Figure 1:
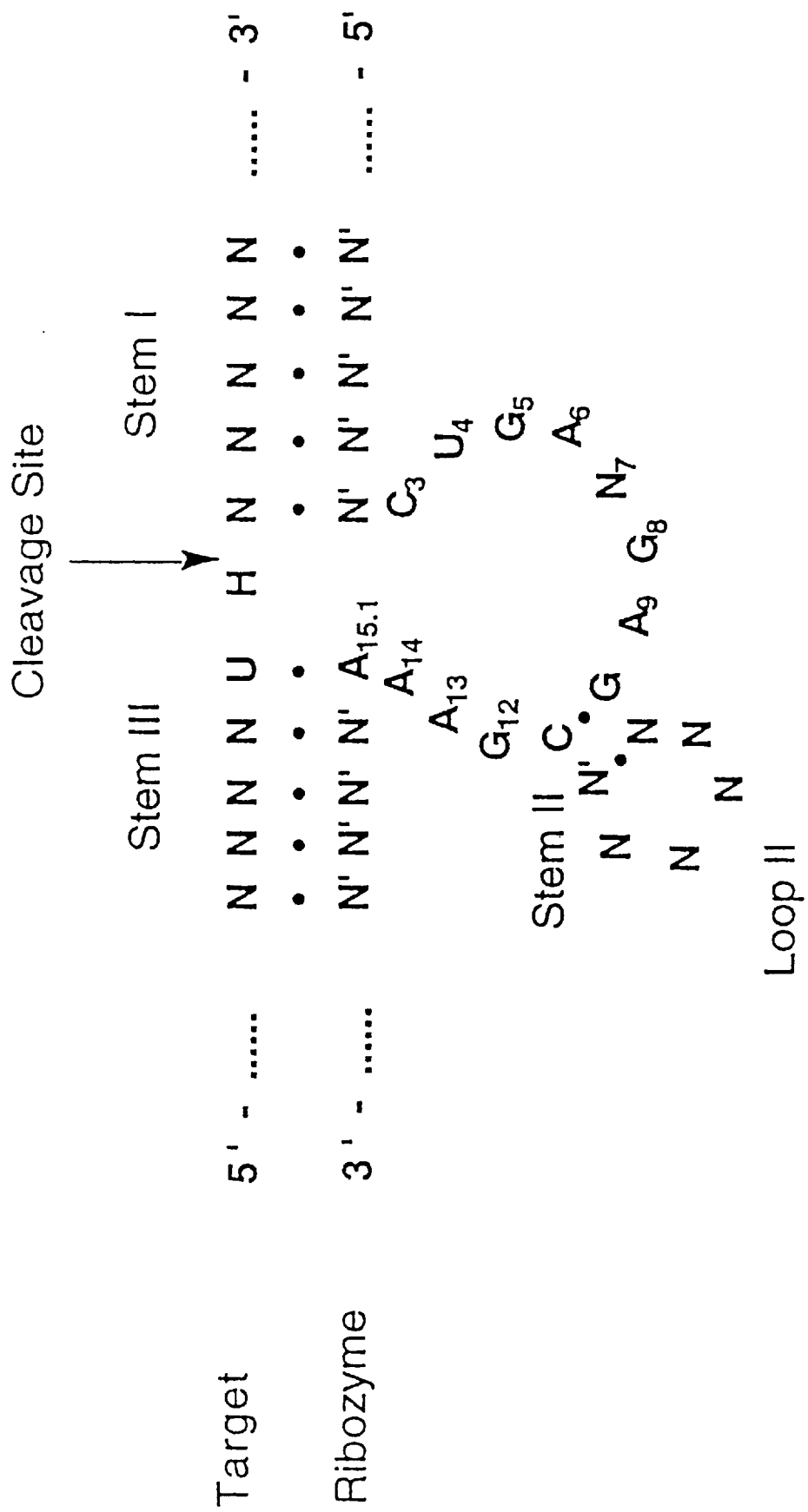

United States Patent [19]

Stinchcomb et al.

[11] Patent Number: 5,807,743
[45] Date of Patent: Sep. 15, 1998

[54] INTERLEUKIN-2 RECEPTOR GAMMA-CHAIN RIBOZYMES

[75] Inventors: Dan T. Stinchcomb, Fort Collins; James A. McSwiggen, Boulder, both of Colo.

[73] Assignee: Ribozyme Pharmaceuticals, Inc., Boulder, Colo.

[21] Appl. No.: 758,306

[22] Filed: Dec. 3, 1996

[51] Int. Cl.$^6$ ............................ C07H 21/09; C12Q 1/68; C12N 15/85

[52] U.S. Cl. .......................... 435/366; 435/6; 435/91.31; 435/172.3; 435/320.1; 435/325; 536/23.1; 536/23.2; 536/24.5

[58] Field of Search .......................... 435/6, 91.1, 91.31, 435/172.3, 325, 366, 320.1; 536/23.1, 23.2, 24.1, 24.5; 514/44

[56] References Cited

U.S. PATENT DOCUMENTS

| | | | |
|---|---|---|---|
| 4,987,071 | 1/1991 | Cech et al. | 435/91.31 |
| 5,135,917 | 8/1992 | Burch | 514/44 |
| 5,334,711 | 8/1994 | Sproat et al. | 536/24.5 |
| 5,359,051 | 10/1994 | Cook et al. | 435/6 |
| 5,525,468 | 6/1996 | McSwiggen | 435/6 |

FOREIGN PATENT DOCUMENTS

| | | |
|---|---|---|
| 0360257 | 3/1990 | European Pat. Off. . |
| 0578932 | 4/1993 | European Pat. Off. . |
| 9103162 | 3/1991 | WIPO . |
| 9207065 | 4/1992 | WIPO . |
| 9213886 | 8/1992 | WIPO . |
| 8900168 | 1/1993 | WIPO . |
| 9314218 | 7/1993 | WIPO . |
| 9315187 | 8/1993 | WIPO . |
| 9323057 | 11/1993 | WIPO . |
| 9323569 | 11/1993 | WIPO . |
| 9402595 | 2/1994 | WIPO . |
| 9506731 | 3/1995 | WIPO . |
| 9511910 | 5/1995 | WIPO . |
| 9513378 | 5/1995 | WIPO . |
| 9513380 | 5/1995 | WIPO . |
| 9523225 | 8/1995 | WIPO . |
| 9531541 | 11/1995 | WIPO . |
| 9618736 | 6/1996 | WIPO . |
| 9622689 | 8/1996 | WIPO . |

OTHER PUBLICATIONS

Arima et al., *J. Exp. Med.* 176:1265 (1992).

Caine, "Immunosuppression for Organ Grafting," *Transplantation Proceedings* 24:1260–1262 (1992).

Campen et al., *Arthritis Rheum* 31:1358 (1988).

Carlson et al., "Effects of Orally Administered Rapamycin in Animal Models of Arthritis and Other Autoimmune Diseases," in *Immunomodulating Drugs: Annals of the New York Academy of Sciences* 685:86–113 (1993).

Carter, "Adeno–Associated Virus Vectors," *Curr Opi. Biotech.* 3:533–539 (1992).

Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20:4581–4589 (1992).

Chowrira and Burke, "Extensive Phosphorothioate Substitution Yields Highly Active and Nuclease–Resisant Hairpin Ribozymes," *Nucleic Acids Research* 20:2835–2840 (1992).

Chowrira et al., "In Vitro and in Vivo Comparison of Hammerhead, Hairpin, and Hepatitis Delta Virus Self–Processing Ribozyme Cassettes," *J. Biol. Chem.* 269:25856–25864 (1994).

Collins and Olive, "Reaction Conditions and Kinetics of Self–Cleavage of a Ribozyme Derived From Neurospora VS RNA," *Biochemistry* 32:2795–2799 (1993).

Dropulic et al., "Functional Characterization of a U5 Ribozyme: Intracellular Suppression of Human Immunodeficiency Virus Type I Expression," *Journal of Virology* 66:1432–1441 (1992).

Duval–Valentin, "Specific inhibition of transcription by triple helix–forming oligonucleotides," *Proc. Natl. Acad. Sci. USA* 89:504–508 (1992).

Egholm et al., "PNA hybridizes to complementary oligonucleotides obeying the Watson–Crick hydrogen–bonding rules," *Nature* 365:566–568 (1993).

Elroy–Stein and Moss, "Cytoplasmic Expression System Based on Constitutive Synthesis of Bacteriophage T7 RNA Polymerase in Mammalian Cells," *Proc. Natl. Acad. Sci. USA* 87:6743–6747 (1990).

Feldstein et al., "Two sequences participating in the autolytic processing of satellite tobacco ringspot virus complementary RNA," *Gene* 82:53–61 (1989).

Finck et al., "Treatment of Murine Lupus with CTLA41g," *Science* 265:1225–1227 (1994).

Fodor et al., "Expression of a functional human complement inhibitor in a transgenic pig as a model for the prevention of xenogenic hyperacute organ rejection," *Proc. Natl. Acad. Sci. USA* 91:11153–11157 (1994).

Forster and Altman, "External Guide Sequences for an RNA Enzyme," *Science* 249:783–786 (1990).

Fulehian et al., "Cyclosporin A Inhibits CD40 Ligand Expression in T Lymphocytes," *J. Clin. Invest.* 93:1315–1320 (1994).

Gao and Huang, "Cytoplasmic Expression of a Reporter Gene by Co–Delivery of T7 RNA Polymerase and T7 Promoter Sequence with Cationic Liposomes," *Nucleic Acids Research* 21:2867–2872 (1993).

Gottlieb et al., *Nature Medicine* 1:442 (1995)2.

(List continued on next page.)

Primary Examiner—John L. LeGuyader
Attorney, Agent, or Firm—Lyon & Lyon LLP

[57] ABSTRACT

A nucleic acid molecule which blocks synthesis and/or expression of an IL-2R encoded RNA, wherein said nucleic acid molecule is used to treat graft rejection, an autoimmune disease, cancer, psoriasis, an allergy or other inflammatory disease.

15 Claims, 6 Drawing Sheets

OTHER PUBLICATIONS

Griffin et al., "Group II intron ribozymes that cleave DNA and RNA linkages with similar efficiency, and lack contacts with substrate 2'-hydroxyl groups," *Chemistry & Biology*, 2:761–770 (1995).

Guerrier–Takada et al., "The RNA Moiety of Ribonuclease P Is the Catalytic Subunit of the Enzyme," *Cell* 35:849–857 (1983).

Guo and Collins, "Efficent trans–cleavage of stem–loop RNA substrate by a ribozyme derived from Neurospora VS RNA," *EMBO J.* 14:368–376 (1995).

Hampel et al., "'Hairpin' Catalytic RNA Model: Evidence for Helices and Sequence Requirement for Substrate RNA," *Nucleic Acids Research* 18:299–304 (1990).

Hampel and Tritz, "RNA Catalytic Properties of the Minimum (–)s TRSV Sequence," *Biochemistry* 28:4929–4933 (1989).

Haseloff and Gerlach, "Simple RNA Enzymes with New and Highly Specific Endoribonuclease Activities," *Nature* 334:585–591 (1988).

Haseloff and Gerlach, "Sequences required for self–catalysed cleavage of the satellite RNA of tobacco ringspot virus," *Gene* 82:43–52 (1989).

Hatakeyama et al., *Science* 244:551 (1989).

Hertel et al., "Numbering System for the Hammerhead," *Nucleic Acids Research* 20:3252 (1992).

Izant and Weintraub, "Constitutive and Conditional Suppression of Exogenous and Endogeneous Genes by Anti–Sense RNA," *Science* 229:345–352 (1985).

Jaeger et al., "Improved Predictions of Secondary Structures for RNA," *Proc. Natl. Acad. Sci. USA* 86:7706–7710 (1989).

Jeffries and Symons, "A Catalytic 13–mer Ribozyme," *Nucleic Acids Research* 17:1371–1377 (1989).

Kashani–Sabet et al., "Reversal of the Malignant Phenotype by an Anti–ras Ribozyme," *Antisense Research & Development* 2:3–15 (1992).

Kelly et al., *J. Immunol.* 140:59 (1988).

Kemeny and Diaz–Sanchez, "Can persistent IgE responses be suppressed?" *Clin. Exp. Immunol.* 82:423–426 (1990).

Keystone et al., *Arthritis Rheum* 31:844 (1988).

Kondo et al., *Science* 262:1874 (1993).

Kuus–Reichel et al., *Hybridoma* 13:115 (1994).

L'Huillier et al., "Cytoplasmic Delivery of Ribozymes Lead to Efficient Reduction in α–Lactalbumin mRNA Levels in C1271 Mouse," *Embo J.* 11:4411–4418 (1992).

Leonard et al., *Nature* 311:626 (1984).

Li and Altman, "Cleavage by RNase P of gene N mRNA reduce bacteriophage λ burst size," *Nucleic Acids Research* 24:835–842 (1996).

Lieber et al., "Stable High–Level Gene Expression in Mammalian Cells by T7 Phage RNA Polymerase," *Methods Enzymol.* 217:47–66 (1993).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A* 90:8000–8004 (1993).

McGarry and Lindquist, "Inhibition of heat shock protein synthesis by heat–inducible antisense RNA," *Proc. Natl. Acad. Sci. USA* 83:399–403 (1986).

Michels and Pyle, "Conversion of a Group II Intron into a New Multiple–Turnover Ribozyme that Selectively Cleaves Oligonucleotides: Elucidation of Reaction Mechanism and Structure/Function Relationships," *Biochemistry* 34:2965–2977 (1995).

Milligan and Uhlenbeck, "Synthesis of Small RNAs Using T7 RNA Polymerase," *Methods Enzymol.* 180:51–62 (1989).

Nelson and Kurman, *Proc. Soc. Exp. Biol. Med.* 206:309 (1994).

Nikaido et al., *Nature* 311:631 (1984).

Noguchi et al., *Science* 262:1877 (1993).

Noguchi et al., *Cell* 73:147 (1993).

Nowak, *Science* 262:1818 (1993).

Nowak, "Xenotransplants Set to Resume," *Science* 266:1148–1151 (1994).

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Pachecho–Silva et al., *Eur. J. Immunol.* 22:697 (1992).

Perreault et al., "Mixed Deoxyribo–and Ribo–Oligonucleotides with Catalytic Activity," *Nature* 344:565–567 (1990).

Perrotta and Been, "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease-Resistant 2'–Modified Hammerhead Ribozymes," *Science* 253:314–317 (1991).

Pretolani et al., "Cytokines—Eosinophil Interactions in Experimental Allergy," *Cells and Cytokines in Lung Inflammation: Annals of the New York Academy of Sciences* 725:247–258 (1994).

Rossi et al., "Ribozymes as Anti–HIV–1 Therapeutic Agents: Principles, Applications, and Problems," *Acids Research and Human Retroviruses* 8:183–189 (1992).

Rubin and Nelson, *Annals. Int. Med.* 113:619 (1990).

Russell et al., *Science* 262:1880 (1993).

Sarver et al., "Ribozymes as Potential Anti–HIV–1 Therapeutic Agents" *Science* 247:1222–1225 (1990).

Saville and Collins, "A Site–Specific Self–Cleavage Reaction Performed by a Novel RNA in Neurospora Mitochondria," *Cell* 61;685–696 (1990).

Saville and Collins, "RNA–Mediated Ligation of Self–Cleavage Products of a Neurospora Mitochondrial Plasmid Transcript," *Proc. Natl. Acad. Sci. USA* 88:8826–8830 (1991).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18;5433–5441 (1990).

Stein and Cheng, "Antisense Oligonucleotides as Therapeutic Agents—Is the Bullet Really Magical?" *Science* 261:1004–1288 (1993).

Taira et al., "Construction of a novel RNA–transcript–trimming plasmid which can be used both in vitro in place of run–off and (G)–free transcriptions and in vivo as multi–sequences transcription vectors," *Nucleic Acids Research* 19:5125–5130 (1991).

Takeshita et al., *Science* 257:379 (1992).

Taniguchi and Minami, *Cell* 73:5–8 (1993).

Thompson et al., "Improved accumulation and activity of ribozymes expressed from a tRNA–based RNA polymerase III promoter," *Nucleic Acids Research* 23:2259–2268 (1995).

Torrence et al., "Targeting RNA for degradation with a (2'–5') oligoadenylate–antisense chimera," *Proc. Natl. Acad. Sci. USA* 90:1300–1304 (1993).

Uhlenbeck, "A Small Catalytic Oligoribonucleotide," *Nature* 328:596–600 (1987).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Usman et al., "Chemical modification of hammerhead ribozymes: activity and nuclease resistance," *Nucleic Acids Syposium Series* 31:163–164 (1994).

Usman and Cedergren, "Exploiting the chemical synthesis of RNA," *TIBS* 17:334–339 (1992).

van Laar et al., "Towards T Cell Vaccination in Rheumatoid Arthritis," *Chem. Immunol.* 58:206–235 (1994).

Van Gool et al., "Synergy Between Cyclosporin A and a Monoclonal Antibody to B7 in Blocking Alloantigen–Induced T–Cell Activation," *Blood* 83:176–183 (1994).

Ventura et al., "Activation of HIV–Specific Ribozyme Activity by Self–Cleavage," *Nucleic Acids Research* 21:3249–3255 (1993).

Waldmann, *JAMA* 263:272 (1990).

Weerasinghe et al., "Resistance to Human Immunodeficiency Virus Type 1 (HIV–1) Infection in Human CD4$^+$ Lymphocyte–Derived Cell Lines Conferred by Using Retroviral Vectors Expressing an HIV–1 RNA–Specific Ribozyme," *Journal of Virology* 65:5531–5534 (1994).

Wekerle et al., "Animal Models," *Ann. Neurol.* 36:s47–s53 (1994).

Wincott et al., "Synthesis, deprotection, analysis and purification of RNA and ribozymes," *Nucleic Acids Research* 23:2677–2684 (1995).

Wolf and Brelsford, *Arthritis Rheum* 31:729 (1988).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zabner et al., "Adenovirus–Mediated Gene Transfer Transiently Corrects the Chloride Transport Defect in Nasal Epithelia of Patients with Cystic Fibrosis," *Cell* 75:207–216 (1993).

Zhou et al., "Synthesis of Functional mRNA in Mammalian Cells by Bacteriophage T3 RNA Polymerase," *Mol. Cell. Biol.* 10:4529–4537 (1990).

Stall et al. Pharm. Res. 12: 465–483 (1995).

Gewirtz et al. PNAS 93: 3161–3163 (1996).

Rojanasakul Adv. Drug. Delivery Reviews 18 (1996) 115–131.

- Body-labeled transcript (not purified)
- DNA oligo (10 nM, 100 nM and 1000 nM)
- RNAse H (0.08 -1.0 u/µl)
- 37°C, 10 min

INTERLEUKIN-2 RECEPTOR GAMMA-CHAIN RIBOZYMES

BACKGROUND OF THE INVENTION

This invention relates to methods for the prevention of graft rejection, and autoimmune diseases, inflammatory disorders, cancer, psoriasis and allergies, in particular, by inhibition of expression of the γ-chain of the interleukin-2 receptor (IL-2Rγ).

The following is a discussion of relevant art, none of which is admitted to be prior art to the present invention. All references cited herein are hereby incorporated by reference herein in their entirety, including drawings.

An adaptive immune response requires activation, clonal expansion, and differentiation of a class of cells termed T lymphocytes (T cells). T cell activation is a multi-step process requiring several signaling events between the T cell and an antigen presenting cell. The ensuing discussion details signals that are exchanged between T cells and antigen presenting B cells. Similar pathways are thought to occur between T cells, monocytes, follicular dendritic cells and other antigen presenting cells.

T cell activation is initiated when the T-cell receptor (TCR) binds to a specific antigen that is associated with the MHC proteins on the surface of an antigen presenting cell. Complete T cell activation via the T cell receptor and costimulatory molecules leads to cytokine secretion, clonal expansion, and differentiation.

A variety of cytokines (polypeptide hormones) are secreted during the activation of lymphocytes, including IL-2. These cytokines interact with specific, high-affinity cell surface receptors to stimulate T-cell growth and differentiation.

IL-2 exerts its influence on cells by interacting with specific, high-affinity cell-surface receptors termed IL-2 receptor (IL-2R). The IL-2R is that it is made up of at least three distinct components or chains: IL-2 alpha chain (IL-2Rα), IL-2 beta chain (IL-2Rβ) and IL-2 gamma chain (IL-2Rγ) [for a review see Taniguchi and Minami, 1993 Cell 73, 5–8; and Nakamura et al., European Patent Application EP 0578 932). Non-covalent association of the three IL-2R chains on the cell surface give rise to a functional IL-2R complex. IL-2Rα chain is a 55 kd protein (Leonard et al., 1984 Nature 311, 626; Nikaido et al., 1984 Nature 311, 631) which is usually not expressed in resting T-cells. However, upon activation of the T-cell, high level expression of IL-2 and IL-2Rα is observed in activated T-cells. IL-2Rβ chain is a 75 kd protein (Hatakeyama et al., 1989 Science 244, 551) which is constitutively expressed in CD8+ cytotoxic T cells. However, the expression of IL-2Rβ is not detectable in CD4+ helper T cells. High level of IL-2Rβ expression is often observed in activated T-cells. IL-2Rγ is a 64 kd protein (Nakamura et al., European Patent Publication EP 0578932 A2, Takeshita et al., 1992 Science 257, 379) which is constitutively expressed in lymphoid cells. The three subunits of IL-2R associate with each other in various combinations to yield three families of receptors based on their affinity towards IL-2. IL-2Rα alone binds to IL-2 with "low" affinity (Kd=$10^{-8}$M); IL-2Rβ and IL-2Rγ interact with each other to bind IL-2 with "intermediate" affinity (Kd=$10^{-9}$M); IL-2Rα, IL-2Rβ and IL-2Rγ interact with each other to bind IL-2 with "high" affinity (Kd=$10^{-11}$M).

IL-2 (15.5 kd) is an important immune regulator, especially involved in the clonal proliferation of T cells. IL-2 also exerts its influence on other lymphoid cells such as thymocytes, B cells, macrophages, natural killer (NK) cells, lymphokine-activated killer (LAK) cells, monocytes, early or mature granulocytes and others. Additionally, certain cells of non-lymphoid origin are also stimulated by IL-2 (for reviews see Taniguchi and Minami, supra; Nakamura et al., supra; Nelson and Kurman, 1994 Proc. Soc. Exp. Biol. Med. 206, 309) and are therefore likely to express high-affinity IL-2 receptors.

IL-2γ is a key player in the IL-2-induced signal transduction pathway (see Taniguchi and Minami supra for review). Takeshita et al., supra demonstrated that IL-2γ is essential for receptor-mediated internalization of IL-2. Arima et al., 1992 J. Exp. Med., 176, 1265 reported that a cell line that expresses IL-2Rα, and IL-2Rβ but not IL-2Rγ does not respond to IL-2 stimulation. Recently, Noguchi et al., 1993 Cell 73, 147, showed evidence for the involvement of IL-2Rγ in X-linked severe combined immunodeficiency (XSCID). XSCID involves severe depletion of mature and immature T-cells. It appears therefore that IL-2Rγ plays a critical role in the maturation of T-cells.

The role of IL-2Rγ in signal transduction is not limited to the IL-2 system. It was recently shown by several groups that IL-2Rγ is an active component of several cytokine receptors such as the receptors for IL-4, IL-7, IL-9 and IL-13 (Kondo et al., 1993 Science 262, 1874; Noguchi et al., 1993 Science 262, 1877; Russell et al., 1993 Science 262, 1880; Nowak, 1993 Science 262, 1818).

The presence of activated T cells expressing high level of IL-2R has been associated with certain forms of lymphoid neoplasia, autoimmune diseases, psoriasis and T-cells that participate in graft rejection (for a review see Waldmann, 1990 JAMA 263, 272; Rubin and Nelson, 1990 Annals Int. Med. 113,619; Pacheco-Silva et al., 1992 Eur. J. Immunol. 22, 697; Jacques et al., PCT Publication WO 92/13886; Nelson and Kurman, 1994 Proc. Soc. Exp. Biol. Med. 206, 309; Nakamura et al., supra; Kuus-Reichel et al., 1994 Hybridoma 13, 115; Gottlieb et al., 1995 Nature Medicine 1, 442). Thus down-modulating IL-2Rγ expression on T cells in patients with these conditions is likely to reverse the state of T cell activation and repress T cell proliferation and alleviate disease.

Rubin and Nelson, supra state that:

"Patients with an HTLV-1 associated, non-malignant spastic myelopathy, a neurologic disorder complicated by unusual pulmonary involvement featuring broncoalveolar T lymphocytosis, have elevated levels of serum sIL-2R and measurable sIL-2R in the bronchoalveolar lavage fluid . . . . Measurement of sIL-2R levels has also been useful in the management of other hematologic neoplasms, particularly hairy cell leukemia."

Elevated levels of IL-2R have been associated with rheumatoid arthritis and systemic lupus erythematosus (Keystone et al., 1988 Arthritis Rheum 31, 844; Campen et al., 1988 Arthritis Rheum 31, 1358; Wolf and Brelsford, 1988 Arthritis Rheum 31, 729).

Insulin-dependent diabetes mellitus (IDDM) is T-cell associated autoimmune disease, where insulin-producing b cells are selectively targeted by T-cells (Pacheco-Silva et al., supra). They state that:

Expression of the high-affinity IL-2R is a universal feature of recently activated but not resting T-cells. An ideal therapeutic for diabetes should rapidly and selectively destroy the activated, autoregressive T-cells. Our previous studies established that diabetogenic cells express IL-2R in vivo . . . . Therefore we reasoned that specific elimination of IL-2R+ T cells should abort diabetogenic process . . . IL-2R-targeted therapy may be an attractive alternative to the immunosuppressive agents currently available.

Administration of anti-IL-2R antibody prevents insulitis in non-obese diabetic (NOD) mice (Kelly et al., 1988 *J. Immunol* 140, 59; Pacheco-Silva et al., 1992 supra). Recently, Kuus-Reichel et al., 1994 supra used a bifunctional antibody with specificities for mouse IL-2R and vinca alkaloids as a means to block diabetes in mice.

Psoriasis is a an inflammatory disease characterized by excessive scaling and inflammation in the skin (Gottlieb et al., 1995 supra). Psoriasis appears to be an autoimmune disease where activated $CD8^+$ T cells directly invade the epidermis and dermis of the skin. Gottlieb et al., supra explored the role of IL-2 receptor-expressing T cells using a "fusion" protein, wherein the receptor binding domain of diphtheria toxin is replaced with IL-2. This chimeric protein specifically targets the destruction of cells bearing high affinity IL-2R. This protein was used to selectively deplete activated T-cells in psoriatic tissue and cause regression of the disease. Thus, the activated T cells are necessary for maintenance of the psoriatic lesions.

Successful organ transplantation currently requires suppression of the recipient's immune system in order to prevent graft rejection and maintain good graft function. The available therapies, including cyclosporin A, FK506 and various monoclonal antibodies, all have side effects (Caine, 1992 *Transplantation Proceedings* 24, 1260; Fuleihan et al., 1994 *J. Clin. Invest.* 93, 1315; Van Gool et al., 1994 *Blood* 83, 176). Since organ graft rejection is mediated by T cell effector function, the goal is to block the activation and expansion of the T cells that recognize donor antigens.

By "transplantation" is meant grafting of tissues and/or organ from the body of an individual to a different place within the same or different individual. Transplantation can be grafting of tissues and/or organs from one area of the body to another. Transplantation of tissues and/or organs between genetically dissimilar animals of the same species is termed as allogeneic transplantation. Transplantation of animal organs into humans is termed xenotransplants (for a review see Nowak, 1994 *Science* 266, 1148). Another major limitation in the field of transplantation is the supply of donor organs (Id.). The ability to induce tolerance would substantially increase the chances of successful xenographs, thereby greatly increasing the donor pool.

By "graft" is meant implantation or transplantation of tissue and/or organs.

Therapeutic agents used to prevent rejection of a transplanted organ include cytotoxic compounds or antibodies designed to suppress the cell-mediated immune system. The side effects of these agents are those of immunosuppression and infections. The primary approved agents are azathioprine, corticosteroids, and cyclosporine, all of which have outward effects on tissues outside the immune system; the antibodies are antilymphocyte or antithymocyte globulins. All of these are given to individuals who have been as closely matched as possible to their donors by both major and minor histocompatibility typing. Since the principal problem in transplantation is an antigenic mismatch and the resulting need for cytotoxic therapy, any therapeutic improvement which specifically decreases the local immune response is useful.

Cyclosporine

At the end of the 1970's and early 1980's the introduction of cyclosporine revolutionized the transplantation field. It is a potent immunosuppressant which can inhibit immunocompetent lymphocytes specifically and reversibly. Its primary mechanism of action appears to be inhibition of the production and release of interleukin-2 by T helper cells. In addition it also interferes with the release of interleukin-1 by macrophages, as well as proliferation of B lymphocytes. It was approved by the FDA in 1983 and by 1989 was almost universally given to transplant recipients. At first it was believed that the toxicity and side effects from cyclosporine were minimal and it was hailed as a "wonder drug." Numerous side effects have been progressively cited, including the appearance of lymphomas, especially in the gastrointestinal tract; acute and chronic nephrotoxcicity; hypertension; hepatotoxicity; hirsutism; anemia; neurotoxicity; endocrine and neurological complications; and gastrointestinal distress. It is now acknowledged that the non-specific side effects of the drug demand caution and close monitoring of its use. One-year survival rates for cadaver kidney transplants treated with cyclosporine is 80%, much better than the 50–60% rates without the drug. The one-year survival is almost 90% for transplants with related donors and the use of cyclosporine.

Azathioprine

In addition to cyclosporine, azathioprine is used for transplant patients. Azathioprine is one of the mercaptopurine class of drugs and inhibits nucleic acid synthesis. Patients are maintained indefinitely on daily doses of 1 mg/kg or less, with a dosage adjusted in accordance with the white cell count. The drug may cause depression of bone marrow elements and may cause jaundice.

Corticosteroids

Prednisone, used in almost all transplant recipients, is usually given in association with azathioprine and cyclosporine. The dosage must be regulated carefully so as so prevent complications such as infection, development of cushingoid features, and hypertension. Usually the initial maintenance prednisone dosage is 0.5 mg/kg/d. This dosage is usually further decreased in the outpatient clinic until maintenance levels of about 10 mg/d for adults are obtained. The exact site of action of corticosteroids on the immune response is not known.

Antithymoblast or antilymphocyte globulin (ALG) and antithymocyte globulin (ATG)

These are important adjunctive immunosuppressants. They are effective, particularly in induction of immunosuppressive therapy and in the treatment of corticosteroid-resistant rejection. Both ALG and ATG can be made by immunizing horses, rabbits, or sheep; the main source is horses. Lymphocytes from human peripheral blood, spleen, lymph nodes, or thymus serve as the immunogen.

Tacrolimus

On Apr. 13, 1994 the Food and Drug Administration approved another drug to help prevent the rejection of organ transplants. The drug, tacrolimus, was approved only for use in liver transplant patients. An alternative to cyclosporine, the macrolide immunosuppressant tacrolimus is a powerful and selective anti-T-lymphocyte agent that was discovered in 1984. Tacrolimus, isolated from the fungus *Streptomyces tsukubaensis*, possesses immunodepressant properties similar to but more potent than cyclosporine. It inhibits both cell-mediated and humoral immune responses. Like cyclosporine, tacrolimus demonstrates considerable interindividual variation in its pharmacokinetic profile. Some clinical studies with tacrolimus have neither been published in their entirety nor subjected to extensive peer review; there are only a few published randomized investigations of tacrolimus vs. cyclosporine, particularly in renal transplantation. Despite these drawbacks, tacrolimus has shown notable efficacy as a rescue or primary immunosuppressant therapy when combined with corticosteroids. The potential for reductional withdrawal of corticosteroid therapy with tacrolimus appears to be a distinct advantage compared with the cyclosporine. This benefit may be enhanced by reduced incidence of infectious complications, hypertension and hypercholesterolemia reported by some investigators. In other respects, the tolerability profile of tacrolimus appears to be broadly similar to that of cyclosporine.

In addition to induction of graft tolerance, inhibition of the common IL-2Rγ chain can be used to reverse autoimmune diseases, multiple sclerosis, cancer and allergies which are mediated by immune response to self-antigens (Finck et al., Science 265:1225–1227 (1994).

Burch, U.S. Pat. No. 5.135,917, disclose antisense oligonucleotides that inhibit IL-1 receptor. The oligonucleotide compounds of the Burch patent bind to the messenger RNA coding for human IL-1 receptors and inhibit expression of the receptors.

Waldmann and Leonard, PCT Publication WO 89/00168, describe the use of anti-IL-2Rβ antibodies to block the high-affinity binding of IL-2. They describe a method for neutralizing or killing p70–75 expressing cells by reacting p70–75 expressing cells with an effective amount of anti-p70–75 antibody to neutralize or kill the cells.

Jaques et al., WO 92/13886 state:

The compositions, which is comprised of at least two antibodies . . . directed against the interleukin-e receiver . . . [is] useful as active agent against rejection of members and marrow grafting, against leukemia and positive CD25 lymphomas as well as against autoimmune pathologies such as type 1 diabetes, rheumatoid polyarthritis, ankylosing spondylarthritis, multiple sclerosis and myasthenia gravis.

Nakamura et al., European Patent Publication EP 0578932A2 describe purification of an IL-2 receptor γ chain molecule, and further describe an antibody capable of binding to an IL-2 receptor γ chain molecule. Nakamura et al. suggest that such an antibody would be useful to cure autoimmune diseases and to prevent graft-rejection.

Sullivan et al., WO 94/02595 describe an enzymatic RNA molecule (or ribozyme) which cleaves mRNA associated with development or maintenance of a psoriatic or asthmatic condition. Specifically, the described ribozymes cleave mRNA encoding TNF-α, IL-5, IL-1, IL-3, IL-4, IL-6, IL-8, glycerol transferase, selectins, E-selectin, MEL-14, ICAM-1, ELAM-1, VCAM-1, GMP-140, MAM, TGFβ, TNFaR, IL-1R, α-, β- or γ-interferon, GM-CSF and protein kinase C.

Stinchcomb et al., WO 95/23225 describe enzymatic nucleic acid molecules which cleave mRNA associated with development or maintenance of an autoimmune disease, and which can be used to increase graft tolerance.

Stinchcomb et al., WO 95/31541 describes enzymatic nucleic acid molecules which cleave mRNA associated with restenosis and cancer.

Beigelman et al., WO 96/18736 describes enzymatic nucleic acid molecules which cleave RNA associated with development and maintenance of an arthritic condition, induction of graft tolerance, or reversal of an immune response.

Draper et al., WO 95/13380 describes enzymatic nucleic acid molecules which cleave RNA associated with development and maintenance of an arthritic condition.

The references cited above are distinct from the presently claimed invention since they do not disclose the use of ribozymes to cleave IL-2Rγ chain RNA.

SUMMARY OF THE INVENTION

The invention features novel nucleic acid-based techniques [e.g., enzymatic nucleic acid molecules (ribozymes), antisense nucleic acids, 2-5A antisense chimeras, triplex DNA, nucleic acid decoys, antisense nucleic acids containing RNA cleaving chemical groups (Cook et al., U.S. Pat. No. 5,359,051)] and methods for their use to induce graft tolerance, to treat autoimmune diseases such as lupus, rheumatoid arthritis, multiple sclerosis, certain cancers, psoriasis and to treatment of allergies.

In a preferred embodiment, the invention features use of nucleic acid-based techniques to induce graft tolerance by inhibiting or reducing the synthesis of IL-2Rγ.

By "inhibit" is meant that the activity of IL-2Rγ or the level of mRNAs encoded by IL-2Rγ is reduced below that observed in the absence of the nucleic acid.

In one embodiment, inhibition with ribozymes preferably is below that level observed in the presence of an enzymatically inactive RNA molecule able to bind to the same site on the mRNA, but unable to cleave that RNA.

By "antisense nucleic acid" is meant a non-enzymatic nucleic acid molecule that binds to another RNA (target RNA) by means of RNA-RNA or RNA-DNA or RNA-PNA (protein nucleic acid; Egholm et al., 1993 Nature 365, 566) interactions and alters the activity of the target RNA (for a review see Stein and Cheng, 1993 Science 261, 1004).

By "2-5A antisense chimera" is meant, an antisense oligonucleotide containing a 5' phosphorylated 2'-5'-linked adenylate residues. These chimeras bind to target RNA in a sequence-specific manner and activate a cellular 2-5A-dependent ribonuclease which in turn cleaves the target RNA (Torrence et al., 1993 Proc. Natl. Acad. Sci. USA 90, 1300).

By "triplex DNA" is meant an oligonucleotide that can bind to a double-stranded DNA in a sequence-specific manner to form a triple-strand helix. Triple-helix formation has been shown to inhibit transcription of the targeted gene (Duval-Valentin et al., 1992 Proc. Natl. Acad. Sci. USA 89, 504).

By "decoy nucleic acid" is meant a nucleic molecule that mimics the natural binding domain for a ligand. The decoy RNA therefore competes with natural binding target for the binding of a specific ligand.

By "gene" is meant a nucleic acid that encodes an RNA.

By "complementarity" is meant a nucleic acid that can form hydrogen bond(s) with other RNA sequence by either traditional Watson-Crick or other non-traditional types (for example, Hoogsteen type) of base-paired interactions.

By "enzymatic RNA molecule" it is meant an RNA molecule which has complementarity in a substrate binding region to a specified gene target, and also has an enzymatic activity which is active to specifically cleave RNA in that target. That is, the enzymatic RNA molecule is able to intermolecularly cleave RNA and thereby inactivate a target RNA molecule. This complementarity functions to allow sufficient hybridization of the enzymatic RNA molecule to the target RNA to allow the cleavage to occur. One hundred percent complementarity is preferred, but complementarity as low as 50–75% may also be useful in this invention. Such an RNA molecule may include one or more ribonucleotides, and other types of nucleotides and even sugar molecules without a nucleotide base attached. See, e.g., Usman et al., WO 95/06731, and WO 95/13378; Dudycz et al., WO 95/11910; and Eckstein et al., WO 92/07065; all hereby incorporated by reference herein.

By "equivalent" RNA to IL-2Rγ is meant to include those naturally occurring RNA molecules associated with graft rejection and auto immune disorders in various animals, including human, mice, rats, rabbits, primates and pigs.

Seven basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, since the concentration of ribozyme necessary to affect a therapeutic treatment may be lower. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base-pairing mechanism of binding to the target RNA, but also on the mechanism of target RNA cleavage. Single mismatches, or base-substitutions, near the site of cleavage can completely eliminate catalytic activity of a ribozyme.

Ribozymes that cleave the specified sites in IL-2Rγ RNAs represent a novel therapeutic approach to induce graft tolerance, and treat autoimmune diseases, allergies, cancer and other inflammatory conditions. Applicant indicates that ribozymes are able to inhibit the activity of IL-2Rγ and that the catalytic activity of the ribozymes is required for their inhibitory effect. Those of ordinary skill in the art, will find that it is clear from the examples described that other ribozymes that cleave these sites in IL-2Rγ RNAs may be readily designed and are within the scope of this invention.

In one of the preferred embodiments of the inventions herein, the enzymatic nucleic acid molecule is formed in a hammerhead or hairpin motif, but may also be formed in the motif of a hepatitis d virus, group I intron, group II intron or RNaseP RNA (in association with an RNA guide sequence) or *Neurospora* VS RNA. Examples of such hammerhead motifs are described by Dreyfus, supra, Rossi et al, 1992, *AIDS Research and Human Retroviruses* 8, 183; of hairpin motifs by Hampel et al., EP0360257, Hampel and Tritz, 1989 *Biochemistry* 28, 4929, Feldstein et al., 1989, *Gene* 82, 53, Haseloff and Gerlach, 1989, *Gene,* 82, 43, and Hampel et al, 1990 *Nucleic Acids Res.* 18, 299; of the hepatitis d virus motif is described by Perrotta and Been, 1992 *Biochemistry* 31,16; of the RNaseP motif by Guerrier-Takada et al, 1983 *Cell* 35, 849; Forster and Altman, 1990, *Science* 249, 783; Li and Altman, 1996, *Nucleic Acids* Res. 24, 835; *Neurospora* VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry 32, 2795–2799*; Guo and Collins, 1995, *EMBO. J* 14, 363); Group II introns are described by Griffin et al., 1995, *Chem. Biol.* 2, 761; Michels and Pyle, 1995, *Biochemistry* 34, 2965; Pyle et al., International PCT Publication No. WO 96/22689; and of the Group I intron by Cech et al, U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

In a preferred embodiment the invention provides a method for producing a class of enzymatic cleaving agents which exhibit a high degree of specificity for the RNA of a desired target. The enzymatic nucleic acid molecule is preferably targeted to a highly conserved sequence region of target mRNAs encoding IL-2Rγ proteins such that specific treatment of a disease or condition can be provided with either one or several enzymatic nucleic acids. Such enzymatic nucleic acid molecules can be delivered exogenously to specific cells as required. Alternatively, the ribozymes can be expressed from DNA/RNA vectors that are delivered to specific cells.

Synthesis of nucleic acids greater than 100 nucleotides in length is difficult using automated methods, and the therapeutic cost of such molecules is prohibitive. In this invention, small nucleic acid motifs (e.g., antisense oligonucleotides, hammerhead or the hairpin ribozymes) are used for exogenous delivery. The simple structure of these molecules increases the ability of the nucleic acid to invade targeted regions of the mRNA structure. However, these nucleic acid molecules can also be expressed within cells from eukaryotic promoters (e.g., Izant and Weintraub, 1985 *Science* 229, 345; McGarry and Lindquist, 1986 *Proc. Natl. Acad. Sci. USA* 83, 399; Scanlon et al., 1991, *Proc. Natl. Acad. Sci. USA,* 88,10591/5; Kashani-Sabet et al, 1992 *Antisense Res. Dev.,* 2, 3–15; Dropulic et al., 1992 *J. Virol,* 66, 1432–41; Weerasinghe et al., 1991 *J. Virol,* 65, 5531–4; Ojwang et al, 1992 *Proc. Natl. Acad. Sci. USA* 89, 10802–6; Chen et al, 1992 *Nucleic Acids Res.,* 20, 4581–9; Sarver et al., 1990 *Science* 247, 1222–1225; Thompson et al, 1995 *Nucleic Acids Res.* 23, 2259). Those skilled in the art realize that any nucleic acid can be expressed in eukaryotic cells from the appropriate DNA/RNA vector. The activity of such nucleic acids can be augmented by their release from the primary transcript by a ribozyme (Draper et al., PCT WO93/23569, and Sullivan et al., PCT WO94/02595, both hereby incorporated in their totality by reference herein; Ohkawa et al, 1992 *Nucleic Acids Symp. Ser.,* 27, 15–6; Taira et al., 1991, *Nucleic Acids Res.,* 19, 5125–30; Ventura et al, 1993 *Nucleic Acids Res.,* 21, 3249–55; Chowrira et al., 1994 *J. Biol. Chem.* 269, 25856).

Such ribozymes are useful for the prevention of the diseases and conditions discussed above, and any other diseases or conditions that are associated with the levels of IL-2Rγ activity in a cell or tissue. By "associated" is meant that the inhibition of IL-2Rγ RNAs and thus reduction in the level respective protein activity will relieve to some extent the symptoms of the is disease or condition. It may also mean that the occurrence of such symptoms is correlated with the level of such RNAs.

Ribozymes are added directly, or can be complexed with cationic lipids, packaged within liposomes, or otherwise delivered to target cells. The nucleic acid or nucleic acid complexes can be locally administered to relevant tissues ex vivo, or in vivo through injection, infusion pump or stent, with or without their incorporation in biopolymers. In preferred embodiments, the ribozymes have binding arms which are complementary to the sequences in Tables II–VII (odd numbered Seq. ID. Nos. from 9-1379). Examples of such ribozymes are also shown in Tables II–VII (even numbered Seq. ID. Nos. from 8-1378). Examples of such ribozymes consist essentially of sequences defined in these Tables. By "consists essentially of" is meant that the active ribozyme contains an enzymatic center (or core) equivalent to those in the examples, and binding arms able to bind mRNA such that cleavage at the target site occurs. Other sequences may be present which do not interfere with such cleavage.

In another aspect of the invention, ribozymes that cleave target molecules and inhibit IL-2Rγ activity are expressed from transcription units inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described above, and persist in target cells. Alternatively Target Sites Targets for useful ribozymes can be determined as disclosed in Draper et al., WO 93/23569; Sullivan et al., WO 93/23057; Thompson et al., WO 94/02595 and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described.

The sequence of human, mouse and canine IL-2Rγ RNAs were screened for optimal ribozyme target sites using a computer folding algorithm. Hammerhead or hairpin ribozyme cleavage sites were identified. These sites are shown in Tables II–VII (All sequences are 5' to 3' in the tables) The nucleotide base position is noted in the Tables as that site to be cleaved by the designated type of ribozyme. While mouse, canine and human sequences can be screened and ribozymes thereafter designed, the human targeted sequences are of most utility. However, as discussed in Stinchcomb et al., "Method and Composition for Treatment of Restenosis and Cancer Using Ribozymes," International PCT Publication No. WO 95/31541, mouse targeted ribozymes may be useful to test efficacy of action of the ribozyme prior to testing in humans. The nucleotide base position is noted in the Tables as that site to be cleaved by the designated type of ribozyme.

Hammerhead or hairpin ribozymes were designed that could bind and were individually analyzed by computer folding (Jaeger et al., 1989 *Proc. Natl. Acad. Sci. USA*, 86, 7706) to assess whether the ribozyme sequences fold into the appropriate secondary structure. Those ribozymes with unfavorable intramolecular interactions between the binding arms and the catalytic core were eliminated from consideration. Varying binding arm lengths can be chosen to optimize activity. Generally, at least 5 bases on each arm are able to bind to, or otherwise interact with, the target RNA.

Figure 6:
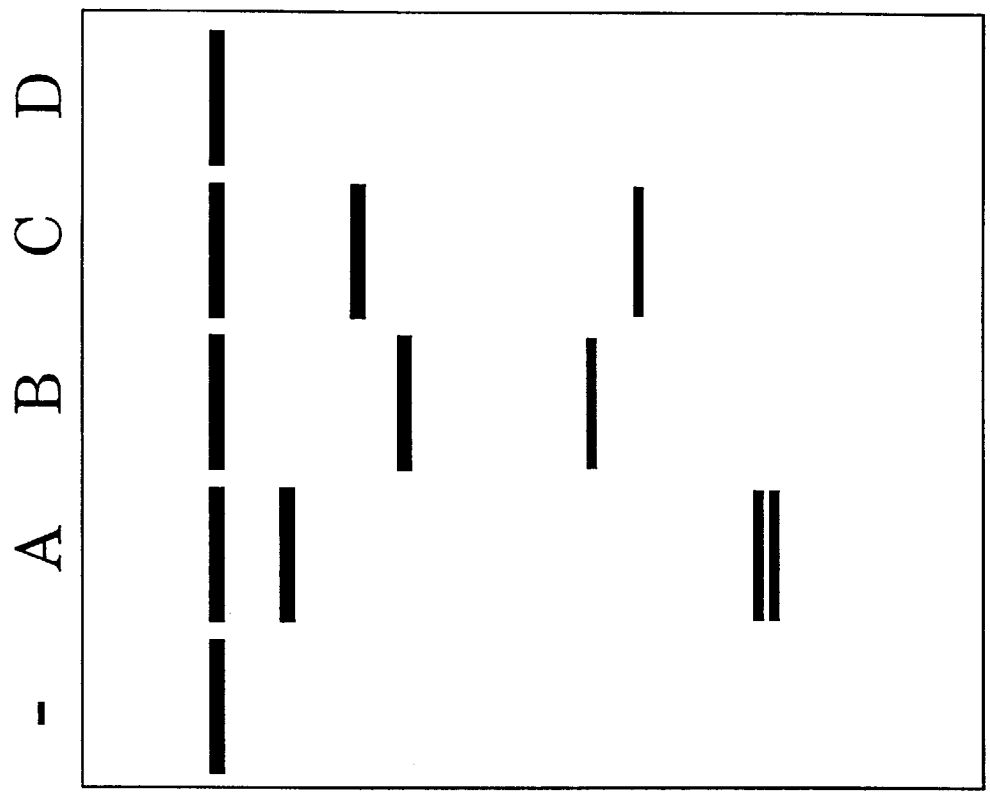
Figure 6:
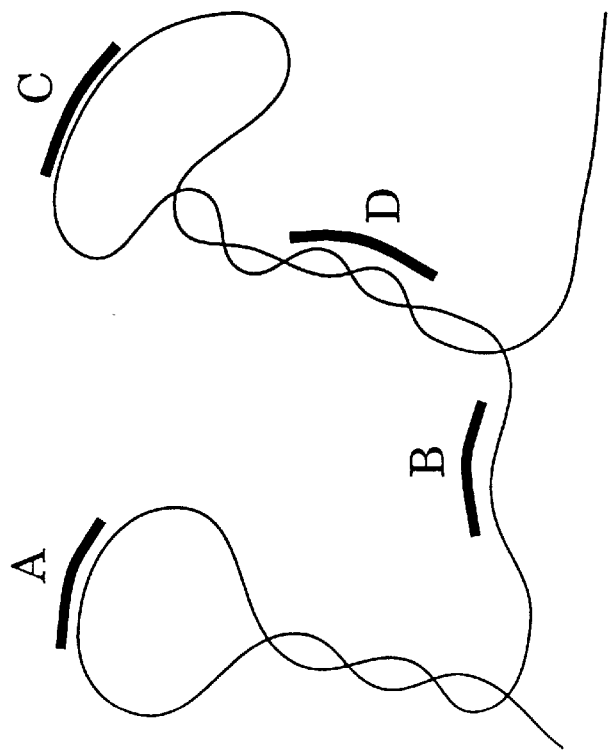

Referring to FIG. 6, mRNA is screened for accessible cleavage sites by the method described generally in Draper et al., supra, hereby incorporated by reference herein. Briefly, DNA oligonucleotides representing potential hammerhead or hairpin ribozyme cleavage sites were synthesized. A polymerase chain reaction was used to generate substrates for T7 RNA polymerase transcription from human, canine and mouse IL-2Rγ cDNA clones. Labeled RNA transcripts were synthesized in vitro from the templates. The oligonucleotides and the labeled transcripts were annealed, RNAseH was added and the mixtures were incubated for the designated times at 37° C. Reactions were stopped and RNA separated on sequencing polyacrylamide gels. The percentage of the substrate cleaved is determined by autoradiographic quantitation using a PhosphorImaging system. From these data, hammerhead or hairpin ribozyme sites were chosen as the most accessible.

Ribozymes of the hammerhead or hairpin motif were designed to anneal to various sites in the mRNA message. The binding arms are complementary to the target site sequences described above. The ribozymes were chemically synthesized. The method of synthesis used follows the procedure for normal RNA synthesis as described in Usman et al., 1987 *J. Am. Chem. Soc.*, 109, 7845; Scaringe et al, 1990 *Nucleic Acids Res.*, 18, 5433; and Wincoft et al., 1995 *Nucleic Acids Res.* 23, 2677–2684 and makes use of common nucleic acid protecting and coupling groups, such as dimethoxytrityl at the 5'-end, and phosphoramidites at the 3'-end. Small scale synthesis were conducted on a 394 Applied Biosystems, Inc. synthesizer using a modified 2.5 μmol scale protocol with a 5 min coupling step for alkylsilyl protected nucleotides and 2.5 min coupling step for 2'-O-methylated nucleotides. Table VIII outlines the amounts, and the contact times, of the reagents used in the synthesis cycle. A 6.5-fold excess (163 μL of 0.1M=16.3 μmol) of phosphoramidite and a 24-fold excess of S-ethyl tetrazole (238 μL of 0.25M=59.5 μmol) relative to polymer-bound 5'-hydroxyl was used in each coupling cycle. Average coupling yields on the 394 Applied Biosystems, Inc. synthesizer, determined by calorimetric quantitation of the trityl fractions, were 97.5–99%. Other oligonucleotide synthesis reagents for the 394 Applied Biosystems, Inc. synthesizer: detritylation solution was 2% TCA in methylene chloride (ABI); capping was performed with 16% N-methyl imidazole in THF (ABI) and 10% acetic anhydride/10% 2,6-lutidine in THF (ABI); oxidation solution was 16.9 mM $I_2$, 49 mM pyridine, 9% water in THF (Millipore). B & J Synthesis Grade acetonitrile was used directly from the reagent bottle. S-Ethyl tetrazole solution (0.25M in acetonitrile) was made up from the solid obtained from American International Chemical, Inc.

Deprotection of the RNA was performed as follows. The polymer-bound oligoribonucleotide, trityl-off, was transferred from the synthesis column to a 4 mL glass screw top vial and suspended in a solution of methylamine (MA) at 65° C. for 10 min. After cooling to −20° C., the supernatant was removed from the polymer support. The support was washed three times with 1.0 mL of EtOH:MeCN:$H_2O$/3:1:1, vortexed and the supernatant was then added to the first supernatant. The combined supernatants, containing the oligoribonucleotide, were dried to a white powder.

The base-deprotected oligoribonucleotide was resuspended in anhydrous TEA↑HF/NMP solution (250 μL of a solution of 1.5 mL N-methylpyrrolidinone, 750 μL TEA and 1.0 mL TEA↑3HF to provide a 1.4M HF concentration) and heated to 65° C. for 1.5 h. The resulting, fully deprotected, oligomer was quenched with 50 mM TEAB (9 mL) prior to anion exchange desalting.

For anion exchange desalting of the deprotected oligomer, the TEAB solution was loaded onto a Qiagen 500® anion exchange cartridge (Qiagen Inc.) that was prewashed with 50 mM TEAB (10 mL). After washing the loaded cartridge with 50 mM TEAB (10 mL), the RNA was eluted with 2M TEAB (10 mL) and dried down to a white powder.

Inactive hammerhead ribozymes were synthesized by substituting a U for $G_5$ and a U for $A_{14}$ (numbering from Hertel, K. J., et al., 1992, *Nucleic Acids Res.*, 20, 3252).

The average stepwise coupling yields were >98% (Wincott et al, 1995 *Nucleic Acids Res.* 23, 2677–2684).

Hairpin ribozymes are synthesized in two parts and annealed to reconstruct the active ribozyme (Chowrira and Burke, 1992 *Nucleic Acids Res.*, 20, 2835–2840). Ribozymes are also synthesized from DNA templates using bacteriophage T7 RNA polymerase (Milligan and Uhlenbeck, 1989, *Methods Enzymol.* 180, 51).

All ribozymes are modified extensively to enhance stability by modification with nuclease resistant groups, for example, 2'-amino, 2'-C-allyl, 2'-flouro, 2'-O-methyl, 2'-H (for a review see Usman and Cedergren, 1992 TIBS 17, 34; Usman et al, 1994 *Nucleic Acids Symp. Ser* 31, 163). Ribozymes are purified by gel electrophoresis using general methods or are purified by high pressure liquid chromatography (HPLC; See Usman et al., "Synthesis, deprotection, analysis and purification of RNA and ribozymes", filed May, 18, 1994, U.S. application Ser. No. 08/245,736; and U.S. application Ser. No. 08/380,734, filed Jan. 30, 1995; and Usman et al, WO 95/23225, filed Feb. 23, 1995; the totality of these applications is hereby incorporated herein by reference;) and are resuspended in water.

The sequences of the ribozymes that are chemically synthesized, useful in this study, are shown in Tables II-VII (even numbered SEQ ID Nos. from 8 to 1378). Those in the art will recognize that these sequences are representative only of many more such sequences where the enzymatic portion of the ribozyme (all but the binding arms) is altered to affect activity. For example, stem-loop II sequence of hammerhead ribozymes can be altered (substitution, deletion, and/or insertion) to contain any sequences provided a minimum of two base-paired stem structure can form. Similarly, stem-loop IV sequence of hairpin ribozymes listed in Tables VI and VII (5'-CACGUUGUG-3') can be altered (substitution, deletion, and/or insertion) to contain any sequence, provided a minimum of two base-paired stem structure can form. The sequences listed in Tables II-VII may be formed of ribonucleotides or other nucleotides or non-nucleotides. Such ribozymes are equivalent to the ribozymes described specifically in the Tables.

Optimizing Ribozyme Activity

Figure 2B:
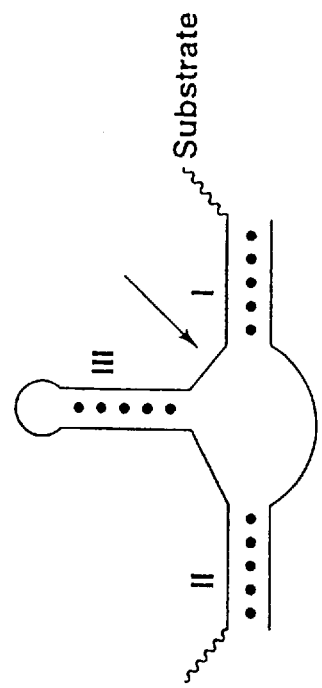
Figure 2D:
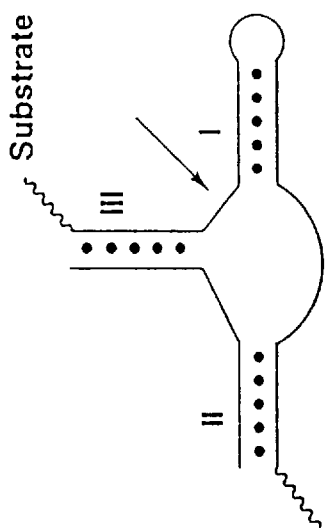
Figure 2A:
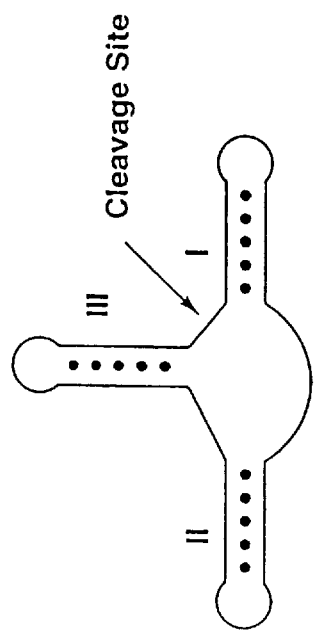
Figure 2C:
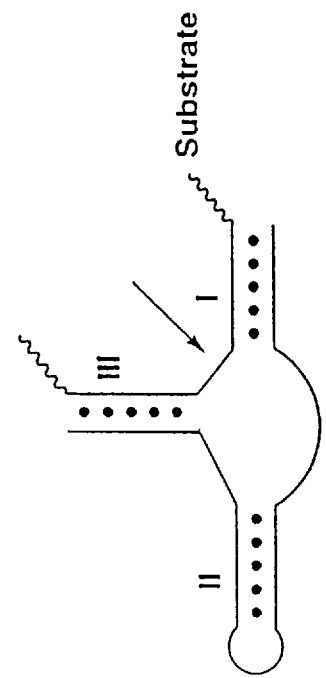

Ribozyme activity can be optimized as described by Draper et al., supra. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et al, 1990 *Nature* 344, 565; Pieken et al., 1991 *Science* 253, 314; Usman and Cedergren, 1992 *Trends in Biochem. Sci* 17, 334; Usman et al., International Publication No. WO 93/15187; and Rossi et al., International Publication No. WO 91/03162 and Sproat, U.S. Pat. No. 5,334,711 which describe various chemical modifications that can be made to the sugar moieties of enzymatic RNA molecules. Modifications which enhance their efficacy in cells, and removal of stem 11 bases to shorten RNA synthesis times and reduce chemical requirements are desired. (All these publications are hereby incorporated by reference herein.), Sullivan, et al, supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al, supra and Draper et al, supra which have been incorporated by reference herein.

In another preferred embodiments, the ribozyme is administered to the site of IL-2Rγ expression (T cells) in an appropriate lipid vesicle. Cells isolated from donor (for example) are treated with the ribozyme preparation (or other nucleic acid therapeutics) ex vivo and the treated cells are infused into recipient. Alternatively, cells, tissues or organs are directly treated with nucleic acids of the present invention prior to transplantation into a recipient.

Another means of accumulating high concentrations of a ribozyme(s) within cells is to incorporate the ribozyme-encoding sequences into a DNA or RNA expression vector. Transcription of the ribozyme sequences are driven from a promoter for eukaryotic RNA polymerase I (pol I), RNA polymerase II (pol II), or RNA polymerase III (po III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. USA*, 87, 6743–7; Gao and Huang 1993 *Nucleic Acids Res.*, 21, 2867–72; Lieber et al., 1993 *Methods Enzymol.*, 217, 47–66; Zhou et al., 1990 *Mol. Cell. Biol.*, 10, 4529–37). Several investigators have demonstrated that ribozymes expressed from such promoters can function in mammalian cells (e.g. Kashani-Sabet et al., 1992 *Antisense Res. Dev.*, 2, 3–15; Ojwang et al., 1992 *Proc. Natl. Acad. Sci. USA*, 89, 10802–6; Chen et al., 1992 *Nucleic Acids Res.*, 20, 4581–9; Yu et al., 1993 *Proc. Natl. Acad. Sci. USA*, 90, 6340–4; L'Huillier et al., 1992 *EMBO J.* 11, 4411–8; Lisziewicz et al, 1993 *Proc. Natl. Acad. Sci. U.S.A.*, 90, 8000–4). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors).

In a preferred embodiment of the invention, a transcription unit expressing a ribozyme that cleaves mRNAs encoded by IL-2Rγ are inserted into a plasmid DNA vector or an adenovirus or adeno-associated virus DNA viral vector or a retroviral or alpha viral RNA vector. Viral vectors have been used to transfer genes and lead to either transient or long term gene expression (Zabner et al., 1993 *Cell* 75, 207; Carter, 1992 *Curr. Opi. Biotech.* 3, 533). The adenovirus vector is delivered as recombinant adenoviral particles. The DNA may be delivered alone or complexed with vehicles (as described for RNA above). The recombinant adenovirus or AAV particles are locally administered to the site of treatment, e.g., through incubation or inhalation in vivo or by direct application to cells or tissues ex vivo. Retroviral vectors have also been used to express ribozymes in mammalian cells (Ojwang et al, 1992 supra; Thompson et al., 1995 supra).

IL-2Rγ is attractive as a nucleic acid therapeutic target by several criteria. The molecular mechanism of T cell activation is well-established. Efficacy can be tested in well-defined and predictive animal models. The clinical end-point of graft rejection is clear. Finally, the disease condition is serious and current therapies are inadequate.

Similarly, autoimmune diseases and allergies can be prevented or treated by reversing the devastating course of immune response to self-antigens. Specifically, nucleic acids of this inventions can dampen the response to naturally occurring antigens.

EXAMPLE 1

IL-2Rγ Hammerhead and Hairpin ribozymes

By engineering ribozyme motifs we have designed several ribozymes directed against IL-2Rγ encoded mRNA sequences. These ribozymes were synthesized with modifications that improve their nuclease resistance. The ability of ribozymes to cleave target sequences in vitro was evaluated.

Several common human cell lines are available that can be induced to express endogenous IL-2Rγ. Alternatively, murine splenic cells can be isolated and induced, to express IL-2Rγ, with IL-2 for example. IL-2Rγ can be detected easily with monoclonal antibodies. Use of appropriate flourescent antibody reagents and flourescence-activated cell-sorting (FACS) will permit direct quantitation of surface IL-2Rγ on a cell-by-cell basis. Active ribozymes are expected to directly reduce IL-2Rγ expression and can be measured by a variety of techniques. Ribozymes targeted to IL-2Rγ would prevent induction of T-cells and proliferation in response to IL-2.

Several animal models of autoimmune disorders are available—allergic encephalomyelitis (EAE) in Lewis rats (Carlson et al., 1993 Ann. N.Y. Acad. Sci. 685, 86); animal models of multiple sclerosis (Wekerle et al., 1994 Ann. Neurol. 36, s47) and rheumatoid arthritis (van Laar et al., 1994 Chem. Immunol. 58, 206).

Several animal models of transplantation are available—Porcine model (Fodor et al., 1994, *Proc. Natl. Acad. Sci. USA* 91, 11153); Baboon (reviewed by Nowak, 1994 *Science* 266, 1148). IL-2Rγ protein levels can be measured clinically or experimentally by FACS analysis. IL-2Rγ encoded mRNA levels will be assessed by Northern analysis, RNase-protection, primer extension analysis and/or quantitative RT-PCR. Ribozymes that block the induction of IL-2Rγ activity and/or IL-2Rγ protein encoding mRNAs by more than 20% in vitro will be identified.

Several animal models of allergy are available and are reviewed by Kemeny and Diaz-Sanchez, 1990, Clin. Exp. Immunol. 82, 423 and Pretolani et al., 1994 Ann. N.Y. Acad. Sci. 725, 247).

RNA ribozymes and/or genes encoding them will be delivered by either free delivery, liposome delivery, cationic lipid delivery, adeno-associated virus vector delivery, adenovirus vector delivery, retrovirus vector delivery or plasmid vector delivery in these animal model experiments. One dose of a ribozyme vector that constitutively expresses the ribozyme or one or more doses of a stable anti-IL-2Rγ ribozyme or a transiently expressing ribozyme vector may reduce the incidence of graft rejection. Alternatively, graft tissues may be treated as described above prior to transplantation.

Diagnostic uses

Ribozymes of this invention may be used as diagnostic tools to examine genetic drift and mutations within diseased cells or to detect the presence of IL-2Rγ RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with IL-2Rγ related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., IL-2Rγ) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE I

Characteristics of Ribozymes

Group I Introns
  Size: ~200 to >1000 nucleotides.
  Requires a U in the target sequence immediately 5' of the cleavage site.
  Binds 4–6 nucleotides at 5' side of cleavage site.
  Over 75 known members of this class. Found in *Tetrahymena thermophila* rRNA, fungal mitochondria, chloroplasts, phage T4, blue-green algae, and others.

RNAseP RNA (M1 RNA)
  Size: ~290 to 400 nucleotides.
  RNA portion of a ribonucleoprotein enzyme. Cleaves tRNA precursors to form mature tRNA.
  Roughly 10 known members of this group all are bacterial in origin.

Hammerhead Ribozyme
  Size: ~13 to 40 nucleotides.
  Requires the target sequence U in the target sequence immediately 5' of the cleavage site. Binds a variable number nucleotides on both sides of the cleavage site.
  14 known members of this class. Found in a number of plant pathogens (virusoids) that use RNA as the infectious agent (FIGS. 1 and 2)

Figure 3:
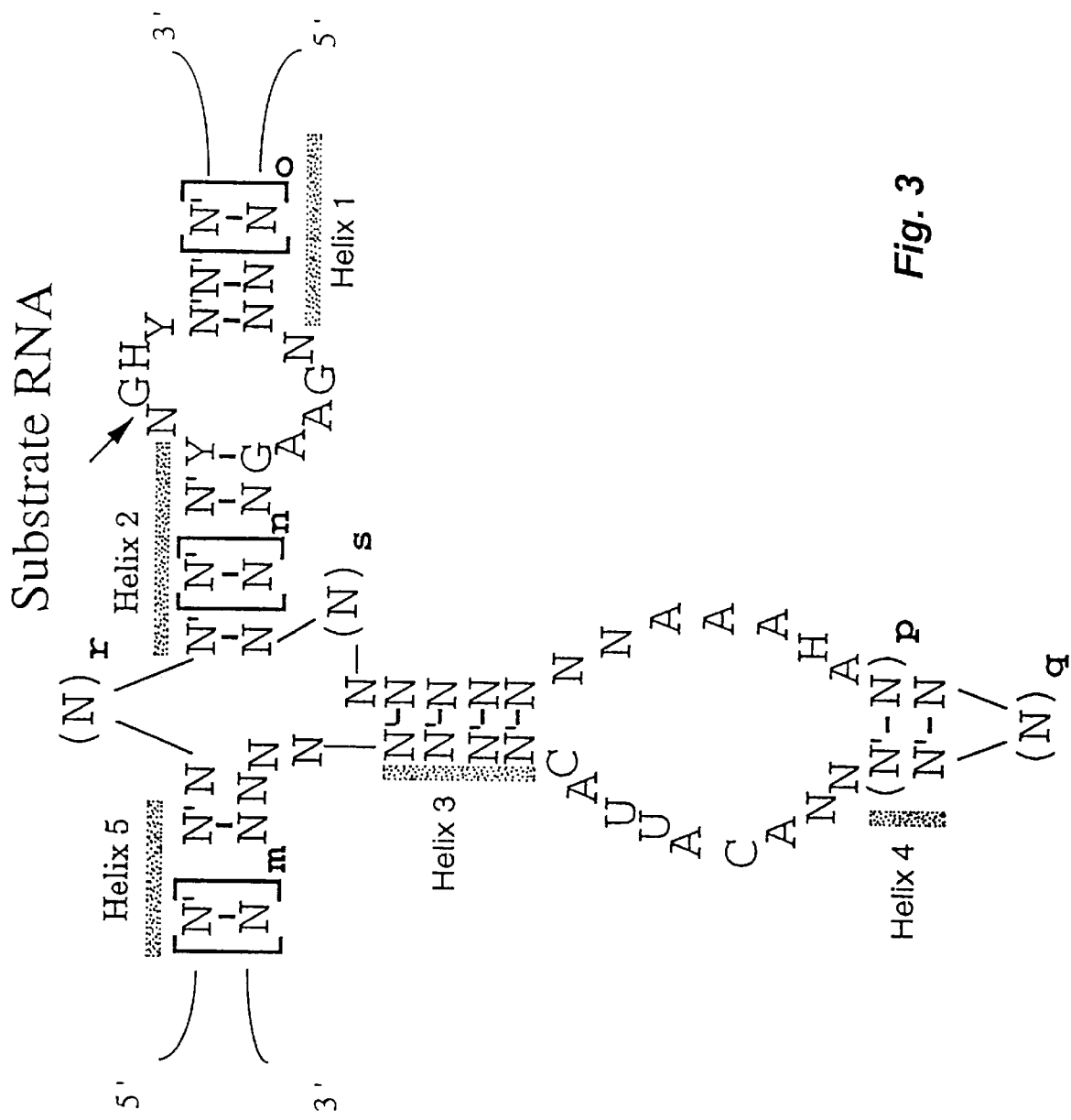

Hairpin Ribozyme
  Size: ~50 nucleotides.
  Requires the target sequence GUC immediately 3' of the cleavage site. Binds 4–6 nucleotides at 5' side of the cleavage site and a variable number to the 3' side of the cleavage site.
  Only 3 known member of this class. Found in three plant pathogen (satellite RNAs of the tobacco ringspot virus, arabis mosaic virus and chicory yellow mottle virus) which uses RNA as the infectious agent (FIG. 3).

Figure 4:
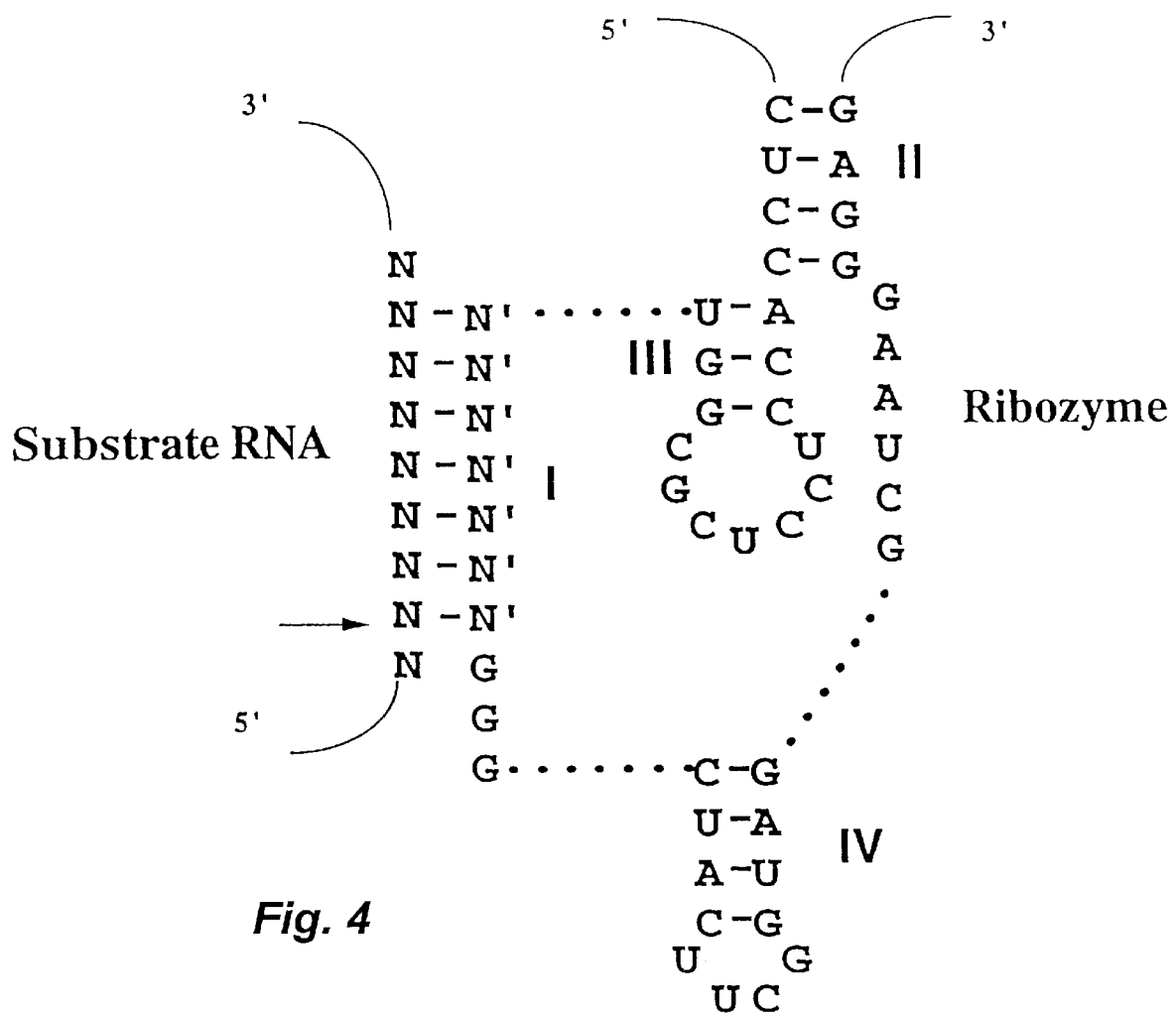

Hepatitis Delta Virus (HDV) Ribozyme
  Size: 50–60 nucleotides (at present).
  Cleavage of target RNAs recently demonstrated. Sequence requirements not fully determined. Binding sites and structural requirements not fully determined, although no sequences 5' of cleavage site are required. Only 1 known member of this class. Found in human HDV (FIG. 4).

Neurospora VS RNA Ribozyme

Size: ~144 nucleotides (at present)

Cleavage of target RNAs recently demonstrated.

Sequence requirements not fully determined.

Figure 5:
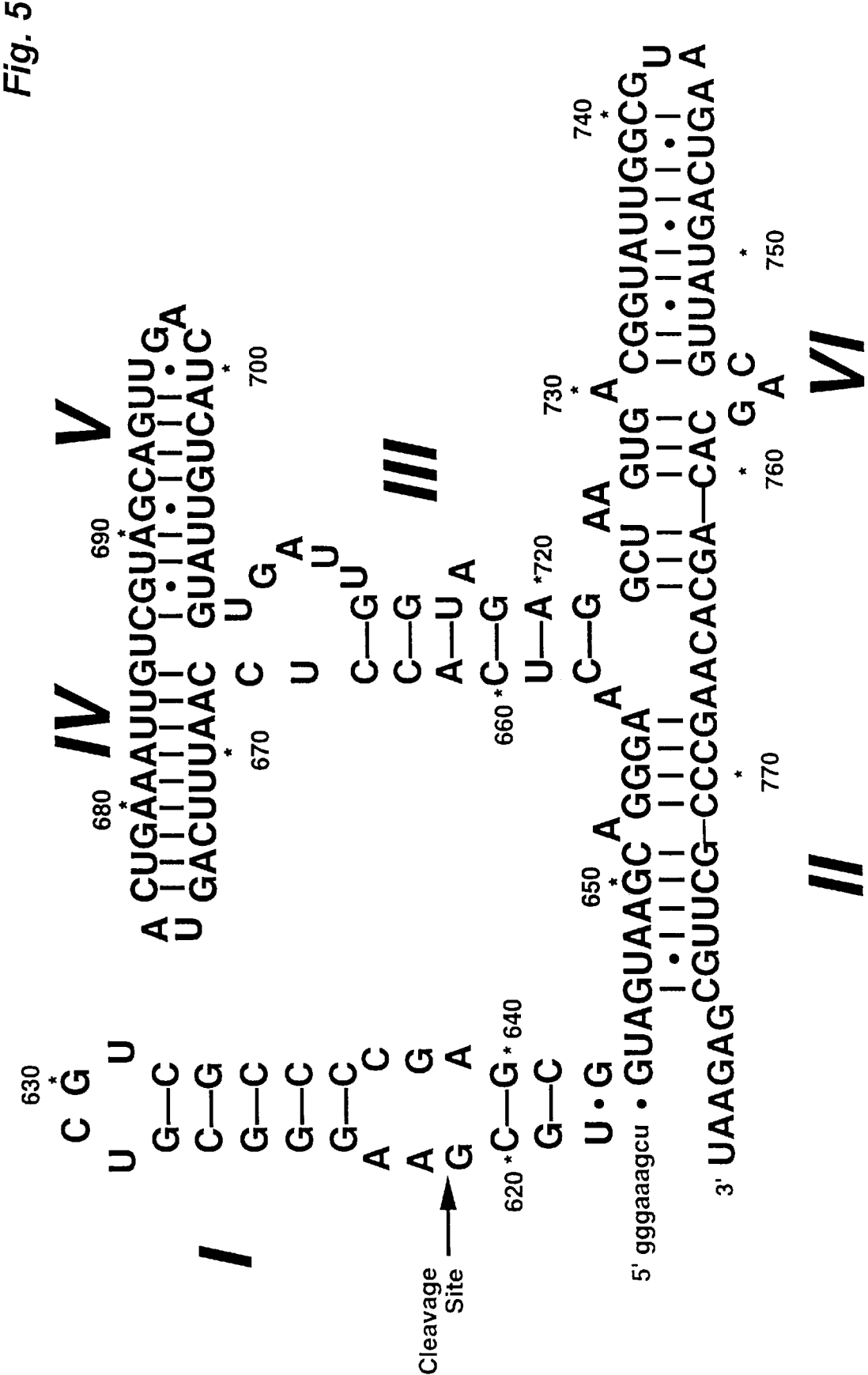

Binding sites and structural requirements not fully determined. Only 1 known member of this class. Found in Neurospora VS RNA (FIG. 5).

TABLE II

Human IL-2 Receptor g-Chain Hammerhead Ribozyme and Substrate Sequence

| nt. Position | HH Ribozyme Sequence | | | | Seq. ID No. | Substrate | | Seq. ID No. |
|---|---|---|---|---|---|---|---|---|
| 19 | AUGGCUUC | CUGAUGA | X | GAA ACAUGGCG | 8 | CGCCAUGUU | GAAGCCAU | 9 |
| 28 | AUGGUAAU | CUGAUGA | X | GAA AUGGCUUC | 10 | GAAGCCAUC | AUUACCAU | 11 |
| 31 | UGAAUGGU | CUGAUGA | X | GAA AUGAUGGC | 12 | GCCAUCAUU | ACCAUUCA | 13 |
| 32 | GUGAAUGG | CUGAUGA | X | GAA AAUGAUGG | 14 | CCAUCAUUA | CCAUUCAC | 15 |
| 37 | GGGAUGUG | CUGAUGA | X | GAA AUGGUAAU | 16 | AUUACCAUU | CACAUCCC | 17 |
| 38 | AGGGAUGU | CUGAUGA | X | GAA AAUGGUAA | 18 | UUACCAUUC | ACAUCCCU | 19 |
| 43 | AUAAGAGG | CUGAUGA | X | GAA AUGUGAAU | 20 | AUUCACAUC | CCUCUUAU | 21 |
| 47 | AGGAAUAA | CUGAUGA | X | GAA AGGGAUGU | 22 | ACAUCCCUC | UUAUUCCU | 23 |
| 49 | GCAGGAAU | CUGAUGA | X | GAA AGAGGGAU | 24 | AUCCCUCUU | AUUCCUGC | 25 |
| 50 | UGCAGGAA | CUGAUGA | X | GAA AAGAGGGA | 26 | UCCCUCUUA | UUCCUGCA | 27 |
| 52 | GCUGCAGG | CUGAUGA | X | GAA AUAAGAGG | 28 | CCUCUUAUU | CCUGCAGC | 29 |
| 53 | AGCUGCAG | CUGAUGA | X | GAA AAUAAGAG | 30 | CUCUUAUUC | CUGCAGCU | 31 |
| 95 | GGCGUCAG | CUGAUGA | X | GAA AUUGUCGU | 32 | ACGACAAUU | CUGACGCC | 33 |
| 96 | GGGCGUCA | CUGAUGA | X | GAA AAUUGUCG | 34 | CGACAAUUC | UGACGCCC | 35 |
| 132 | CAGGAAGA | CUGAUGA | X | GAA AUCAGCUG | 36 | CAGCUGAUU | UCUUCCUG | 37 |
| 133 | UCAGGAAG | CUGAUGA | X | GAA AAUCAGCU | 38 | AGCUGAUUU | CUUCCUGA | 39 |
| 134 | GUCAGGAA | CUGAUGA | X | GAA AAAUCAGC | 40 | GCUGAUUUC | UUCCUGAC | 41 |
| 136 | UGGUCAGG | CUGAUGA | X | GAA AGAAAUCA | 42 | UGAUUUCUU | CCUGACCA | 43 |
| 137 | GUGGUCAG | CUGAUGA | X | GAA AAGAAAUC | 44 | GAUUUCUUC | CUGACCAC | 45 |
| 147 | AGUGGGCA | CUGAUGA | X | GAA AGUGGUCA | 46 | UGACCACUA | UGCCCACU | 47 |
| 160 | CACUGAGG | CUGAUGA | X | GAA AGUCAGUG | 48 | CACUGACUC | CCUCAGUG | 49 |
| 164 | GAAACACU | CUGAUGA | X | GAA AGGGAGUC | 50 | GACUCCCUC | AGUGUUUC | 51 |
| 170 | AGAGUGGA | CUGAUGA | X | GAA ACACUGAG | 52 | CUCAGUGUU | UCCACUCU | 53 |
| 171 | CAGAGUGG | CUGAUGA | X | GAA AACACUGA | 54 | UCAGUGUUU | CCACUCUG | 55 |
| 172 | GCAGAGUG | CUGAUGA | X | GAA AAACACUG | 56 | CAGUGUUUC | CACUCUGC | 57 |
| 177 | GAGGGGCA | CUGAUGA | X | GAA AGUGGAAA | 58 | UUUCCACUC | UGCCCCUC | 59 |
| 185 | ACCUCUGG | CUGAUGA | X | GAA AGGGGCAG | 60 | CUGCCCCUC | CCAGAGGU | 61 |
| 194 | AAACACUG | CUGAUGA | X | GAA ACCUCUGG | 62 | CCAGAGGUU | CAGUGUUU | 63 |
| 195 | AAAACACU | CUGAUGA | X | GAA AACCUCUG | 64 | CAGAGGUUC | AGUGUUUU | 65 |
| 201 | GAACACAA | CUGAUGA | X | GAA ACACUGAA | 66 | UUCAGUGUU | UUGUGUUC | 67 |
| 202 | UGAACACA | CUGAUGA | X | GAA AACACUGA | 68 | UCAGUGUUU | UGUGUUCA | 69 |
| 203 | UUGAACAC | CUGAUGA | X | GAA AAACACUG | 70 | CAGUGUUUU | GUGUUCAA | 71 |
| 208 | CGACAUUG | CUGAUGA | X | GAA ACACAAAA | 72 | UUUUGUGUU | CAAUGUCG | 73 |
| 209 | UCGACAUU | CUGAUGA | X | GAA AACACAAA | 74 | UUUGUGUUC | AAUGUCGA | 75 |
| 215 | AUGUACUC | CUGAUGA | X | GAA ACAUUGAA | 76 | UUCAAUGUC | GAGUACAU | 77 |
| 220 | AAUUCAUG | CUGAUGA | X | GAA ACUCGACA | 78 | UGUCGAGUA | CAUGAAUU | 79 |
| 228 | CCAAGUGC | CUGAUGA | X | GAA AUUCAUGU | 80 | ACAUGAAUU | GCACUUGG | 81 |
| 234 | GCUGUUCC | CUGAUGA | X | GAA AGUGCAAU | 82 | AUUGCACUU | GGAACAGC | 83 |
| 247 | GGGGCUCA | CUGAUGA | X | GAA AGCUGCUG | 84 | CAGCAGCUC | UGAGCCCC | 85 |
| 261 | GAGGUGGG | CUGAUGA | X | GAA AGGCUGGG | 86 | CCCAGCCUA | CCAACCUC | 87 |
| 269 | UGCAGAGU | CUGAUGA | X | GAA AGGUUGGU | 88 | ACCAACCUC | ACUCUGCA | 89 |
| 273 | AUAAUGCA | CUGAUGA | X | GAA AGUGAGGU | 90 | ACCUCACUC | UGCAUUAU | 91 |
| 279 | GUACCAAU | CUGAUGA | X | GAA AUGCAGAG | 92 | CUCUGCAUU | AUUGGUAC | 93 |
| 280 | UGUACCAA | CUGAUGA | X | GAA AAUGCAGA | 94 | UCUGCAUUA | UUGGUACA | 95 |
| 282 | CUUGUACC | CUGAUGA | X | GAA AUAAUGCA | 96 | UGCAUUAUU | GGUACAAG | 97 |
| 286 | AGUUCUUG | CUGAUGA | X | GAA ACCAAUAA | 98 | UUAUUGGUA | CAAGAACU | 99 |
| 295 | CAUUAUCC | CUGAUGA | X | GAA AGUUCUUG | 100 | CAAGAACUC | GGAUAAUG | 101 |
| 300 | UUUAUCAU | CUGAUGA | X | GAA AUCCGAGU | 102 | ACUCGGAUA | AUGAUAAA | 103 |
| 308 | CUGGACUU | CUGAUGA | X | GAA AUCAUUAU | 104 | AUAAUGAUA | AAGUCCAG | 105 |
| 311 | CACUUCUG | CUGAUGA | X | GAA ACUUUAUC | 106 | GAUAAAGUC | CAGAAGUG | 107 |
| 328 | AGAAUAGA | CUGAUGA | X | GAA AGUGGCUG | 108 | CAGCCACUA | UCUAUUCU | 109 |
| 330 | AGAGAAUA | CUGAUGA | X | GAA AUAGUGGC | 110 | GCCACUAUC | UAUUCUCU | 111 |
| 332 | UCAGAGAA | CUGAUGA | X | GAA AGAUAGUG | 112 | CACUAUCUA | UUCUCUGA | 113 |
| 334 | CUUCAGAG | CUGAUGA | X | GAA AUAGAUAG | 114 | CUAUCUAUU | CUCUGAAG | 115 |
| 335 | UCUUCAGA | CUGAUGA | X | GAA AAUAGAUA | 116 | UAUCUAUUC | UCUGAAGA | 117 |
| 337 | UUUCUUCA | CUGAUGA | X | GAA AGAAUAGA | 118 | UCUAUUCUC | UGAAGAAA | 119 |
| 347 | CCAGAAGU | CUGAUGA | X | GAA AUUUCUUC | 120 | GAAGAAAUC | ACUUCUGG | 121 |
| 351 | ACAGCCAG | CUGAUGA | X | GAA AGUGAUUU | 122 | AAAUCACUU | CUGGCUGU | 123 |
| 352 | GACAGCCA | CUGAUGA | X | GAA AAGUGAUU | 124 | AAUCACUUC | UGGCUGUC | 125 |
| 360 | UUGCAACU | CUGAUGA | X | GAA ACAGCCAG | 126 | CUGGCUGUC | AGUUGCAA | 127 |
| 364 | UUUUUUGC | CUGAUGA | X | GAA ACUGACAG | 128 | CUGUCAGUU | GCAAAAAA | 129 |
| 380 | UAGAGGUG | CUGAUGA | X | GAA AUCUCCUU | 130 | AAGGAGAUC | CACCUCUA | 131 |
| 386 | GUUUGGUA | CUGAUGA | X | GAA AGGUGGAU | 132 | AUCCACCUC | UACCAAAC | 133 |
| 388 | AUGUUUGG | CUGAUGA | X | GAA AGAGGUGG | 134 | CCACCUCUA | CCAAACAU | 135 |
| 397 | GAACAACA | CUGAUGA | X | GAA AUGUUUGG | 136 | CCAAACAUU | UGUUGUUC | 137 |

TABLE II-continued

Human IL-2 Receptor g-Chain Hammerhead Ribozyme and Substrate Sequence

| nt. Position | HH Ribozyme Sequence | Seq. ID No. | Substrate | Seq. ID No. |
|---|---|---|---|---|
| 398 | UGAACAAC CUGAUGA X GAA AAUGUUUG | 138 | CAAACAUUU GUUGUUCA | 139 |
| 401 | AGCUGAAC CUGAUGA X GAA ACAAAUGU | 140 | ACAUUUGUU GUUCAGCU | 141 |
| 404 | UGGAGCUG CUGAUGA X GAA ACAACAAA | 142 | UUUGUUGUU CAGCUCCA | 143 |
| 405 | CUGGAGCU CUGAUGA X GAA AACAACAA | 144 | UUGUUGUUC AGCUCCAG | 145 |
| 410 | GGGUCCUG CUGAUGA X GAA AGCUGAAC | 146 | GUUCAGCUC CAGGACCC | 147 |
| 452 | UGCAGUUU CUGAUGA X GAA AGCAUCUG | 148 | CAGAUGCUA AAACUGCA | 149 |
| 465 | GAUCACCA CUGAUGA X GAA AUUCUGCA | 150 | UGCAGAAUC UGGUGAUC | 151 |
| 473 | GCCCAGGG CUGAUGA X GAA AUCACCAG | 152 | CUGGUGAUC CCCUGGGC | 153 |
| 483 | GUUCUCUG CUGAUGA X GAA AGCCCAGG | 154 | CCUGGGCUC CAGAGAAC | 155 |
| 494 | UGAAGUGU CUGAUGA X GAA AGGUUCUC | 156 | GAGAACCUA ACACUUCA | 157 |
| 500 | AGUUUGUG CUGAUGA X GAA AGUGUUAG | 158 | CUAACACUU CACAAACU | 159 |
| 501 | CAGUUUGU CUGAUGA X GAA AAGUGUUA | 160 | UAACACUUC ACAAACUG | 161 |
| 517 | CUAGCUGG CUGAUGA X GAA AUUCACUC | 162 | GAGUGAAUC CCAGCUAG | 163 |
| 524 | UUCAGUUC CUGAUGA X GAA AGCUGGGA | 164 | UCCCAGCUA GAACUGAA | 165 |
| 547 | GGUUCAAG CUGAUGA X GAA AUCUGUUG | 166 | CAACAGAUU CUUGAACC | 167 |
| 548 | UGGUUCAA CUGAUGA X GAA AAUCUGUU | 168 | AACAGAUUC UUGAACCA | 169 |
| 550 | AGUGGUUC CUGAUGA X GAA AGAAUCUG | 170 | CAGAUUCUU GAACCACU | 171 |
| 561 | GUGCUCCA CUGAUGA X GAA ACAGUGGU | 172 | ACCACUGUU UGGAGCAC | 173 |
| 562 | AGUGCUCC CUGAUGA X GAA AACAGUGG | 174 | CCACUGUUU GGAGCACU | 175 |
| 571 | ACUGCACC CUGAUGA X GAA AGUGCUCC | 176 | GGAGCACUU GGUGCAGU | 177 |
| 580 | CAGUCCGG CUGAUGA X GAA ACUGCACC | 178 | GGUGCAGUA CCGGACUG | 179 |
| 616 | AAUCCACU CUGAUGA X GAA AAUGUUCA | 180 | UGAACAAUC AGUGGAUU | 181 |
| 624 | AUGUCUAU CUGAUGA X GAA AUCCACUG | 182 | CAGUGGAUU AUAGACAU | 183 |
| 625 | UAUGUCUA CUGAUGA X GAA AAUCCACU | 184 | AGUGGAUUA UAGACAUA | 185 |
| 627 | CUUAUGUC CUGAUGA X GAA AUAAUCCA | 186 | UGGAUUAUA GACAUAAG | 187 |
| 633 | GGAGAACU CUGAUGA X GAA AUGUCUAU | 188 | AUAGACAUA AGUUCUCC | 189 |
| 637 | GCAAGGAG CUGAUGA X GAA ACUUAUGU | 190 | ACAUAAGUU CUCCUUGC | 191 |
| 638 | GGCAAGGA CUGAUGA X GAA AACUUAUG | 192 | CAUAAGUUC UCCUUGCC | 193 |
| 640 | UAGGCAAG CUGAUGA X GAA AGAACUUA | 194 | UAAGUUCUC CUUGCCUA | 195 |
| 643 | CACUAGGC CUGAUGA X GAA AGGAGAAC | 196 | GUUCUCCUU GCCUAGUG | 197 |
| 648 | AUCCACAC CUGAUGA X GAA AGGCAAGG | 198 | CCUUGCCUA GUGUGGAU | 199 |
| 670 | GAAACGUG CUGAUGA X GAA AGCGUUUC | 200 | GAAACGCUA CACGUUUC | 201 |
| 676 | GAACACGA CUGAUGA X GAA ACGUGUAG | 202 | CUACACGUU UCGUGUUC | 203 |
| 677 | CGAACACG CUGAUGA X GAA AACGUGUA | 204 | UACACGUUU CGUGUUCG | 205 |
| 678 | CCGAACAC CUGAUGA X GAA AAACGUGU | 206 | ACACGUUUC GUGUUCGG | 207 |
| 683 | CGGCUCCG CUGAUGA X GAA ACACGAAA | 208 | UUUCGUGUU CGGAGCCG | 209 |
| 684 | GCGGCUCC CUGAUGA X GAA AACACGAA | 210 | UUCGUGUUC GGAGCCGC | 211 |
| 694 | GUGGGUUA CUGAUGA X GAA AGCGGCUC | 212 | GAGCCGCUU UAACCCAC | 213 |
| 695 | AGUGGGUU CUGAUGA X GAA AAGCGGCU | 214 | AGCCGCUUU AACCCACU | 215 |
| 696 | GAGUGGGU CUGAUGA X GAA AAAGCGGC | 216 | GCCGCUUUA ACCCACUC | 217 |
| 704 | CUUCCACA CUGAUGA X GAA AGUGGGUU | 218 | AACCCACUC UGUGGAAG | 219 |
| 717 | CCAAUGCU CUGAUGA X GAA AGCACUUC | 220 | GAAGUGCUC AGCAUUGG | 221 |
| 723 | UUCACUCC CUGAUGA X GAA AUGCUGAG | 222 | CUCAGCAUU GGAGUGAA | 223 |
| 746 | CCCCAGUG CUGAUGA X GAA AUUGGGUG | 224 | CACCCAAUC CACUGGGG | 225 |
| 762 | UUUUGAAG CUGAUGA X GAA AUUGCUCC | 226 | GGAGCAAUA CUUCAAAA | 227 |
| 765 | CUCUUUUG CUGAUGA X GAA AGUAUUGC | 228 | GCAAUACUU CAAAAGAG | 229 |
| 766 | UCUCUUUU CUGAUGA X GAA AAGUAUUG | 230 | CAAUACUUC AAAAGAGA | 231 |
| 777 | CAGGAAAG CUGAUGA X GAA AUUCUCUU | 232 | AAGAGAAUC CUUUCCUG | 233 |
| 780 | AAACAGGA CUGAUGA X GAA AGGAUUCU | 234 | AGAAUCCUU UCCUGUUU | 235 |
| 781 | CAAACAGG CUGAUGA X GAA AAGGAUUC | 236 | GAAUCCUUU CCUGUUUG | 237 |
| 782 | GCAAACAG CUGAUGA X GAA AAAGGAUU | 238 | AAUCCUUUC CUGUUUGC | 239 |
| 787 | CCAAUGCA CUGAUGA X GAA ACAGGAAA | 240 | UUUCCUGUU UGCAUUGG | 241 |
| 788 | UCCAAUGC CUGAUGA X GAA AACAGGAA | 242 | UUCCUGUUU GCAUUGGA | 243 |
| 793 | CGGCUUCC CUGAUGA X GAA AUGCAAAC | 244 | GUUUGCAUU GGAAGCCG | 245 |
| 806 | ACAGAGAU CUGAUGA X GAA ACCACGGC | 246 | GCCGUGGUU AUCUCUGU | 247 |
| 807 | AACAGAGA CUGAUGA X GAA AACCACGG | 248 | CCGUGGUUA UCUCUGUU | 249 |
| 809 | CCAACAGA CUGAUGA X GAA AUAACCAC | 250 | GUGGUUAUC UCUGUUGG | 251 |
| 811 | AGCCAACA CUGAUGA X GAA AGAUAACC | 252 | GGUUAUCUC UGUUGGCU | 253 |
| 815 | AUGGAGCC CUGAUGA X GAA ACAGAGAU | 254 | AUCUCUGUU GGCUCCAU | 255 |
| 820 | AUCCCAUG CUGAUGA X GAA AGCCAACA | 256 | UGUUGGCUC CAUGGGAU | 257 |
| 829 | UGAUAAUC CUGAUGA X GAA AUCCCAUG | 258 | CAUGGGAUU GAUUAUCA | 259 |
| 833 | AGGCUGAU CUGAUGA X GAA AUCAAUCC | 260 | GGAUUGAUU AUCAGCCU | 261 |
| 834 | AAGGCUGA CUGAUGA X GAA AAUCAAUC | 262 | GAUUGAUUA UCAGCCUU | 263 |
| 836 | AGAAGGCU CUGAUGA X GAA AUAAUCAA | 264 | UUGAUUAUC AGCCUUCU | 265 |
| 842 | ACACAGAG CUGAUGA X GAA AGGCUGAU | 266 | AUCAGCCUU CUCUGUGU | 267 |
| 843 | CACACAGA CUGAUGA X GAA AAGGCUGA | 268 | UCAGCCUUC UCUGUGUG | 269 |
| 845 | UACACACA CUGAUGA X GAA AGAAGGCU | 270 | AGCCUUCUC UGUGUGUA | 271 |
| 853 | GCCAGAAA CUGAUGA X GAA ACACACAG | 272 | CUGUGUGUA UUUCGGC | 273 |
| 855 | CAGCCAGA CUGAUGA X GAA AUACACAC | 274 | GUGUGUAUU UCUGGCUG | 275 |
| 856 | CCAGCCAG CUGAUGA X GAA AAUACACA | 276 | UGUGUAUUU CUGGCUGG | 277 |
| 857 | UCCAGCCA CUGAUGA X GAA AAAUACAC | 278 | GUGUAUUUC UGGCUGGA | 279 |
| 884 | AGGGUGGG CUGAUGA X GAA AUUCGGGG | 280 | CCCCGAAUU CCCACCCU | 281 |
| 885 | CAGGGUGG CUGAUGA X GAA AAUUCGGG | 282 | CCCGAAUUC CCACCCUG | 283 |

TABLE II-continued

Human IL-2 Receptor g-Chain Hammerhead Ribozyme and Substrate Sequence

| nt. Position | HH Ribozyme Sequence | Seq. ID No. | Substrate | Seq. ID No. |
|---|---|---|---|---|
| 902 | AGAUCCUC CUGAUGA X GAA AGGUUCUU | 284 | AAGAACCUA GAGGAUCU | 285 |
| 909 | AGUAACAA CUGAUGA X GAA AUCCUCUA | 286 | UAGAGGAUC UUGUUACU | 287 |
| 911 | UCAGUAAC CUGAUGA X GAA AGAUCCUC | 288 | GAGGAUCUU GUUACUGA | 289 |
| 914 | UAUUCAGU CUGAUGA X GAA ACAAGAUC | 290 | GAUCUUGUU ACUGAAUA | 291 |
| 915 | GUAUUCAG CUGAUGA X GAA AACAAGAU | 292 | AUCUUGUUA CUGAAUAC | 293 |
| 922 | UCCCGUGG CUGAUGA X GAA AUUCAGUA | 294 | UACUGAAUA CCACGGGA | 295 |
| 934 | AGGCCGAA CUGAUGA X GAA AGUUCCCG | 296 | CGGGAACUU UUCGGCCU | 297 |
| 935 | CAGGCCGA CUGAUGA X GAA AAGUUCCC | 298 | GGGAACUUU UCGGCCUG | 299 |
| 936 | CCAGGCCG CUGAUGA X GAA AAAGUUCC | 300 | GGAACUUUU CGGCCUGG | 301 |
| 937 | UCCAGGCC CUGAUGA X GAA AAAAGUUC | 302 | GAACUUUUC GGCCUGGA | 303 |
| 955 | GUCCCUUA CUGAUGA X GAA ACACACCA | 304 | UGGUGUGUC UAAGGGAC | 305 |
| 957 | CAGUCCCU CUGAUGA X GAA AGACACAC | 306 | GUGUGUCUA AGGGACUG | 307 |
| 975 | UGGCUGCA CUGAUGA X GAA ACUCUCAG | 308 | CUGAGAGUC UGCAGCCA | 309 |
| 988 | GUUCACUG CUGAUGA X GAA AGUCUGGC | 310 | GCCAGACUA CAGUGAAC | 311 |
| 1001 | ACGAGGCA CUGAUGA X GAA AGUCGUUC | 312 | GAACGACUC UGCCUCGU | 313 |
| 1007 | UCACUGAC CUGAUGA X GAA AGGCAGAG | 314 | CUCUGCCUC GUCAGUGA | 315 |
| 1010 | AUCUCACU CUGAUGA X GAA ACGAGGCA | 316 | UGCCUCGUC AGUGAGAU | 317 |
| 1019 | UUUGGGGG CUGAUGA X GAA AUCUCACU | 318 | AGUGAGAUU CCCCCAAA | 319 |
| 1020 | UUUUGGGG CUGAUGA X GAA AAUCUCAC | 320 | GUGAGAUUC CCCCAAAA | 321 |
| 1040 | CCCUCCCC CUGAUGA X GAA AGGGCCCC | 322 | GGGGCCCUU GGGGAGGG | 323 |
| 1060 | UGCAUGGG CUGAUGA X GAA AGGCCCCA | 324 | UGGGGCCUC CCCAUGCA | 325 |
| 1077 | GUAGGGGC CUGAUGA X GAA AUGCUGGU | 326 | ACCAGCAUA GCCCCUAC | 327 |
| 1084 | GGGCCCAG CUGAUGA X GAA AGGGGCUA | 328 | UAGCCCCUA CUGGGCCC | 329 |
| 1101 | UAGGGUGU CUGAUGA X GAA ACAUGGGG | 330 | CCCCAUGUU ACACCCUA | 331 |
| 1102 | UUAGGGUG CUGAUGA X GAA AACAUGGG | 332 | CCCAUGUUA CACCCUAA | 333 |
| 1109 | UCAGGCUU CUGAUGA X GAA AGGGUGUA | 334 | UACACCCUA AAGCCUGA | 335 |
| 1133 | UGUCAGAG CUGAUGA X GAA AUUGGGGU | 336 | ACCCCAAUC CUCUGACA | 337 |
| 1136 | UUCUGUCA CUGAUGA X GAA AGGAUUGG | 338 | CCAAUCCUC UGACAGAA | 339 |
| 1157 | GGCUACAG CUGAUGA X GAA ACCCUGGG | 340 | CCCAGGGUC CUGUAGCC | 341 |
| 1162 | CUUAGGGC CUGAUGA X GAA ACAGGACC | 342 | GGUCCUGUA GCCCUAAG | 343 |
| 1168 | GUACCACU CUGAUGA X GAA AGGGCUAC | 344 | GUAGCCCUA AGUGGUAC | 345 |
| 1175 | AAAGUUAG CUGAUGA X GAA ACCACUUA | 346 | UAAGUGGUA CUAACUUU | 347 |
| 1178 | AGGAAAGU CUGAUGA X GAA AGUACCAC | 348 | GUGGUACUA ACUUUCCU | 349 |
| 1182 | AUGAAGGA CUGAUGA X GAA AGUUAGUA | 350 | UACUAACUU UCCUUCAU | 351 |
| 1183 | AAUGAAGG CUGAUGA X GAA AAGUUAGU | 352 | ACUAACUUU CCUUCAUU | 353 |
| 1184 | GAAUGAAG CUGAUGA X GAA AAAGUUAG | 354 | CUAACUUUC CUUCAUUC | 355 |
| 1187 | GUUGAAUG CUGAUGA X GAA AGGAAAGU | 356 | ACUUUCCUU CAUUCAAC | 357 |
| 1188 | GGUUGAAU CUGAUGA X GAA AAGGAAAG | 358 | CUUUCCUUC AUUCAACC | 359 |
| 1191 | GUGGGUUG CUGAUGA X GAA AUGAAGGA | 360 | UCCUUCAUU CAACCCAC | 361 |
| 1192 | GGUGGGUU CUGAUGA X GAA AAUGAAGG | 362 | CCUUCAUUC AACCCACC | 363 |
| 1206 | GAGUAUGA CUGAUGA X GAA ACGCAGGU | 364 | ACCUGCGUC UCAUACUC | 365 |
| 1208 | GUGAGUAU CUGAUGA X GAA AGACGCAG | 366 | CUGCGUCUC AUACUCAC | 367 |
| 1211 | GAGGUGAG CUGAUGA X GAA AUGAGACG | 368 | CGUCUCAUA CUCACCUC | 369 |
| 1214 | GGUGAGGU CUGAUGA X GAA AGUAUGAG | 370 | CUCAUACUC ACCUCACC | 371 |
| 1219 | AGUGGGGU CUGAUGA X GAA AGGUGAGU | 372 | ACUCACCUC ACCCCACU | 373 |
| 1237 | AAAUUCCA CUGAUGA X GAA AUCAGCCA | 374 | UGGCUGAUU UGGAAUUU | 375 |
| 1238 | AAAAUUCC CUGAUGA X GAA AAUCAGCC | 376 | GGCUGAUUU GGAAUUUU | 377 |
| 1244 | GGGCACAA CUGAUGA X GAA AUUCCAAA | 378 | UUUGGAAUU UUGUGCCC | 379 |
| 1245 | GGGGCACA CUGAUGA X GAA AAUUCCAA | 380 | UUGGAAUUU UGUGCCCC | 381 |
| 1246 | GGGGGCAC CUGAUGA X GAA AAAUUCCA | 382 | UGGAAUUUU GUGCCCCC | 383 |
| 1259 | GGGGUGCU CUGAUGA X GAA ACAUGGGG | 384 | CCCCAUGUA AGCACCCC | 385 |
| 1269 | GCCAAAUG CUGAUGA X GAA AGGGGUGC | 386 | GCACCCCUU CAUUGGC | 387 |
| 1270 | UGCCAAAU CUGAUGA X GAA AAGGGGUG | 388 | CACCCCUUC AUUUGGCA | 389 |
| 1273 | GAAUGCCA CUGAUGA X GAA AUGAAGGG | 390 | CCCUUCAUU UGGCAUUC | 391 |
| 1274 | GGAAUGCC CUGAUGA X GAA AAUGAAGG | 392 | CCUUCAUUU GGCAUUCC | 393 |
| 1280 | AAGUGGGG CUGAUGA X GAA AUGCCAAA | 394 | UUUGGCAUU CCCACUU | 395 |
| 1281 | CAAGUGGG CUGAUGA X GAA AAUGCCAA | 396 | UUGGCAUUC CCACUUG | 397 |
| 1288 | UAAUUCUC CUGAUGA X GAA AGUGGGGA | 398 | UCCCCACUU GAGAAUUA | 399 |
| 1295 | AAAAGGGU CUGAUGA X GAA AUUCUCAA | 400 | UUGAGAAUU ACCCUUUU | 401 |
| 1296 | CAAAAGGG CUGAUGA X GAA AAUUCUCA | 402 | UGAGAAUUA CCCUUUUG | 403 |
| 1301 | CGGGGCAA CUGAUGA X GAA AGGGUAAU | 404 | AUUACCCUU UUGCCCCG | 405 |
| 1302 | UCGGGGCA CUGAUGA X GAA AAGGGUAA | 406 | UUACCCUUU UGCCCCGA | 407 |
| 1303 | UUCGGGGC CUGAUGA X GAA AAAGGGUA | 408 | UACCCUUUU GCCCCGAA | 409 |
| 1317 | AGAAGAAA CUGAUGA X GAA ACAUGUUC | 410 | GAACAUGUU UUUCUUCU | 411 |
| 1318 | GAGAAGAA CUGAUGA X GAA AACAUGUU | 412 | AACAUGUUU UCUUCUC | 413 |
| 1319 | GGAGAAGA CUGAUGA X GAA AAACAUGU | 414 | ACAUGUUUU UCUUCUCC | 415 |
| 1320 | GGGAGAAG CUGAUGA X GAA AAAACAUG | 416 | CAUGUUUUU CUUCUCCU | 417 |
| 1321 | AGGGAGAA CUGAUGA X GAA AAAAACAU | 418 | AUGUUUUUC UUCUCCCU | 419 |
| 1323 | UGAGGGAG CUGAUGA X GAA AGAAAAAC | 420 | GUUUUCUU CUCCCUCA | 421 |
| 1324 | CUGAGGGA CUGAUGA X GAA AAGAAAAA | 422 | UUUUUCUUC UCCCUCAG | 423 |
| 1326 | GACUGAGG CUGAUGA X GAA AGAAGAAA | 424 | UUUCUUCUC CCUCAGUC | 425 |
| 1330 | GCCAGACU CUGAUGA X GAA AGGGAGAA | 426 | UUCUCCCUC AGUCUGGC | 427 |
| 1334 | AAGGGCCA CUGAUGA X GAA ACUGAGGG | 428 | CCCUCAGUC UGGCCCUU | 429 |

TABLE II-continued

Human IL-2 Receptor g-Chain Hammerhead Ribozyme and Substrate Sequence

| nt. Position | HH Ribozyme Sequence | | | | Seq. ID No. | Substrate | | Seq. ID No. |
|---|---|---|---|---|---|---|---|---|
| 1342 | CGAAAAGG | CUGAUGA | X | GAA | AGGGCCAG | 430 | CUGGCCCUU | CCUUUUCG | 431 |
| 1343 | GCGAAAAG | CUGAUGA | X | GAA | AAGGGCCA | 432 | UGGCCCUUC | CUUUUCGC | 433 |
| 1346 | CCUGCGAA | CUGAUGA | X | GAA | AGGAAGGG | 434 | CCCUUCCUU | UUCGCAGG | 435 |
| 1347 | UCCUGCGA | CUGAUGA | X | GAA | AAGGAAGG | 435 | CCUUCCUUU | UCGCAGGA | 437 |
| 1348 | AUCCUGCG | CUGAUGA | X | GAA | AAAGGAAG | 438 | CUUCCUUUU | CGCAGGAU | 439 |
| 1349 | AAUCCUGC | CUGAUGA | X | GAA | AAAAGGAA | 440 | UUCCUUUUC | GCAGGAUU | 441 |
| 1357 | GGAGGAAG | CUGAUGA | X | GAA | AUCCUGCG | 442 | CGCAGGAUU | CUUCCUCC | 443 |
| 1358 | GGGAGGAA | CUGAUGA | X | GAA | AAUCCUGC | 444 | GCAGGAUUC | UUCCUCCC | 445 |
| 1360 | GAGGGAGG | CUGAUGA | X | GAA | AGAAUCCU | 446 | AGGAUUCUU | CCUCCCUC | 447 |
| 1361 | GGAGGGAG | CUGAUGA | X | GAA | AAGAAUCC | 448 | GGAUUCUUC | CUCCCUCC | 449 |
| 1364 | GAGGGAGG | CUGAUGA | X | GAA | AGGAAGAA | 450 | UUCUUCCUC | CCUCCCUC | 451 |
| 1368 | GAAAGAGG | CUGAUGA | X | GAA | AGGGAGGA | 452 | UCCUCCCUC | CCUCUUUC | 453 |
| 1372 | GAGGGAAA | CUGAUGA | X | GAA | AGGGAGGG | 454 | CCCUCCCUC | UUUCCCUC | 455 |
| 1374 | GGGAGGGA | CUGAUGA | X | GAA | AGAGGGAG | 456 | CUCCCUCUU | UCCCUCCC | 457 |
| 1375 | AGGGAGGG | CUGAUGA | X | GAA | AAGAGGGA | 458 | UCCCUCUUU | CCCUCCCU | 459 |
| 1376 | AAGGGAGG | CUGAUGA | X | GAA | AAAGAGGG | 460 | CCCUCUUUC | CCUCCCUU | 461 |
| 1380 | GAGGGAGG | CUGAUGA | X | GAA | AGGGAAAG | 462 | CUUUCCCUC | CCUUCCUC | 463 |
| 1384 | GAAAGAGG | CUGAUGA | X | GAA | AGGGAGGG | 464 | CCCUCCCUU | CCUCUUUC | 465 |
| 1385 | GGAAAGAG | CUGAUGA | X | GAA | AAGGGAGG | 466 | CCUCCCUUC | CUCUUUCC | 467 |
| 1388 | GAUGGAAA | CUGAUGA | X | GAA | AGGAAGGG | 468 | CCCUUCCUC | UUUCCAUC | 469 |
| 1390 | UAGAUGGA | CUGAUGA | X | GAA | AGAGGAAG | 470 | CUUCCUCUU | UCCAUCUA | 471 |
| 1391 | GUAGAUGG | CUGAUGA | X | GAA | AAGAGGAA | 472 | UUCCUCUUU | CCAUCUAC | 473 |
| 1392 | GGUAGAUG | CUGAUGA | X | GAA | AAAGAGGA | 474 | UCCUCUUUC | CAUCUACC | 475 |
| 1396 | GGAGGGUA | CUGAUGA | X | GAA | AUGGAAAG | 476 | CUUUCCAUC | UACCCUCC | 477 |
| 1398 | UCGGAGGG | CUGAUGA | X | GAA | AGAUGGAA | 478 | UUCCAUCUA | CCCUCCGA | 479 |
| 1403 | AACAAUCG | CUGAUGA | X | GAA | AGGGUAGA | 480 | UCUACCCUC | CGAUUGUU | 481 |
| 1408 | UCAGGAAC | CUGAUGA | X | GAA | AUCGGAGG | 482 | CCUCCGAUU | GUUCCUGA | 483 |
| 1411 | GGUUCAGG | CUGAUGA | X | GAA | ACAAUCGG | 484 | CCGAUUGUU | CCUGAACC | 485 |
| 1412 | CGGUUCAG | CUGAUGA | X | GAA | AACAAUCG | 486 | CGAUUGUUC | CUGAACCG | 487 |
| 1430 | AGAAACUU | CUGAUGA | X | GAA | AUUUCUCA | 488 | UGAGAAAUA | AAGUUUCU | 489 |
| 1435 | UCAACAGA | CUGAUGA | X | GAA | ACUUUAUU | 490 | AAUAAAGUU | UCUGUUGA | 491 |
| 1436 | AUCAACAG | CUGAUGA | X | GAA | AACUUUAU | 492 | AUAAAGUUU | CUGUUGAU | 493 |
| 1437 | UAUCAACA | CUGAUGA | X | GAA | AAACUUUA | 494 | UAAAGUUUC | UGUUGAUA | 495 |
| 1441 | UGAUUAUC | CUGAUGA | X | GAA | ACAGAAAC | 496 | GUUUCUGUU | GAUAAUCA | 497 |

Where "X" represents stem II region of a HH ribozyme (Hertel et al., 1992 Nucleic Acids Res. 20 3252). The length of stem II may be ≧ 2 base-pairs.

TABLE III

Human IL-2 Receptor g-Chain Hairpin Ribozyme and Substrate Sequence

| nt. Position | Hairpin Ribozyme Sequence | Seq. ID No. | Substrate | Seq. ID No. |
|---|---|---|---|---|
| 58 | GCAGGGGC AGAA GCAGGA ACCAGAGAAACACACGUUGUGGUACAUUACCUGGUA UCCUGCA | 498 | GCU GCCCUGC | 499 |
| 61 | CCAGCAGG AGAA GCUGCA ACCAGAGAAACACACGUUGUGGUACAUUACCUGGUA UGCAGCU | 500 | GCC CCUGCUGG | 501 |
| 67 | CCACUCCC AGAA GGGGCA ACCAGAGAAACACACGUUGUGGUACAUUACCUGGUA UGCCCCU | 502 | GCU GGGAGUGG | 503 |
| 97 | CAUUGGGC AGAA GAAUUG ACCAGAGAAACACACGUUGUGGUACAUUACCUGGUA CAAUUCU | 504 | GAC GCCCAAUG | 505 |
| 125 | AAGAAAUC AGAA GUGUUG ACCAGAGAAACACACGUUGUGGUACAUUACCUGGUA CACCACA | 506 | GCU GAUUUCUU | 507 |
| 128 | AGGAAGAA AGAA GCUGUG ACCAGAGAAACACACGUUGUGGUACAUUACCUGGUA CACAGCU | 508 | GAU UUCUUCCU | 509 |
| 139 | GCAUAGUG AGAA GGAAGA ACCAGAGAAACACACGUUGUGGUACAUUACCUGGUA UCUUCCU | 510 | GAC CACUAUGC | 511 |
| 155 | CUGAGGGA AGAA GUGGGC ACCAGAGAAACACACGUUGUGGUACAUUACCUGGUA GCCACUG | 512 | GAC UCCCUCAG | 513 |
| 178 | CUGGGAGG AGAA GAGUGG ACCAGAGAAACACACGUUGUGGUACAUUACCUGGUA CCACUCU | 514 | GCC CCUCCAG | 515 |
| 243 | GGGUCUCAG AGAA GCUGUU ACCAGAGAAACACACGUUGUGGUACAUUACCUGGUA AACAGCA | 516 | GCU CUGAGCCC | 517 |
| 256 | GGUUGGUA AGAA GGGGCU ACCAGAGAAACACACGUUGUGGUACAUUACCUGGUA AGCCCCA | 518 | GCC UACCAACC | 519 |
| 361 | UUUUUGC AGAA GACAGC ACCAGAGAAACACACGUUGUGGUACAUUACCUGGUA GCUGUCA | 520 | GUU GCAAAAAA | 521 |
| 406 | GGUCCUGG AGAA GAACAA ACCAGAGAAACACACGUUGUGGUACAUUACCUGGUA UUGUUCA | 522 | GCU CCAGGACC | 523 |
| 445 | GUUUUAGC AGAA GUGUGG ACCAGAGAAACACACGUUGUGGUACAUUACCUGGUA CCACACA | 524 | GAU GCUAAAAC | 525 |
| 543 | GUUCAAGA AGAA GUUGUU ACCAGAGAAACACACGUUGUGGUACAUUACCUGGUA AACAACA | 526 | GAU UCUUGAAC | 527 |
| 558 | GUGCUCCA AGAA GUGGUU ACCAGAGAAACACACGUUGUGGUACAUUACCUGGUA AACCACU | 528 | GUU UGGAGCAC | 529 |
| 583 | CCCAGUCA AGAA GGUACU ACCAGAGAAACACACGUUGUGGUACAUUACCUGGUA AGUACCG | 530 | GAC UGACUGGG | 531 |
| 587 | UGGUCCCA AGAA GUCCGG ACCAGAGAAACACACGUUGUGGUACAUUACCUGGUA CCGGACU | 532 | GAC UGGGACCA | 533 |
| 600 | UUCAGUCC AGAA GUGGUC ACCAGAGAAACACACGUUGUGGUACAUUACCUGGUA GACCACA | 534 | GCU GGACUGAA | 535 |
| 690 | UGGGUUAA AGAA GCUCCG ACCAGAGAAACACACGUUGUGGUACAUUACCUGGUA CGGAGCC | 536 | GCU UUAACCCA | 537 |
| 784 | CCAAUGCA AGAA GGAAAG ACCAGAGAAACACACGUUGUGGUACAUUACCUGGUA CUUUCCU | 538 | GUU UGCAUUGG | 539 |
| 812 | AUGGAGCC AGAA GAGAUA ACCAGAGAAACACACGUUGUGGUACAUUACCUGGUA UAUCUCU | 540 | GUU GGCUCCAU | 541 |
| 837 | ACAGAGAA AGAA GAUAAU ACCAGAGAAACACACGUUGUGGUACAUUACCUGGUA AUUAUCA | 542 | GCC UUCUCUGU | 543 |
| 868 | GGGGCAUC AGAA GUUCCA ACCAGAGAAACACACGUUGUGGUACAUUACCUGGUA UGGAACG | 544 | GAC GAUGCCCC | 545 |
| 938 | CCACUCCA AGAA GAAAAG ACCAGAGAAACACACGUUGUGGUACAUUACCUGGUA CUUUUCG | 546 | GCC UGGAGUGG | 547 |
| 983 | UCACUGUA AGAA GGCUGC ACCAGAGAAACACACGUUGUGGUACAUUACCUGGUA GCAGCCA | 548 | GAC UACAGUGA | 549 |
| 1002 | ACUGACGA AGAA GAGUCG ACCAGAGAAACACACGUUGUGGUACAUUACCUGGUA CGACUCU | 550 | GCC UCGUCAGU | 551 |
| 1233 | AAUUCCAA AGAA GCCACA ACCAGAGAAACACACGUUGUGGUACAUUACCUGGUA UGUGGCU | 552 | GAU UUGGAAUU | 553 |
| 1331 | AAGGGCCA AGAA GAGGGA ACCAGAGAAACACACGUUGUGGUACAUUACCUGGUA UCCCUCA | 554 | GUC UGGCCCUU | 555 |
| 1404 | CAGGAACA AGAA GAGGGU ACCAGAGAAACACACGUUGUGGUACAUUACCUGGUA ACCUCCC | 556 | GAU UGUUCCUG | 557 |
| 1419 | UAUUUCUC AGAA GUCAG ACCAGAGAAACACACGUUGUGGUACAUUACCUGGUA CUGAACC | 558 | GAU GAGAAAUA | 559 |
| 1438 | UGAUUAUC AGAA GAAACU ACCAGAGAAACACACGUUGUGGUACAUUACCUGGUA AGUUUCU | 560 | GUU GAUAAUCA | 561 |

TABLE IV

Mouse IL-2 Receptor g-Chain Hammerhead Ribozyme and Substrate Sequence

| nt. Position | HH Ribozyme Sequence | Seq. ID No. | Substrate | Seq. ID No. |
|---|---|---|---|---|
| 12  | AUAGUUUC CUGAUGA X GAA ACAUGGUG | 562 | CACCAUGUU GAAACUAU | 563 |
| 19  | GACAAUAA CUGAUGA X GAA AGUUUCAA | 564 | UUGAAACUA UUAUUGUC | 565 |
| 21  | GUGACAAU CUGAUGA X GAA AUAGUUUC | 566 | GAAACUAUU AUUGUCAC | 567 |
| 22  | GGUGACAA CUGAUGA X GAA AAUAGUUU | 568 | AAACUAUUA UUGUCACC | 569 |
| 24  | UAGGUGAC CUGAUGA X GAA AUAAUAGU | 570 | ACUAUUAUU GUCACCUA | 571 |
| 27  | AUCUAGGU CUGAUGA X GAA ACAAUAAU | 572 | AUUAUUGUC ACCUAGAU | 573 |
| 32  | GAAGGAUC CUGAUGA X GAA AGGUGACA | 574 | UGUCACCUA GAUCCUUC | 575 |
| 36  | CUAAGAAG CUGAUGA X GAA AUCUAGGU | 576 | ACCUAGAUC CUUCUUAG | 577 |
| 39  | GGACUAAG CUGAUGA X GAA AGGAUCUA | 578 | UAGAUCCUU CUUAGUCC | 579 |
| 40  | AGGACUAA CUGAUGA X GAA AAGGAUCU | 580 | AGAUCCUUC UUAGUCCU | 581 |
| 42  | GAAGGACU CUGAUGA X GAA AGAAGGAU | 582 | AUCCUUCUU AGUCCUUC | 583 |
| 43  | UGAAGGAC CUGAUGA X GAA AAGAAGGA | 584 | UCCUUCUUA GUCCUUCA | 585 |
| 46  | AGCUGAAG CUGAUGA X GAA ACUAAGAA | 586 | UUCUUAGUC CUUCAGCU | 587 |
| 49  | AGCAGCUG CUGAUGA X GAA AGGACUAA | 588 | UUAGUCCUU CAGCUGCU | 589 |
| 50  | GAGCAGCU CUGAUGA X GAA AAGGACUA | 590 | UAGUCCUUC AGCUGCUC | 591 |
| 58  | CUCAGCAG CUGAUGA X GAA AGCAGCUG | 592 | CAGCUGCUC CUGCUGAG | 593 |
| 81  | GGACCUUG CUGAUGA X GAA AGCUCCAC | 594 | GUGGAGCUC CAAGGUCC | 595 |
| 88  | GACAUGAG CUGAUGA X GAA ACCUUGGA | 596 | UCCAAGGUC CUCAUGUC | 597 |
| 91  | CUGGACAU CUGAUGA X GAA AGGACCUU | 598 | AAGGUCCUC AUGUCCAG | 599 |
| 96  | UCGCACUG CUGAUGA X GAA ACAUGAGG | 600 | CCUCAUGUC CAGUGCGA | 601 |
| 115 | UCAGCUUU CUGAUGA X GAA AUGUCUUC | 602 | GAAGACAUC AAAGCUGA | 603 |
| 125 | CAGGAUCA CUGAUGA X GAA AUCAGCUU | 604 | AAGCUGAUU UGAUCCUG | 605 |
| 126 | UCAGGAUC CUGAUGA X GAA AAUCAGCU | 606 | AGCUGAUUU GAUCCUGA | 607 |
| 130 | GAAGUCAG CUGAUGA X GAA AUCAAAUC | 608 | GAUUUGAUC CUGACUUC | 609 |
| 137 | GGCUGUAG CUGAUGA X GAA AGUCAGGA | 610 | UCCUGACUU CUACAGCC | 611 |
| 138 | GGGCUGUA CUGAUGA X GAA AAGUCAGG | 612 | CCUGACUUC UACAGCCC | 613 |
| 140 | AGGGGCUG CUGAUGA X GAA AGAAGUCA | 614 | UGACUUCUA CAGCCCCU | 615 |
| 157 | GGAGCACU CUGAUGA X GAA AGGUGUUC | 616 | GAACACCUC AGUGCUCC | 617 |
| 164 | CAGAGUAG CUGAUGA X GAA AGCACUGA | 618 | UCAGUGCUC CUACUCUG | 619 |
| 167 | GGGCAGAG CUGAUGA X GAA AGGAGCAC | 620 | GUGCUCCUA CUCUGCCC | 621 |
| 170 | AAGGGGCA CUGAUGA X GAA AGUAGGAG | 622 | CUCCUACUC UGCCCCUU | 623 |
| 178 | ACCUCUGG CUGAUGA X GAA AGGGGCAG | 624 | CUGCCCCUU CCAGAGGU | 625 |
| 179 | AACCUCUG CUGAUGA X GAA AAGGGGCA | 626 | UGCCCCUUC CAGAGGUU | 627 |
| 187 | AAGCACUG CUGAUGA X GAA ACCUCUGG | 628 | CCAGAGGUU CAGUGCUU | 629 |
| 188 | AAAGCACU CUGAUGA X GAA AACCUCUG | 630 | CAGAGGUUC AGUGCUUU | 631 |
| 195 | UGAACACA CUGAUGA X GAA AGCACUGA | 632 | UCAGUGCUU UGUGUUCA | 633 |
| 196 | UUGAACAC CUGAUGA X GAA AAGCACUG | 634 | CAGUGCUUU GUGUUCAA | 635 |
| 201 | CUAUGUUG CUGAUGA X GAA ACACAAAG | 636 | CUUUGUGUU CAACAUAG | 637 |
| 202 | UCUAUGUU CUGAUGA X GAA AACACAAA | 638 | UUUGUGUUC AACAUAGA | 639 |
| 208 | AUGUACUC CUGAUGA X GAA AUGUUGAA | 640 | UUCAACAUA GAGUACAU | 641 |
| 213 | AAUUCAUG CUGAUGA X GAA ACUCUAUG | 642 | CAUAGAGUA CAUGAAUU | 643 |
| 221 | CCAAGUGC CUGAUGA X GAA AUUCAUGU | 644 | ACAUGAAUU GCACUUGG | 645 |
| 227 | GCUAUUCC CUGAUGA X GAA AGUGCAAU | 646 | AUUGCACAU GGAAUAGC | 647 |
| 233 | AGAACUGC CUGAUGA X GAA AUUCCAAG | 648 | CUUGGAAUA GCAGUUCU | 649 |
| 239 | AGGCUCAG CUGAUGA X GAA ACUGCUAU | 650 | AUAGCAGUU CUGAGCCU | 651 |
| 240 | GAGGCUCA CUGAUGA X GAA AACUGCUA | 652 | UAGCAGUUC UGAGCCUC | 653 |
| 248 | GGUUGCCU CUGAUGA X GAA AGGCUCAG | 654 | CUGAGCCUC AGGCAACC | 655 |
| 262 | UGCAGCGU CUGAUGA X GAA AGGUUGGU | 656 | ACCAACCUC ACGCUGCA | 657 |
| 273 | UGUACCUA CUGAUGA X GAA AGUGCAGC | 658 | GCUGCACUA UAGGUACA | 659 |
| 275 | CUUGUACC CUGAUGA X GAA AUAGUGCA | 660 | UGCACUAUA GGUACAAG | 661 |
| 279 | AUACCUUG CUGAUGA X GAA ACCUAUAG | 662 | CUAUAGGUA CAAGGUAU | 663 |
| 286 | UUAUCAGA CUGAUGA X GAA ACCUUGUA | 664 | UACAAGGUA UCUGAUAA | 665 |
| 288 | UAUUAUCA CUGAUGA X GAA AUACCUUG | 666 | CAAGGUAUC UGAUAAUA | 667 |
| 293 | UGUAUUAU CUGAUGA X GAA AUCAGAUA | 668 | UAUCUGAUA AUAAUACA | 669 |
| 296 | GAAUGUAU CUGAUGA X GAA AUUAUCAG | 670 | CUGAUAAUA AUACAUUC | 671 |
| 299 | CUGGAAUG CUGAUGA X GAA AUUAUUAU | 672 | AUAAUAAUA CAUUCCAG | 673 |
| 303 | ACUCCUGG CUGAUGA X GAA AUGUAUUA | 674 | UAAUACAUU CCAGGAGU | 675 |
| 304 | CACUCCUG CUGAUGA X GAA AAUGUAUU | 676 | AAUACAUUC CAGGAGUG | 677 |
| 317 | CAAAUAGU CUGAUGA X GAA ACUGCACU | 678 | AGUGCAGUC ACUAUUUG | 679 |
| 321 | AGAACAAA CUGAUGA X GAA AGUGACUG | 680 | CAGUCACUA UUUGUUCU | 681 |
| 323 | GGAGAACA CUGAUGA X GAA AUAGUGAC | 682 | GUCACUAUU UGUUCUCC | 683 |
| 324 | UGGAGAAC CUGAUGA X GAA AAUAGUGA | 684 | UCACUAUUU GUUCUCCA | 685 |
| 327 | CUUUGGAG CUGAUGA X GAA ACAAAUAG | 686 | CUAUUUGUU CUCCAAAG | 687 |
| 328 | UCUUUGGA CUGAUGA X GAA AACAAAUA | 688 | UAUUUGUUC UCCAAAGA | 689 |
| 330 | UCUCUUUG CUGAUGA X GAA AGAACAAA | 690 | UUUGUUCUC CAAAGAGA | 691 |
| 340 | CCAGAAGU CUGAUGA X GAA AUCUCUUU | 692 | AAAGAGAUU ACUUCUGG | 693 |
| 341 | GCCAGAAG CUGAUGA X GAA AAUCUCUU | 694 | AAGAGAUUA CUUCUGGC | 695 |
| 344 | ACAGCCAG CUGAUGA X GAA AGUAAUCU | 696 | AGAUUACUU CUGGCUGU | 697 |
| 345 | GACAGCCA CUGAUGA X GAA AAGUAAUC | 698 | GAUUACUUC UGGCUGUC | 699 |
| 353 | UUGUAUCU CUGAUGA X GAA ACAGCCAG | 700 | CUGGCUGUC AGAUACAA | 701 |
| 358 | UCUUUUUG CUGAUGA X GAA AUCUGACA | 702 | UGUCAGAUA CAAAAAGA | 703 |
| 371 | GAGCUGGA CUGAUGA X GAA AUCUUCUU | 704 | AAGAAGAUA UCCAGCUC | 705 |
| 373 | UAGCUGGA CUGAUGA X GAA AUAUCUUC | 706 | GAAGAUAUC CAGCUCUA | 707 |
| 379 | GUCUGGUA CUGAUGA X GAA AGCUGGAU | 708 | AUCCAGCUC UACCAGAC | 709 |

TABLE IV-continued

Mouse IL-2 Receptor g-Chain Hammerhead Ribozyme and Substrate Sequence

| nt. Position | HH Ribozyme Sequence | | | | | Seq. ID No. | Substrate | | Seq. ID No. |
|---|---|---|---|---|---|---|---|---|---|
| 381 | AUGUCUGG | CUGAUGA | X | GAA | AGAGCUGG | 710 | CCAGCUCUA | CCAGACAU | 711 |
| 390 | GGACAACA | CUGAUGA | X | GAA | AUGUCUGG | 712 | CCAGACAUU | UGUUGUCC | 713 |
| 391 | UGGACAAC | CUGAUGA | X | GAA | AAUGUCUG | 714 | CAGACAUUU | GUUGUCCA | 715 |
| 394 | AGCUGGAC | CUGAUGA | X | GAA | ACAAAUGU | 716 | ACAUUUGUU | GUCCAGCU | 717 |
| 397 | UGGAGCUG | CUGAUGA | X | GAA | ACAACAAA | 718 | UUUGUUGUC | CAGCUCCA | 719 |
| 403 | GGGUCCUG | CUGAUGA | X | GAA | AGCUGGAC | 720 | GUCCAGCUC | CAGGACCC | 721 |
| 436 | AGCUUCUG | CUGAUGA | X | GAA | ACAGCUCG | 722 | CGAGCUGUA | CAGAAGCU | 723 |
| 445 | UGUAGGUU | CUGAUGA | X | GAA | AGCUUCUG | 724 | CAGAAGCUA | AACCUACA | 725 |
| 451 | AGAUUCUG | CUGAUGA | X | GAA | AGGUUUAG | 726 | CUAAACCUA | CAGAAUCU | 727 |
| 458 | GAUCACAA | CUGAUGA | X | GAA | AUUCUGUA | 728 | UACAGAAUC | UUGUGAUC | 729 |
| 460 | GGGAUCAC | CUGAUGA | X | GAA | AGAUUCUG | 730 | CAGAAUCUU | GUGAUCCC | 731 |
| 466 | GCCCGUGG | CUGAUGA | X | GAA | AUCACAAG | 732 | CUUGUGAUC | CCACGGGC | 733 |
| 476 | AUUUCUG | CUGAUGA | X | GAA | AGCCCGUG | 734 | CACGGGCUC | CAGAAAAU | 735 |
| 485 | GAGUGUUA | CUGAUGA | X | GAA | AUUUUCUG | 736 | CAGAAAAUC | UAACACUC | 737 |
| 487 | CUGAGUGU | CUGAUGA | X | GAA | AGAUUUUC | 738 | GAAAAUCUA | ACACUCAG | 739 |
| 493 | AGAUUGCU | CUGAUGA | X | GAA | AGUGUUAG | 740 | CUAACACUC | AGCAAUCU | 741 |
| 500 | UUCACUCA | CUGAUGA | X | GAA | AUUGCUGA | 742 | UCAGCAAUC | UGAGUGAA | 743 |
| 510 | CUAGCUGG | CUGAUGA | X | GAA | AUUCACUC | 744 | GAGUGAAUC | CCAGCUAG | 745 |
| 517 | CUCAGCUC | CUGAUGA | X | GAA | AGCUGGGA | 746 | UCCCAGCUA | GAGCUGAG | 747 |
| 542 | UUCUUUAA | CUGAUGA | X | GAA | AUGUCUGC | 748 | GCAGACAUA | UUAAAGAA | 749 |
| 544 | CGUUCUUU | CUGAUGA | X | GAA | AUAUGUCU | 750 | AGACAUAUU | AAAGAACG | 751 |
| 545 | GCGUUCUU | CUGAUGA | X | GAA | AAUAUGUC | 752 | GACAUAUUA | AAGAACGC | 753 |
| 557 | GUAUUGUA | CUGAUGA | X | GAA | ACAGCGUU | 754 | AACGCUGUU | UACAAUAC | 755 |
| 558 | AGUAUUGU | CUGAUGA | X | GAA | AACAGCGU | 756 | ACGCUGUUU | ACAAUACU | 757 |
| 559 | AAGUAUUG | CUGAUGA | X | GAA | AAACAGCG | 758 | CGCUGUUUA | CAAUACUU | 759 |
| 564 | GCACCAAG | CUGAUGA | X | GAA | AUUGUAAA | 760 | UUUACAAUA | CUUGGUGC | 761 |
| 567 | ACUGCACC | CUGAUGA | X | GAA | AGUAUUGU | 762 | ACAAUACUU | GGUGCAGU | 763 |
| 576 | UGCUCCGG | CUGAUGA | X | GAA | ACUGCACC | 764 | GGUGCAGUA | CCGGAGCA | 765 |
| 593 | CCAGCUUC | CUGAUGA | X | GAA | AUCUCUGU | 766 | ACAGAGUAC | GAAGCUGG | 767 |
| 610 | UUCACUAU | CUGAUGA | X | GAA | AGUUCCGU | 768 | ACGGAACUA | AUAGUGAA | 769 |
| 613 | UGAUUCAC | CUGAUGA | X | GAA | AUUAGUUC | 770 | GAACUAAUA | GUGAAUCA | 771 |
| 620 | AGGUUCAU | CUGAUGA | X | GAA | AUUCACUA | 772 | UAGUGAAUC | AUGAACCU | 773 |
| 629 | GGAGAAUC | CUGAUGA | X | GAA | AGGUUCAU | 774 | AUGAACCUA | GAUUCUCC | 775 |
| 633 | GCAGGGAG | CUGAUGA | X | GAA | AUCUAGGU | 776 | ACCUAGAUU | CUCCCUGC | 777 |
| 634 | GGCAGGGA | CUGAUGA | X | GAA | AAUCUAGG | 778 | CCUAGAUUC | UCCCUGCC | 779 |
| 636 | UAGGCAGG | CUGAUGA | X | GAA | AGAAUCUA | 780 | UAGAUUCUC | CCUGCCUA | 781 |
| 644 | AUCCACAC | CUGAUGA | X | GAA | AGGCAGGG | 782 | CCCUGCCUA | GUGUGGAU | 783 |
| 666 | GAAAUGUG | CUGAUGA | X | GAA | ACCGUUUC | 784 | GAAACGGUA | CACAUUUC | 785 |
| 672 | GAACCCGA | CUGAUGA | X | GAA | AUGUGUAC | 786 | GUACACAUU | UCGGGUAC | 787 |
| 673 | CGAACCCG | CUGAUGA | X | GAA | AAUGUGUA | 788 | UACACAUUU | CGGGUUCG | 789 |
| 674 | CCGAACCC | CUGAUGA | X | GAA | AAAUGUGU | 790 | ACACAUUUC | GGGUUCGG | 791 |
| 679 | CGGCUCCG | CUGAUGA | X | GAA | ACCCGAAA | 792 | UUUCGGGUU | CGGAGCCG | 793 |
| 680 | GCGGCUCC | CUGAUGA | X | GAA | AACCCGAA | 794 | UUCGGGUUC | GGAGCCGC | 795 |
| 690 | UUGGGUUA | CUGAUGA | X | GAA | AGCGGCUC | 796 | GAGCCGCUA | UAACCCAA | 797 |
| 692 | GAUUGGGU | CUGAUGA | X | GAA | AUAGCGGC | 798 | GCCGCUAUA | ACCCAAUC | 799 |
| 700 | CUUCCACA | CUGAUGA | X | GAA | AUUGGGUU | 800 | AACCCAAUC | UGUGGAAG | 801 |
| 710 | CUGUUGAG | CUGAUGA | X | GAA | ACUUCCAC | 802 | GUGGAAGUU | CUCAACAG | 803 |
| 711 | ACUGUUGA | CUGAUGA | X | GAA | AACUUCCA | 804 | UGGAAGUUC | UCAACAGU | 805 |
| 713 | CCACUGUU | CUGAUGA | X | GAA | AGAACUUC | 806 | GAAGUUCUC | AACAGUGG | 807 |
| 725 | GCUCCAUU | CUGAUGA | X | GAA | ACUCCACU | 808 | AGUGGAGUA | AAUGGAGC | 809 |
| 742 | CCCCAGUG | CUGAUGA | X | GAA | ACAGGCUG | 810 | CAGCCUGUC | CACUGGGG | 811 |
| 755 | UACAGUAU | CUGAUGA | X | GAA | ACUCCCCC | 812 | GGGGGAGUC | AUACUGUA | 813 |
| 758 | CUCUACAG | CUGAUGA | X | GAA | AUGACUCC | 814 | GGAGUCAUA | CUGUAGAG | 815 |
| 763 | UUCUCCUC | CUGAUGA | X | GAA | ACAGUAUG | 816 | CAUACUGUA | GAGGAGAA | 817 |
| 773 | CAAGGAAG | CUGAUGA | X | GAA | AUUCUCCU | 818 | AGGAGAAUC | CUUCCUUG | 819 |
| 776 | AAACAAGG | CUGAUGA | X | GAA | AGGAUUCU | 820 | AGAAUCCUU | CCUUGUUU | 821 |
| 777 | CAAACAAG | CUGAUGA | X | GAA | AAGGAUUC | 822 | GAAUCCUUC | CUUGUUUG | 823 |
| 780 | GUGCAAAC | CUGAUGA | X | GAA | AGGAAGGA | 824 | UCCUUCCUU | GUUUGCAC | 825 |
| 783 | CCAGUGCA | CUGAUGA | X | GAA | ACAAGGAA | 826 | UUCCUUGUU | UGCACUGG | 827 |
| 784 | UCCAGUGC | CUGAUGA | X | GAA | AACAAGGA | 828 | UCCUUGUUU | GCACUGGA | 829 |
| 802 | ACAGGGAU | CUGAUGA | X | GAA | AGCACAGC | 830 | GCUGUGCUU | AUCCCUGU | 831 |
| 803 | AACAGGGA | CUGAUGA | X | GAA | AAGCACAG | 832 | CUGUGCUUA | UCCCUGUU | 833 |
| 805 | CCAACAGG | CUGAUGA | X | GAA | AUAAGCAC | 834 | GUGCUUAUC | CCUGUUGG | 835 |
| 811 | AUGGUGCC | CUGAUGA | X | GAA | ACAGGGAU | 836 | AUCCCUGUU | GGCACCAU | 837 |
| 825 | UAAUAAUC | CUGAUGA | X | GAA | ACCCCAUG | 838 | CAUGGGGUU | GAUUAUUA | 839 |
| 829 | AGGGUAAU | CUGAUGA | X | GAA | AUCAACCC | 840 | GGGUUGAUU | AUUACCCU | 841 |
| 830 | CAGGGUAA | CUGAUGA | X | GAA | AAUCAACC | 842 | GGUUGAUUA | UUACCCUG | 843 |
| 832 | AUCAGGGU | CUGAUGA | X | GAA | AUAAUCAA | 844 | UUGAUUAUU | ACCCUGAU | 845 |
| 833 | GAUCAGGG | CUGAUGA | X | GAA | AAUAAUCA | 846 | UGAUUAUUA | CCCUGAUC | 847 |
| 841 | UACACAAA | CUGAUGA | X | GAA | AUCAGGGU | 848 | ACCCUGAUC | UUUGUGUA | 849 |
| 843 | AGUACACA | CUGAUGA | X | GAA | AGAUCAGG | 850 | CCUGAUCUU | UGUGUACU | 851 |
| 844 | CAGUACAC | CUGAUGA | X | GAA | AAGAUCAG | 852 | CUGAUCUUU | GUGUACUG | 853 |
| 849 | ACCAACAG | CUGAUGA | X | GAA | ACACAAAG | 854 | CUUUGUGUA | CUGUUGGU | 855 |
| 854 | UUCCAACC | CUGAUGA | X | GAA | ACAGUACA | 856 | UGUACUGUU | GGUUGGAA | 857 |

TABLE IV-continued

Mouse IL-2 Receptor g-Chain Hammerhead Ribozyme and Substrate Sequence

| nt. Position | HH Ribozyme Sequence | | | | | Seq. ID No. | Substrate | | Seq. ID No. |
|---|---|---|---|---|---|---|---|---|---|
| 858 | UUCGUUCC | CUGAUGA | X | GAA | ACCAACAG | 858 | CUGUUGGUU | GGAACGAA | 859 |
| 872 | GGGAAUUG | CUGAUGA | X | GAA | AGGCAUUC | 860 | GAAUGCCUC | CAAUUCCC | 861 |
| 877 | AUGGGGGG | CUGAUGA | X | GAA | AUUGGAGG | 862 | CCUCCAAUU | CCCCCCAU | 863 |
| 878 | GAUGGGGG | CUGAUGA | X | GAA | AAUUGGAG | 864 | CUCCAAUUC | CCCCCAUC | 865 |
| 886 | AGAUUCUU | CUGAUGA | X | GAA | AUGGGGGG | 866 | CCCCCCAUC | AAGAAUCU | 867 |
| 893 | AUCCUCUA | CUGAUGA | X | GAA | AUUCUUGA | 868 | UCAAGAAUC | UAGAGGAU | 869 |
| 895 | AGACCUC | CUGAUGA | X | GAA | AGAUUCUU | 870 | AAGAAUCUA | GAGGAUCU | 871 |
| 902 | AGUAACCA | CUGAUGA | X | GAA | AUCCUCUA | 872 | UAGAGGAUC | UGGUUACU | 873 |
| 907 | UAUUCAGU | CUGAUGA | X | GAA | ACCAGAUC | 874 | GAUCUGGUU | ACUGAAUA | 875 |
| 908 | GUAUUCAG | CUGAUGA | X | GAA | AUUCAGUA | 876 | AUCUGGUUA | CUGAAUAC | 877 |
| 915 | UCCCUUGG | CUGAUGA | X | GAA | AUUCAGUA | 878 | UACUGAAUA | CCAAGGGA | 879 |
| 927 | AGGCCGAA | CUGAUGA | X | GAA | AGUUCCCU | 880 | AGGGAACUU | UUCGGCCU | 881 |
| 928 | CAGGCCGA | CUGAUGA | X | GAA | AAGUUCCC | 882 | GGGAACUUU | UCGGCCUG | 883 |
| 929 | CCAGGCCG | CUGAUGA | X | GAA | AAAGUUCC | 884 | GGAACUUUU | CGGCCUGG | 885 |
| 930 | UCCAGGCC | CUGAUGA | X | GAA | AAAAGUUC | 886 | GAACUUUUC | GGCCUGGA | 887 |
| 948 | GCCCUUUA | CUGAUGA | X | GAA | ACACACCA | 888 | UGGUGUGUC | UAAAGGGC | 889 |
| 950 | CAGCCCUU | CUGAUGA | X | GAA | AGACACAC | 890 | GUGUGUCUA | AAGGGCUG | 891 |
| 968 | UGGCUGCA | CUGAUGA | X | GAA | ACUCUCAG | 892 | CUGAGAGUC | UGCAGCCA | 893 |
| 981 | GUUCACUG | CUGAUGA | X | GAA | AGUCUGGC | 894 | GCCAGACUA | CAGUGAAC | 895 |
| 993 | CGUGGCAG | CUGAUGA | X | GAA | ACCGUUCA | 896 | UGAACGGUU | CUGCCACG | 897 |
| 994 | ACGUGGCA | CUGAUGA | X | GAA | AACCGUUC | 898 | GAACGGUUC | UGCCACGU | 899 |
| 1003 | AUCUCGCU | CUGAUGA | X | GAA | ACGUGGCA | 900 | UGCCACGUC | AGCGAGAU | 901 |
| 1012 | UUGGGGGG | CUGAUGA | X | GAA | AUCUCGCU | 902 | AGCGAGAUU | CCCCCCAA | 903 |
| 1013 | UUUGGGGG | CUGAUGA | X | GAA | AAUCUCGC | 904 | GCGAGAUUC | CCCCCAAA | 905 |
| 1033 | CCCUCUCC | CUGAUGA | X | GAA | AGGGCCCC | 906 | GGGGCCCUA | GGAGAGGG | 907 |
| 1052 | GCAAGGAG | CUGAUGA | X | GAA | ACCUCCAG | 908 | CUGGAGGUU | CUCCUUGC | 909 |
| 1053 | UGCAAGGA | CUGAUGA | X | GAA | AACCUCCA | 910 | UGGAGGUUC | UCCUUGCA | 911 |
| 1055 | GCUGCAAG | CUGAUGA | X | GAA | AGAACCUC | 912 | GAGGUUCUC | CUUGCAGC | 913 |
| 1058 | CAGGCUGC | CUGAUGA | X | GAA | AGGAGAAC | 914 | GUUCUCCUU | GCAGCCUG | 915 |
| 1070 | GUAAGGGC | CUGAUGA | X | GAA | AUGCAGGC | 916 | GCCUGCAUA | GCCCUUAC | 917 |
| 1076 | AGGCCAGU | CUGAUGA | X | GAA | AGGGCUAU | 918 | AUAGCCCUU | ACUGGCCU | 919 |
| 1077 | GAGGCCAG | CUGAUGA | X | GAA | AAGGGCUA | 920 | UAGCCCUUA | CUGGCCUC | 921 |
| 1085 | ACAUGGGG | CUGAUGA | X | GAA | AGGCCAGU | 922 | ACUGGCCUC | CCCCAUGU | 923 |
| 1094 | CAGAGAAU | CUGAUGA | X | GAA | ACAUGGGG | 924 | CCCCAUGUU | AUUCUCUG | 925 |
| 1095 | UCAGAGAA | CUGAUGA | X | GAA | AACAUGGG | 926 | CCCAUGUUA | UUCUCUGA | 927 |
| 1097 | CUUCAGAG | CUGAUGA | X | GAA | AUAACAUG | 928 | CAUGUUAUU | CUCUGAAG | 929 |
| 1098 | GCUUCAGA | CUGAUGA | X | GAA | AAUAACAU | 930 | AUGUUAUUC | UCUGAAGC | 931 |
| 1100 | CGGCUUCA | CUGAUGA | X | GAA | AGAAUAAC | 932 | GUUAUUCUC | UGAAGCCG | 933 |
| 1122 | AAAGGAUU | CUGAUGA | X | GAA | AUGUUCAG | 934 | CUGAACAUC | AAUCCUUU | 935 |
| 1126 | CAUCAAAG | CUGAUGA | X | GAA | AUUGAUGU | 936 | ACAUCAAUC | CUUUGAUG | 937 |
| 1129 | UUCCAUCA | CUGAUGA | X | GAA | AGGAUUGA | 938 | UCAAUCCUU | UGAUGGAA | 939 |
| 1130 | GUUCCAUC | CUGAUGA | X | GAA | AAGGAUUG | 940 | CAAUCCUUU | GAUGGAAC | 941 |
| 1141 | AGGACUUU | CUGAUGA | X | GAA | AGGUUCCA | 942 | UGGAACCUC | AAAGUCCU | 943 |
| 1147 | GACUAUAG | CUGAUGA | X | GAA | ACCUUGAG | 944 | CUCAAAGUC | CUAUAGUC | 945 |
| 1150 | UAGGACUA | CUGAUGA | X | GAA | AGGACUUU | 946 | AAAGUCCUA | UAGUCCUA | 947 |
| 1152 | CUUAGGAC | CUGAUGA | X | GAA | AUAGGACU | 948 | AGUCCUAUA | GUCCUAAG | 949 |
| 1155 | UCACUUAG | CUGAUGA | X | GAA | ACUAUAGG | 950 | CCUAUAGUC | CUAAGUGA | 951 |

Where "X" represents stem II region of a HH ribozyme (Hertel et al., 1992 Nucleic Acids Res. 20 3252). The Length of stem II may be ≥ 2 base-pairs.

TABLE V

Mouse IL-2 Receptor g-Chain Hairpin Ribozyme and Substrate Sequence

| nt. Position | Hairpin Ribozyme Sequence | | | Seq. ID NO. | Substrate | | Seq. ID NO. |
|---|---|---|---|---|---|---|---|
| 51 | GCAGGAGC | AGAA | GAAGGA | ACCAGAGAAACACGUUGUGGUACAUUACCUGGUA | 952 | UCCUUCA | GCU | GCUCCUGC | 953 |
| 54 | UCAGCAGG | AGAA | GCUGAA | ACCAGAGAAACACGUUGUGGUACAUUACCUGGUA | 954 | UUCAGCU | GCU | CCUGCUGA | 955 |
| 60 | CUGCCCUC | AGAA | GGAGCA | ACCAGAGAAACACGUUGUGGUACAUUACCUGGUA | 956 | UGCUCCU | GCU | GAGGGCAG | 957 |
| 121 | AGGAUCAA | AGAA | GCUUUG | ACCAGAGAAACACGUUGUGGUACAUUACCUGGUA | 958 | CAAAGCU | GAU | UUGAUCCU | 959 |
| 132 | CUGUAGAA | AGAA | GGAUCA | ACCAGAGAAACACGUUGUGGUACAUUACCUGGUA | 960 | UGAUCCU | GAC | UUCUACAG | 961 |
| 142 | UGUUCAGG | AGAA | GUAGAA | ACCAGAGAAACACGUUGUGGUACAUUACCUGGUA | 962 | UUCUACA | GCC | CCUGAACA | 963 |
| 171 | CUGGAAGG | AGAA | GAGUAG | ACCAGAGAAACACGUUGUGGUACAUUACCUGGUA | 964 | CUACUCU | GCC | CCUUCCAG | 965 |
| 236 | AGGCUCAG | AGAA | GCUAUU | ACCAGAGAAACACGUUGUGGUACAUUACCUGGUA | 966 | AAUAGCA | GUU | CUGAGCCU | 967 |
| 375 | UCUGGUAG | AGAA | GGAUAU | ACCAGAGAAACACGUUGUGGUACAUUACCUGGUA | 968 | AUAUCCA | GCU | CUACCAGA | 969 |
| 399 | GGUCCUGG | AGAA | GGACAA | ACCAGAGAAACACGUUGUGGUACAUUACCUGGUA | 970 | UUGUCCA | GCU | CCAGGACC | 971 |
| 554 | GUAUUGUA | AGAA | GCGUUC | ACCAGAGAAACACGUUGUGGUACAUUACCUGGUA | 972 | GAACGCU | GUU | UACAAUAC | 973 |
| 639 | CCACACUA | AGAA | GGGAGA | ACCAGAGAAACACGUUGUGGUACAUUACCUGGUA | 974 | UCUCCCU | GCC | UAGUGUGG | 975 |
| 735 | AGUGGACA | AGAA | GCUCC  | ACCAGAGAAACACGUUGUGGUACAUUACCUGGUA | 976 | GGAGCCA | GCC | UGUCCACU | 977 |
| 739 | CCCCAGUG | AGAA | GGCUGG | ACCAGAGAAACACGUUGUGGUACAUUACCUGGUA | 978 | CCAGCCU | GUC | CACUGGGG | 979 |
| 808 | AUGGUGCC | AGAA | GGGAUA | ACCAGAGAAACACGUUGUGGUACAUUACCUGGUA | 980 | UAUCCCU | GCC | GGCACCAU | 981 |
| 837 | ACACAAAG | AGAA | GGUAA  | ACCAGAGAAACACGUUGUGGUACAUUACCUGGUA | 982 | UUACCCU | GAU | CUUUGUGU | 983 |
| 851 | UUCCAACC | AGAA | GUACAC | ACCAGAGAAACACGUUGUGGUACAUUACCUGGUA | 984 | GUGUACU | GUU | GGUUGGAA | 985 |
| 931 | CCACUCCA | AGAA | GAAAAG | ACCAGAGAAACACGUUGUGGUACAUUACCUGGUA | 986 | CUUUUCG | GCC | UGGAGUGG | 987 |
| 957 | GACUCUCA | AGGA | GCCCUU | ACCAGAGAAACACGUUGUGGUACAUUACCUGGUA | 988 | AAGGGCU | GAC | UGAGAGUC | 989 |
| 976 | UCACUGUA | AGAA | GGCUGC | ACCAGAGAAACACGUUGUGGUACAUUACCUGGUA | 990 | GCAGCCA | GAC | UACAGUGA | 991 |
| 990 | CGUGGCAG | AGAA | GUUCAC | ACCAGAGAAACACGUUGUGGUACAUUACCUGGUA | 992 | GUGAACG | GUU | CUGCCACG | 993 |
| 1061 | GCUAUGCA | AGAA | GCAAGG | ACCAGAGAAACACGUUGUGGUACAUUACCUGGUA | 994 | CCUUGCA | GCC | UGCAUAGC | 995 |

TABLE VI

Canine IL-2 Receptor g-Chain Hammerhead Ribozyme and Substrate Sequence

| nt. Position | HH Ribozyme Sequence | | | | | Seq. ID No. | Substrate | | Seq. ID No. |
|---|---|---|---|---|---|---|---|---|---|
| 17 | UGAGUGGC | CUGAUGA | X | GAA | AUGGUGGC | 996 | GCCACCAUU | GCCACUCA | 997 |
| 24 | AGGGAUCU | CUGAUGA | X | GAA | AGUGGCAA | 998 | UUGCCACUC | AGAUCCCU | 999 |
| 29 | AUAAGAGG | CUGAUGA | X | GAA | AUCUGAGU | 1000 | ACUCAGAUC | CCUCUUAU | 1001 |
| 33 | AGGAAUAA | CUGAUGA | X | GAA | AGGGAUCU | 1002 | AGAUCCCUC | UUAUUCCU | 1003 |
| 35 | GCAGGAAU | CUGAUGA | X | GAA | AGAGGGAU | 1004 | AUCCCUCUU | AUUCCUGC | 1005 |
| 36 | UGCAGGAA | CUGAUGA | X | GAA | AAGAGGGA | 1006 | UCCCUCUUA | UUCCUGCA | 1007 |
| 38 | GCUGCAGG | CUGAUGA | X | GAA | AUAAGAGG | 1008 | CCUCUUAUU | CCUGCAGC | 1009 |
| 39 | AGCUGCAG | CUGAUGA | X | GAA | AAUAAGAG | 1010 | CUCUUAUUC | CUGCAGCU | 1011 |
| 50 | CCAGCAGA | CUGAUGA | X | GAA | ACAGCUGC | 1012 | GCAGCUGUC | UCUGCUGG | 1013 |
| 52 | CCCCAGCA | CUGAUGA | X | GAA | AGACAGCU | 1014 | AGCUGUCUC | UGCUGGGG | 1015 |
| 74 | GGACCGUG | CUGAUGA | X | GAA | AGUUCAGC | 1016 | GCUGAACUC | CACGGUCC | 1017 |
| 81 | GGCAUGGG | CUGAUGA | X | GAA | ACCGUGGA | 1018 | UCCACGGUC | CCCAUGCC | 1019 |
| 108 | UCAGGUGU | CUGAUGA | X | GAA | AUGUCUUC | 1020 | GAAGACAUC | ACACCUGA | 1021 |
| 118 | CAGGAAGA | CUGAUGA | X | GAA | AUCAGGUG | 1022 | CACCUGAUU | UCUUCCUG | 1023 |
| 119 | UCAGGAAG | CUGAUGA | X | GAA | AAUCAGGU | 1024 | ACCUGAUUU | CUUCCUGA | 1025 |
| 120 | GUCAGGAA | CUGAUGA | X | GAA | AAAUCAGG | 1026 | CCUGAUUUC | UUCCUGAC | 1027 |
| 122 | CGGUCAGG | CUGAUGA | X | GAA | AGAAAUCA | 1028 | UGAUUUCUU | CCUGACCG | 1029 |
| 123 | GCGGUCAG | CUGAUGA | X | GAA | AAGAAAUC | 1030 | GAUUUCUUC | CUGACCGC | 1031 |
| 133 | GGAGGGUG | CUGAUGA | X | GAA | AGCGGUCA | 1032 | UGACCGCUA | CACCCUCC | 1033 |
| 140 | GGGUCUCG | CUGAUGA | X | GAA | AGGGUGUA | 1034 | UACACCCUC | CGAGACCC | 1035 |
| 150 | GAAACACU | CUGAUGA | X | GAA | AGGGUCUC | 1036 | GAGACCCUC | AGUGUUUC | 1037 |
| 156 | AGGGAGGA | CUGAUGA | X | GAA | ACACUGAG | 1038 | CUCAGUGUU | UCCUCCCU | 1039 |
| 157 | CAGGGAGG | CUGAUGA | X | GAA | AACACUGA | 1040 | UCAGUGUUU | CCUCCCUG | 1041 |
| 158 | GCAGGGAG | CUGAUGA | X | GAA | AAACACUG | 1042 | CAGUGUUUC | CUCCCUGC | 1043 |
| 161 | GGGGCAGG | CUGAUGA | X | GAA | AGGAAACA | 1044 | UGUUUCCUC | CCUGCCCC | 1045 |
| 171 | ACCUCUGG | CUGAUGA | X | GAA | AGGGGCAG | 1046 | CUGCCCCUC | CCAGAGGU | 1047 |
| 180 | AAACACUG | CUGAUGA | X | GAA | ACCUCUGG | 1048 | CCAGAGGUC | CAGUGUUU | 1049 |
| 187 | GAACACAA | CUGAUGA | X | GAA | ACACUGGA | 1050 | UCCAGUGUU | UUGUGUUC | 1051 |
| 188 | UGAACACA | CUGAUGA | X | GAA | AACACUGG | 1052 | CCAGUGUUU | UGUGUUCA | 1053 |
| 189 | UUGAACAC | CUGAUGA | X | GAA | AAACACUG | 1054 | CAGUGUUUU | GUGUUCAA | 1055 |
| 194 | CAACAUUG | CUGAUGA | X | GAA | ACACAAAA | 1056 | UUUUGUGUU | CAAUGUUG | 1057 |
| 195 | UCAACAUU | CUGAUGA | X | GAA | AACACAAA | 1058 | UUUGUGUUC | AAUGUUGA | 1059 |
| 201 | AUGUACUC | CUGAUGA | X | GAA | ACAUUGAA | 1060 | UUCAAUGUU | GAGUACAU | 1061 |
| 206 | AAUUCAUG | CUGAUGA | X | GAA | ACUCAACA | 1062 | UGUUGAGUA | CAUGAAUU | 1063 |
| 214 | CCAAGUGC | CUGAUGA | X | GAA | AUUCAUGU | 1064 | ACAUGAAUU | GCACUUGG | 1065 |
| 220 | GCUGUUCC | CUGAUGA | X | GAA | AGUGCAAU | 1066 | AUUGCACUU | GGAACAGC | 1067 |
| 233 | GGGGCUCA | CUGAUGA | X | GAA | AGCUGCUG | 1068 | CAGCAGCUC | UGAGCCCC | 1069 |
| 266 | UAUACCAG | CUGAUGA | X | GAA | AGUGCAGG | 1070 | CCUGCACUA | CUGGUAUA | 1071 |
| 272 | AGUUCUUA | CUGAUGA | X | GAA | ACCAGUAG | 1072 | CUACUGGUA | UAAGAACU | 1073 |
| 274 | GGAGUUCU | CUGAUGA | X | GAA | AUACCAGU | 1074 | ACUGGUAUA | AGAACUCC | 1075 |
| 281 | CAUCAUUG | CUGAUGA | X | GAA | AGUUCUUA | 1076 | UAAGAACUC | CAAUGAUG | 1077 |
| 292 | CUGGACUU | CUGAUGA | X | GAA | AUCAUCAU | 1078 | AUGAUGAUA | AAGUCCAG | 1079 |
| 297 | CACUCCUG | CUGAUGA | X | GAA | ACUUUAUC | 1080 | GAUAAAGUC | CAGGAGUG | 1081 |
| 314 | AGAAUAGG | CUGAUGA | X | GAA | AGUGGCCA | 1082 | UGGCCACUA | CCUAUUCU | 1083 |
| 318 | CUAGAGAA | CUGAUGA | X | GAA | AGGUAGUG | 1084 | CACUACCUA | UUCUCUAG | 1085 |
| 320 | CUCUAGAG | CUGAUGA | X | GAA | AUAGGUAG | 1086 | CUACCUAUU | CUCUAGAG | 1087 |
| 321 | UCUCUAGA | CUGAUGA | X | GAA | AAUAGGUA | 1088 | UACCUAUUC | UCUAGAGA | 1089 |
| 323 | CCUCUCUA | CUGAUGA | X | GAA | AGAAUAGG | 1090 | CCUAUUCUC | UAGAGAGG | 1091 |
| 325 | GACCUCUC | CUGAUGA | X | GAA | AGAGAAUA | 1092 | UAUUCUCUA | GAGAGGUC | 1093 |
| 333 | CCAGCAGU | CUGAUGA | X | GAA | ACCUCUCU | 1094 | AGAGAGGUC | ACUGCUGG | 1095 |
| 346 | CUGCAACC | CUGAUGA | X | GAA | ACAGCCAG | 1096 | CUGGCUGUU | GGUUGCAG | 1097 |
| 350 | CCUUCUGC | CUGAUGA | X | GAA | ACCAACAG | 1098 | CUGUUGGUU | GCAGAAGG | 1099 |
| 366 | UAGAGAUG | CUGAUGA | X | GAA | AUCUCCUC | 1100 | GAGGAGAUC | CAUCUCUA | 1101 |
| 370 | UUCGUAGA | CUGAUGA | X | GAA | AUGGAUCU | 1102 | AGAUCCAUC | UCUACGAA | 1103 |
| 372 | GUUUCGUA | CUGAUGA | X | GAA | AGAUGGAU | 1104 | AUCCAUCUC | UACGAAAC | 1105 |
| 374 | AUGUUUCG | CUGAUGA | X | GAA | AGAGAUGG | 1106 | CCAUCUCUA | CGAAACAU | 1107 |
| 383 | GGACAACA | CUGAUGA | X | GAA | AUGUUUCG | 1108 | CGAAACAUU | UGUUGUCC | 1109 |
| 384 | UGGACAAC | CUGAUGA | X | GAA | AAUGUUUC | 1110 | GAAACAUUU | GUUGUCCA | 1111 |
| 387 | AGCUGGAC | CUGAUGA | X | GAA | ACAAAUGU | 1112 | ACAUUUGUU | GUCCAGCU | 1113 |
| 390 | CGGAGCUG | CUGAUGA | X | GAA | ACAACAAA | 1114 | UUUGUUGUC | CAGCUCCG | 1115 |
| 396 | GGGUCCCG | CUGAUGA | X | GAA | AGCUGGAC | 1116 | GUCCAGCUC | CGGGACCC | 1117 |
| 425 | UCUGUGUG | CUGAUGA | X | GAA | ACUGCCUC | 1118 | GAGGCAGUC | CACACAGA | 1119 |
| 438 | UGCAGUUU | CUGAUGA | X | GAA | AGCUUCUG | 1120 | CAGAAGCUA | AAACUGCA | 1121 |
| 451 | GAUCACCA | CUGAUGA | X | GAA | AUUUUGCA | 1122 | UGCAAAAUC | UGGUGAUC | 1123 |
| 459 | GCCCAGGG | CUGAUGA | X | GAA | AUCACCAG | 1124 | CUGGUGAUC | CCCUGGGC | 1125 |
| 469 | GUUCUCCG | CUGAUGA | X | GAA | AGCCCAGG | 1126 | CCUGGGCUC | CGGAGAAC | 1127 |
| 480 | UGAAGGGU | CUGAUGA | X | GAA | AGGUUCUC | 1128 | GAGAACCUA | ACCCUUCA | 1129 |
| 486 | AGGUUGUG | CUGAUGA | X | GAA | AGGGUUAG | 1130 | CUAACCCUU | CACAACCU | 1131 |
| 487 | CAGGUUGU | CUGAUGA | X | GAA | AAGGGUUA | 1132 | UAACCCUUC | ACAACCUG | 1133 |
| 503 | CUAGCUGG | CUGAUGA | X | GAA | AUUCGCUC | 1134 | GAGCGAAUC | CCAGCUAG | 1135 |
| 510 | CUCAGUUC | CUGAUGA | X | GAA | AGCUGGGA | 1136 | UCCCAGCUA | GAACUGAG | 1137 |
| 536 | AGUGGUCC | CUGAUGA | X | GAA | AGUGUCUG | 1138 | CAGACACUU | GGACCACU | 1139 |
| 547 | AUGCUCCA | CUGAUGA | X | GAA | ACAGUGGU | 1140 | ACCACUGUU | UGGAGCAU | 1141 |

TABLE VI-continued

Canine IL-2 Receptor g-Chain Hammerhead Ribozyme and Substrate Sequence

| nt. Position | HH Ribozyme Sequence | | | | | Seq. ID No. | Substrate | | Seq. ID No. |
|---|---|---|---|---|---|---|---|---|---|
| 548 | CAUGCUCC | CUGAUGA | X | GAA | AACAGUGG | 1142 | CCACUGUUU | GGAGCAUG | 1143 |
| 558 | UACUGCAC | CUGAUGA | X | GAA | ACAUGCUC | 1144 | GAGCAUGUU | GUGCAGUA | 1145 |
| 566 | CACUCCGG | CUGAUGA | X | GAA | ACUGCACA | 1146 | UGUGCAGUA | CCGGAGUG | 1147 |
| 602 | GGUCCACU | CUGAUGA | X | GAA | ACUGUUCA | 1148 | UGAACAGUC | AGUGGACC | 1149 |
| 619 | AGAGAAGC | CUGAUGA | X | GAA | AUUUCGGU | 1150 | ACCGAAAUA | GCUUCUCU | 1151 |
| 623 | GCAGAGAG | CUGAUGA | X | GAA | AGCUAUUU | 1152 | AAAUAGCUU | CUCUCUGC | 1153 |
| 624 | GGCAGAGA | CUGAUGA | X | GAA | AAGCUAUU | 1154 | AAUAGCUUC | UCUCUGCC | 1155 |
| 626 | UAGGCAGA | CUGAUGA | X | GAA | AGAAGCUA | 1156 | UAGCUUCUC | UCUGCCUA | 1157 |
| 628 | GCUAGGCA | CUGAUGA | X | GAA | AGAGAAGC | 1158 | GCUUCUCUC | UGCCUAGC | 1159 |
| 634 | AUCCACGC | CUGAUGA | X | GAA | AGGCAGAG | 1160 | CUCUGCCUA | GCGUGGAU | 1161 |
| 653 | ACGUGUAG | CUGAUGA | X | GAA | ACUUCUGC | 1162 | GCAGAAGUU | CUACACGU | 1163 |
| 654 | AACGUGUA | CUGAUGA | X | GAA | AACUUCUG | 1164 | CAGAAGUUC | UACACGUU | 1165 |
| 656 | GGAACGUG | CUGAUGA | X | GAA | AGAACUUC | 1166 | GAAGUUCUA | CACGUUCC | 1167 |
| 662 | GGACACGG | CUGAUGA | X | GAA | ACGUGUAG | 1168 | CUACACGUU | CCGUGUCC | 1169 |
| 663 | CGGACACG | CUGAUGA | X | GAA | AACGUGUA | 1170 | UACACGUUC | CGUGUCCG | 1171 |
| 669 | CGGCUUCG | CUGAUGA | X | GAA | ACACGGAA | 1172 | UUCCGUGUC | CGAAGCCG | 1173 |
| 680 | GUGGGUUA | CUGAUGA | X | GAA | AGCGGCUU | 1174 | AAGCCGCUA | UAACCCAC | 1175 |
| 682 | GAGUGGGU | CUGAUGA | X | GAA | AUAGCGGC | 1176 | GCCGCUAUA | ACCCACUC | 1177 |
| 690 | CUUCCACA | CUGAUGA | X | GAA | AGUGGGUU | 1178 | AACCCACUC | UGUGGAAG | 1179 |
| 703 | CCAACGCU | CUGAUGA | X | GAA | AGCGCUUC | 1180 | GAAGCGCUC | AGCGUUGG | 1181 |
| 709 | UUCACUCC | CUGAUGA | X | GAA | ACGCUGAG | 1182 | CUCAGCGUU | GGAGUGAA | 1183 |
| 730 | CCAGUGGA | CUGAUGA | X | GAA | AGGGUGGC | 1184 | GCCACCCUA | UCCACUGG | 1185 |
| 732 | CCCCAGUG | CUGAUGA | X | GAA | AUAGGGUG | 1186 | CACCCUAUC | CACUGGGG | 1187 |
| 748 | CUUGGAGG | CUGAUGA | X | GAA | AUUGCUCC | 1188 | GGAGCAAUA | CCUCCAAG | 1189 |
| 752 | UCUCCUUG | CUGAUGA | X | GAA | AGGUAUUG | 1190 | CAAUACCUC | CAAGGAGA | 1191 |
| 763 | AAACAAAG | CUGAUGA | X | GAA | AUUCUCCU | 1192 | AGGAGAAUC | CUUUGUUU | 1193 |
| 766 | UGCAAACA | CUGAUGA | X | GAA | AGGAUUCU | 1194 | AGAAUCCUU | UGUUUGCA | 1195 |
| 767 | AUGCAAAC | CUGAUGA | X | GAA | AAGGAUUC | 1196 | GAAUCCUUU | GUUUGCAU | 1197 |
| 770 | CCGAUGCA | CUGAUGA | X | GAA | ACAAAGGA | 1198 | UCCUUUGUU | UGCAUCGG | 1199 |
| 771 | UCCGAUGC | CUGAUGA | X | GAA | AACAAAGG | 1200 | CCUUUGUUU | GCAUCGGA | 1201 |
| 776 | CAGCUUCC | CUGAUGA | X | GAA | AUGCAAAC | 1202 | GUUUGCAUC | GGAAGCUG | 1203 |
| 789 | AGGGGGAU | CUGAUGA | X | GAA | AGCACAGC | 1204 | GCUGUGCUU | AUCCCCCU | 1205 |
| 790 | AAGGGGGA | CUGAUGA | X | GAA | AAGCACAG | 1206 | CUGUGCUUA | UCCCCCUU | 1207 |
| 792 | CCAAGGGG | CUGAUGA | X | GAA | AUAAGCAC | 1208 | GUGCUUAUC | CCCCUUGG | 1209 |
| 798 | AUGGAGCC | CUGAUGA | X | GAA | AGGGGGAU | 1210 | AUCCCCCUU | GGCUCCAU | 1211 |
| 803 | AUCCCAUG | CUGAUGA | X | GAA | AGCCAAGG | 1212 | CCUUGGCUC | CAUGGGAU | 1213 |
| 812 | UAAUAAUC | CUGAUGA | X | GAA | AUCCCAUG | 1214 | CAUGGGAUU | GAUUAUUA | 1215 |
| 816 | AGGCUAAU | CUGAUGA | X | GAA | AUCAAUCC | 1216 | GGAUUGAUU | AUUAGCCU | 1217 |
| 817 | AAGGCUAA | CUGAUGA | X | GAA | AAUCAAUC | 1218 | GAUUGAUUA | UUAGCCUU | 1219 |
| 819 | AUAAGGCU | CUGAUGA | X | GAA | AUAAUCAA | 1220 | UUGAUUAUU | AGCCUUAU | 1221 |
| 820 | GAUAAGGC | CUGAUGA | X | GAA | AAUAAUCA | 1222 | UGAUUAUUA | GCCUUAUC | 1223 |
| 825 | ACACAGAU | CUGAUGA | X | GAA | AGGCUAAU | 1224 | AUUAGCCUU | AUCUGUGU | 1225 |
| 826 | CACACAGA | CUGAUGA | X | GAA | AAGGCUAA | 1226 | UUAGCCUUA | UCUGUGUG | 1227 |
| 828 | UACACACA | CUGAUGA | X | GAA | AUAAGGCU | 1228 | AGCCUUAUC | UGUGUGUA | 1229 |
| 836 | GCCAGUAG | CUGAUGA | X | GAA | ACACACAG | 1230 | CUGUGUGUA | CUACUGGC | 1231 |
| 839 | CCAGCCAG | CUGAUGA | X | GAA | AGUACACA | 1232 | UGUGUACUA | CUGGCUGG | 1233 |
| 854 | GGGGGAUC | CUGAUGA | X | GAA | ACCGUUCC | 1234 | GGAACGGUC | GAUCCCCC | 1235 |
| 858 | AUUCGGGG | CUGAUGA | X | GAA | AUCGACCG | 1236 | CGGUCGAUC | CCCCGAAU | 1237 |
| 867 | AGGGUAGG | CUGAUGA | X | GAA | AUUCGGGG | 1238 | CCCCGAAUU | CCUACCCU | 1239 |
| 868 | GAGGGUAG | CUGAUGA | X | GAA | AAUUCGGG | 1240 | CCCGAAUUC | CUACCCUC | 1241 |
| 871 | CUUGCAGGG | CUGAUGA | X | GAA | AGGAAUUC | 1242 | GAAUUCCUA | CCCUCAAG | 1243 |
| 876 | AGGUUCUU | CUGAUGA | X | GAA | AGGGUAGG | 1244 | CCUACCCUC | AAGAACCU | 1245 |
| 892 | AGUAACCA | CUGAUGA | X | GAA | AUCCUCCA | 1246 | UGGAGGAUC | UGGUUACU | 1247 |
| 897 | UAUUCAGU | CUGAUGA | X | GAA | ACCAGAUC | 1248 | GAUCUGGUU | ACUGAAUA | 1249 |
| 898 | AUAUUCAG | CUGAUGA | X | GAA | AACCAGAU | 1250 | AUCUGGUUA | CUGAAUAU | 1251 |
| 905 | UCCCGUGA | CUGAUGA | X | GAA | AUUCAGUA | 1252 | UACUGAAUA | UCACGGGA | 1253 |
| 907 | AUCCCGU | CUGAUGA | X | GAA | AUAUUCAG | 1254 | CUGAAUAUC | ACGGGAAU | 1255 |
| 916 | GGCCGAAA | CUGAUGA | X | GAA | AUUCCCGU | 1256 | ACGGGAAUU | UUUCGGCC | 1257 |
| 917 | AGGCCGAA | CUGAUGA | X | GAA | AAUUCCCG | 1258 | CGGGAAUUU | UCGGCCU | 1259 |
| 918 | CAGGCCGA | CUGAUGA | X | GAA | AAAUUCCC | 1260 | GGGAAUUUU | UCGGCCUG | 1261 |
| 919 | CCAGGCCG | CUGAUGA | X | GAA | AAAAUUCC | 1262 | GGAAUUUUU | CGGCCUGG | 1263 |
| 920 | UCCAGGCC | CUGAUGA | X | GAA | AAAAAUUC | 1264 | GAAUUUUUC | GGCCUGGA | 1265 |
| 938 | GUCCCUUA | CUGAUGA | X | GAA | ACACUCCA | 1266 | UGGAGUGUC | UAAGGGAC | 1267 |
| 940 | CAGUCCCU | CUGAUGA | X | GAA | AGACACUC | 1268 | GAGUGUCUA | AGGGACUG | 1269 |
| 958 | UGGCUGCA | CUGAUGA | X | GAA | ACUCUCCG | 1270 | CGGAGAGUC | UGCAGCCA | 1271 |
| 971 | AUUCACUG | CUGAUGA | X | GAA | AGUCUGGC | 1272 | GCCAGACUA | CAGUGAAU | 1273 |
| 984 | ACGUGGCA | CUGAUGA | X | GAA | AGCCAUUC | 1274 | GAAUGGCUC | UGCCACGU | 1275 |
| 993 | AUCUCACU | CUGAUGA | X | GAA | ACGUGGCA | 1276 | UGCCACGUC | AGUGAGAU | 1277 |
| 1002 | UUUGGGGG | CUGAUGA | X | GAA | AUCUCACU | 1278 | AGUGAGAUU | CCCCCAAA | 1279 |
| 1003 | UUUUGGGG | CUGAUGA | X | GAA | AAUCUCAC | 1280 | GUGAGAUUC | CCCCAAAA | 1281 |
| 1021 | CUCCCCUG | CUGAUGA | X | GAA | AGCCCCUC | 1282 | GAGGGGCUC | CAGGGGAG | 1283 |
| 1033 | GCCCCCAG | CUGAUGA | X | GAA | ACCCUCCC | 1284 | GGGAGGGUC | CUGGGGC | 1285 |
| 1043 | UGCAGGGG | CUGAUGA | X | GAA | AGCCCCCA | 1286 | UGGGGGCUC | CCCCUGCA | 1287 |

TABLE VI-continued

Canine IL-2 Receptor g-Chain Hammerhead Ribozyme and Substrate Sequence

| nt. Position | HH Ribozyme Sequence | | | | | Seq. ID No. | Substrate | | Seq. ID No. |
|---|---|---|---|---|---|---|---|---|---|
| 1060 | GUAGGGGC | CUGAUGA | X | GAA | AUGCUGGC | 1288 | GCCAGCAUA | GCCCCUAC | 1289 |
| 1067 | GAGCCCAG | CUGAUGA | X | GAA | AGGGGCUA | 1290 | UAGCCCCUA | CUGGGCUC | 1291 |
| 1075 | ACAUGGGG | CUGAUGA | X | GAA | AGCCCAGU | 1292 | ACUGGGCUC | CCCCAUGU | 1293 |
| 1084 | CAGGGUAU | CUGAUGA | X | GAA | ACAUGGGG | 1294 | CCCCAUGUU | AUACCCUG | 1295 |
| 1085 | UCAGGGUA | CUGAUGA | X | GAA | AACAUGGG | 1296 | CCCAUGUUA | UACCCUGA | 1297 |
| 1087 | UUUCAGGG | CUGAUGA | X | GAA | AUAACAUG | 1298 | CAUGUUAUA | CCCUGAAA | 1299 |
| 1116 | UGUCAGGG | CUGAUGA | X | GAA | AUCAGGGC | 1300 | GCCCUGAUA | CCCUGACA | 1301 |
| 1131 | AGGACUCU | CUGAUGA | X | GAA | AGGUUCUG | 1302 | CAGAACCUC | AGAGUCCU | 1303 |
| 1137 | GAGGACAG | CUGAUGA | X | GAA | ACUCUGAG | 1304 | CUCAGAGUC | CUGUCCUC | 1305 |
| 1142 | UAUAGGAG | CUGAUGA | X | GAA | ACAGGACU | 1306 | AGUCCUGUC | CUCCUAUA | 1307 |
| 1145 | CAAUAUAG | CUGAUGA | X | GAA | AGGACAGG | 1308 | CCUGUCCUC | CUAUAUUG | 1309 |
| 1148 | GUACAAUA | CUGAUGA | X | GAA | AGGAGGAC | 1310 | GUCCUCCUA | UAUUGUAC | 1311 |
| 1150 | UAGUACAA | CUGAUGA | X | GAA | AUAGGAGG | 1312 | CCUCCUAUA | UUGUACUA | 1313 |
| 1152 | GUUAGUAC | CUGAUGA | X | GAA | AUAUAGGA | 1314 | UCCUAUAUU | GUACUAAC | 1315 |
| 1155 | GAAGUUAG | CUGAUGA | X | GAA | ACAAUAUA | 1316 | UAUAUUGUA | CUAACUUC | 1317 |
| 1158 | GGGGAAGU | CUGAUGA | X | GAA | AGUACAAU | 1318 | AUUGUACUA | ACUUCCCC | 1319 |
| 1162 | AUAAGGGG | CUGAUGA | X | GAA | AGUUAGUA | 1320 | UACUAACUU | CCCCUUAU | 1321 |
| 1163 | GAUAAGGG | CUGAUGA | X | GAA | AAGUUAGU | 1322 | ACUAACUUC | CCCUUAUC | 1323 |
| 1168 | GGUUAGAU | CUGAUGA | X | GAA | AGGGGAAG | 1324 | CUUCCCCUU | AUCUAACC | 1325 |
| 1169 | UGGUUAGA | CUGAUGA | X | GAA | AAGGGGAA | 1326 | UUCCCCUUA | UCUAACCA | 1327 |
| 1171 | GUUGGUUA | CUGAUGA | X | GAA | AUAAGGGG | 1328 | CCCCUUAUC | UAACCAAC | 1329 |
| 1173 | AGGUUGGU | CUGAUGA | X | GAA | AGAUAAGG | 1330 | CCUUAUCUA | ACCAACCU | 1331 |
| 1186 | GAGCAUUG | CUGAUGA | X | GAA | ACCCAGGU | 1332 | ACCUGGGUC | CAAUGCUC | 1333 |
| 1194 | GGCGAGGU | CUGAUGA | X | GAA | AGCAUUGG | 1334 | CCAAUGCUC | ACCUCGCC | 1335 |

Where "X" represents stem II region of a HH ribozyme (Hertel et al., 1992 Nucleic Acids Res. 20 3252). The length of stem II may be ≧2 base-pairs.

TABLE VII

Canine IL-2 Receptor g-Chain Hairpin Ribozyme and Substrate Sequence

| nt. Position | Hairpin Ribozyme Sequence | | | | Seq. ID No. |
|---|---|---|---|---|---|
| 25 | UAAGAGGG | AGAA | GAGUGG | ACCAGAGAAACACACGUUGUGGUACAUUACCUGGUA | 1336 |
| 44 | GCAGAGAC | AGAA | GCAGGA | ACCAGAGAAACACACGUUGUGGUACAUUACCUGGUA | 1338 |
| 47 | CCAGCAGA | AGAA | GCUGCA | ACCAGAGAAACACACGUUGUGGUACAUUACCUGGUA | 1340 |
| 53 | CCACCCCC | AGAA | GAGACA | ACCAGAGAAACACACGUUGUGGUACAUUACCUGGUA | 1342 |
| 78 | GGCAUGGG | AGAA | GUGGAG | ACCAGAGAAACACACGUUGUGGUACAUUACCUGGUA | 1344 |
| 114 | AGGAAGAA | AGAA | GGUGUG | ACCAGAGAAACACACGUUGUGGUACAUUACCUGGUA | 1346 |
| 125 | GUGUAGCG | AGAA | GGAAGA | ACCAGAGAAACACACGUUGUGGUACAUUACCUGGUA | 1348 |
| 164 | CUGGGAGG | AGAA | GGGAGG | ACCAGAGAAACACACGUUGUGGUACAUUACCUGGUA | 1350 |
| 229 | GGGCUCAG | AGAA | GCUGUU | ACCAGAGAAACACACGUUGUGGUACAUUACCUGGUA | 1352 |
| 242 | GGUUGGUG | AGAA | GGGGCU | ACCAGAGAAACACACGUUGUGGUACAUUACCUGGUA | 1354 |
| 254 | AGUGCAGG | AGAA | GGUUGG | ACCAGAGAAACACACGUUGUGGUACAUUACCUGGUA | 1356 |
| 336 | CAACAGCC | AGAA | GUGACC | ACCAGAGAAACACACGUUGUGGUACAUUACCUGGUA | 1358 |
| 343 | CUGCAACC | AGAA | GCCAGC | ACCAGAGAAACACACGUUGUGGUACAUUACCUGGUA | 1360 |
| 392 | GGUCCCGG | AGAA | GGACAA | ACCAGAGAAACACACGUUGUGGUACAUUACCUGGUA | 1362 |
| 422 | UCUGUGUG | AGAA | GCCUCC | ACCAGAGAAACACACGUUGUGGUACAUUACCUGGUA | 1364 |
| 544 | AUGCUCCA | AGAA | GUGGUC | ACCAGAGAAACACACGUUGUGGUACAUUACCUGGUA | 1366 |
| 586 | UUCAGUCC | AGAA | GCGGUC | ACCAGAGAAACACACGUUGUGGUACAUUACCUGGUA | 1368 |
| 629 | CCACGCUA | AGAA | GAGAGA | ACCAGAGAAACACACGUUGUGGUACAUUACCUGGUA | 1370 |
| 851 | GGGGGAUC | AGAA | GUUCCA | ACCAGAGAAACACACGUUGUGGUACAUUACCUGGUA | 1372 |
| 921 | CCACUCCA | AGAA | GAAAAA | ACCAGAGAAACACACGUUGUGGUACAUUACCUGGUA | 1374 |
| 966 | UCACUGUA | AGAA | GGCUGC | ACCAGAGAAACACACGUUGUGGUACAUUACCUGGUA | 1376 |
| 1139 | UAUAGGAG | AGAA | GGACUC | ACCAGAGAAACACACGUUGUGGUACAUUACCUGGUA | 1378 |

| nt. Position | Substrate | | | Seq. ID No. |
|---|---|---|---|---|
| 25 | CCACUCA | GAU | CCCUCUUA | 1337 |
| 44 | UCCUGCA | GCU | GUCUCUGC | 1339 |
| 47 | UGCAGCU | GUC | UCUGCUGG | 1341 |
| 53 | UGUCUCU | GCU | GGGGGUGG | 1343 |
| 78 | CUCCACG | GUC | CCCAUGCC | 1345 |
| 114 | CACACCU | GAU | UUCUUCCU | 1347 |
| 125 | UCUUCCU | GAC | CGCUACAC | 1349 |
| 164 | CCUCCCU | GCC | CCUCCCAG | 1351 |
| 229 | AACAGCA | GCU | CUGAGCCC | 1353 |
| 242 | AGCCCCG | GCC | CACCAACC | 1355 |

TABLE VII-continued

| Canine IL-2 Receptor g-Chain Hairpin Ribozyme and Substrate Sequence | | | | |
|---|---|---|---|---|
| 254 | CCAACCU | GAC | CCUGCACU | 1357 |
| 336 | GGUCACU | GCU | GGCUGUUG | 1359 |
| 343 | GCUGGCU | GUU | GGUUGCAG | 1361 |
| 392 | UUGUCCA | GCU | CCGGGACC | 1363 |
| 422 | GGAGGCA | GUC | CACACAGA | 1365 |
| 544 | GACCACU | GUU | UGGAGCAU | 1367 |
| 586 | GACCGCA | GCU | GGACUGAA | 1369 |
| 629 | UCUCUCU | GCC | UAGCGUGG | 1371 |
| 851 | UGGAACG | GUC | GAUCCCCC | 1373 |
| 921 | UUUUUCG | GCC | UGGAGUGG | 1375 |
| 966 | GCAGCCA | GAC | UACAGUGA | 1377 |
| 1139 | GAGUCCU | GUC | CUCCUAUA | 1379 |

TABLE VIII

| 2.5 $\mu$mol RNA Synthesis Cycle | | | |
|---|---|---|---|
| Reagent | Equivalents | Amount | Wait Time* |
| Phosphoramidites | 6.5 | 163 $\mu$L | 2.5 |
| S-Ethyl Tetrazole | 23.8 | 238 $\mu$L | 2.5 |
| Acetic Anhydride | 100 | 233 $\mu$L | 5 sec |
| N-Methyl Imidazole | 186 | 233 $\mu$L | 5 sec |
| TCA | 83.2 | 1.73 mL | 21 sec |
| Iodine | 8.0 | 1.18 mL | 45 sec |
| Acetonitrile | NA | 6.67 mL | NA |

*Wait time does not include contact time during delivery.

We claim:

1. An enzymatic nucleic acid molecule which specifically modulates synthesis and/or expression of an IL-2Rγ encoded RNA.

2. The enzymatic nucleic acid molecule of claim 1, wherein said enzymatic nucleic acid molecule specifically cleaves the IL-2Rγ encoded RNA.

3. The enzymatic nucleic acid molecule of claim 1, wherein, the binding arms of said enzymatic nucleic acid molecule comprise sequences complementary to an oligonucleotide having a nucleotide base sequence selected from odd numbered Seq ID Nos from Seq ID No 9-1379.

4. The enzymatic nucleic acid molecule of claim 1, wherein said enzymatic nucleic acid molecule is in a hammerhead motif.

5. The enzymatic nucleic acid molecule of claim 4, wherein said enzymatic nucleic acid molecule specifically cleaves RNA having a sequence selected from the group consisting of: odd numbered Seq ID Nos from Seq ID No 9 to Seq ID No 497; odd numbered Seq ID Nos from Seq ID No 563 to Seq ID No 951; and odd numbered Seq ID Nos from Seq ID No 997 to Seq ID No 1335.

6. The enzymatic nucleic acid molecule of claim 1, wherein said enzymatic nucleic acid molecule is in a hairpin, hepatitis virus, group I intron, group II intron, VS nucleic acid or RNaseP nucleic acid motif.

7. The enzymatic nucleic acid molecule of claim 6, wherein said enzymatic nucleic acid molecule is in a hairpin motif, and wherein said enzymatic nucleic acid molecule specifically cleaves RNA having a sequence selected from the group consisting of: odd numbered Seq ID Nos from Seq ID No 499 to Seq ID No 561; odd numbered Seq ID Nos from Seq ID No 953 to Seq ID No 995; and odd numbered Seq ID Nos from Seq ID No 1337 to Seq ID No 1379.

8. The enzymatic nucleic acid molecule of claim 1, wherein said enzymatic nucleic acid molecule comprises between 12 and 100 bases complementary to the IL-2Rγ encoded RNA.

9. The enzymatic nucleic acid of claim 1, wherein said enzymatic nucleic acid molecule comprises between 14 and 24 bases complementary to the IL-2Rγ encoded RNA.

10. The enzymatic nucleic acid molecule of claim 1, consisting essentially of a nucleotide sequence selected from even numbered Seq ID Nos from Seq ID No 8 to Seq ID No 1378.

11. A mammalian cell including an enzymatic nucleic acid molecule of claim 1.

12. The mammalian cell of claim 11, wherein said mammalian cell is a human cell.

13. An expression vector comprising nucleic acid sequence encoding the enzymatic nucleic acid molecule of claim 1, in a manner which allows expression and/or delivery of that enzymatic RNA molecule within a mammalian cell.

14. A mammalian cell including the expression vector of claim 3.

15. The mammalian cell of claim 14, wherein said mammalian cell is a human cell.

* * * * *

UNITED STATES PATENT AND TRADEMARK OFFICE
CERTIFICATE OF CORRECTION

PATENT NO. : 5,807,743

DATED : September 15, 1998

INVENTOR(S) : Dan T. Stinchcomb et al.

It is certified that error appears in the above-indentified patent and that said Letters Patent is hereby corrected as shown below:

Column 551, Line 62: delete "hepatitis virus" and insert --hepatitis delta virus--

Column 552, Line 63: delete "claim 3" and insert --claim 13--

Signed and Sealed this

Sixteenth Day of November, 1999

Attest:

Q. TODD DICKINSON

Attesting Officer     Acting Commissioner of Patents and Trademarks

SEQUENCE LISTING ( 1 ) GENERAL INFORMATION:

( i i i ) NUMBER OF SEQUENCES: 1379

( 2 ) INFORMATION FOR SEQ ID NO: 1:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.
        The letter "H"stands for C, A or U.

( x i ) SEQUENCE DESCRIPTION: SEQ ID NO: 1:

NNNNUHNNNN N          1 1

( 2 ) INFORMATION FOR SEQ ID NO: 2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.

( x i ) SEQUENCE DESCRIPTION: SEQ ID NO: 2:

NNNNNCUGAN GAGNNNNNNC GAAANNNN 28

(2) INFORMATION FOR SEQ ID NO: 3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ix) FEATURE:
        (D) OTHER INFORMATION: The letter "N"stands for any base.
        The leter "Y"is stands for U or C.
        The letter "H"stands for A, U or C.

(xi) SEQUENCE DESCRIPTION: SEQ ID NO: 3:

NNNNNNNYNG HYNNN 15

(2) INFORMATION FOR SEQ ID NO: 4:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ix) FEATURE:
        (D) OTHER INFORMATION: The letter "N"stands for any base.
        The letter "H"stands for A, U or C.

(xi) SEQUENCE DESCRIPTION: SEQ ID NO: 4:

NNNNGAAGNN NNNNNNNNA AAHANNNNN NACAUUACNN NNNNNNN 47

(2) INFORMATION FOR SEQ ID NO: 5:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ix) FEATURE:
        (D) OTHER INFORMATION: The letter "N"stands for any base.

(xi) SEQUENCE DESCRIPTION: SEQ ID NO: 5:

NNNNNNNNN 9

(2) INFORMATION FOR SEQ ID NO: 6:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ix) FEATURE:
        (D) OTHER INFORMATION: The letter "N"stands for any base.

(xi) SEQUENCE DESCRIPTION: SEQ ID NO: 6:

CUCCACCUCC UCGCGGUNNN NNNNGGGCUA CUUCGGUAGG CUAAGGGAG 49

(2) INFORMATION FOR SEQ ID NO: 7:

(i) SEQUENCE CHARACTERISTICS:
        (A) LENGTH: 176 base pairs
        (B) TYPE: nucleic acid
        (C) STRANDEDNESS: single
        (D) TOPOLOGY: linear (xi) SEQUENCE DESCRIPTION: SEQ ID NO: 7:

GGGAAAGCUU GCGAAGGGCG UCGUCGCCCC GAGCGGUAGU AAGCAGGGAA CUCACCUCCA 60

AUUUCAGUAC UGAAAUUGUC GUAGCAGUUG ACUACUGUUA UGUGAUUGGU AGAGGCUAAG 120

UGACGGUAUU GGCGUAAGUC AGUAUUGCAG CACAGCACAA GCCCGCUUGC GAGAAU 176

( 2 ) INFORMATION FOR SEQ ID NO: 8:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 8:

AUGGCUUCCU GAUGANGAAA CAUGGCG 27

( 2 ) INFORMATION FOR SEQ ID NO: 9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 9:

CGCCAUGUUG AAGCCAU 17

( 2 ) INFORMATION FOR SEQ ID NO: 10:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 10:

AUGGUAAUCU GAUGANGAAA UGGCUUC 27

( 2 ) INFORMATION FOR SEQ ID NO: 11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 11:

GAAGCCAUCA UUACCAU 17

( 2 ) INFORMATION FOR SEQ ID NO: 12:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 12:

UGAAUGGUCU GAUGANGAAA UGAUGGC 27

( 2 ) INFORMATION FOR SEQ ID NO: 13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 13:

GCCAUCAUUA CCAUUCA 17

( 2 ) INFORMATION FOR SEQ ID NO: 14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 14:

GUGAAUGGCU GAUGANGAAA AUGAUGG 27

( 2 ) INFORMATION FOR SEQ ID NO: 15:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 15:

CCAUCAUUAC CAUUCAC 17

( 2 ) INFORMATION FOR SEQ ID NO: 16:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 16:

GGGAUGUGCU GAUGANGAAA UGGUAAU 27

( 2 ) INFORMATION FOR SEQ ID NO: 17:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 17:

AUUACCAUUC ACAUCCC 17

( 2 ) INFORMATION FOR SEQ ID NO: 18:

( i ) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 18:

AGGGAUGUCU GAUGANGAAA AUGGUAA 27

(2) INFORMATION FOR SEQ ID NO: 19:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 19:

UUACCAUUCA CAUCCCU 17

(2) INFORMATION FOR SEQ ID NO: 20:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 20:

AUAAGAGGCU GAUGANGAAA UGUGAAU 27

(2) INFORMATION FOR SEQ ID NO: 21:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 21:

AUUCACAUCC CUCUUAU 17

(2) INFORMATION FOR SEQ ID NO: 22:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 22:

AGGAAUAACU GAUGANGAAA GGGAUGU 27

(2) INFORMATION FOR SEQ ID NO: 23:

(i) SEQUENCE CHARACTERISTICS:
(A) LENGTH: 17 base pairs
(B) TYPE: nucleic acid
(C) STRANDEDNESS: single ( D ) TOPOLOGY: linear ( x i ) SEQUENCE DESCRIPTION: SEQ ID NO: 23:

ACAUCCCUCU UAUUCCU 17

( 2 ) INFORMATION FOR SEQ ID NO: 24:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 24:

GCAGGAAUCU GAUGANGAAA GAGGGAU 27

( 2 ) INFORMATION FOR SEQ ID NO: 25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 25:

AUCCCUCUUA UUCCUGC 17

( 2 ) INFORMATION FOR SEQ ID NO: 26:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 26:

UGCAGGAACU GAUGANGAAA AGAGGGA 27

( 2 ) INFORMATION FOR SEQ ID NO: 27:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 27:

UCCCUCUUAU UCCUGCA 17

( 2 ) INFORMATION FOR SEQ ID NO: 28:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 28:

GCUGCAGGCU GAUGANGAAA UAAGAGG 27

(2) INFORMATION FOR SEQ ID NO: 29:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 29:

CCUCUUAUUC CUGCAGC 17

(2) INFORMATION FOR SEQ ID NO: 30:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 30:

AGCUGCAGCU GAUGANGAAA AUAAGAG 27

(2) INFORMATION FOR SEQ ID NO: 31:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 31:

CUCUUAUUCC UGCAGCU 17

(2) INFORMATION FOR SEQ ID NO: 32:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 32:

GGCGUCAGCU GAUGANGAAA UUGUCGU 27

(2) INFORMATION FOR SEQ ID NO: 33:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 33:

ACGACAAUUC UGACGCC 17

(2) INFORMATION FOR SEQ ID NO: 34:

(i) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 34:

GGGCGUCACU GAUGANGAAA AUUGUCG  27

(2) INFORMATION FOR SEQ ID NO: 35:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 35:

CGACAAUUCU GACGCCC  17

(2) INFORMATION FOR SEQ ID NO: 36:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 36:

CAGGAAGACU GAUGANGAAA UCAGCUG  27

(2) INFORMATION FOR SEQ ID NO: 37:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 37:

CAGCUGAUUU CUUCCUG  17

(2) INFORMATION FOR SEQ ID NO: 38:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 38:

UCAGGAAGCU GAUGANGAAA AUCAGCU  27

(2) INFORMATION FOR SEQ ID NO: 39:

(i) SEQUENCE CHARACTERISTICS:
(A) LENGTH: 17 base pairs
(B) TYPE: nucleic acid
(C) STRANDEDNESS: single (D) TOPOLOGY: linear (x i) SEQUENCE DESCRIPTION: SEQ ID NO: 39:

AGCUGAUUUC UUCCUGA     17

(2) INFORMATION FOR SEQ ID NO: 40:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i x) FEATURE:
        (D) OTHER INFORMATION: The letter "N"stands for the stem II region of a HH ribozyme.

(x i) SEQUENCE DESCRIPTION: SEQ ID NO: 40:

GUCAGGAACU GAUGANGAAA AAUCAGC     27

(2) INFORMATION FOR SEQ ID NO: 41:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 41:

GCUGAUUUCU UCCUGAC     17

(2) INFORMATION FOR SEQ ID NO: 42:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i x) FEATURE:
        (D) OTHER INFORMATION: The letter "N"stands for the stem II region of a HH ribozyme.

(x i) SEQUENCE DESCRIPTION: SEQ ID NO: 42:

UGGUCAGGCU GAUGANGAAA GAAAUCA     27

(2) INFORMATION FOR SEQ ID NO: 43:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 43:

UGAUUUCUUC CUGACCA     17

(2) INFORMATION FOR SEQ ID NO: 44:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i x) FEATURE:
        (D) OTHER INFORMATION: The letter "N"stands for the stem II region of a HH ribozyme.

(x i) SEQUENCE DESCRIPTION: SEQ ID NO: 44:

GUGGUCAGCU GAUGANGAAA AGAAAUC 27

(2) INFORMATION FOR SEQ ID NO: 45:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 45:

GAUUUCUUCC UGACCAC 17

(2) INFORMATION FOR SEQ ID NO: 46:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N"stands for the stem II
            region of a HH ribozyme.

(xi) SEQUENCE DESCRIPTION: SEQ ID NO: 46:

AGUGGGCACU GAUGANGAAA GUGGUCA 27

(2) INFORMATION FOR SEQ ID NO: 47:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 47:

UGACCACUAU GCCCACU 17

(2) INFORMATION FOR SEQ ID NO: 48:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N"stands for the stem II
            region of a HH ribozyme.

(xi) SEQUENCE DESCRIPTION: SEQ ID NO: 48:

CACUGAGGCU GAUGANGAAA GUCAGUG 27

(2) INFORMATION FOR SEQ ID NO: 49:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 49:

CACUGACUCC CUCAGUG 17

(2) INFORMATION FOR SEQ ID NO: 50:

(i) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 50:

GAAACACUCU GAUGANGAAA GGGAGUC     27

(2) INFORMATION FOR SEQ ID NO: 51:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 51:

GACUCCCUCA GUGUUUC     17

(2) INFORMATION FOR SEQ ID NO: 52:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 52:

AGAGUGGACU GAUGANGAAA CACUGAG     27

(2) INFORMATION FOR SEQ ID NO: 53:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 53:

CUCAGUGUUU CCACUCU     17

(2) INFORMATION FOR SEQ ID NO: 54:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 54:

CAGAGUGGCU GAUGANGAAA ACACUGA     27

(2) INFORMATION FOR SEQ ID NO: 55:

(i) SEQUENCE CHARACTERISTICS:
(A) LENGTH: 17 base pairs
(B) TYPE: nucleic acid
(C) STRANDEDNESS: single (D) TOPOLOGY: linear (xi) SEQUENCE DESCRIPTION: SEQ ID NO: 55:

UCAGUGUUUC CACUCUG                    17

(2) INFORMATION FOR SEQ ID NO: 56:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II region of a HH ribozyme.

(xi) SEQUENCE DESCRIPTION: SEQ ID NO: 56:

GCAGAGUGCU GAUGANGAAA AACACUG         27

(2) INFORMATION FOR SEQ ID NO: 57:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 57:

CAGUGUUUCC ACUCUGC                    17

(2) INFORMATION FOR SEQ ID NO: 58:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II region of a HH ribozyme.

(xi) SEQUENCE DESCRIPTION: SEQ ID NO: 58:

GAGGGGCACU GAUGANGAAA GUGGAAA         27

(2) INFORMATION FOR SEQ ID NO: 59:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 59:

UUUCCACUCU GCCCCUC                    17

(2) INFORMATION FOR SEQ ID NO: 60:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II region of a HH ribozyme.

(xi) SEQUENCE DESCRIPTION: SEQ ID NO: 60:

ACCUCUGGCU GAUGANGAAA GGGGCAG                27

( 2 ) INFORMATION FOR SEQ ID NO: 61:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 61:

CUGCCCCUCC CAGAGGU                17

( 2 ) INFORMATION FOR SEQ ID NO: 62:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 62:

AAACACUGCU GAUGANGAAA CCUCUGG                27

( 2 ) INFORMATION FOR SEQ ID NO: 63:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 63:

CCAGAGGUUC AGUGUUU                17

( 2 ) INFORMATION FOR SEQ ID NO: 64:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 64:

AAAACACUCU GAUGANGAAA ACCUCUG                27

( 2 ) INFORMATION FOR SEQ ID NO: 65:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 65:

CAGAGGUUCA GUGUUUU                17

( 2 ) INFORMATION FOR SEQ ID NO: 66:

( i ) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 66:

GAACACAACU GAUGANGAAA CACUGAA 27

(2) INFORMATION FOR SEQ ID NO: 67:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 67:

UUCAGUGUUU UGUGUUC 17

(2) INFORMATION FOR SEQ ID NO: 68:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 68:

UGAACACACU GAUGANGAAA ACACUGA 27

(2) INFORMATION FOR SEQ ID NO: 69:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 69:

UCAGUGUUUU GUGUUCA 17

(2) INFORMATION FOR SEQ ID NO: 70:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 70:

UUGAACACCU GAUGANGAAA AACACUG 27

(2) INFORMATION FOR SEQ ID NO: 71:

(i) SEQUENCE CHARACTERISTICS:
(A) LENGTH: 17 base pairs
(B) TYPE: nucleic acid
(C) STRANDEDNESS: single (D) TOPOLOGY: linear (xi) SEQUENCE DESCRIPTION: SEQ ID NO: 71:

CAGUGUUUUG UGUUCAA								17

(2) INFORMATION FOR SEQ ID NO: 72:

(i) SEQUENCE CHARACTERISTICS:
  (A) LENGTH: 27 base pairs
  (B) TYPE: nucleic acid
  (C) STRANDEDNESS: single
  (D) TOPOLOGY: linear (ix) FEATURE:
  (D) OTHER INFORMATION: The letter "N" stands for the stem II
   region of a HH ribozyme.

(xi) SEQUENCE DESCRIPTION: SEQ ID NO: 72:

CGACAUUGCU GAUGANGAAA CACAAAA							27

(2) INFORMATION FOR SEQ ID NO: 73:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (xi) SEQUENCE DESCRIPTION: SEQ ID NO: 73:

UUUUGUGUUC AAUGUCG								17

(2) INFORMATION FOR SEQ ID NO: 74:

(i) SEQUENCE CHARACTERISTICS:
  (A) LENGTH: 27 base pairs
  (B) TYPE: nucleic acid
  (C) STRANDEDNESS: single
  (D) TOPOLOGY: linear (ix) FEATURE:
  (D) OTHER INFORMATION: The letter "N" stands for the stem II
   region of a HH ribozyme.

(xi) SEQUENCE DESCRIPTION: SEQ ID NO: 74:

UCGACAUUCU GAUGANGAAA ACACAAA							27

(2) INFORMATION FOR SEQ ID NO: 75:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (xi) SEQUENCE DESCRIPTION: SEQ ID NO: 75:

UUUGUGUUCA AUGUCGA								17

(2) INFORMATION FOR SEQ ID NO: 76:

(i) SEQUENCE CHARACTERISTICS:
  (A) LENGTH: 27 base pairs
  (B) TYPE: nucleic acid
  (C) STRANDEDNESS: single
  (D) TOPOLOGY: linear (ix) FEATURE:
  (D) OTHER INFORMATION: The letter "N" stands for the stem II
   region of a HH ribozyme.

(xi) SEQUENCE DESCRIPTION: SEQ ID NO: 76:

AUGUACUCCU GAUGANGAAA CAUUGAA                                                27

( 2 ) INFORMATION FOR SEQ ID NO: 77:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 77:

UUCAAUGUCG AGUACAU                                                           17

( 2 ) INFORMATION FOR SEQ ID NO: 78:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i x ) FEATURE:
            ( D ) OTHER INFORMATION: The letter "N"stands for the stem II
                region of a HH ribozyme.

( x i ) SEQUENCE DESCRIPTION: SEQ ID NO: 78:

AAUUCAUGCU GAUGANGAAA CUCGACA                                                27

( 2 ) INFORMATION FOR SEQ ID NO: 79:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 79:

UGUCGAGUAC AUGAAUU                                                           17

( 2 ) INFORMATION FOR SEQ ID NO: 80:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i x ) FEATURE:
            ( D ) OTHER INFORMATION: The letter "N"stands for the stem II
                region of a HH ribozyme.

( x i ) SEQUENCE DESCRIPTION: SEQ ID NO: 80:

CCAAGUGCCU GAUGANGAAA UUCAUGU                                                27

( 2 ) INFORMATION FOR SEQ ID NO: 81:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 81:

ACAUGAAUUG CACUUGG                                                           17

( 2 ) INFORMATION FOR SEQ ID NO: 82:

( i ) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N"stands for the stem II region of a HH ribozyme.

(xi) SEQUENCE DESCRIPTION: SEQ ID NO: 82:

GCUGUUCCCU GAUGANGAAA GUGCAAU                27

(2) INFORMATION FOR SEQ ID NO: 83:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 83:

AUUGCACUUG GAACAGC                            17

(2) INFORMATION FOR SEQ ID NO: 84:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N"stands for the stem II region of a HH ribozyme.

(xi) SEQUENCE DESCRIPTION: SEQ ID NO: 84:

GGGGCUCACU GAUGANGAAA GCUGCUG                27

(2) INFORMATION FOR SEQ ID NO: 85:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 85:

CAGCAGCUCU GAGCCCC                            17

(2) INFORMATION FOR SEQ ID NO: 86:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N"stands for the stem II region of a HH ribozyme.

(xi) SEQUENCE DESCRIPTION: SEQ ID NO: 86:

GAGGUUGGCU GAUGANGAAA GGCUGGG                27

(2) INFORMATION FOR SEQ ID NO: 87:

(i) SEQUENCE CHARACTERISTICS:
(A) LENGTH: 17 base pairs
(B) TYPE: nucleic acid
(C) STRANDEDNESS: single (  D  ) TOPOLOGY: linear (  x i  ) SEQUENCE DESCRIPTION: SEQ ID NO: 87:

CCCAGCCUAC CAACCUC 17

(  2  ) INFORMATION FOR SEQ ID NO: 88:

(  i  ) SEQUENCE CHARACTERISTICS:
        (  A  ) LENGTH: 27 base pairs
        (  B  ) TYPE: nucleic acid
        (  C  ) STRANDEDNESS: single
        (  D  ) TOPOLOGY: linear (  i x  ) FEATURE:
        (  D  ) OTHER INFORMATION: The letter "N"stands for the stem II
            region of a HH ribozyme.

(  x i  ) SEQUENCE DESCRIPTION: SEQ ID NO: 88:

UGCAGAGUCU GAUGANGAAA GGUUGGU 27

(  2  ) INFORMATION FOR SEQ ID NO: 89:

(  i  ) SEQUENCE CHARACTERISTICS:
        (  A  ) LENGTH: 17 base pairs
        (  B  ) TYPE: nucleic acid
        (  C  ) STRANDEDNESS: single
        (  D  ) TOPOLOGY: linear (  x i  ) SEQUENCE DESCRIPTION: SEQ ID NO: 89:

ACCAACCUCA CUCUGCA 17

(  2  ) INFORMATION FOR SEQ ID NO: 90:

(  i  ) SEQUENCE CHARACTERISTICS:
        (  A  ) LENGTH: 27 base pairs
        (  B  ) TYPE: nucleic acid
        (  C  ) STRANDEDNESS: single
        (  D  ) TOPOLOGY: linear (  i x  ) FEATURE:
        (  D  ) OTHER INFORMATION: The letter "N"stands for the stem II
            region of a HH ribozyme.

(  x i  ) SEQUENCE DESCRIPTION: SEQ ID NO: 90:

AUAAUGCACU GAUGANGAAA GUGAGGU 27

(  2  ) INFORMATION FOR SEQ ID NO: 91:

(  i  ) SEQUENCE CHARACTERISTICS:
        (  A  ) LENGTH: 17 base pairs
        (  B  ) TYPE: nucleic acid
        (  C  ) STRANDEDNESS: single
        (  D  ) TOPOLOGY: linear (  x i  ) SEQUENCE DESCRIPTION: SEQ ID NO: 91:

ACCUCACUCU GCAUUAU 17

(  2  ) INFORMATION FOR SEQ ID NO: 92:

(  i  ) SEQUENCE CHARACTERISTICS:
        (  A  ) LENGTH: 27 base pairs
        (  B  ) TYPE: nucleic acid
        (  C  ) STRANDEDNESS: single
        (  D  ) TOPOLOGY: linear (  i x  ) FEATURE:
        (  D  ) OTHER INFORMATION: The letter "N"stands for the stem II
            region of a HH ribozyme.

(  x i  ) SEQUENCE DESCRIPTION: SEQ ID NO: 92:

GUACCAAUCU GAUGANGAAA UGCAGAG 27

( 2 ) INFORMATION FOR SEQ ID NO: 93:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 93:

CUCUGCAUUA UUGGUAC 17

( 2 ) INFORMATION FOR SEQ ID NO: 94:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 94:

UGUACCAACU GAUGANGAAA AUGCAGA 27

( 2 ) INFORMATION FOR SEQ ID NO: 95:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 95:

UCUGCAUUAU UGGUACA 17

( 2 ) INFORMATION FOR SEQ ID NO: 96:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 96:

CUUGUACCCU GAUGANGAAA UAAUGCA 27

( 2 ) INFORMATION FOR SEQ ID NO: 97:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 97:

UGCAUUAUUG GUACAAG 17

( 2 ) INFORMATION FOR SEQ ID NO: 98:

( i ) SEQUENCE CHARACTERISTICS:

(A) LENGTH: 27 base pairs
          (B) TYPE: nucleic acid
          (C) STRANDEDNESS: single
          (D) TOPOLOGY: linear (ix) FEATURE:
          (D) OTHER INFORMATION: The letter "N" stands for the stem II
              region of a HH ribozyme.

(xi) SEQUENCE DESCRIPTION: SEQ ID NO: 98:

AGUUCUUGCU GAUGANGAAA CCAAUAA                                    27

(2) INFORMATION FOR SEQ ID NO: 99:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (xi) SEQUENCE DESCRIPTION: SEQ ID NO: 99:

UUAUUGGUAC AAGAACU                                                17

(2) INFORMATION FOR SEQ ID NO: 100:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ix) FEATURE:
          (D) OTHER INFORMATION: The letter "N" stands for the stem II
              region of a HH ribozyme.

(xi) SEQUENCE DESCRIPTION: SEQ ID NO: 100:

CAUUACCCU GAUGANGAAA GUUCUUG                                     27

(2) INFORMATION FOR SEQ ID NO: 101:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (xi) SEQUENCE DESCRIPTION: SEQ ID NO: 101:

CAAGAACUCG GAUAAUG                                                17

(2) INFORMATION FOR SEQ ID NO: 102:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ix) FEATURE:
          (D) OTHER INFORMATION: The letter "N" stands for the stem II
              region of a HH ribozyme.

(xi) SEQUENCE DESCRIPTION: SEQ ID NO: 102:

UUUAUCAUCU GAUGANGAAA UCCGAGU                                    27

(2) INFORMATION FOR SEQ ID NO: 103:

(i) SEQUENCE CHARACTERISTICS:
          (A) LENGTH: 17 base pairs
          (B) TYPE: nucleic acid
          (C) STRANDEDNESS: single ( D ) TOPOLOGY: linear ( x i ) SEQUENCE DESCRIPTION: SEQ ID NO: 103:

ACUCGGAUAA UGAUAAA 17

( 2 ) INFORMATION FOR SEQ ID NO: 104:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 104:

CUGGACUUCU GAUGANGAAA UCAUUAU 27

( 2 ) INFORMATION FOR SEQ ID NO: 105:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 105:

AUAAUGAUAA AGUCCAG 17

( 2 ) INFORMATION FOR SEQ ID NO: 106:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 106:

CACUUCUGCU GAUGANGAAA CUUUAUC 27

( 2 ) INFORMATION FOR SEQ ID NO: 107:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 107:

GAUAAAGUCC AGAAGUG 17

( 2 ) INFORMATION FOR SEQ ID NO: 108:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 108:

AGAAUAGACU GAUGANGAAA GUGGCUG 27

( 2 ) INFORMATION FOR SEQ ID NO: 109:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 109:

CAGCCACUAU CUAUUCU 17

( 2 ) INFORMATION FOR SEQ ID NO: 110:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 110:

AGAGAAUACU GAUGANGAAA UAGUGGC 27

( 2 ) INFORMATION FOR SEQ ID NO: 111:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 111:

GCCACUAUCU AUUCUCU 17

( 2 ) INFORMATION FOR SEQ ID NO: 112:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 112:

UCAGAGAACU GAUGANGAAA GAUAGUG 27

( 2 ) INFORMATION FOR SEQ ID NO: 113:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 113:

CACUAUCUAU UCUCUGA 17

( 2 ) INFORMATION FOR SEQ ID NO: 114:

( i ) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 114:

CUUCAGAGCU GAUGANGAAA UAGAUAG 27

(2) INFORMATION FOR SEQ ID NO: 115:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 115:

CUAUCUAUUC UCUGAAG 17

(2) INFORMATION FOR SEQ ID NO: 116:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 116:

UCUUCAGACU GAUGANGAAA AUAGAUA 27

(2) INFORMATION FOR SEQ ID NO: 117:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 117:

UAUCUAUUCU CUGAAGA 17

(2) INFORMATION FOR SEQ ID NO: 118:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 118:

UUUCUUCACU GAUGANGAAA GAAUAGA 27

(2) INFORMATION FOR SEQ ID NO: 119:

(i) SEQUENCE CHARACTERISTICS:
(A) LENGTH: 17 base pairs
(B) TYPE: nucleic acid
(C) STRANDEDNESS: single (D) TOPOLOGY: linear (x i) SEQUENCE DESCRIPTION: SEQ ID NO: 119:

UCUAUUCUCU GAAGAAA  17

(2) INFORMATION FOR SEQ ID NO: 120:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i x) FEATURE:
        (D) OTHER INFORMATION: The letter "N"stands for the stem II region of a HH ribozyme.

(x i) SEQUENCE DESCRIPTION: SEQ ID NO: 120:

CCAGAAGUCU GAUGANGAAA UUUCUUC  27

(2) INFORMATION FOR SEQ ID NO: 121:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 121:

GAAGAAAUCA CUUCUGG  17

(2) INFORMATION FOR SEQ ID NO: 122:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i x) FEATURE:
        (D) OTHER INFORMATION: The letter "N"stands for the stem II region of a HH ribozyme.

(x i) SEQUENCE DESCRIPTION: SEQ ID NO: 122:

ACAGCCAGCU GAUGANGAAA GUGAUUU  27

(2) INFORMATION FOR SEQ ID NO: 123:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 123:

AAAUCACUUC UGGCUGU  17

(2) INFORMATION FOR SEQ ID NO: 124:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i x) FEATURE:
        (D) OTHER INFORMATION: The letter "N"stands for the stem II region of a HH ribozyme.

(x i) SEQUENCE DESCRIPTION: SEQ ID NO: 124:

GACAGCCACU GAUGANGAAA AGUGAUU 27

( 2 ) INFORMATION FOR SEQ ID NO: 125:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 125:

AAUCACUUCU GGCUGUC 17

( 2 ) INFORMATION FOR SEQ ID NO: 126:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 126:

UUGCAACUCU GAUGANGAAA CAGCCAG 27

( 2 ) INFORMATION FOR SEQ ID NO: 127:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 127:

CUGGCUGUCA GUUGCAA 17

( 2 ) INFORMATION FOR SEQ ID NO: 128:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 128:

UUUUUUGCCU GAUGANGAAA CUGACAG 27

( 2 ) INFORMATION FOR SEQ ID NO: 129:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 129:

CUGUCAGUUG CAAAAAA 17

( 2 ) INFORMATION FOR SEQ ID NO: 130:

( i ) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II
region of a HH ribozyme.

(xi) SEQUENCE DESCRIPTION: SEQ ID NO: 130:

UAGAGGUGCU GAUGANGAAA UCUCCUU                27

(2) INFORMATION FOR SEQ ID NO: 131:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 131:

AAGGAGAUCC ACCUCUA                            17

(2) INFORMATION FOR SEQ ID NO: 132:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II
region of a HH ribozyme.

(xi) SEQUENCE DESCRIPTION: SEQ ID NO: 132:

GUUUGGUACU GAUGANGAAA GGUGGAU                27

(2) INFORMATION FOR SEQ ID NO: 133:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 133:

AUCCACCUCU ACCAAAC                            17

(2) INFORMATION FOR SEQ ID NO: 134:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II
region of a HH ribozyme.

(xi) SEQUENCE DESCRIPTION: SEQ ID NO: 134:

AUGUUUGGCU GAUGANGAAA GAGGUGG                27

(2) INFORMATION FOR SEQ ID NO: 135:

(i) SEQUENCE CHARACTERISTICS:
(A) LENGTH: 17 base pairs
(B) TYPE: nucleic acid
(C) STRANDEDNESS: single ( D ) TOPOLOGY: linear ( x i ) SEQUENCE DESCRIPTION: SEQ ID NO: 135:

CCACCUCUAC CAAACAU                                                                                                    17

( 2 ) INFORMATION FOR SEQ ID NO: 136:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 136:

GAACAACACU GAUGANGAAA UGUUUGG                                                                                         27

( 2 ) INFORMATION FOR SEQ ID NO: 137:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 137:

CCAAACAUUU GUUGUUC                                                                                                    17

( 2 ) INFORMATION FOR SEQ ID NO: 138:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 138:

UGAACAACCU GAUGANGAAA AUGUUUG                                                                                         27

( 2 ) INFORMATION FOR SEQ ID NO: 139:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 139:

CAAACAUUUG UUGUUCA                                                                                                    17

( 2 ) INFORMATION FOR SEQ ID NO: 140:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 140:

AGCUGAACCU GAUGANGAAA CAAAUGU 27

( 2 ) INFORMATION FOR SEQ ID NO: 141:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 141:

ACAUUUGUUG UUCAGCU 17

( 2 ) INFORMATION FOR SEQ ID NO: 142:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II
          region of a HH ribozyme.

( x i ) SEQUENCE DESCRIPTION: SEQ ID NO: 142:

UGGAGCUGCU GAUGANGAAA CAACAAA 27

( 2 ) INFORMATION FOR SEQ ID NO: 143:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 143:

UUUGUUGUUC AGCUCCA 17

( 2 ) INFORMATION FOR SEQ ID NO: 144:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II
          region of a HH ribozyme.

( x i ) SEQUENCE DESCRIPTION: SEQ ID NO: 144:

CUGGAGCUCU GAUGANGAAA ACAACAA 27

( 2 ) INFORMATION FOR SEQ ID NO: 145:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 145:

UUGUUGUUCA GCUCCAG 17

( 2 ) INFORMATION FOR SEQ ID NO: 146:

( i ) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 146:

GGGUCCUGCU GAUGANGAAA GCUGAAC 27

(2) INFORMATION FOR SEQ ID NO: 147:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 147:

GUUCAGCUCC AGGACCC 17

(2) INFORMATION FOR SEQ ID NO: 148:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 148:

UGCAGUUUCU GAUGANGAAA GCAUCUG 27

(2) INFORMATION FOR SEQ ID NO: 149:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 149:

CAGAUGCUAA AACUGCA 17

(2) INFORMATION FOR SEQ ID NO: 150:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 150:

GAUCACCACU GAUGANGAAA UUCUGCA 27

(2) INFORMATION FOR SEQ ID NO: 151:

(i) SEQUENCE CHARACTERISTICS:
(A) LENGTH: 17 base pairs
(B) TYPE: nucleic acid
(C) STRANDEDNESS: single ( D ) TOPOLOGY: linear ( x i ) SEQUENCE DESCRIPTION: SEQ ID NO: 151:

UGCAGAAUCU GGUGAUC                                                      17

( 2 ) INFORMATION FOR SEQ ID NO: 152:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 152:

GCCCAGGGCU GAUGANGAAA UCACCAG                                           27

( 2 ) INFORMATION FOR SEQ ID NO: 153:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 153:

CUGGUGAUCC CCUGGGC                                                      17

( 2 ) INFORMATION FOR SEQ ID NO: 154:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 154:

GUUCUCUGCU GAUGANGAAA GCCCAGG                                           27

( 2 ) INFORMATION FOR SEQ ID NO: 155:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 155:

CCUGGGCUCC AGAGAAC                                                      17

( 2 ) INFORMATION FOR SEQ ID NO: 156:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 156:

UGAAGUGUCU GAUGANGAAA GGUUCUC 27

( 2 ) INFORMATION FOR SEQ ID NO: 157:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 157:

GAGAACCUAA CACUUCA 17

( 2 ) INFORMATION FOR SEQ ID NO: 158:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 158:

AGUUUGUGCU GAUGANGAAA GUGUUAG 27

( 2 ) INFORMATION FOR SEQ ID NO: 159:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 159:

CUAACACUUC ACAAACU 17

( 2 ) INFORMATION FOR SEQ ID NO: 160:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 160:

CAGUUUGUCU GAUGANGAAA AGUGUUA 27

( 2 ) INFORMATION FOR SEQ ID NO: 161:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 161:

UAACACUUCA CAAACUG 17

( 2 ) INFORMATION FOR SEQ ID NO: 162:

( i ) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 162:

CUAGCUGGCU GAUGANGAAA UUCACUC 27

(2) INFORMATION FOR SEQ ID NO: 163:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 163:

GAGUGAAUCC CAGCUAG 17

(2) INFORMATION FOR SEQ ID NO: 164:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 164:

UUCAGUUCCU GAUGANGAAA GCUGGGA 27

(2) INFORMATION FOR SEQ ID NO: 165:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 165:

UCCCAGCUAG AACUGAA 17

(2) INFORMATION FOR SEQ ID NO: 166:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 166:

GGUUCAAGCU GAUGANGAAA UCUGUUG 27

(2) INFORMATION FOR SEQ ID NO: 167:

(i) SEQUENCE CHARACTERISTICS:
(A) LENGTH: 17 base pairs
(B) TYPE: nucleic acid
(C) STRANDEDNESS: single ( D ) TOPOLOGY: linear ( x i ) SEQUENCE DESCRIPTION: SEQ ID NO: 167:

CAACAGAUUC UUGAACC                                                                                      17

( 2 ) INFORMATION FOR SEQ ID NO: 168:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i x ) FEATURE:
                ( D ) OTHER INFORMATION: The letter "N" stands for the stem II
                        region of a HH ribozyme.

( x i ) SEQUENCE DESCRIPTION: SEQ ID NO: 168:

UGGUUCAACU GAUGANGAAA AUCUGUU                                                                           27

( 2 ) INFORMATION FOR SEQ ID NO: 169:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 169:

AACAGAUUCU UGAACCA                                                                                      17

( 2 ) INFORMATION FOR SEQ ID NO: 170:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i x ) FEATURE:
                ( D ) OTHER INFORMATION: The letter "N" stands for the stem II
                        region of a HH ribozyme.

( x i ) SEQUENCE DESCRIPTION: SEQ ID NO: 170:

AGUGGUUCCU GAUGANGAAA GAAUCUG                                                                           27

( 2 ) INFORMATION FOR SEQ ID NO: 171:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 171:

CAGAUUCUUG AACCACU                                                                                      17

( 2 ) INFORMATION FOR SEQ ID NO: 172:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i x ) FEATURE:
                ( D ) OTHER INFORMATION: The letter "N" stands for the stem II
                        region of a HH ribozyme.

( x i ) SEQUENCE DESCRIPTION: SEQ ID NO: 172:

GUGCUCCACU GAUGANGAAA CAGUGGU 27

( 2 ) INFORMATION FOR SEQ ID NO: 173:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 173:

ACCACUGUUU GGAGCAC 17

( 2 ) INFORMATION FOR SEQ ID NO: 174:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 174:

AGUGCUCCCU GAUGANGAAA ACAGUGG 27

( 2 ) INFORMATION FOR SEQ ID NO: 175:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 175:

CCACUGUUUG GAGCACU 17

( 2 ) INFORMATION FOR SEQ ID NO: 176:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 176:

ACUGCACCCU GAUGANGAAA GUGCUCC 27

( 2 ) INFORMATION FOR SEQ ID NO: 177:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 177:

GGAGCACUUG GUGCAGU 17

( 2 ) INFORMATION FOR SEQ ID NO: 178:

( i ) SEQUENCE CHARACTERISTICS:

(A) LENGTH: 27 base pairs
                (B) TYPE: nucleic acid
                (C) STRANDEDNESS: single
                (D) TOPOLOGY: linear (ix) FEATURE:
                (D) OTHER INFORMATION: The letter "N" stands for the stem II
                        region of a HH ribozyme.

(xi) SEQUENCE DESCRIPTION: SEQ ID NO: 178:

CAGUCCGGCU GAUGANGAAA CUGCACC                                                                27

(2) INFORMATION FOR SEQ ID NO: 179:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO: 179:

GGUGCAGUAC CGGACUG                                                                           17

(2) INFORMATION FOR SEQ ID NO: 180:

(i) SEQUENCE CHARACTERISTICS:
                (A) LENGTH: 27 base pairs
                (B) TYPE: nucleic acid
                (C) STRANDEDNESS: single
                (D) TOPOLOGY: linear (ix) FEATURE:
                (D) OTHER INFORMATION: The letter "N" stands for the stem II
                        region of a HH ribozyme.

(xi) SEQUENCE DESCRIPTION: SEQ ID NO: 180:

AAUCCACUCU GAUGANGAAA UUGUUCA                                                                27

(2) INFORMATION FOR SEQ ID NO: 181:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO: 181:

UGAACAAUCA GUGGAUU                                                                           17

(2) INFORMATION FOR SEQ ID NO: 182:

(i) SEQUENCE CHARACTERISTICS:
                (A) LENGTH: 27 base pairs
                (B) TYPE: nucleic acid
                (C) STRANDEDNESS: single
                (D) TOPOLOGY: linear (ix) FEATURE:
                (D) OTHER INFORMATION: The letter "N" stands for the stem II
                        region of a HH ribozyme.

(xi) SEQUENCE DESCRIPTION: SEQ ID NO: 182:

AUGUCUAUCU GAUGANGAAA UCCACUG                                                                27

(2) INFORMATION FOR SEQ ID NO: 183:

(i) SEQUENCE CHARACTERISTICS:
                (A) LENGTH: 17 base pairs
                (B) TYPE: nucleic acid
                (C) STRANDEDNESS: single (D) TOPOLOGY: linear (xi) SEQUENCE DESCRIPTION: SEQ ID NO: 183:

CAGUGGAUUA UAGACAU 17

(2) INFORMATION FOR SEQ ID NO: 184:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II region of a HH ribozyme.

(xi) SEQUENCE DESCRIPTION: SEQ ID NO: 184:

UAUGUCACU GAUGANGAAA AUCCACU 27

(2) INFORMATION FOR SEQ ID NO: 185:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 185:

AGUGGAUUAU AGACAUA 17

(2) INFORMATION FOR SEQ ID NO: 186:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II region of a HH ribozyme.

(xi) SEQUENCE DESCRIPTION: SEQ ID NO: 186:

CUUAUGUCCU GAUGANGAAA UAAUCCA 27

(2) INFORMATION FOR SEQ ID NO: 187:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 187:

UGGAUUAUAG ACAUAAG 17

(2) INFORMATION FOR SEQ ID NO: 188:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II region of a HH ribozyme.

(xi) SEQUENCE DESCRIPTION: SEQ ID NO: 188:

GGAGAACUCU GAUGANGAAA UGUCUAU                                    27

(2) INFORMATION FOR SEQ ID NO: 189:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 189:

AUAGACAUAA GUUCUCC                                               17

(2) INFORMATION FOR SEQ ID NO: 190:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
        region of a HH ribozyme.

(xi) SEQUENCE DESCRIPTION: SEQ ID NO: 190:

GCAAGGAGCU GAUGANGAAA CUUAUGU                                    27

(2) INFORMATION FOR SEQ ID NO: 191:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 191:

ACAUAAGUUC UCCUUGC                                               17

(2) INFORMATION FOR SEQ ID NO: 192:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
        region of a HH ribozyme.

(xi) SEQUENCE DESCRIPTION: SEQ ID NO: 192:

GGCAAGGACU GAUGANGAAA ACUUAUG                                    27

(2) INFORMATION FOR SEQ ID NO: 193:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 193:

CAUAAGUUCU CCUUGCC                                               17

(2) INFORMATION FOR SEQ ID NO: 194:

(i) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 194:

UAGGCAAGCU GAUGANGAAA GAACUUA 27

(2) INFORMATION FOR SEQ ID NO: 195:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 195:

UAAGUUCUCC UUGCCUA 17

(2) INFORMATION FOR SEQ ID NO: 196:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 196:

CACUAGGCCU GAUGANGAAA GGAGAAC 27

(2) INFORMATION FOR SEQ ID NO: 197:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 197:

GUUCUCCUUG CCUAGUG 17

(2) INFORMATION FOR SEQ ID NO: 198:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 198:

AUCCACACCU GAUGANGAAA GGCAAGG 27

(2) INFORMATION FOR SEQ ID NO: 199:

(i) SEQUENCE CHARACTERISTICS:
        (A) LENGTH: 17 base pairs
        (B) TYPE: nucleic acid
        (C) STRANDEDNESS: single ( D ) TOPOLOGY: linear ( x i ) SEQUENCE DESCRIPTION: SEQ ID NO: 199:

CCUUGCCUAG UGUGGAU 17

( 2 ) INFORMATION FOR SEQ ID NO: 200:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 200:

GAAACGUGCU GAUGANGAAA GCGUUUC 27

( 2 ) INFORMATION FOR SEQ ID NO: 201:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 201:

GAAACGCUAC ACGUUUC 17

( 2 ) INFORMATION FOR SEQ ID NO: 202:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 202:

GAACACGACU GAUGANGAAA CGUGUAG 27

( 2 ) INFORMATION FOR SEQ ID NO: 203:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 203:

CUACACGUUU CGUGUUC 17

( 2 ) INFORMATION FOR SEQ ID NO: 204:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 204:

CGAACACGCU GAUGANGAAA ACGUGUA                    27

( 2 ) INFORMATION FOR SEQ ID NO: 205:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 205:

UACACGUUUC GUGUUCG                               17

( 2 ) INFORMATION FOR SEQ ID NO: 206:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 206:

CCGAACACCU GAUGANGAAA AACGUGU                    27

( 2 ) INFORMATION FOR SEQ ID NO: 207:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 207:

ACACGUUUCG UGUUCGG                               17

( 2 ) INFORMATION FOR SEQ ID NO: 208:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 208:

CGGCUCCGCU GAUGANGAAA CACGAAA                    27

( 2 ) INFORMATION FOR SEQ ID NO: 209:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 209:

UUUCGUGUUC GGAGCCG                               17

( 2 ) INFORMATION FOR SEQ ID NO: 210:

( i ) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 210:

GCGGCUCCCU GAUGANGAAA ACACGAA 27

(2) INFORMATION FOR SEQ ID NO: 211:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 211:

UUCGUGUUCG GAGCCGC 17

(2) INFORMATION FOR SEQ ID NO: 212:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 212:

GUGGGUUACU GAUGANGAAA GCGGCUC 27

(2) INFORMATION FOR SEQ ID NO: 213:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 213:

GAGCCGCUUU AACCCAC 17

(2) INFORMATION FOR SEQ ID NO: 214:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 214:

AGUGGGUUCU GAUGANGAAA AGCGGCU 27

(2) INFORMATION FOR SEQ ID NO: 215:

(i) SEQUENCE CHARACTERISTICS:
(A) LENGTH: 17 base pairs
(B) TYPE: nucleic acid
(C) STRANDEDNESS: single ( D ) TOPOLOGY: linear ( x i ) SEQUENCE DESCRIPTION: SEQ ID NO: 215:

AGCCGCUUUA ACCCACU 17

( 2 ) INFORMATION FOR SEQ ID NO: 216:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 216:

GAGUGGGUCU GAUGANGAAA AAGCGGC 27

( 2 ) INFORMATION FOR SEQ ID NO: 217:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 217:

GCCGCUUUAA CCCACUC 17

( 2 ) INFORMATION FOR SEQ ID NO: 218:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 218:

CUUCCACACU GAUGANGAAA GUGGGUU 27

( 2 ) INFORMATION FOR SEQ ID NO: 219:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 219:

AACCCACUCU GUGGAAG 17

( 2 ) INFORMATION FOR SEQ ID NO: 220:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 220:

CCAAUGCUCU GAUGANGAAA GCACUUC                                                27

( 2 ) INFORMATION FOR SEQ ID NO: 221:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 221:

GAAGUGCUCA GCAUUGG                                                           17

( 2 ) INFORMATION FOR SEQ ID NO: 222:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 222:

UUCACUCCCU GAUGANGAAA UGCUGAG                                                27

( 2 ) INFORMATION FOR SEQ ID NO: 223:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 223:

CUCAGCAUUG GAGUGAA                                                           17

( 2 ) INFORMATION FOR SEQ ID NO: 224:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 224:

CCCCAGUGCU GAUGANGAAA UUGGGUG                                                27

( 2 ) INFORMATION FOR SEQ ID NO: 225:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 225:

CACCCAAUCC ACUGGGG                                                           17

( 2 ) INFORMATION FOR SEQ ID NO: 226:

( i ) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 226:

UUUUGAAGCU GAUGANGAAA UUGCUCC    27

(2) INFORMATION FOR SEQ ID NO: 227:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 227:

GGAGCAAUAC UUCAAAA    17

(2) INFORMATION FOR SEQ ID NO: 228:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 228:

CUCUUUUGCU GAUGANGAAA GUAUUGC    27

(2) INFORMATION FOR SEQ ID NO: 229:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 229:

GCAAUACUUC AAAAGAG    17

(2) INFORMATION FOR SEQ ID NO: 230:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 230:

UCUCUUUUCU GAUGANGAAA AGUAUUG    27

(2) INFORMATION FOR SEQ ID NO: 231:

(i) SEQUENCE CHARACTERISTICS:
(A) LENGTH: 17 base pairs
(B) TYPE: nucleic acid
(C) STRANDEDNESS: single (D) TOPOLOGY: linear (xi) SEQUENCE DESCRIPTION: SEQ ID NO: 231:

CAAUACUUCA AAAGAGA 17

(2) INFORMATION FOR SEQ ID NO: 232:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N"stands for the stem II
        region of a HH ribozyme.

(xi) SEQUENCE DESCRIPTION: SEQ ID NO: 232:

CAGGAAAGCU GAUGANGAAA UUCUCUU 27

(2) INFORMATION FOR SEQ ID NO: 233:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 233:

AAGAGAAUCC UUUCCUG 17

(2) INFORMATION FOR SEQ ID NO: 234:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N"stands for the stem II
        region of a HH ribozyme.

(xi) SEQUENCE DESCRIPTION: SEQ ID NO: 234:

AAACAGGACU GAUGANGAAA GGAUUCU 27

(2) INFORMATION FOR SEQ ID NO: 235:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 235:

AGAAUCCUUU CCUGUUU 17

(2) INFORMATION FOR SEQ ID NO: 236:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N"stands for the stem II
        region of a HH ribozyme.

(xi) SEQUENCE DESCRIPTION: SEQ ID NO: 236:

CAAACAGGCU GAUGANGAAA AGGAUUC                27

(2) INFORMATION FOR SEQ ID NO: 237:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 237:

GAAUCCUUUC CUGUUUG                17

(2) INFORMATION FOR SEQ ID NO: 238:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 238:

GCAAACAGCU GAUGANGAAA AAGGAUU                27

(2) INFORMATION FOR SEQ ID NO: 239:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 239:

AAUCCUUUCC UGUUUGC                17

(2) INFORMATION FOR SEQ ID NO: 240:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 240:

CCAAUGCACU GAUGANGAAA CAGGAAA                27

(2) INFORMATION FOR SEQ ID NO: 241:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 241:

UUUCCUGUUU GCAUUGG                17

(2) INFORMATION FOR SEQ ID NO: 242:

(i) SEQUENCE CHARACTERISTICS:

(A) LENGTH: 27 base pairs
                (B) TYPE: nucleic acid
                (C) STRANDEDNESS: single
                (D) TOPOLOGY: linear (ix) FEATURE:
                (D) OTHER INFORMATION: The letter "N" stands for the stem II
                    region of a HH ribozyme.

(xi) SEQUENCE DESCRIPTION: SEQ ID NO: 242:

UCCAAUGCCU GAUGANGAAA ACAGGAA                                                                           27

(2) INFORMATION FOR SEQ ID NO: 243:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO: 243:

UUCCUGUUUG CAUUGGA                                                                                      17

(2) INFORMATION FOR SEQ ID NO: 244:

(i) SEQUENCE CHARACTERISTICS:
                (A) LENGTH: 27 base pairs
                (B) TYPE: nucleic acid
                (C) STRANDEDNESS: single
                (D) TOPOLOGY: linear (ix) FEATURE:
                (D) OTHER INFORMATION: The letter "N" stands for the stem II
                    region of a HH ribozyme.

(xi) SEQUENCE DESCRIPTION: SEQ ID NO: 244:

CGGCUUCCCU GAUGANGAAA UGCAAAC                                                                           27

(2) INFORMATION FOR SEQ ID NO: 245:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO: 245:

GUUUGCAUUG GAAGCCG                                                                                      17

(2) INFORMATION FOR SEQ ID NO: 246:

(i) SEQUENCE CHARACTERISTICS:
                (A) LENGTH: 27 base pairs
                (B) TYPE: nucleic acid
                (C) STRANDEDNESS: single
                (D) TOPOLOGY: linear (ix) FEATURE:
                (D) OTHER INFORMATION: The letter "N" stands for the stem II
                    region of a HH ribozyme.

(xi) SEQUENCE DESCRIPTION: SEQ ID NO: 246:

ACAGAGAUCU GAUGANGAAA CCACGGC                                                                           27

(2) INFORMATION FOR SEQ ID NO: 247:

(i) SEQUENCE CHARACTERISTICS:
                (A) LENGTH: 17 base pairs
                (B) TYPE: nucleic acid
                (C) STRANDEDNESS: single (D) TOPOLOGY: linear (xi) SEQUENCE DESCRIPTION: SEQ ID NO: 247:

GCCGUGGUUA UCUCUGU 17

(2) INFORMATION FOR SEQ ID NO: 248:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II region of a HH ribozyme.

(xi) SEQUENCE DESCRIPTION: SEQ ID NO: 248:

AACAGAGACU GAUGANGAAA ACCACGG 27

(2) INFORMATION FOR SEQ ID NO: 249:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 249:

CCGUGGUUAU CUCUGUU 17

(2) INFORMATION FOR SEQ ID NO: 250:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II region of a HH ribozyme.

(xi) SEQUENCE DESCRIPTION: SEQ ID NO: 250:

CCAACAGACU GAUGANGAAA UAACCAC 27

(2) INFORMATION FOR SEQ ID NO: 251:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 251:

GUGGUUAUCU CUGUUGG 17

(2) INFORMATION FOR SEQ ID NO: 252:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II region of a HH ribozyme.

(xi) SEQUENCE DESCRIPTION: SEQ ID NO: 252:

AGCCAACACU GAUGANGAAA GAUAACC                                   27

( 2 ) INFORMATION FOR SEQ ID NO: 253:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 253:

GGUUAUCUCU GUUGGCU                                              17

( 2 ) INFORMATION FOR SEQ ID NO: 254:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II
            region of a HH ribozyme.

( x i ) SEQUENCE DESCRIPTION: SEQ ID NO: 254:

AUGGAGCCCU GAUGANGAAA CAGAGAU                                   27

( 2 ) INFORMATION FOR SEQ ID NO: 255:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 255:

AUCUCUGUUG GCUCCAU                                              17

( 2 ) INFORMATION FOR SEQ ID NO: 256:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II
            region of a HH ribozyme.

( x i ) SEQUENCE DESCRIPTION: SEQ ID NO: 256:

AUCCCAUGCU GAUGANGAAA GCCAACA                                   27

( 2 ) INFORMATION FOR SEQ ID NO: 257:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 257:

UGUUGGCUCC AUGGGAU                                              17

( 2 ) INFORMATION FOR SEQ ID NO: 258:

( i ) SEQUENCE CHARACTERISTICS:

( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for the stem II region of a HH ribozyme.

( x i ) SEQUENCE DESCRIPTION: SEQ ID NO: 258:

UGAUAAUCCU GAUGANGAAA UCCCAUG 27

( 2 ) INFORMATION FOR SEQ ID NO: 259:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 259:

CAUGGGAUUG AUUAUCA 17

( 2 ) INFORMATION FOR SEQ ID NO: 260:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for the stem II region of a HH ribozyme.

( x i ) SEQUENCE DESCRIPTION: SEQ ID NO: 260:

AGGCUGAUCU GAUGANGAAA UCAAUCC 27

( 2 ) INFORMATION FOR SEQ ID NO: 261:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 261:

GGAUUGAUUA UCAGCCU 17

( 2 ) INFORMATION FOR SEQ ID NO: 262:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for the stem II region of a HH ribozyme.

( x i ) SEQUENCE DESCRIPTION: SEQ ID NO: 262:

AAGGCUGACU GAUGANGAAA AUCAAUC 27

( 2 ) INFORMATION FOR SEQ ID NO: 263:

( i ) SEQUENCE CHARACTERISTICS:
( A ) LENGTH: 17 base pairs
( B ) TYPE: nucleic acid
( C ) STRANDEDNESS: single -continued (D) TOPOLOGY: linear (x i) SEQUENCE DESCRIPTION: SEQ ID NO: 263:

GAUUGAUUAU CAGCCUU                17

(2) INFORMATION FOR SEQ ID NO: 264:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i x) FEATURE:
        (D) OTHER INFORMATION: The letter "N"stands for the stem II
            region of a HH ribozyme.

(x i) SEQUENCE DESCRIPTION: SEQ ID NO: 264:

AGAAGGCUCU GAUGANGAAA UAAUCAA                27

(2) INFORMATION FOR SEQ ID NO: 265:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 265:

UUGAUUAUCA GCCUUCU                17

(2) INFORMATION FOR SEQ ID NO: 266:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i x) FEATURE:
        (D) OTHER INFORMATION: The letter "N"stands for the stem II
            region of a HH ribozyme.

(x i) SEQUENCE DESCRIPTION: SEQ ID NO: 266:

ACACAGAGCU GAUGANGAAA GGCUGAU                27

(2) INFORMATION FOR SEQ ID NO: 267:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 267:

AUCAGCCUUC UCUGUGU                17

(2) INFORMATION FOR SEQ ID NO: 268:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i x) FEATURE:
        (D) OTHER INFORMATION: The letter "N"stands for the stem II
            region of a HH ribozyme.

(x i) SEQUENCE DESCRIPTION: SEQ ID NO: 268:

CACACAGACU GAUGANGAAA AGGCUGA 27

( 2 ) INFORMATION FOR SEQ ID NO: 269:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 269:

UCAGCCUUCU CUGUGUG 17

( 2 ) INFORMATION FOR SEQ ID NO: 270:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 270:

UACACACACU GAUGANGAAA GAAGGCU 27

( 2 ) INFORMATION FOR SEQ ID NO: 271:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 271:

AGCCUUCUCU GUGUGUA 17

( 2 ) INFORMATION FOR SEQ ID NO: 272:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 272:

GCCAGAAACU GAUGANGAAA CACACAG 27

( 2 ) INFORMATION FOR SEQ ID NO: 273:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 273:

CUGUGUGUAU UUCUGGC 17

( 2 ) INFORMATION FOR SEQ ID NO: 274:

( i ) SEQUENCE CHARACTERISTICS:

( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for the stem II region of a HH ribozyme.

( x i ) SEQUENCE DESCRIPTION: SEQ ID NO: 274:

CAGCCAGACU GAUGANGAAA UACACAC 27

( 2 ) INFORMATION FOR SEQ ID NO: 275:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 275:

GUGUGUAUUU CUGGCUG 17

( 2 ) INFORMATION FOR SEQ ID NO: 276:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for the stem II region of a HH ribozyme.

( x i ) SEQUENCE DESCRIPTION: SEQ ID NO: 276:

CCAGCCAGCU GAUGANGAAA AUACACA 27

( 2 ) INFORMATION FOR SEQ ID NO: 277:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 277:

UGUGUAUUUC UGGCUGG 17

( 2 ) INFORMATION FOR SEQ ID NO: 278:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for the stem II region of a HH ribozyme.

( x i ) SEQUENCE DESCRIPTION: SEQ ID NO: 278:

UCCAGCCACU GAUGANGAAA AAUACAC 27

( 2 ) INFORMATION FOR SEQ ID NO: 279:

( i ) SEQUENCE CHARACTERISTICS:
( A ) LENGTH: 17 base pairs
( B ) TYPE: nucleic acid
( C ) STRANDEDNESS: single (D) TOPOLOGY: linear (xi) SEQUENCE DESCRIPTION: SEQ ID NO: 279:

GUGUAUUUCU GGCUGGA                                                              17

(2) INFORMATION FOR SEQ ID NO: 280:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 280:

AGGGUGGGCU GAUGANGAAA UUCGGGG                                                   27

(2) INFORMATION FOR SEQ ID NO: 281:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 281:

CCCCGAAUUC CCACCCU                                                              17

(2) INFORMATION FOR SEQ ID NO: 282:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 282:

CAGGGUGGCU GAUGANGAAA AUUCGGG                                                   27

(2) INFORMATION FOR SEQ ID NO: 283:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 283:

CCCGAAUUCC CACCCUG                                                              17

(2) INFORMATION FOR SEQ ID NO: 284:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 284:

AGAUCCUCCU GAUGANGAAA GGUUCUU 27

(2) INFORMATION FOR SEQ ID NO: 285:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 285:

AAGAACCUAG AGGAUCU 17

(2) INFORMATION FOR SEQ ID NO: 286:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 286:

AGUAACAACU GAUGANGAAA UCCUCUA 27

(2) INFORMATION FOR SEQ ID NO: 287:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 287:

UAGAGGAUCU UGUUACU 17

(2) INFORMATION FOR SEQ ID NO: 288:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 288:

UCAGUAACCU GAUGANGAAA GAUCCUC 27

(2) INFORMATION FOR SEQ ID NO: 289:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 289:

GAGGAUCUUG UUACUGA 17

(2) INFORMATION FOR SEQ ID NO: 290:

(i) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 290:

UAUUCAGUCU GAUGANGAAA CAAGAUC    27

(2) INFORMATION FOR SEQ ID NO: 291:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 291:

GAUCUUGUUA CUGAAUA    17

(2) INFORMATION FOR SEQ ID NO: 292:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 292:

GUAUUCAGCU GAUGANGAAA ACAAGAU    27

(2) INFORMATION FOR SEQ ID NO: 293:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 293:

AUCUUGUUAC UGAAUAC    17

(2) INFORMATION FOR SEQ ID NO: 294:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 294:

UCCCGUGGCU GAUGANGAAA UUCAGUA    27

(2) INFORMATION FOR SEQ ID NO: 295:

(i) SEQUENCE CHARACTERISTICS:
(A) LENGTH: 17 base pairs
(B) TYPE: nucleic acid
(C) STRANDEDNESS: single ( D ) TOPOLOGY: linear ( x i ) SEQUENCE DESCRIPTION: SEQ ID NO: 295:

UACUGAAUAC CACGGGA                                                                                           17

( 2 ) INFORMATION FOR SEQ ID NO: 296:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 296:

AGGCCGAACU GAUGANGAAA GUUCCCG                                                                                27

( 2 ) INFORMATION FOR SEQ ID NO: 297:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 297:

CGGGAACUUU UCGGCCU                                                                                           17

( 2 ) INFORMATION FOR SEQ ID NO: 298:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 298:

CAGGCCGACU GAUGANGAAA AGUUCCC                                                                                27

( 2 ) INFORMATION FOR SEQ ID NO: 299:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 299:

GGGAACUUUU CGGCCUG                                                                                           17

( 2 ) INFORMATION FOR SEQ ID NO: 300:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 300:

CCAGGCCGCU GAUGANGAAA AAGUUCC                27

(2) INFORMATION FOR SEQ ID NO: 301:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 301:

GGAACUUUUC GGCCUGG                17

(2) INFORMATION FOR SEQ ID NO: 302:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 302:

UCCAGGCCCU GAUGANGAAA AAAGUUC                27

(2) INFORMATION FOR SEQ ID NO: 303:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 303:

GAACUUUUCG GCCUGGA                17

(2) INFORMATION FOR SEQ ID NO: 304:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 304:

GUCCCUUACU GAUGANGAAA CACACCA                27

(2) INFORMATION FOR SEQ ID NO: 305:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 305:

UGGUGUGUCU AAGGGAC                17

(2) INFORMATION FOR SEQ ID NO: 306:

(i) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 306:

CAGUCCCUCU GAUGANGAAA GACACAC 27

(2) INFORMATION FOR SEQ ID NO: 307:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 307:

GUGUGUCUAA GGGACUG 17

(2) INFORMATION FOR SEQ ID NO: 308:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 308:

UGGCUGCACU GAUGANGAAA CUCUCAG 27

(2) INFORMATION FOR SEQ ID NO: 309:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 309:

CUGAGAGUCU GCAGCCA 17

(2) INFORMATION FOR SEQ ID NO: 310:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 310:

GUUCACUGCU GAUGANGAAA GUCUGGC 27

(2) INFORMATION FOR SEQ ID NO: 311:

(i) SEQUENCE CHARACTERISTICS:
(A) LENGTH: 17 base pairs
(B) TYPE: nucleic acid
(C) STRANDEDNESS: single ( D ) TOPOLOGY: linear ( x i ) SEQUENCE DESCRIPTION: SEQ ID NO: 311:

GCCAGACUAC AGUGAAC 17

( 2 ) INFORMATION FOR SEQ ID NO: 312:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 312:

ACGAGGCACU GAUGANGAAA GUCGUUC 27

( 2 ) INFORMATION FOR SEQ ID NO: 313:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 313:

GAACGACUCU GCCUCGU 17

( 2 ) INFORMATION FOR SEQ ID NO: 314:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 314:

UCACUGACCU GAUGANGAAA GGCAGAG 27

( 2 ) INFORMATION FOR SEQ ID NO: 315:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 315:

CUCUGCCUCG UCAGUGA 17

( 2 ) INFORMATION FOR SEQ ID NO: 316:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 316:

```
AUCUCACUCU GAUGANGAAA CGAGGCA                                                    27
```

( 2 ) INFORMATION FOR SEQ ID NO: 317:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 317:

```
UGCCUCGUCA GUGAGAU                                                               17
```

( 2 ) INFORMATION FOR SEQ ID NO: 318:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 318:

```
UUUGGGGCU GAUGANGAAA UCUCACU                                                     27
```

( 2 ) INFORMATION FOR SEQ ID NO: 319:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 319:

```
AGUGAGAUUC CCCCAAA                                                               17
```

( 2 ) INFORMATION FOR SEQ ID NO: 320:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 320:

```
UUUUGGGCU GAUGANGAAA AUCUCAC                                                     27
```

( 2 ) INFORMATION FOR SEQ ID NO: 321:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 321:

```
GUGAGAUUCC CCCAAAA                                                               17
```

( 2 ) INFORMATION FOR SEQ ID NO: 322:

( i ) SEQUENCE CHARACTERISTICS:

( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for the stem II
region of a HH ribozyme.

( x i ) SEQUENCE DESCRIPTION: SEQ ID NO: 322:

CCCUCCCCU GAUGANGAAA GGGCCCC 27

( 2 ) INFORMATION FOR SEQ ID NO: 323:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 323:

GGGGCCCUUG GGGAGGG 17

( 2 ) INFORMATION FOR SEQ ID NO: 324:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for the stem II
region of a HH ribozyme.

( x i ) SEQUENCE DESCRIPTION: SEQ ID NO: 324:

UGCAUGGGCU GAUGANGAAA GGCCCCA 27

( 2 ) INFORMATION FOR SEQ ID NO: 325:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 325:

UGGGGCCUCC CCAUGCA 17

( 2 ) INFORMATION FOR SEQ ID NO: 326:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for the stem II
region of a HH ribozyme.

( x i ) SEQUENCE DESCRIPTION: SEQ ID NO: 326:

GUAGGGGCCU GAUGANGAAA UGCUGGU 27

( 2 ) INFORMATION FOR SEQ ID NO: 327:

( i ) SEQUENCE CHARACTERISTICS:
( A ) LENGTH: 17 base pairs
( B ) TYPE: nucleic acid
( C ) STRANDEDNESS: single (D) TOPOLOGY: linear (x i) SEQUENCE DESCRIPTION: SEQ ID NO: 327:

ACCAGCAUAG CCCCUAC 17

(2) INFORMATION FOR SEQ ID NO: 328:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i x) FEATURE:
        (D) OTHER INFORMATION: The letter "N" stands for the stem II region of a HH ribozyme.

(x i) SEQUENCE DESCRIPTION: SEQ ID NO: 328:

GGGCCCAGCU GAUGANGAAA GGGGCUA 27

(2) INFORMATION FOR SEQ ID NO: 329:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 329:

UAGCCCUAC UGGGCCC 17

(2) INFORMATION FOR SEQ ID NO: 330:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i x) FEATURE:
        (D) OTHER INFORMATION: The letter "N" stands for the stem II region of a HH ribozyme.

(x i) SEQUENCE DESCRIPTION: SEQ ID NO: 330:

UAGGGUGUCU GAUGANGAAA CAUGGGG 27

(2) INFORMATION FOR SEQ ID NO: 331:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (x i) SEQUENCE DESCRIPTION: SEQ ID NO: 331:

CCCCAUGUUA CACCCUA 17

(2) INFORMATION FOR SEQ ID NO: 332:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i x) FEATURE:
        (D) OTHER INFORMATION: The letter "N" stands for the stem II region of a HH ribozyme.

(x i) SEQUENCE DESCRIPTION: SEQ ID NO: 332:

UUAGGGUGCU GAUGANGAAA ACAUGGG 27

( 2 ) INFORMATION FOR SEQ ID NO: 333:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 333:

CCCAUGUUAC ACCCUAA 17

( 2 ) INFORMATION FOR SEQ ID NO: 334:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 334:

UCAGGCUUCU GAUGANGAAA GGGUGUA 27

( 2 ) INFORMATION FOR SEQ ID NO: 335:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 335:

UACACCCUAA AGCCUGA 17

( 2 ) INFORMATION FOR SEQ ID NO: 336:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 336:

UGUCAGAGCU GAUGANGAAA UUGGGGU 27

( 2 ) INFORMATION FOR SEQ ID NO: 337:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 337:

ACCCCAAUCC UCUGACA 17

( 2 ) INFORMATION FOR SEQ ID NO: 338:

( i ) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 338:

UUCUGUCACU GAUGANGAAA GGAUUGG    27

(2) INFORMATION FOR SEQ ID NO: 339:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 339:

CCAAUCCUCU GACAGAA    17

(2) INFORMATION FOR SEQ ID NO: 340:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 340:

GGCUACAGCU GAUGANGAAA CCCUGGG    27

(2) INFORMATION FOR SEQ ID NO: 341:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 341:

CCCAGGGUCC UGUAGCC    17

(2) INFORMATION FOR SEQ ID NO: 342:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 342:

CUUAGGGCCU GAUGANGAAA CAGGACC    27

(2) INFORMATION FOR SEQ ID NO: 343:

(i) SEQUENCE CHARACTERISTICS:
(A) LENGTH: 17 base pairs
(B) TYPE: nucleic acid
(C) STRANDEDNESS: single ( D ) TOPOLOGY: linear ( x i ) SEQUENCE DESCRIPTION: SEQ ID NO: 343:

GGUCCUGUAG CCCUAAG 17

( 2 ) INFORMATION FOR SEQ ID NO: 344:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 344:

GUACCACUCU GAUGANGAAA GGGCUAC 27

( 2 ) INFORMATION FOR SEQ ID NO: 345:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 345:

GUAGCCCUAA GUGGUAC 17

( 2 ) INFORMATION FOR SEQ ID NO: 346:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 346:

AAAGUUAGCU GAUGANGAAA CCACUUA 27

( 2 ) INFORMATION FOR SEQ ID NO: 347:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 347:

UAAGUGGUAC UAACUUU 17

( 2 ) INFORMATION FOR SEQ ID NO: 348:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 348:

AGGAAAGUCU GAUGANGAAA GUACCAC 27

( 2 ) INFORMATION FOR SEQ ID NO: 349:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 349:

GUGGUACUAA CUUUCCU 17

( 2 ) INFORMATION FOR SEQ ID NO: 350:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 350:

AUGAAGGACU GAUGANGAAA GUUAGUA 27

( 2 ) INFORMATION FOR SEQ ID NO: 351:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 351:

UACUAACUUU CCUUCAU 17

( 2 ) INFORMATION FOR SEQ ID NO: 352:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 352:

AAUGAAGGCU GAUGANGAAA AGUUAGU 27

( 2 ) INFORMATION FOR SEQ ID NO: 353:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 353:

ACUAACUUUC CUUCAUU 17

( 2 ) INFORMATION FOR SEQ ID NO: 354:

( i ) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 354:

GAAUGAAGCU GAUGANGAAA AAGUUAG        27

(2) INFORMATION FOR SEQ ID NO: 355:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 355:

CUAACUUUCC UUCAUUC        17

(2) INFORMATION FOR SEQ ID NO: 356:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 356:

GUUGAAUGCU GAUGANGAAA GGAAAGU        27

(2) INFORMATION FOR SEQ ID NO: 357:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 357:

ACUUUCCUUC AUUCAAC        17

(2) INFORMATION FOR SEQ ID NO: 358:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 358:

GGUUGAAUCU GAUGANGAAA AGGAAAG        27

(2) INFORMATION FOR SEQ ID NO: 359:

(i) SEQUENCE CHARACTERISTICS:
(A) LENGTH: 17 base pairs
(B) TYPE: nucleic acid
(C) STRANDEDNESS: single ( D ) TOPOLOGY: linear ( x i ) SEQUENCE DESCRIPTION: SEQ ID NO: 359:

CUUUCCUUCA UUCAACC                                                                                              17

( 2 ) INFORMATION FOR SEQ ID NO: 360:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i x ) FEATURE:
            ( D ) OTHER INFORMATION: The letter "N"stands for the stem II
                  region of a HH ribozyme.

( x i ) SEQUENCE DESCRIPTION: SEQ ID NO: 360:

GUGGGUUGCU GAUGANGAAA UGAAGGA                                                                                   27

( 2 ) INFORMATION FOR SEQ ID NO: 361:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 361:

UCCUUCAUUC AACCCAC                                                                                              17

( 2 ) INFORMATION FOR SEQ ID NO: 362:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i x ) FEATURE:
            ( D ) OTHER INFORMATION: The letter "N"stands for the stem II
                  region of a HH ribozyme.

( x i ) SEQUENCE DESCRIPTION: SEQ ID NO: 362:

GGUGGGUUCU GAUGANGAAA AUGAAGG                                                                                   27

( 2 ) INFORMATION FOR SEQ ID NO: 363:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 363:

CCUUCAUUCA ACCCACC                                                                                              17

( 2 ) INFORMATION FOR SEQ ID NO: 364:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i x ) FEATURE:
            ( D ) OTHER INFORMATION: The letter "N"stands for the stem II
                  region of a HH ribozyme.

( x i ) SEQUENCE DESCRIPTION: SEQ ID NO: 364:

GAGUAUGACU GAUGANGAAA CGCAGGU 27

( 2 ) INFORMATION FOR SEQ ID NO: 365:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 365:

ACCUGCGUCU CAUACUC 17

( 2 ) INFORMATION FOR SEQ ID NO: 366:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 366:

GUGAGUAUCU GAUGANGAAA GACGCAG 27

( 2 ) INFORMATION FOR SEQ ID NO: 367:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 367:

CUGCGUCUCA UACUCAC 17

( 2 ) INFORMATION FOR SEQ ID NO: 368:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 368:

GAGGUGAGCU GAUGANGAAA UGAGACG 27

( 2 ) INFORMATION FOR SEQ ID NO: 369:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 369:

CGUCUCAUAC UCACCUC 17

( 2 ) INFORMATION FOR SEQ ID NO: 370:

( i ) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 370:

GGUGAGGUCU GAUGANGAAA GUAUGAG 27

(2) INFORMATION FOR SEQ ID NO: 371:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 371:

CUCAUACUCA CCUCACC 17

(2) INFORMATION FOR SEQ ID NO: 372:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 372:

AGUGGGGUCU GAUGANGAAA GGUGAGU 27

(2) INFORMATION FOR SEQ ID NO: 373:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 373:

ACUCACCUCA CCCCACU 17

(2) INFORMATION FOR SEQ ID NO: 374:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 374:

AAAUUCCACU GAUGANGAAA UCAGCCA 27

(2) INFORMATION FOR SEQ ID NO: 375:

(i) SEQUENCE CHARACTERISTICS:
(A) LENGTH: 17 base pairs
(B) TYPE: nucleic acid
(C) STRANDEDNESS: single (D) TOPOLOGY: linear (xi) SEQUENCE DESCRIPTION: SEQ ID NO: 375:

UGGCUGAUUU GGAAUUU    17

(2) INFORMATION FOR SEQ ID NO: 376:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N"stands for the stem II region of a HH ribozyme.

(xi) SEQUENCE DESCRIPTION: SEQ ID NO: 376:

AAAAUCCCU GAUGANGAAA AUCAGCC    27

(2) INFORMATION FOR SEQ ID NO: 377:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 377:

GGCUGAUUUG GAAUUUU    17

(2) INFORMATION FOR SEQ ID NO: 378:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N"stands for the stem II region of a HH ribozyme.

(xi) SEQUENCE DESCRIPTION: SEQ ID NO: 378:

GGGCACAACU GAUGANGAAA UUCCAAA    27

(2) INFORMATION FOR SEQ ID NO: 379:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 379:

UUUGGAAUUU UGUGCCC    17

(2) INFORMATION FOR SEQ ID NO: 380:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N"stands for the stem II region of a HH ribozyme.

(xi) SEQUENCE DESCRIPTION: SEQ ID NO: 380:

GGGGCACACU GAUGANGAAA AUUCCAA 27

( 2 ) INFORMATION FOR SEQ ID NO: 381:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 381:

UUGGAAUUUU GUGCCCC 17

( 2 ) INFORMATION FOR SEQ ID NO: 382:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 382:

GGGGGCACCU GAUGANGAAA AAUUCCA 27

( 2 ) INFORMATION FOR SEQ ID NO: 383:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 383:

UGGAAUUUUG UGCCCCC 17

( 2 ) INFORMATION FOR SEQ ID NO: 384:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 384:

GGGGUGCUCU GAUGANGAAA CAUGGGG 27

( 2 ) INFORMATION FOR SEQ ID NO: 385:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 385:

CCCCAUGUAA GCACCCC 17

( 2 ) INFORMATION FOR SEQ ID NO: 386:

( i ) SEQUENCE CHARACTERISTICS:

( A ) LENGTH: 27 base pairs
                    ( B ) TYPE: nucleic acid
                    ( C ) STRANDEDNESS: single
                    ( D ) TOPOLOGY: linear ( i x ) FEATURE:
                    ( D ) OTHER INFORMATION: The letter "N"stands for the stem II
                        region of a HH ribozyme.

( x i ) SEQUENCE DESCRIPTION: SEQ ID NO: 386:

GCCAAAUGCU GAUGANGAAA GGGGUGC                                                                    27

( 2 ) INFORMATION FOR SEQ ID NO: 387:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO: 387:

GCACCCCUUC AUUUGGC                                                                                17

( 2 ) INFORMATION FOR SEQ ID NO: 388:

( i ) SEQUENCE CHARACTERISTICS:
                    ( A ) LENGTH: 27 base pairs
                    ( B ) TYPE: nucleic acid
                    ( C ) STRANDEDNESS: single
                    ( D ) TOPOLOGY: linear ( i x ) FEATURE:
                    ( D ) OTHER INFORMATION: The letter "N"stands for the stem II
                        region of a HH ribozyme.

( x i ) SEQUENCE DESCRIPTION: SEQ ID NO: 388:

UGCCAAAUCU GAUGANGAAA AGGGGUG                                                                    27

( 2 ) INFORMATION FOR SEQ ID NO: 389:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO: 389:

CACCCCUUCA UUUGGCA                                                                                17

( 2 ) INFORMATION FOR SEQ ID NO: 390:

( i ) SEQUENCE CHARACTERISTICS:
                    ( A ) LENGTH: 27 base pairs
                    ( B ) TYPE: nucleic acid
                    ( C ) STRANDEDNESS: single
                    ( D ) TOPOLOGY: linear ( i x ) FEATURE:
                    ( D ) OTHER INFORMATION: The letter "N"stands for the stem II
                        region of a HH ribozyme.

( x i ) SEQUENCE DESCRIPTION: SEQ ID NO: 390:

GAAUGCCACU GAUGANGAAA UGAAGGG                                                                    27

( 2 ) INFORMATION FOR SEQ ID NO: 391:

( i ) SEQUENCE CHARACTERISTICS:
                    ( A ) LENGTH: 17 base pairs
                    ( B ) TYPE: nucleic acid
                    ( C ) STRANDEDNESS: single ( D ) TOPOLOGY: linear ( x i ) SEQUENCE DESCRIPTION: SEQ ID NO: 391:

CCCUUCAUUU GGCAUUC    17

( 2 ) INFORMATION FOR SEQ ID NO: 392:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 392:

GGAAUGCCCU GAUGANGAAA AUGAAGG    27

( 2 ) INFORMATION FOR SEQ ID NO: 393:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 393:

CCUUCAUUUG GCAUUCC    17

( 2 ) INFORMATION FOR SEQ ID NO: 394:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 394:

AAGUGGGGCU GAUGANGAAA UGCCAAA    27

( 2 ) INFORMATION FOR SEQ ID NO: 395:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 395:

UUUGGCAUUC CCCACUU    17

( 2 ) INFORMATION FOR SEQ ID NO: 396:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 396:

CAAGUGGGCU GAUGANGAAA AUGCCAA 27

( 2 ) INFORMATION FOR SEQ ID NO: 397:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 397:

UUGGCAUUCC CCACUUG 17

( 2 ) INFORMATION FOR SEQ ID NO: 398:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 398:

UAAUUCUCCU GAUGANGAAA GUGGGGA 27

( 2 ) INFORMATION FOR SEQ ID NO: 399:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 399:

UCCCCACUUG AGAAUUA 17

( 2 ) INFORMATION FOR SEQ ID NO: 400:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 400:

AAAAGGGUCU GAUGANGAAA UUCUCAA 27

( 2 ) INFORMATION FOR SEQ ID NO: 401:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 401:

UUGAGAAUUA CCCUUUU 17

( 2 ) INFORMATION FOR SEQ ID NO: 402:

( i ) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 402:

CAAAAGGGCU GAUGANGAAA AUUCUCA　　　　　　　　　　　　　　　　　　　　27

(2) INFORMATION FOR SEQ ID NO: 403:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 403:

UGAGAAUUAC CCUUUUG　　　　　　　　　　　　　　　　　　　　　　　　　　17

(2) INFORMATION FOR SEQ ID NO: 404:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 404:

CGGGGCAACU GAUGANGAAA GGGUAAU　　　　　　　　　　　　　　　　　　　　27

(2) INFORMATION FOR SEQ ID NO: 405:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 405:

AUUACCCUUU UGCCCCG　　　　　　　　　　　　　　　　　　　　　　　　　　17

(2) INFORMATION FOR SEQ ID NO: 406:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 406:

UCGGGGCACU GAUGANGAAA AGGGUAA　　　　　　　　　　　　　　　　　　　　27

(2) INFORMATION FOR SEQ ID NO: 407:

(i) SEQUENCE CHARACTERISTICS:
(A) LENGTH: 17 base pairs
(B) TYPE: nucleic acid
(C) STRANDEDNESS: single ( D ) TOPOLOGY: linear ( x i ) SEQUENCE DESCRIPTION: SEQ ID NO: 407:

UUACCCUUUU GCCCCGA        17

( 2 ) INFORMATION FOR SEQ ID NO: 408:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 408:

UUCGGGGCCU GAUGANGAAA AAGGGUA        27

( 2 ) INFORMATION FOR SEQ ID NO: 409:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 409:

UACCCUUUUG CCCCGAA        17

( 2 ) INFORMATION FOR SEQ ID NO: 410:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 410:

AGAAGAAACU GAUGANGAAA CAUGUUC        27

( 2 ) INFORMATION FOR SEQ ID NO: 411:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 411:

GAACAUGUUU UUCUUCU        17

( 2 ) INFORMATION FOR SEQ ID NO: 412:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 412:

GAGAAGAACU GAUGANGAAA ACAUGUU 27

( 2 ) INFORMATION FOR SEQ ID NO: 413:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 413:

AACAUGUUUU UCUUCUC 17

( 2 ) INFORMATION FOR SEQ ID NO: 414:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 414:

GGAGAAGACU GAUGANGAAA AACAUGU 27

( 2 ) INFORMATION FOR SEQ ID NO: 415:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 415:

ACAUGUUUUU CUUCUCC 17

( 2 ) INFORMATION FOR SEQ ID NO: 416:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 416:

GGGAGAAGCU GAUGANGAAA AAACAUG 27

( 2 ) INFORMATION FOR SEQ ID NO: 417:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 417:

CAUGUUUUUC UUCUCCC 17

( 2 ) INFORMATION FOR SEQ ID NO: 418:

( i ) SEQUENCE CHARACTERISTICS:

( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for the stem II
region of a HH ribozyme.

( x i ) SEQUENCE DESCRIPTION: SEQ ID NO: 418:

AGGGAGAACU GAUGANGAAA AAAACAU  27

( 2 ) INFORMATION FOR SEQ ID NO: 419:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 419:

AUGUUUUUCU UCUCCCU  17

( 2 ) INFORMATION FOR SEQ ID NO: 420:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for the stem II
region of a HH ribozyme.

( x i ) SEQUENCE DESCRIPTION: SEQ ID NO: 420:

UGAGGGAGCU GAUGANGAAA GAAAAAC  27

( 2 ) INFORMATION FOR SEQ ID NO: 421:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 421:

GUUUUUCUUC UCCCUCA  17

( 2 ) INFORMATION FOR SEQ ID NO: 422:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for the stem II
region of a HH ribozyme.

( x i ) SEQUENCE DESCRIPTION: SEQ ID NO: 422:

CUGAGGGACU GAUGANGAAA AGAAAAA  27

( 2 ) INFORMATION FOR SEQ ID NO: 423:

( i ) SEQUENCE CHARACTERISTICS:
( A ) LENGTH: 17 base pairs
( B ) TYPE: nucleic acid
( C ) STRANDEDNESS: single (D) TOPOLOGY: linear (xi) SEQUENCE DESCRIPTION: SEQ ID NO: 423:

UUUUUCUUCU CCCUCAG 17

(2) INFORMATION FOR SEQ ID NO: 424:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 424:

GACUGAGGCU GAUGANGAAA GAAGAAA 27

(2) INFORMATION FOR SEQ ID NO: 425:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 425:

UUUCUUCUCC CUCAGUC 17

(2) INFORMATION FOR SEQ ID NO: 426:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 426:

GCCAGACUCU GAUGANGAAA GGGAGAA 27

(2) INFORMATION FOR SEQ ID NO: 427:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 427:

UUCUCCCUCA GUCUGGC 17

(2) INFORMATION FOR SEQ ID NO: 428:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 428:

AAGGGCCACU GAUGANGAAA CUGAGGG                                                                27

( 2 ) INFORMATION FOR SEQ ID NO: 429:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 429:

CCCUCAGUCU GGCCCUU                                                                            17

( 2 ) INFORMATION FOR SEQ ID NO: 430:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 430:

CGAAAAGGCU GAUGANGAAA GGGCCAG                                                                27

( 2 ) INFORMATION FOR SEQ ID NO: 431:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 431:

CUGGCCCUUC CUUUUCG                                                                            17

( 2 ) INFORMATION FOR SEQ ID NO: 432:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 432:

GCGAAAAGCU GAUGANGAAA AGGGCCA                                                                27

( 2 ) INFORMATION FOR SEQ ID NO: 433:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 433:

UGGCCCUUCC UUUUCGC                                                                            17

( 2 ) INFORMATION FOR SEQ ID NO: 434:

( i ) SEQUENCE CHARACTERISTICS:

(A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 434:

CCUGCGAACU GAUGANGAAA GGAAGGG                                                                27

(2) INFORMATION FOR SEQ ID NO: 435:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 435:

CCCUUCCUUU UCGCAGG                                                                            17

(2) INFORMATION FOR SEQ ID NO: 436:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 436:

UCCUGCGACU GAUGANGAAA AGGAAGG                                                                27

(2) INFORMATION FOR SEQ ID NO: 437:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 437:

CCUUCCUUUU CGCAGGA                                                                            17

(2) INFORMATION FOR SEQ ID NO: 438:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 438:

AUCCUGCGCU GAUGANGAAA AAGGAAG                                                                27

(2) INFORMATION FOR SEQ ID NO: 439:

(i) SEQUENCE CHARACTERISTICS:
        (A) LENGTH: 17 base pairs
        (B) TYPE: nucleic acid
        (C) STRANDEDNESS: single ( D ) TOPOLOGY: linear ( x i ) SEQUENCE DESCRIPTION: SEQ ID NO: 439:

CUUCCUUUUC GCAGGAU    17

( 2 ) INFORMATION FOR SEQ ID NO: 440:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 440:

AAUCCUGCCU GAUGANGAAA AAAGGAA    27

( 2 ) INFORMATION FOR SEQ ID NO: 441:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 441:

UUCCUUUUCG CAGGAUU    17

( 2 ) INFORMATION FOR SEQ ID NO: 442:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 442:

GGAGGAAGCU GAUGANGAAA UCCUGCG    27

( 2 ) INFORMATION FOR SEQ ID NO: 443:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 443:

CGCAGGAUUC UUCCUCC    17

( 2 ) INFORMATION FOR SEQ ID NO: 444:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 444:

GGGAGGAACU GAUGANGAAA AUCCUGC 27

(2) INFORMATION FOR SEQ ID NO: 445:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 445:

GCAGGAUUCU UCCUCCC 17

(2) INFORMATION FOR SEQ ID NO: 446:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N"stands for the stem II
            region of a HH ribozyme.

(xi) SEQUENCE DESCRIPTION: SEQ ID NO: 446:

GAGGGAGGCU GAUGANGAAA GAAUCCU 27

(2) INFORMATION FOR SEQ ID NO: 447:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 447:

AGGAUUCUUC CUCCCUC 17

(2) INFORMATION FOR SEQ ID NO: 448:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N"stands for the stem II
            region of a HH ribozyme.

(xi) SEQUENCE DESCRIPTION: SEQ ID NO: 448:

GGAGGGAGCU GAUGANGAAA AGAAUCC 27

(2) INFORMATION FOR SEQ ID NO: 449:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 449:

GGAUUCUUCC UCCCUCC 17

(2) INFORMATION FOR SEQ ID NO: 450:

(i) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 450:

GAGGGAGGCU GAUGANGAAA GGAAGAA 27

(2) INFORMATION FOR SEQ ID NO: 451:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 451:

UUCUUCCUCC CUCCCUC 17

(2) INFORMATION FOR SEQ ID NO: 452:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 452:

GAAAGAGGCU GAUGANGAAA GGGAGGA 27

(2) INFORMATION FOR SEQ ID NO: 453:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 453:

UCCUCCCUCC CUCUUUC 17

(2) INFORMATION FOR SEQ ID NO: 454:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 454:

GAGGGAAACU GAUGANGAAA GGGAGGG 27

(2) INFORMATION FOR SEQ ID NO: 455:

(i) SEQUENCE CHARACTERISTICS:
(A) LENGTH: 17 base pairs
(B) TYPE: nucleic acid
(C) STRANDEDNESS: single ( D ) TOPOLOGY: linear ( x i ) SEQUENCE DESCRIPTION: SEQ ID NO: 455:

CCCUCCCUCU UUCCCUC 17

( 2 ) INFORMATION FOR SEQ ID NO: 456:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II region of a HH ribozyme.

( x i ) SEQUENCE DESCRIPTION: SEQ ID NO: 456:

GGGAGGGACU GAUGANGAAA GAGGGAG 27

( 2 ) INFORMATION FOR SEQ ID NO: 457:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 457:

CUCCCUCUUU CCCUCCC 17

( 2 ) INFORMATION FOR SEQ ID NO: 458:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II region of a HH ribozyme.

( x i ) SEQUENCE DESCRIPTION: SEQ ID NO: 458:

AGGGAGGGCU GAUGANGAAA AGAGGGA 27

( 2 ) INFORMATION FOR SEQ ID NO: 459:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 459:

UCCCUCUUUC CCUCCCU 17

( 2 ) INFORMATION FOR SEQ ID NO: 460:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II region of a HH ribozyme.

( x i ) SEQUENCE DESCRIPTION: SEQ ID NO: 460:

AAGGGAGGCU GAUGANGAAA AAGAGGG                                                              27

( 2 ) INFORMATION FOR SEQ ID NO: 461:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 461:

C C C U C U U U C C   C U C C C U U                                                       17

( 2 ) INFORMATION FOR SEQ ID NO: 462:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i x ) FEATURE:
                ( D ) OTHER INFORMATION: The letter "N"stands for the stem II
                        region of a HH ribozyme.

( x i ) SEQUENCE DESCRIPTION: SEQ ID NO: 462:

GAGGAAGGCU GAUGANGAAA GGGAAAG                                                              27

( 2 ) INFORMATION FOR SEQ ID NO: 463:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 463:

C U U U C C C U C C   C U U C C U C                                                       17

( 2 ) INFORMATION FOR SEQ ID NO: 464:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i x ) FEATURE:
                ( D ) OTHER INFORMATION: The letter "N"stands for the stem II
                        region of a HH ribozyme.

( x i ) SEQUENCE DESCRIPTION: SEQ ID NO: 464:

GAAAGAGGCU GAUGANGAAA GGGAGGG                                                              27

( 2 ) INFORMATION FOR SEQ ID NO: 465:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 465:

C C C U C C C U U C   C U C U U U C                                                       17

( 2 ) INFORMATION FOR SEQ ID NO: 466:

( i ) SEQUENCE CHARACTERISTICS:

(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 466:

GGAAAGAGCU GAUGANGAAA AGGGAGG 27

(2) INFORMATION FOR SEQ ID NO: 467:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 467:

CCUCCCUUCC UCUUUCC 17

(2) INFORMATION FOR SEQ ID NO: 468:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 468:

GAUGGAAACU GAUGANGAAA GGAAGGG 27

(2) INFORMATION FOR SEQ ID NO: 469:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 469:

CCCUUCCUCU UUCCAUC 17

(2) INFORMATION FOR SEQ ID NO: 470:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 470:

UAGAUGGACU GAUGANGAAA GAGGAAG 27

(2) INFORMATION FOR SEQ ID NO: 471:

(i) SEQUENCE CHARACTERISTICS:
(A) LENGTH: 17 base pairs
(B) TYPE: nucleic acid
(C) STRANDEDNESS: single (D) TOPOLOGY: linear (xi) SEQUENCE DESCRIPTION: SEQ ID NO: 471:

CUUCCUCUUU CCAUCUA    17

(2) INFORMATION FOR SEQ ID NO: 472:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II region of a HH ribozyme.

(xi) SEQUENCE DESCRIPTION: SEQ ID NO: 472:

GUAGAUGGCU GAUGANGAAA AGAGGAA    27

(2) INFORMATION FOR SEQ ID NO: 473:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 473:

UUCCUCUUUC CAUCUAC    17

(2) INFORMATION FOR SEQ ID NO: 474:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II region of a HH ribozyme.

(xi) SEQUENCE DESCRIPTION: SEQ ID NO: 474:

GGUAGAUGCU GAUGANGAAA AAGAGGA    27

(2) INFORMATION FOR SEQ ID NO: 475:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 475:

UCCUCUUUCC AUCUACC    17

(2) INFORMATION FOR SEQ ID NO: 476:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II region of a HH ribozyme.

(xi) SEQUENCE DESCRIPTION: SEQ ID NO: 476:

GGAGGGUACU GAUGANGAAA UGGAAAG 27

( 2 ) INFORMATION FOR SEQ ID NO: 477:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 477:

CUUUCCAUCU ACCCUCC 17

( 2 ) INFORMATION FOR SEQ ID NO: 478:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 478:

UCGGAGGGCU GAUGANGAAA GAUGGAA 27

( 2 ) INFORMATION FOR SEQ ID NO: 479:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 479:

UUCCAUCUAC CCUCCGA 17

( 2 ) INFORMATION FOR SEQ ID NO: 480:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 480:

AACAAUCGCU GAUGANGAAA GGGUAGA 27

( 2 ) INFORMATION FOR SEQ ID NO: 481:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 481:

UCUACCCUCC GAUUGUU 17

( 2 ) INFORMATION FOR SEQ ID NO: 482:

( i ) SEQUENCE CHARACTERISTICS:

( A ) LENGTH: 27 base pairs
                    ( B ) TYPE: nucleic acid
                    ( C ) STRANDEDNESS: single
                    ( D ) TOPOLOGY: linear ( i x ) FEATURE:
                    ( D ) OTHER INFORMATION: The letter "N"stands for the stem II
                          region of a HH ribozyme.

( x i ) SEQUENCE DESCRIPTION: SEQ ID NO: 482:

UCAGGAACCU GAUGANGAAA UCGGAGG                                                                    27

( 2 ) INFORMATION FOR SEQ ID NO: 483:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO: 483:

CCUCCGAUUG UUCCUGA                                                                               17

( 2 ) INFORMATION FOR SEQ ID NO: 484:

( i ) SEQUENCE CHARACTERISTICS:
                    ( A ) LENGTH: 27 base pairs
                    ( B ) TYPE: nucleic acid
                    ( C ) STRANDEDNESS: single
                    ( D ) TOPOLOGY: linear ( i x ) FEATURE:
                    ( D ) OTHER INFORMATION: The letter "N"stands for the stem II
                          region of a HH ribozyme.

( x i ) SEQUENCE DESCRIPTION: SEQ ID NO: 484:

GGUUCAGGCU GAUGANGAAA CAAUCGG                                                                    27

( 2 ) INFORMATION FOR SEQ ID NO: 485:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO: 485:

CCGAUUGUUC CUGAACC                                                                               17

( 2 ) INFORMATION FOR SEQ ID NO: 486:

( i ) SEQUENCE CHARACTERISTICS:
                    ( A ) LENGTH: 27 base pairs
                    ( B ) TYPE: nucleic acid
                    ( C ) STRANDEDNESS: single
                    ( D ) TOPOLOGY: linear ( i x ) FEATURE:
                    ( D ) OTHER INFORMATION: The letter "N"stands for the stem II
                          region of a HH ribozyme.

( x i ) SEQUENCE DESCRIPTION: SEQ ID NO: 486:

CGGUUCAGCU GAUGANGAAA ACAAUCG                                                                    27

( 2 ) INFORMATION FOR SEQ ID NO: 487:

( i ) SEQUENCE CHARACTERISTICS:
                    ( A ) LENGTH: 17 base pairs
                    ( B ) TYPE: nucleic acid
                    ( C ) STRANDEDNESS: single ( D ) TOPOLOGY: linear ( x i ) SEQUENCE DESCRIPTION: SEQ ID NO: 487:

CGAUUGUUCC UGAACCG 17

( 2 ) INFORMATION FOR SEQ ID NO: 488:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i x ) FEATURE:
  ( D ) OTHER INFORMATION: The letter "N"stands for the stem II region of a HH ribozyme.

( x i ) SEQUENCE DESCRIPTION: SEQ ID NO: 488:

AGAAACUUCU GAUGANGAAA UUUCUCA 27

( 2 ) INFORMATION FOR SEQ ID NO: 489:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 489:

UGAGAAAUAA AGUUUCU 17

( 2 ) INFORMATION FOR SEQ ID NO: 490:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i x ) FEATURE:
  ( D ) OTHER INFORMATION: The letter "N"stands for the stem II region of a HH ribozyme.

( x i ) SEQUENCE DESCRIPTION: SEQ ID NO: 490:

UCAACAGACU GAUGANGAAA CUUUAUU 27

( 2 ) INFORMATION FOR SEQ ID NO: 491:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 491:

AAUAAAGUUU CUGUUGA 17

( 2 ) INFORMATION FOR SEQ ID NO: 492:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i x ) FEATURE:
  ( D ) OTHER INFORMATION: The letter "N"stands for the stem II region of a HH ribozyme.

( x i ) SEQUENCE DESCRIPTION: SEQ ID NO: 492:

AUCAACAGCU GAUGANGAAA ACUUUAU 27

(2) INFORMATION FOR SEQ ID NO: 493:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 493:

AUAAAGUUUC UGUUGAU 17

(2) INFORMATION FOR SEQ ID NO: 494:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N"stands for the stem II
            region of a HH ribozyme.

(xi) SEQUENCE DESCRIPTION: SEQ ID NO: 494:

UAUCAACACU GAUGANGAAA AACUUUA 27

(2) INFORMATION FOR SEQ ID NO: 495:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 495:

UAAAGUUUCU GUUGAUA 17

(2) INFORMATION FOR SEQ ID NO: 496:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N"stands for the stem II
            region of a HH ribozyme.

(xi) SEQUENCE DESCRIPTION: SEQ ID NO: 496:

UGAUUAUCCU GAUGANGAAA CAGAAAC 27

(2) INFORMATION FOR SEQ ID NO: 497:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 497:

GUUUCUGUUG AUAAUCA 17

(2) INFORMATION FOR SEQ ID NO: 498:

(i) SEQUENCE CHARACTERISTICS:

(A) LENGTH: 54 base pairs
(B) TYPE: nucleic acid
(C) STRANDEDNESS: single
(D) TOPOLOGY: linear (xi) SEQUENCE DESCRIPTION: SEQ ID NO: 498:

GCAGGGGCAG AAGCAGGAAC CAGAGAAACA CACGUUGUGG UACAUUACCU GGUA    54

(2) INFORMATION FOR SEQ ID NO: 499:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO: 499:

UCCUGCAGCU GCCCCUGC    18

(2) INFORMATION FOR SEQ ID NO: 500:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO: 500:

CCAGCAGGAG AAGCUGCAAC CAGAGAAACA CACGUUGUGG UACAUUACCU GGUA    54

(2) INFORMATION FOR SEQ ID NO: 501:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO: 501:

UGCAGCUGCC CCUGCUGG    18

(2) INFORMATION FOR SEQ ID NO: 502:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO: 502:

CCACUCCCAG AAGGGGCAAC CAGAGAAACA CACGUUGUGG UACAUUACCU GGUA    54

(2) INFORMATION FOR SEQ ID NO: 503:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO: 503:

UGCCCCUGCU GGGAGUGG    18

(2) INFORMATION FOR SEQ ID NO: 504:

(i) SEQUENCE CHARACTERISTICS:
(A) LENGTH: 54 base pairs
(B) TYPE: nucleic acid ( C ) STRANDEDNESS: single
( D ) TOPOLOGY: linear ( x i ) SEQUENCE DESCRIPTION: SEQ ID NO: 504:

CAUUGGGCAG AAGAAUUGAC CAGAGAAACA CACGUUGUGG UACAUUACCU GGUA          54

( 2 ) INFORMATION FOR SEQ ID NO: 505:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO: 505:

CAAUUCUGAC GCCCAAUG          18

( 2 ) INFORMATION FOR SEQ ID NO: 506:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO: 506:

AAGAAAUCAG AAGUGGUGAC CAGAGAAACA CACGUUGUGG UACAUUACCU GGUA          54

( 2 ) INFORMATION FOR SEQ ID NO: 507:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO: 507:

CACCACAGCU GAUUUCUU          18

( 2 ) INFORMATION FOR SEQ ID NO: 508:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO: 508:

AGGAAGAAAG AAGCUGUGAC CAGAGAAACA CACGUUGUGG UACAUUACCU GGUA          54

( 2 ) INFORMATION FOR SEQ ID NO: 509:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO: 509:

CACAGCUGAU UUCUUCCU          18

( 2 ) INFORMATION FOR SEQ ID NO: 510:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO: 510:

GCAUAGUGAG AAGGAAGAAC CAGAGAAACA CACGUUGUGG UACAUUACCU GGUA        54

( 2 ) INFORMATION FOR SEQ ID NO: 511:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 511:

UCUUCCUGAC CACUAUGC        18

( 2 ) INFORMATION FOR SEQ ID NO: 512:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 512:

CUGAGGGAAG AAGUGGCAC CAGAGAAACA CACGUUGUGG UACAUUACCU GGUA        54

( 2 ) INFORMATION FOR SEQ ID NO: 513:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 513:

GCCCACUGAC UCCCUCAG        18

( 2 ) INFORMATION FOR SEQ ID NO: 514:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 514:

CUGGGAGGAG AAGAGUGGAC CAGAGAAACA CACGUUGUGG UACAUUACCU GGUA        54

( 2 ) INFORMATION FOR SEQ ID NO: 515:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 515:

CCACUCUGCC CCUCCCAG        18

( 2 ) INFORMATION FOR SEQ ID NO: 516:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 516:

```
GGGCUCAGAG  AAGCUGUUAC  CAGAGAAACA  CACGUUGUGG  UACAUUACCU  GGUA                54
```

( 2 ) INFORMATION FOR SEQ ID NO: 517:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 517:

```
AACAGCAGCU  CUGAGCCC                                                            18
```

( 2 ) INFORMATION FOR SEQ ID NO: 518:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 518:

```
GGUUGGUAAG  AAGGGCUAC   CAGAGAAACA  CACGUUGUGG  UACAUUACCU  GGUA                54
```

( 2 ) INFORMATION FOR SEQ ID NO: 519:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 519:

```
AGCCCAGCC   UACCAACC                                                            18
```

( 2 ) INFORMATION FOR SEQ ID NO: 520:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 520:

```
UUUUUUGCAG  AAGACAGCAC  CAGAGAAACA  CACGUUGUGG  UACAUUACCU  GGUA                54
```

( 2 ) INFORMATION FOR SEQ ID NO: 521:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 521:

```
GCUGUCAGUU  GCAAAAAA                                                            18
```

( 2 ) INFORMATION FOR SEQ ID NO: 522:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 522:

```
GGUCCUGGAG  AAGAACAAAC  CAGAGAAACA  CACGUUGUGG  UACAUUACCU  GGUA                54
```

( 2 ) INFORMATION FOR SEQ ID NO: 523:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 523:

UUGUUCAGCU CCAGGACC                                  18

( 2 ) INFORMATION FOR SEQ ID NO: 524:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 524:

GUUUUAGCAG AAGUGUGGAC CAGAGAAACA CACGUUGUGG UACAUUACCU GGUA      54

( 2 ) INFORMATION FOR SEQ ID NO: 525:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 525:

CCACACAGAU GCUAAAAC                                     18

( 2 ) INFORMATION FOR SEQ ID NO: 526:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 526:

GUUCAAGAAG AAGUUGUUAC CAGAGAAACA CACGUUGUGG UACAUUACCU GGUA      54

( 2 ) INFORMATION FOR SEQ ID NO: 527:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 527:

AACAACAGAU UCUUGAAC                                     18

( 2 ) INFORMATION FOR SEQ ID NO: 528:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 528:

GUGCUCCAAG AAGUGGUUAC CAGAGAAACA CACGUUGUGG UACAUUACCU GGUA      54

( 2 ) INFORMATION FOR SEQ ID NO: 529:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 529:

AACCACUGUU UGGAGCAC                                                  18

( 2 ) INFORMATION FOR SEQ ID NO: 530:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 530:

CCCAGUCAAG AAGGUACUAC CAGAGAAACA CACGUUGUGG UACAUUACCU GGUA    54

( 2 ) INFORMATION FOR SEQ ID NO: 531:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 531:

AGUACCGGAC UGACUGGG                                                  18

( 2 ) INFORMATION FOR SEQ ID NO: 532:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 532:

UGGUCCCAAG AAGUCCGGAC CAGAGAAACA CACGUUGUGG UACAUUACCU GGUA    54

( 2 ) INFORMATION FOR SEQ ID NO: 533:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 533:

CCGGACUGAC UGGGACCA                                                  18

( 2 ) INFORMATION FOR SEQ ID NO: 534:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 534:

UUCAGUCCAG AAGUGGUCAC CAGAGAAACA CACGUUGUGG UACAUUACCU GGUA    54

( 2 ) INFORMATION FOR SEQ ID NO: 535:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 535:

GACCACAGCU GGACUGAA 18

( 2 ) INFORMATION FOR SEQ ID NO: 536:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 536:

UGGGUUAAAG AAGCUCCGAC CAGAGAAACA CACGUUGUGG UACAUUACCU GGUA 54

( 2 ) INFORMATION FOR SEQ ID NO: 537:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 537:

CGGAGCCGCU UUAACCCA 18

( 2 ) INFORMATION FOR SEQ ID NO: 538:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 538:

CCAAUGCAAG AAGGAAAGAC CAGAGAAACA CACGUUGUGG UACAUUACCU GGUA 54

( 2 ) INFORMATION FOR SEQ ID NO: 539:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 539:

CUUUCCUGUU UGCAUUGG 18

( 2 ) INFORMATION FOR SEQ ID NO: 540:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 540:

AUGGAGCCAG AAGAGAUAAC CAGAGAAACA CACGUUGUGG UACAUUACCU GGUA 54

( 2 ) INFORMATION FOR SEQ ID NO: 541:

( i ) SEQUENCE CHARACTERISTICS:
    ( A ) LENGTH: 18 base pairs ( B ) TYPE: nucleic acid
        ( C ) STRANDEDNESS: single
        ( D ) TOPOLOGY: linear ( x i ) SEQUENCE DESCRIPTION: SEQ ID NO: 541:

UAUCUCUGUU GGCUCCAU 18

( 2 ) INFORMATION FOR SEQ ID NO: 542:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 542:

ACAGAGAAAG AAGAUAAUAC CAGAGAAACA CACGUUGUGG UACAUUACCU GGUA 54

( 2 ) INFORMATION FOR SEQ ID NO: 543:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 543:

AUUAUCAGCC UUCUCUGU 18

( 2 ) INFORMATION FOR SEQ ID NO: 544:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 544:

GGGGCAUCAG AAGUUCCAAC CAGAGAAACA CACGUUGUGG UACAUUACCU GGUA 54

( 2 ) INFORMATION FOR SEQ ID NO: 545:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 545:

UGGAACGGAC GAUGCCCC 18

( 2 ) INFORMATION FOR SEQ ID NO: 546:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 546:

CCACUCCAAG AAGAAAAGAC CAGAGAAACA CACGUUGUGG UACAUUACCU GGUA 54

( 2 ) INFORMATION FOR SEQ ID NO: 547:

( i ) SEQUENCE CHARACTERISTICS:
        ( A ) LENGTH: 18 base pairs
        ( B ) TYPE: nucleic acid
        ( C ) STRANDEDNESS: single (D) TOPOLOGY: linear (xi) SEQUENCE DESCRIPTION: SEQ ID NO: 547:

CUUUUCGGCC UGGAGUGG 18

(2) INFORMATION FOR SEQ ID NO: 548:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 548:

UCACUGUAAG AAGGCUGCAC CAGAGAAACA CACGUUGUGG UACAUUACCU GGUA 54

(2) INFORMATION FOR SEQ ID NO: 549:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 549:

GCAGCCAGAC UACAGUGA 18

(2) INFORMATION FOR SEQ ID NO: 550:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 550:

ACUGACGAAG AAGAGUCGAC CAGAGAAACA CACGUUGUGG UACAUUACCU GGUA 54

(2) INFORMATION FOR SEQ ID NO: 551:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 551:

CGACUCUGCC UCGUCAGU 18

(2) INFORMATION FOR SEQ ID NO: 552:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 552:

AAUUCCAAAG AAGCCACAAC CAGAGAAACA CACGUUGUGG UACAUUACCU GGUA 54

(2) INFORMATION FOR SEQ ID NO: 553:

(i) SEQUENCE CHARACTERISTICS:
        (A) LENGTH: 18 base pairs
        (B) TYPE: nucleic acid
        (C) STRANDEDNESS: single
        (D) TOPOLOGY: linear ( x i ) SEQUENCE DESCRIPTION: SEQ ID NO: 553:

UGUGGCUGAU UUGGAAUU  18

( 2 ) INFORMATION FOR SEQ ID NO: 554:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 554:

AAGGGCCAAG AAGAGGGAAC CAGAGAAACA CACGUUGUGG UACAUUACCU GGUA  54

( 2 ) INFORMATION FOR SEQ ID NO: 555:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 555:

UCCCUCAGUC UGGCCCUU  18

( 2 ) INFORMATION FOR SEQ ID NO: 556:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 556:

CAGGAACAAG AAGAGGGUAC CAGAGAAACA CACGUUGUGG UACAUUACCU GGUA  54

( 2 ) INFORMATION FOR SEQ ID NO: 557:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 557:

ACCCUCCGAU UGUUCCUG  18

( 2 ) INFORMATION FOR SEQ ID NO: 558:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 558:

UAUUUCUCAG AAGUUCAGAC CAGAGAAACA CACGUUGUGG UACAUUACCU GGUA  54

( 2 ) INFORMATION FOR SEQ ID NO: 559:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 559:

```
CUGAACCGAU GAGAAAUA                                                              18
```

(2) INFORMATION FOR SEQ ID NO: 560:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 560:

```
UGAUUAUCAG AAGAAACUAC CAGAGAAACA CACGUUGUGG UACAUUACCU GGUA                      54
```

(2) INFORMATION FOR SEQ ID NO: 561:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 561:

```
AGUUUCUGUU GAUAAUCA                                                              18
```

(2) INFORMATION FOR SEQ ID NO: 562:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 562:

```
AUAGUUUCCU GAUGANGAAA CAUGGUG                                                    27
```

(2) INFORMATION FOR SEQ ID NO: 563:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 563:

```
CACCAUGUUG AAACUAU                                                               17
```

(2) INFORMATION FOR SEQ ID NO: 564:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 564:

```
GACAAUAACU GAUGANGAAA GUUUCAA                                                    27
```

(2) INFORMATION FOR SEQ ID NO: 565:

(i) SEQUENCE CHARACTERISTICS:
        (A) LENGTH: 17 base pairs (B) TYPE: nucleic acid
(C) STRANDEDNESS: single
(D) TOPOLOGY: linear (xi) SEQUENCE DESCRIPTION: SEQ ID NO: 565:

UUGAAACUAU UAUUGUC                                                                 17

(2) INFORMATION FOR SEQ ID NO: 566:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 566:

GUGACAAUCU GAUGANGAAA UAGUUUC                                                      27

(2) INFORMATION FOR SEQ ID NO: 567:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 567:

GAAACUAUUA UUGUCAC                                                                 17

(2) INFORMATION FOR SEQ ID NO: 568:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 568:

GGUGACAACU GAUGANGAAA AUAGUUU                                                      27

(2) INFORMATION FOR SEQ ID NO: 569:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 569:

AAACUAUUAU UGUCACC                                                                 17

(2) INFORMATION FOR SEQ ID NO: 570:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

( x i ) SEQUENCE DESCRIPTION: SEQ ID NO: 570:

UAGGUGACCU GAUGANGAAA UAAUAGU 27

( 2 ) INFORMATION FOR SEQ ID NO: 571:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 571:

ACUAUUAUUG UCACCUA 17

( 2 ) INFORMATION FOR SEQ ID NO: 572:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 572:

AUCUAGGUCU GAUGANGAAA CAAUAAU 27

( 2 ) INFORMATION FOR SEQ ID NO: 573:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 573:

AUUAUUGUCA CCUAGAU 17

( 2 ) INFORMATION FOR SEQ ID NO: 574:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 574:

GAAGGAUCCU GAUGANGAAA GGUGACA 27

( 2 ) INFORMATION FOR SEQ ID NO: 575:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 575:

UGUCACCUAG AUCCUUC 17

( 2 ) INFORMATION FOR SEQ ID NO: 576:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 576:

CUAAGAAGCU GAUGANGAAA UCUAGGU                                       27

( 2 ) INFORMATION FOR SEQ ID NO: 577:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 577:

ACCUAGAUCC UUCUUAG                                                  17

( 2 ) INFORMATION FOR SEQ ID NO: 578:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 578:

GGACUAAGCU GAUGANGAAA GGAUCUA                                       27

( 2 ) INFORMATION FOR SEQ ID NO: 579:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 579:

UAGAUCCUUC UUAGUCC                                                  17

( 2 ) INFORMATION FOR SEQ ID NO: 580:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 580:

AGGACUAACU GAUGANGAAA AGGAUCU                                       27

( 2 ) INFORMATION FOR SEQ ID NO: 581:

( i ) SEQUENCE CHARACTERISTICS:
        ( A ) LENGTH: 17 base pairs (B) TYPE: nucleic acid
                (C) STRANDEDNESS: single
                (D) TOPOLOGY: linear (xi) SEQUENCE DESCRIPTION: SEQ ID NO: 581:

AGAUCCUUCU UAGUCCU                                                                        17

(2) INFORMATION FOR SEQ ID NO: 582:

(i) SEQUENCE CHARACTERISTICS:
                (A) LENGTH: 27 base pairs
                (B) TYPE: nucleic acid
                (C) STRANDEDNESS: single
                (D) TOPOLOGY: linear (ix) FEATURE:
                (D) OTHER INFORMATION: The letter "N" stands for the stem II
                        region of a HH ribozyme.

(xi) SEQUENCE DESCRIPTION: SEQ ID NO: 582:

GAAGGACUCU GAUGANGAAA GAAGGAU                                                             27

(2) INFORMATION FOR SEQ ID NO: 583:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO: 583:

AUCCUUCUUA GUCCUUC                                                                        17

(2) INFORMATION FOR SEQ ID NO: 584:

(i) SEQUENCE CHARACTERISTICS:
                (A) LENGTH: 27 base pairs
                (B) TYPE: nucleic acid
                (C) STRANDEDNESS: single
                (D) TOPOLOGY: linear (ix) FEATURE:
                (D) OTHER INFORMATION: The letter "N" stands for the stem II
                        region of a HH ribozyme.

(xi) SEQUENCE DESCRIPTION: SEQ ID NO: 584:

UGAAGGACCU GAUGANGAAA AGAAGGA                                                             27

(2) INFORMATION FOR SEQ ID NO: 585:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO: 585:

UCCUUCUUAG UCCUUCA                                                                        17

(2) INFORMATION FOR SEQ ID NO: 586:

(i) SEQUENCE CHARACTERISTICS:
                (A) LENGTH: 27 base pairs
                (B) TYPE: nucleic acid
                (C) STRANDEDNESS: single
                (D) TOPOLOGY: linear (ix) FEATURE:
                (D) OTHER INFORMATION: The letter "N" stands for the stem II
                        region of a HH ribozyme.

( x i ) SEQUENCE DESCRIPTION: SEQ ID NO: 586:

AGCUGAAGCU GAUGANGAAA CUAAGAA 27

( 2 ) INFORMATION FOR SEQ ID NO: 587:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 587:

UUCUUAGUCC UUCAGCU 17

( 2 ) INFORMATION FOR SEQ ID NO: 588:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II
region of a HH ribozyme.

( x i ) SEQUENCE DESCRIPTION: SEQ ID NO: 588:

AGCAGCUGCU GAUGANGAAA GGACUAA 27

( 2 ) INFORMATION FOR SEQ ID NO: 589:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 589:

UUAGUCCUUC AGCUGCU 17

( 2 ) INFORMATION FOR SEQ ID NO: 590:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II
region of a HH ribozyme.

( x i ) SEQUENCE DESCRIPTION: SEQ ID NO: 590:

GAGCAGCUCU GAUGANGAAA AGGACUA 27

( 2 ) INFORMATION FOR SEQ ID NO: 591:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 591:

UAGUCCUUCA GCUGCUC 17

( 2 ) INFORMATION FOR SEQ ID NO: 592:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i x ) FEATURE:
  ( D ) OTHER INFORMATION: The letter "N"stands for the stem II region of a HH ribozyme.

( x i ) SEQUENCE DESCRIPTION: SEQ ID NO: 592:

CUCAGCAGCU GAUGANGAAA GCAGCUG 27

( 2 ) INFORMATION FOR SEQ ID NO: 593:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 593:

CAGCUGCUCC UGCUGAG 17

( 2 ) INFORMATION FOR SEQ ID NO: 594:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 594:

GGACCUUGCU GAUGANGAAA GCUCCAC 27

( 2 ) INFORMATION FOR SEQ ID NO: 595:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 595:

GUGGAGCUCC AAGGUCC 17

( 2 ) INFORMATION FOR SEQ ID NO: 596:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 596:

GACAUGAGCU GAUGANGAAA CCUUGGA 27

( 2 ) INFORMATION FOR SEQ ID NO: 597:

( i ) SEQUENCE CHARACTERISTICS:
    ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO: 597:

UCCAAGGUCC UCAUGUC 17

(2) INFORMATION FOR SEQ ID NO: 598:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 598:

CUGGACAUCU GAUGANGAAA GGACCUU 27

(2) INFORMATION FOR SEQ ID NO: 599:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 599:

AAGGUCCUCA UGUCCAG 17

(2) INFORMATION FOR SEQ ID NO: 600:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 600:

UCGCACUGCU GAUGANGAAA CAUGAGG 27

(2) INFORMATION FOR SEQ ID NO: 601:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 601:

CCUCAUGUCC AGUGCGA 17

(2) INFORMATION FOR SEQ ID NO: 602:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

( x i ) SEQUENCE DESCRIPTION: SEQ ID NO: 602:

UCAGCUUUCU GAUGANGAAA UGUCUUC                27

( 2 ) INFORMATION FOR SEQ ID NO: 603:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 603:

GAAGACAUCA AAGCUGA                17

( 2 ) INFORMATION FOR SEQ ID NO: 604:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 604:

CAGGAUCACU GAUGANGAAA UCAGCUU                27

( 2 ) INFORMATION FOR SEQ ID NO: 605:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 605:

AAGCUGAUUU GAUCCUG                17

( 2 ) INFORMATION FOR SEQ ID NO: 606:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 606:

UCAGGAUCCU GAUGANGAAA AUCAGCU                27

( 2 ) INFORMATION FOR SEQ ID NO: 607:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 607:

AGCUGAUUUG AUCCUGA                17

( 2 ) INFORMATION FOR SEQ ID NO: 608:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II
        region of a HH ribozyme.

( x i ) SEQUENCE DESCRIPTION: SEQ ID NO: 608:

GAAGUCAGCU GAUGANGAAA UCAAAUC 27

( 2 ) INFORMATION FOR SEQ ID NO: 609:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 609:

GAUUUGAUCC UGACUUC 17

( 2 ) INFORMATION FOR SEQ ID NO: 610:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II
        region of a HH ribozyme.

( x i ) SEQUENCE DESCRIPTION: SEQ ID NO: 610:

GGCUGUAGCU GAUGANGAAA GUCAGGA 27

( 2 ) INFORMATION FOR SEQ ID NO: 611:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 611:

UCCUGACUUC UACAGCC 17

( 2 ) INFORMATION FOR SEQ ID NO: 612:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II
        region of a HH ribozyme.

( x i ) SEQUENCE DESCRIPTION: SEQ ID NO: 612:

GGGCUGUACU GAUGANGAAA AGUCAGG 27

( 2 ) INFORMATION FOR SEQ ID NO: 613:

( i ) SEQUENCE CHARACTERISTICS:
    ( A ) LENGTH: 17 base pairs (B) TYPE: nucleic acid
        (C) STRANDEDNESS: single
        (D) TOPOLOGY: linear (xi) SEQUENCE DESCRIPTION: SEQ ID NO: 613:

CCUGACUUCU ACAGCCC 17

(2) INFORMATION FOR SEQ ID NO: 614:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 614:

AGGGGCUGCU GAUGANGAAA GAAGUCA 27

(2) INFORMATION FOR SEQ ID NO: 615:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 615:

UGACUUCUAC AGCCCCU 17

(2) INFORMATION FOR SEQ ID NO: 616:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 616:

GGAGCACUCU GAUGANGAAA GGUGUUC 27

(2) INFORMATION FOR SEQ ID NO: 617:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 617:

GAACACCUCA GUGCUCC 17

(2) INFORMATION FOR SEQ ID NO: 618:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

( x i ) SEQUENCE DESCRIPTION: SEQ ID NO: 618:

CAGAGUAGCU GAUGANGAAA GCACUGA 27

( 2 ) INFORMATION FOR SEQ ID NO: 619:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 619:

UCAGUGCUCC UACUCUG 17

( 2 ) INFORMATION FOR SEQ ID NO: 620:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for the stem II
         region of a HH ribozyme.

( x i ) SEQUENCE DESCRIPTION: SEQ ID NO: 620:

GGGCAGAGCU GAUGANGAAA GGAGCAC 27

( 2 ) INFORMATION FOR SEQ ID NO: 621:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 621:

GUGCUCCUAC UCUGCCC 17

( 2 ) INFORMATION FOR SEQ ID NO: 622:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for the stem II
         region of a HH ribozyme.

( x i ) SEQUENCE DESCRIPTION: SEQ ID NO: 622:

AAGGGGCACU GAUGANGAAA GUAGGAG 27

( 2 ) INFORMATION FOR SEQ ID NO: 623:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 623:

CUCCUACUCU GCCCCUU 17

( 2 ) INFORMATION FOR SEQ ID NO: 624:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i x ) FEATURE:
  ( D ) OTHER INFORMATION: The letter "N" stands for the stem II region of a HH ribozyme.

( x i ) SEQUENCE DESCRIPTION: SEQ ID NO: 624:

ACCUCUGGCU GAUGANGAAA GGGGCAG                                      27

( 2 ) INFORMATION FOR SEQ ID NO: 625:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 625:

CUGCCCCUUC CAGAGGU                                                 17

( 2 ) INFORMATION FOR SEQ ID NO: 626:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 626:

AACCUCUGCU GAUGANGAAA AGGGGCA                                      27

( 2 ) INFORMATION FOR SEQ ID NO: 627:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 627:

UGCCCCUUCC AGAGGUU                                                 17

( 2 ) INFORMATION FOR SEQ ID NO: 628:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 628:

AAGCACUGCU GAUGANGAAA CCUCUGG                                      27

( 2 ) INFORMATION FOR SEQ ID NO: 629:

( i ) SEQUENCE CHARACTERISTICS:
    ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO: 629:

CCAGAGGUUC AGUGCUU                                                                                        17

(2) INFORMATION FOR SEQ ID NO: 630:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ix) FEATURE:
    (D) OTHER INFORMATION: The letter "N" stands for the stem II
        region of a HH ribozyme.

(xi) SEQUENCE DESCRIPTION: SEQ ID NO: 630:

AAAGCACUCU GAUGANGAAA ACCUCUG                                                                             27

(2) INFORMATION FOR SEQ ID NO: 631:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO: 631:

CAGAGGUUCA GUGCUUU                                                                                        17

(2) INFORMATION FOR SEQ ID NO: 632:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ix) FEATURE:
    (D) OTHER INFORMATION: The letter "N" stands for the stem II
        region of a HH ribozyme.

(xi) SEQUENCE DESCRIPTION: SEQ ID NO: 632:

UGAACACACU GAUGANGAAA GCACUGA                                                                             27

(2) INFORMATION FOR SEQ ID NO: 633:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO: 633:

UCAGUGCUUU GUGUUCA                                                                                        17

(2) INFORMATION FOR SEQ ID NO: 634:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ix) FEATURE:
    (D) OTHER INFORMATION: The letter "N" stands for the stem II
        region of a HH ribozyme.

( x i ) SEQUENCE DESCRIPTION: SEQ ID NO: 634:

UUGAACACCU GAUGANGAAA AGCACUG 27

( 2 ) INFORMATION FOR SEQ ID NO: 635:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 635:

CAGUGCUUUG UGUUCAA 17

( 2 ) INFORMATION FOR SEQ ID NO: 636:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 636:

CUAUGUUGCU GAUGANGAAA CACAAAG 27

( 2 ) INFORMATION FOR SEQ ID NO: 637:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 637:

CUUUGUGUUC AACAUAG 17

( 2 ) INFORMATION FOR SEQ ID NO: 638:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 638:

UCUAUGUUCU GAUGANGAAA ACACAAA 27

( 2 ) INFORMATION FOR SEQ ID NO: 639:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 639:

UUUGUGUUCA ACAUAGA 17

( 2 ) INFORMATION FOR SEQ ID NO: 640:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 640:

AUGUACUCCU GAUGANGAAA UGUUGAA 27

( 2 ) INFORMATION FOR SEQ ID NO: 641:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 641:

UUCAACAUAG AGUACAU 17

( 2 ) INFORMATION FOR SEQ ID NO: 642:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II region of a HH ribozyme.

( x i ) SEQUENCE DESCRIPTION: SEQ ID NO: 642:

AAUUCAUGCU GAUGANGAAA CUCUAUG 27

( 2 ) INFORMATION FOR SEQ ID NO: 643:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 643:

CAUAGAGUAC AUGAAUU 17

( 2 ) INFORMATION FOR SEQ ID NO: 644:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II region of a HH ribozyme.

( x i ) SEQUENCE DESCRIPTION: SEQ ID NO: 644:

CCAAGUGCCU GAUGANGAAA UUCAUGU 27

( 2 ) INFORMATION FOR SEQ ID NO: 645:

( i ) SEQUENCE CHARACTERISTICS:
        ( A ) LENGTH: 17 base pairs

-continued ( B ) TYPE: nucleic acid
       ( C ) STRANDEDNESS: single
       ( D ) TOPOLOGY: linear ( x i ) SEQUENCE DESCRIPTION: SEQ ID NO: 645:

ACAUGAAUUG CACUUGG                                                                                        17

( 2 ) INFORMATION FOR SEQ ID NO: 646:

( i ) SEQUENCE CHARACTERISTICS:
       ( A ) LENGTH: 27 base pairs
       ( B ) TYPE: nucleic acid
       ( C ) STRANDEDNESS: single
       ( D ) TOPOLOGY: linear ( i x ) FEATURE:
       ( D ) OTHER INFORMATION: The letter "N"stands for the stem II
             region of a HH ribozyme.

( x i ) SEQUENCE DESCRIPTION: SEQ ID NO: 646:

GCUAUUCCCU GAUGANGAAA GUGCAAU                                                                             27

( 2 ) INFORMATION FOR SEQ ID NO: 647:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO: 647:

AUUGCACUUG GAAUAGC                                                                                        17

( 2 ) INFORMATION FOR SEQ ID NO: 648:

( i ) SEQUENCE CHARACTERISTICS:
       ( A ) LENGTH: 27 base pairs
       ( B ) TYPE: nucleic acid
       ( C ) STRANDEDNESS: single
       ( D ) TOPOLOGY: linear ( i x ) FEATURE:
       ( D ) OTHER INFORMATION: The letter "N"stands for the stem II
             region of a HH ribozyme.

( x i ) SEQUENCE DESCRIPTION: SEQ ID NO: 648:

AGAACUGCCU GAUGANGAAA UUCCAAG                                                                             27

( 2 ) INFORMATION FOR SEQ ID NO: 649:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO: 649:

CUUGGAAUAG CAGUUCU                                                                                        17

( 2 ) INFORMATION FOR SEQ ID NO: 650:

( i ) SEQUENCE CHARACTERISTICS:
       ( A ) LENGTH: 27 base pairs
       ( B ) TYPE: nucleic acid
       ( C ) STRANDEDNESS: single
       ( D ) TOPOLOGY: linear ( i x ) FEATURE:
       ( D ) OTHER INFORMATION: The letter "N"stands for the stem II
             region of a HH ribozyme.

( x i ) SEQUENCE DESCRIPTION: SEQ ID NO: 650:

AGGCUCAGCU GAUGANGAAA CUGCUAU                    27

( 2 ) INFORMATION FOR SEQ ID NO: 651:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 651:

AUAGCAGUUC UGAGCCU                    17

( 2 ) INFORMATION FOR SEQ ID NO: 652:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 652:

GAGGCUCACU GAUGANGAAA ACUGCUA                    27

( 2 ) INFORMATION FOR SEQ ID NO: 653:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 653:

UAGCAGUUCU GAGCCUC                    17

( 2 ) INFORMATION FOR SEQ ID NO: 654:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 654:

GGUUGCCUCU GAUGANGAAA GGCUCAG                    27

( 2 ) INFORMATION FOR SEQ ID NO: 655:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 655:

CUGAGCCUCA GGCAACC                    17

( 2 ) INFORMATION FOR SEQ ID NO: 656:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 656:

UGCAGCGUCU GAUGANGAAA GGUUGGU         27

( 2 ) INFORMATION FOR SEQ ID NO: 657:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 657:

ACCAACCUCA CGCUGCA         17

( 2 ) INFORMATION FOR SEQ ID NO: 658:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 658:

UGUACCUACU GAUGANGAAA GUGCAGC         27

( 2 ) INFORMATION FOR SEQ ID NO: 659:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 659:

GCUGCACUAU AGGUACA         17

( 2 ) INFORMATION FOR SEQ ID NO: 660:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 660:

CUUGUACCCU GAUGANGAAA UAGUGCA         27

( 2 ) INFORMATION FOR SEQ ID NO: 661:

( i ) SEQUENCE CHARACTERISTICS:
        ( A ) LENGTH: 17 base pairs ( B ) TYPE: nucleic acid
( C ) STRANDEDNESS: single
( D ) TOPOLOGY: linear ( x i ) SEQUENCE DESCRIPTION: SEQ ID NO: 661:

UGCACUAUAG GUACAAG 17

( 2 ) INFORMATION FOR SEQ ID NO: 662:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for the stem II region of a HH ribozyme.

( x i ) SEQUENCE DESCRIPTION: SEQ ID NO: 662:

AUACCUUGCU GAUGANGAAA CCUAUAG 27

( 2 ) INFORMATION FOR SEQ ID NO: 663:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 663:

CUAUAGGUAC AAGGUAU 17

( 2 ) INFORMATION FOR SEQ ID NO: 664:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for the stem II region of a HH ribozyme.

( x i ) SEQUENCE DESCRIPTION: SEQ ID NO: 664:

UUAUCAGACU GAUGANGAAA CCUUGUA 27

( 2 ) INFORMATION FOR SEQ ID NO: 665:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 665:

UACAAGGUAU CUGAUAA 17

( 2 ) INFORMATION FOR SEQ ID NO: 666:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for the stem II region of a HH ribozyme.

(x i) SEQUENCE DESCRIPTION: SEQ ID NO: 666:

UAUUAUCACU GAUGANGAAA UACCUUG 27

(2) INFORMATION FOR SEQ ID NO: 667:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (x i) SEQUENCE DESCRIPTION: SEQ ID NO: 667:

CAAGGUAUCU GAUAAUA 17

(2) INFORMATION FOR SEQ ID NO: 668:

(i) SEQUENCE CHARACTERISTICS:
  (A) LENGTH: 27 base pairs
  (B) TYPE: nucleic acid
  (C) STRANDEDNESS: single
  (D) TOPOLOGY: linear (i x) FEATURE:
  (D) OTHER INFORMATION: The letter "N"stands for the stem II region of a HH ribozyme.

(x i) SEQUENCE DESCRIPTION: SEQ ID NO: 668:

UGUAUUAUCU GAUGANGAAA UCAGAUA 27

(2) INFORMATION FOR SEQ ID NO: 669:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (x i) SEQUENCE DESCRIPTION: SEQ ID NO: 669:

UAUCUGAUAA UAAUACA 17

(2) INFORMATION FOR SEQ ID NO: 670:

(i) SEQUENCE CHARACTERISTICS:
  (A) LENGTH: 27 base pairs
  (B) TYPE: nucleic acid
  (C) STRANDEDNESS: single
  (D) TOPOLOGY: linear (i x) FEATURE:
  (D) OTHER INFORMATION: The letter "N"stands for the stem II region of a HH ribozyme.

(x i) SEQUENCE DESCRIPTION: SEQ ID NO: 670:

GAAUGUAUCU GAUGANGAAA UUAUCAG 27

(2) INFORMATION FOR SEQ ID NO: 671:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (x i) SEQUENCE DESCRIPTION: SEQ ID NO: 671:

CUGAUAAUAA UACAUUC 17

(2) INFORMATION FOR SEQ ID NO: 672:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II
    region of a HH ribozyme.

( x i ) SEQUENCE DESCRIPTION: SEQ ID NO: 672:

CUGGAAUGCU GAUGANGAAA UUAUUAU 27

( 2 ) INFORMATION FOR SEQ ID NO: 673:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 673:

AUAAUAAUAC AUUCCAG 17

( 2 ) INFORMATION FOR SEQ ID NO: 674:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II
    region of a HH ribozyme.

( x i ) SEQUENCE DESCRIPTION: SEQ ID NO: 674:

ACUCCUGGCU GAUGANGAAA UGUAUUA 27

( 2 ) INFORMATION FOR SEQ ID NO: 675:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 675:

UAAUACAUUC CAGGAGU 17

( 2 ) INFORMATION FOR SEQ ID NO: 676:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II
    region of a HH ribozyme.

( x i ) SEQUENCE DESCRIPTION: SEQ ID NO: 676:

CACUCCUGCU GAUGANGAAA AUGUAUU 27

( 2 ) INFORMATION FOR SEQ ID NO: 677:

( i ) SEQUENCE CHARACTERISTICS:
    ( A ) LENGTH: 17 base pairs ( B ) TYPE: nucleic acid
            ( C ) STRANDEDNESS: single
            ( D ) TOPOLOGY: linear ( x i ) SEQUENCE DESCRIPTION: SEQ ID NO: 677:

AAUACAUUCC AGGAGUG                                                                              17

( 2 ) INFORMATION FOR SEQ ID NO: 678:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i x ) FEATURE:
            ( D ) OTHER INFORMATION: The letter "N"stands for the stem II
                  region of a HH ribozyme.

( x i ) SEQUENCE DESCRIPTION: SEQ ID NO: 678:

CAAAUAGUCU GAUGANGAAA CUGCACU                                                                   27

( 2 ) INFORMATION FOR SEQ ID NO: 679:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 679:

AGUGCAGUCA CUAUUUG                                                                              17

( 2 ) INFORMATION FOR SEQ ID NO: 680:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i x ) FEATURE:
            ( D ) OTHER INFORMATION: The letter "N"stands for the stem II
                  region of a HH ribozyme.

( x i ) SEQUENCE DESCRIPTION: SEQ ID NO: 680:

AGAACAAACU GAUGANGAAA GUGACUG                                                                   27

( 2 ) INFORMATION FOR SEQ ID NO: 681:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 681:

CAGUCACUAU UUGUUCU                                                                              17

( 2 ) INFORMATION FOR SEQ ID NO: 682:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i x ) FEATURE:
            ( D ) OTHER INFORMATION: The letter "N"stands for the stem II
                  region of a HH ribozyme.

( x i ) SEQUENCE DESCRIPTION: SEQ ID NO: 682:

GGAGAACACU GAUGANGAAA UAGUGAC 27

( 2 ) INFORMATION FOR SEQ ID NO: 683:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 683:

GUCACUAUUU GUUCUCC 17

( 2 ) INFORMATION FOR SEQ ID NO: 684:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II
region of a HH ribozyme.

( x i ) SEQUENCE DESCRIPTION: SEQ ID NO: 684:

UGGAGAACCU GAUGANGAAA AUAGUGA 27

( 2 ) INFORMATION FOR SEQ ID NO: 685:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 685:

UCACUAUUUG UUCUCCA 17

( 2 ) INFORMATION FOR SEQ ID NO: 686:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II
region of a HH ribozyme.

( x i ) SEQUENCE DESCRIPTION: SEQ ID NO: 686:

CUUUGGAGCU GAUGANGAAA CAAAUAG 27

( 2 ) INFORMATION FOR SEQ ID NO: 687:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 687:

CUAUUUGUUC UCCAAAG 17

( 2 ) INFORMATION FOR SEQ ID NO: 688:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i x ) FEATURE:
  ( D ) OTHER INFORMATION: The letter "N" stands for the stem II region of a HH ribozyme.

( x i ) SEQUENCE DESCRIPTION: SEQ ID NO: 688:

UCUUUGGACU GAUGANGAAA ACAAAUA 27

( 2 ) INFORMATION FOR SEQ ID NO: 689:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 689:

UAUUUGUUCU CCAAAGA 17

( 2 ) INFORMATION FOR SEQ ID NO: 690:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 690:

UCUCUUUGCU GAUGANGAAA GAACAAA 27

( 2 ) INFORMATION FOR SEQ ID NO: 691:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 691:

UUUGUUCUCC AAAGAGA 17

( 2 ) INFORMATION FOR SEQ ID NO: 692:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 692:

CCAGAAGUCU GAUGANGAAA UCUCUUU 27

( 2 ) INFORMATION FOR SEQ ID NO: 693:

( i ) SEQUENCE CHARACTERISTICS:
    ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO: 693:

AAAGAGAUUA CUUCUGG 17

(2) INFORMATION FOR SEQ ID NO: 694:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N"stands for the stem II region of a HH ribozyme.

(xi) SEQUENCE DESCRIPTION: SEQ ID NO: 694:

GCCAGAAGCU GAUGANGAAA AUCUCUU 27

(2) INFORMATION FOR SEQ ID NO: 695:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 695:

AAGAGAUUAC UUCUGGC 17

(2) INFORMATION FOR SEQ ID NO: 696:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N"stands for the stem II region of a HH ribozyme.

(xi) SEQUENCE DESCRIPTION: SEQ ID NO: 696:

ACAGCCAGCU GAUGANGAAA GUAAUCU 27

(2) INFORMATION FOR SEQ ID NO: 697:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 697:

AGAUUACUUC UGGCUGU 17

(2) INFORMATION FOR SEQ ID NO: 698:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N"stands for the stem II region of a HH ribozyme.

( x i ) SEQUENCE DESCRIPTION: SEQ ID NO: 698:

GACAGCCACU GAUGANGAAA AGUAAUC                              27

( 2 ) INFORMATION FOR SEQ ID NO: 699:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 699:

GAUUACUUCU GGCUGUC                                          17

( 2 ) INFORMATION FOR SEQ ID NO: 700:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 700:

UUGUAUCUCU GAUGANGAAA CAGCCAG                              27

( 2 ) INFORMATION FOR SEQ ID NO: 701:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 701:

CUGGCUGUCA GAUACAA                                          17

( 2 ) INFORMATION FOR SEQ ID NO: 702:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 702:

UCUUUUUGCU GAUGANGAAA UCUGACA                              27

( 2 ) INFORMATION FOR SEQ ID NO: 703:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 703:

UGUCAGAUAC AAAAAGA                                          17

( 2 ) INFORMATION FOR SEQ ID NO: 704:

( i ) SEQUENCE CHARACTERISTICS:
   ( A ) LENGTH: 27 base pairs
   ( B ) TYPE: nucleic acid
   ( C ) STRANDEDNESS: single
   ( D ) TOPOLOGY: linear ( i x ) FEATURE:
   ( D ) OTHER INFORMATION: The letter "N" stands for the stem II region of a HH ribozyme.

( x i ) SEQUENCE DESCRIPTION: SEQ ID NO: 704:

GAGCUGGACU GAUGANGAAA UCUUCUU 27

( 2 ) INFORMATION FOR SEQ ID NO: 705:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 705:

AAGAAGAUAU CCAGCUC 17

( 2 ) INFORMATION FOR SEQ ID NO: 706:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N" stands for the stem II region of a HH ribozyme.

( x i ) SEQUENCE DESCRIPTION: SEQ ID NO: 706:

UAGAGCUGCU GAUGANGAAA UAUCUUC 27

( 2 ) INFORMATION FOR SEQ ID NO: 707:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 707:

GAAGAUAUCC AGCUCUA 17

( 2 ) INFORMATION FOR SEQ ID NO: 708:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N" stands for the stem II region of a HH ribozyme.

( x i ) SEQUENCE DESCRIPTION: SEQ ID NO: 708:

GUCUGGUACU GAUGANGAAA GCUGGAU 27

( 2 ) INFORMATION FOR SEQ ID NO: 709:

( i ) SEQUENCE CHARACTERISTICS:
      ( A ) LENGTH: 17 base pairs ( B ) TYPE: nucleic acid
        ( C ) STRANDEDNESS: single
        ( D ) TOPOLOGY: linear ( x i ) SEQUENCE DESCRIPTION: SEQ ID NO: 709:

AUCCAGCUCU ACCAGAC 17

( 2 ) INFORMATION FOR SEQ ID NO: 710:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II
              region of a HH ribozyme.

( x i ) SEQUENCE DESCRIPTION: SEQ ID NO: 710:

AUGUCUGGCU GAUGANGAAA GAGCUGG 27

( 2 ) INFORMATION FOR SEQ ID NO: 711:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 711:

CCAGCUCUAC CAGACAU 17

( 2 ) INFORMATION FOR SEQ ID NO: 712:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II
              region of a HH ribozyme.

( x i ) SEQUENCE DESCRIPTION: SEQ ID NO: 712:

GGACAACACU GAUGANGAAA UGUCUGG 27

( 2 ) INFORMATION FOR SEQ ID NO: 713:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 713:

CCAGACAUUU GUUGUCC 17

( 2 ) INFORMATION FOR SEQ ID NO: 714:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II
              region of a HH ribozyme.

( x i ) SEQUENCE DESCRIPTION: SEQ ID NO: 714:

UGGACAACCU GAUGANGAAA AUGUCUG 27

( 2 ) INFORMATION FOR SEQ ID NO: 715:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 715:

CAGACAUUUG UUGUCCA 17

( 2 ) INFORMATION FOR SEQ ID NO: 716:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 716:

AGCUGGACCU GAUGANGAAA CAAAUGU 27

( 2 ) INFORMATION FOR SEQ ID NO: 717:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 717:

ACAUUUGUUG UCCAGCU 17

( 2 ) INFORMATION FOR SEQ ID NO: 718:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 718:

UGGAGCUGCU GAUGANGAAA CAACAAA 27

( 2 ) INFORMATION FOR SEQ ID NO: 719:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 719:

UUUGUUGUCC AGCUCCA 17

( 2 ) INFORMATION FOR SEQ ID NO: 720:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 720:

GGGUCCUGCU GAUGANGAAA GCUGGAC    27

( 2 ) INFORMATION FOR SEQ ID NO: 721:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 721:

GUCCAGCUCC AGGACCC    17

( 2 ) INFORMATION FOR SEQ ID NO: 722:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 722:

AGCUUCUGCU GAUGANGAAA CAGCUCG    27

( 2 ) INFORMATION FOR SEQ ID NO: 723:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 723:

CGAGCUGUAC AGAAGCU    17

( 2 ) INFORMATION FOR SEQ ID NO: 724:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 724:

UGUAGGUUCU GAUGANGAAA GCUUCUG    27

( 2 ) INFORMATION FOR SEQ ID NO: 725:

( i ) SEQUENCE CHARACTERISTICS:
        ( A ) LENGTH: 17 base pairs ( B ) TYPE: nucleic acid
                    ( C ) STRANDEDNESS: single
                    ( D ) TOPOLOGY: linear ( x i ) SEQUENCE DESCRIPTION: SEQ ID NO: 725:

CAGAAGCUAA ACCUACA                                                                                      17

( 2 ) INFORMATION FOR SEQ ID NO: 726:

( i ) SEQUENCE CHARACTERISTICS:
                    ( A ) LENGTH: 27 base pairs
                    ( B ) TYPE: nucleic acid
                    ( C ) STRANDEDNESS: single
                    ( D ) TOPOLOGY: linear ( i x ) FEATURE:
                    ( D ) OTHER INFORMATION: The letter "N" stands for the stem II
                        region of a HH ribozyme.

( x i ) SEQUENCE DESCRIPTION: SEQ ID NO: 726:

AGAUUCUGCU GAUGANGAAA GGUUUAG                                                                           27

( 2 ) INFORMATION FOR SEQ ID NO: 727:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO: 727:

CUAAACCUAC AGAAUCU                                                                                      17

( 2 ) INFORMATION FOR SEQ ID NO: 728:

( i ) SEQUENCE CHARACTERISTICS:
                    ( A ) LENGTH: 27 base pairs
                    ( B ) TYPE: nucleic acid
                    ( C ) STRANDEDNESS: single
                    ( D ) TOPOLOGY: linear ( i x ) FEATURE:
                    ( D ) OTHER INFORMATION: The letter "N" stands for the stem II
                        region of a HH ribozyme.

( x i ) SEQUENCE DESCRIPTION: SEQ ID NO: 728:

GAUCACAACU GAUGANGAAA UUCUGUA                                                                           27

( 2 ) INFORMATION FOR SEQ ID NO: 729:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO: 729:

UACAGAAUCU UGUGAUC                                                                                      17

( 2 ) INFORMATION FOR SEQ ID NO: 730:

( i ) SEQUENCE CHARACTERISTICS:
                    ( A ) LENGTH: 27 base pairs
                    ( B ) TYPE: nucleic acid
                    ( C ) STRANDEDNESS: single
                    ( D ) TOPOLOGY: linear ( i x ) FEATURE:
                    ( D ) OTHER INFORMATION: The letter "N" stands for the stem II
                        region of a HH ribozyme.

( x i ) SEQUENCE DESCRIPTION: SEQ ID NO: 730:

GGGAUCACCU GAUGANGAAA GAUUCUG 27

( 2 ) INFORMATION FOR SEQ ID NO: 731:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 731:

CAGAAUCUUG UGAUCCC 17

( 2 ) INFORMATION FOR SEQ ID NO: 732:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 732:

GCCCGUGGCU GAUGANGAAA UCACAAG 27

( 2 ) INFORMATION FOR SEQ ID NO: 733:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 733:

CUUGUGAUCC CACGGGC 17

( 2 ) INFORMATION FOR SEQ ID NO: 734:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 734:

AUUUCUGCU GAUGANGAAA GCCCGUG 27

( 2 ) INFORMATION FOR SEQ ID NO: 735:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 735:

CACGGGCUCC AGAAAAU 17

( 2 ) INFORMATION FOR SEQ ID NO: 736:

( i ) SEQUENCE CHARACTERISTICS:
   ( A ) LENGTH: 27 base pairs
   ( B ) TYPE: nucleic acid
   ( C ) STRANDEDNESS: single
   ( D ) TOPOLOGY: linear ( i x ) FEATURE:
   ( D ) OTHER INFORMATION: The letter "N"stands for the stem II region of a HH ribozyme.

( x i ) SEQUENCE DESCRIPTION: SEQ ID NO: 736:

GAGUGUUACU GAUGANGAAA UUUCUG    27

( 2 ) INFORMATION FOR SEQ ID NO: 737:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 737:

CAGAAAAUCU AACACUC    17

( 2 ) INFORMATION FOR SEQ ID NO: 738:

( i ) SEQUENCE CHARACTERISTICS:
   ( A ) LENGTH: 27 base pairs
   ( B ) TYPE: nucleic acid
   ( C ) STRANDEDNESS: single
   ( D ) TOPOLOGY: linear ( i x ) FEATURE:
   ( D ) OTHER INFORMATION: The letter "N"stands for the stem II region of a HH ribozyme.

( x i ) SEQUENCE DESCRIPTION: SEQ ID NO: 738:

CUGAGUGUCU GAUGANGAAA GAUUUC    27

( 2 ) INFORMATION FOR SEQ ID NO: 739:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 739:

GAAAAUCUAA CACUCAG    17

( 2 ) INFORMATION FOR SEQ ID NO: 740:

( i ) SEQUENCE CHARACTERISTICS:
   ( A ) LENGTH: 27 base pairs
   ( B ) TYPE: nucleic acid
   ( C ) STRANDEDNESS: single
   ( D ) TOPOLOGY: linear ( i x ) FEATURE:
   ( D ) OTHER INFORMATION: The letter "N"stands for the stem II region of a HH ribozyme.

( x i ) SEQUENCE DESCRIPTION: SEQ ID NO: 740:

AGAUUGCUCU GAUGANGAAA GUGUUAG    27

( 2 ) INFORMATION FOR SEQ ID NO: 741:

( i ) SEQUENCE CHARACTERISTICS:
   ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO: 741:

CUAACACUCA GCAAUCU 17

(2) INFORMATION FOR SEQ ID NO: 742:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 742:

UUCACUCACU GAUGANGAAA UUGCUGA 27

(2) INFORMATION FOR SEQ ID NO: 743:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 743:

UCAGCAAUCU GAGUGAA 17

(2) INFORMATION FOR SEQ ID NO: 744:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 744:

CUAGCUGGCU GAUGANGAAA UUCACUC 27

(2) INFORMATION FOR SEQ ID NO: 745:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 745:

GAGUGAAUCC CAGCUAG 17

(2) INFORMATION FOR SEQ ID NO: 746:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

( x i ) SEQUENCE DESCRIPTION: SEQ ID NO: 746:

CUCAGCUCCU GAUGANGAAA GCUGGGA 27

( 2 ) INFORMATION FOR SEQ ID NO: 747:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 747:

UCCCAGCUAG AGCUGAG 17

( 2 ) INFORMATION FOR SEQ ID NO: 748:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II
      region of a HH ribozyme.

( x i ) SEQUENCE DESCRIPTION: SEQ ID NO: 748:

UUCUUUAACU GAUGANGAAA UGUCUGC 27

( 2 ) INFORMATION FOR SEQ ID NO: 749:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 749:

GCAGACAUAU UAAAGAA 17

( 2 ) INFORMATION FOR SEQ ID NO: 750:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II
      region of a HH ribozyme.

( x i ) SEQUENCE DESCRIPTION: SEQ ID NO: 750:

CGUUCUUUCU GAUGANGAAA UAUGUCU 27

( 2 ) INFORMATION FOR SEQ ID NO: 751:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 751:

AGACAUAUUA AAGAACG 17

( 2 ) INFORMATION FOR SEQ ID NO: 752:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i x ) FEATURE:
  ( D ) OTHER INFORMATION: The letter "N"stands for the stem II region of a HH ribozyme.

( x i ) SEQUENCE DESCRIPTION: SEQ ID NO: 752:

GCGUUCUUCU GAUGANGAAA AUAUGUC    27

( 2 ) INFORMATION FOR SEQ ID NO: 753:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 753:

GACAUAUUAA AGAACGC    17

( 2 ) INFORMATION FOR SEQ ID NO: 754:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i x ) FEATURE:
  ( D ) OTHER INFORMATION: The letter "N"stands for the stem II region of a HH ribozyme.

( x i ) SEQUENCE DESCRIPTION: SEQ ID NO: 754:

GUAUUGUACU GAUGANGAAA CAGCGUU    27

( 2 ) INFORMATION FOR SEQ ID NO: 755:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 755:

AACGCUGUUU ACAAUAC    17

( 2 ) INFORMATION FOR SEQ ID NO: 756:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i x ) FEATURE:
  ( D ) OTHER INFORMATION: The letter "N"stands for the stem II region of a HH ribozyme.

( x i ) SEQUENCE DESCRIPTION: SEQ ID NO: 756:

AGUAUUGUCU GAUGANGAAA ACAGCGU    27

( 2 ) INFORMATION FOR SEQ ID NO: 757:

( i ) SEQUENCE CHARACTERISTICS:
  ( A ) LENGTH: 17 base pairs ( B ) TYPE: nucleic acid
            ( C ) STRANDEDNESS: single
            ( D ) TOPOLOGY: linear ( x i ) SEQUENCE DESCRIPTION: SEQ ID NO: 757:

ACGCUGUUUA CAAUACU 17

( 2 ) INFORMATION FOR SEQ ID NO: 758:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i x ) FEATURE:
            ( D ) OTHER INFORMATION: The letter "N" stands for the stem II
                region of a HH ribozyme.

( x i ) SEQUENCE DESCRIPTION: SEQ ID NO: 758:

AAGUAUUGCU GAUGANGAAA AACAGCG 27

( 2 ) INFORMATION FOR SEQ ID NO: 759:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 759:

CGCUGUUUAC AAUACUU 17

( 2 ) INFORMATION FOR SEQ ID NO: 760:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i x ) FEATURE:
            ( D ) OTHER INFORMATION: The letter "N" stands for the stem II
                region of a HH ribozyme.

( x i ) SEQUENCE DESCRIPTION: SEQ ID NO: 760:

GCACCAAGCU GAUGANGAAA UUGUAAA 27

( 2 ) INFORMATION FOR SEQ ID NO: 761:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 761:

UUUACAAUAC UUGGUGC 17

( 2 ) INFORMATION FOR SEQ ID NO: 762:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i x ) FEATURE:
            ( D ) OTHER INFORMATION: The letter "N" stands for the stem II
                region of a HH ribozyme.

( x i ) SEQUENCE DESCRIPTION: SEQ ID NO: 762:

ACUGCACCCU GAUGANGAAA GUAUUGU 27

( 2 ) INFORMATION FOR SEQ ID NO: 763:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 763:

ACAAUACUUG GUGCAGU 17

( 2 ) INFORMATION FOR SEQ ID NO: 764:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 764:

UGCUCCGGCU GAUGANGAAA CUGCACC 27

( 2 ) INFORMATION FOR SEQ ID NO: 765:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 765:

GGUGCAGUAC CGGAGCA 17

( 2 ) INFORMATION FOR SEQ ID NO: 766:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 766:

CCAGCUUCCU GAUGANGAAA UCUCUGU 27

( 2 ) INFORMATION FOR SEQ ID NO: 767:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 767:

ACAGAGAUCG AAGCUGG 17

( 2 ) INFORMATION FOR SEQ ID NO: 768:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 768:

UUCACUAUCU GAUGANGAAA GUUCCGU    27

( 2 ) INFORMATION FOR SEQ ID NO: 769:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 769:

ACGGAACUAA UAGUGAA    17

( 2 ) INFORMATION FOR SEQ ID NO: 770:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 770:

UGAUUCACCU GAUGANGAAA UUAGUUC    27

( 2 ) INFORMATION FOR SEQ ID NO: 771:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 771:

GAACUAAUAG UGAAUCA    17

( 2 ) INFORMATION FOR SEQ ID NO: 772:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 772:

AGGUUCAUCU GAUGANGAAA UUCACUA    27

( 2 ) INFORMATION FOR SEQ ID NO: 773:

( i ) SEQUENCE CHARACTERISTICS:
    ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO: 773:

UAGUGAAUCA UGAACCU     17

(2) INFORMATION FOR SEQ ID NO: 774:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N"stands for the stem II region of a HH ribozyme.

(xi) SEQUENCE DESCRIPTION: SEQ ID NO: 774:

GGAGAAUCCU GAUGANGAAA GGUUCAU     27

(2) INFORMATION FOR SEQ ID NO: 775:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 775:

AUGAACCUAG AUUCUCC     17

(2) INFORMATION FOR SEQ ID NO: 776:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N"stands for the stem II region of a HH ribozyme.

(xi) SEQUENCE DESCRIPTION: SEQ ID NO: 776:

GCAGGGAGCU GAUGANGAAA UCUAGGU     27

(2) INFORMATION FOR SEQ ID NO: 777:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 777:

ACCUAGAUUC UCCCUGC     17

(2) INFORMATION FOR SEQ ID NO: 778:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N"stands for the stem II region of a HH ribozyme.

( x i ) SEQUENCE DESCRIPTION: SEQ ID NO: 778:

GGCAGGGACU GAUGANGAAA AUCUAGG                                                                                27

( 2 ) INFORMATION FOR SEQ ID NO: 779:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 779:

CCUAGAUUCU CCCUGCC                                                                                            17

( 2 ) INFORMATION FOR SEQ ID NO: 780:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 780:

UAGGCAGGCU GAUGANGAAA GAAUCUA                                                                                27

( 2 ) INFORMATION FOR SEQ ID NO: 781:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 781:

UAGAUUCUCC CUGCCUA                                                                                            17

( 2 ) INFORMATION FOR SEQ ID NO: 782:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 782:

AUCCACACCU GAUGANGAAA GGCAGGG                                                                                27

( 2 ) INFORMATION FOR SEQ ID NO: 783:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 783:

CCCUGCCUAG UGUGGAU                                                                                            17

( 2 ) INFORMATION FOR SEQ ID NO: 784:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 784:

GAAAUGUGCU GAUGANGAAA CCGUUUC      27

( 2 ) INFORMATION FOR SEQ ID NO: 785:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 785:

GAAACGGUAC ACAUUUC      17

( 2 ) INFORMATION FOR SEQ ID NO: 786:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 786:

GAACCCGACU GAUGANGAAA UGUGUAC      27

( 2 ) INFORMATION FOR SEQ ID NO: 787:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 787:

GUACACAUUU CGGGUUC      17

( 2 ) INFORMATION FOR SEQ ID NO: 788:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 788:

CGAACCCGCU GAUGANGAAA AUGUGUA      27

( 2 ) INFORMATION FOR SEQ ID NO: 789:

( i ) SEQUENCE CHARACTERISTICS:
    ( A ) LENGTH: 17 base pairs ( B ) TYPE: nucleic acid
        ( C ) STRANDEDNESS: single
        ( D ) TOPOLOGY: linear ( x i ) SEQUENCE DESCRIPTION: SEQ ID NO: 789:

UACACAUUUC GGGUUCG    17

( 2 ) INFORMATION FOR SEQ ID NO: 790:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 790:

CCGAACCCCU GAUGANGAAA AAUGUGU    27

( 2 ) INFORMATION FOR SEQ ID NO: 791:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 791:

ACACAUUUCG GUUCGG    17

( 2 ) INFORMATION FOR SEQ ID NO: 792:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 792:

CGGCUCCGCU GAUGANGAAA CCCGAAA    27

( 2 ) INFORMATION FOR SEQ ID NO: 793:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 793:

UUUCGGGUUC GGAGCCG    17

( 2 ) INFORMATION FOR SEQ ID NO: 794:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 794:

GCGGCUCCCU GAUGANGAAA ACCCGAA 27

( 2 ) INFORMATION FOR SEQ ID NO: 795:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 795:

UUCGGGUUCG GAGCCGC 17

( 2 ) INFORMATION FOR SEQ ID NO: 796:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 796:

UUGGGUUACU GAUGANGAAA GCGGCUC 27

( 2 ) INFORMATION FOR SEQ ID NO: 797:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 797:

GAGCCGCUAU AACCCAA 17

( 2 ) INFORMATION FOR SEQ ID NO: 798:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 798:

GAUUGGGUCU GAUGANGAAA UAGCGGC 27

( 2 ) INFORMATION FOR SEQ ID NO: 799:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 799:

GCCGCUAUAA CCCAAUC 17

( 2 ) INFORMATION FOR SEQ ID NO: 800:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i x ) FEATURE:
  ( D ) OTHER INFORMATION: The letter "N" stands for the stem II region of a HH ribozyme.

( x i ) SEQUENCE DESCRIPTION: SEQ ID NO: 800:

CUUCCACACU GAUGANGAAA UUGGGUU    27

( 2 ) INFORMATION FOR SEQ ID NO: 801:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 801:

AACCCAAUCU GUGGAAG    17

( 2 ) INFORMATION FOR SEQ ID NO: 802:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 802:

CUGUUGAGCU GAUGANGAAA CUUCCAC    27

( 2 ) INFORMATION FOR SEQ ID NO: 803:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 803:

GUGGAAGUUC UCAACAG    17

( 2 ) INFORMATION FOR SEQ ID NO: 804:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 804:

ACUGUUGACU GAUGANGAAA ACUUCCA    27

( 2 ) INFORMATION FOR SEQ ID NO: 805:

( i ) SEQUENCE CHARACTERISTICS:
    ( A ) LENGTH: 17 base pairs ( B ) TYPE: nucleic acid
        ( C ) STRANDEDNESS: single
        ( D ) TOPOLOGY: linear ( x i ) SEQUENCE DESCRIPTION: SEQ ID NO: 805:

UGGAAGUUCU CAACAGU                                                                                         17

( 2 ) INFORMATION FOR SEQ ID NO: 806:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II
              region of a HH ribozyme.

( x i ) SEQUENCE DESCRIPTION: SEQ ID NO: 806:

CCACUGUUCU GAUGANGAAA GAACUUC                                                                              27

( 2 ) INFORMATION FOR SEQ ID NO: 807:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 807:

GAAGUUCUCA ACAGUGG                                                                                         17

( 2 ) INFORMATION FOR SEQ ID NO: 808:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II
              region of a HH ribozyme.

( x i ) SEQUENCE DESCRIPTION: SEQ ID NO: 808:

GCUCCAUUCU GAUGANGAAA CUCCACU                                                                              27

( 2 ) INFORMATION FOR SEQ ID NO: 809:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 809:

AGUGGAGUAA AUGGAGC                                                                                         17

( 2 ) INFORMATION FOR SEQ ID NO: 810:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II
              region of a HH ribozyme.

( x i ) SEQUENCE DESCRIPTION: SEQ ID NO: 810:

CCCCAGUGCU GAUGANGAAA CAGGCUG 27

( 2 ) INFORMATION FOR SEQ ID NO: 811:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 811:

CAGCCUGUCC ACUGGGG 17

( 2 ) INFORMATION FOR SEQ ID NO: 812:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 812:

UACAGUAUCU GAUGANGAAA CUCCCCC 27

( 2 ) INFORMATION FOR SEQ ID NO: 813:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 813:

GGGGGAGUCA UACUGUA 17

( 2 ) INFORMATION FOR SEQ ID NO: 814:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 814:

CUCUACAGCU GAUGANGAAA UGACUCC 27

( 2 ) INFORMATION FOR SEQ ID NO: 815:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 815:

GGAGUCAUAC UGUAGAG 17

( 2 ) INFORMATION FOR SEQ ID NO: 816:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 816:

UUCUCCUCCU GAUGANGAAA CAGUAUG      27

( 2 ) INFORMATION FOR SEQ ID NO: 817:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 817:

CAUACUGUAG AGGAGAA      17

( 2 ) INFORMATION FOR SEQ ID NO: 818:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 818:

CAAGGAAGCU GAUGANGAAA UUCUCCU      27

( 2 ) INFORMATION FOR SEQ ID NO: 819:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 819:

AGGAGAAUCC UUCCUUG      17

( 2 ) INFORMATION FOR SEQ ID NO: 820:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 820:

AAACAAGGCU GAUGANGAAA GGAUUCU      27

( 2 ) INFORMATION FOR SEQ ID NO: 821:

( i ) SEQUENCE CHARACTERISTICS:
    ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO: 821:

AGAAUCCUUC CUUGUUU                                                              17

(2) INFORMATION FOR SEQ ID NO: 822:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 822:

CAAACAAGCU GAUGANGAAA AGGAUUC                                                   27

(2) INFORMATION FOR SEQ ID NO: 823:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 823:

GAAUCCUUCC UUGUUUG                                                              17

(2) INFORMATION FOR SEQ ID NO: 824:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 824:

GUGCAAACCU GAUGANGAAA GGAAGGA                                                   27

(2) INFORMATION FOR SEQ ID NO: 825:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 825:

UCCUUCCUUG UUUGCAC                                                              17

(2) INFORMATION FOR SEQ ID NO: 826:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

( x i ) SEQUENCE DESCRIPTION: SEQ ID NO: 826:

CCAGUGCACU GAUGANGAAA CAAGGAA     27

( 2 ) INFORMATION FOR SEQ ID NO: 827:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 827:

UUCCUUGUUU GCACUGG     17

( 2 ) INFORMATION FOR SEQ ID NO: 828:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 828:

UCCAGUGCCU GAUGANGAAA ACAAGGA     27

( 2 ) INFORMATION FOR SEQ ID NO: 829:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 829:

UCCUUGUUUG CACUGGA     17

( 2 ) INFORMATION FOR SEQ ID NO: 830:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 830:

ACAGGGAUCU GAUGANGAAA GCACAGC     27

( 2 ) INFORMATION FOR SEQ ID NO: 831:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 831:

GCUGUGCUUA UCCCUGU     17

( 2 ) INFORMATION FOR SEQ ID NO: 832:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 832:

AACAGGGACU GAUGANGAAA AGCACAG 27

( 2 ) INFORMATION FOR SEQ ID NO: 833:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 833:

CUGUGCUUAU CCCUGUU 17

( 2 ) INFORMATION FOR SEQ ID NO: 834:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 834:

CCAACAGGCU GAUGANGAAA UAAGCAC 27

( 2 ) INFORMATION FOR SEQ ID NO: 835:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 835:

GUGCUUAUCC CUGUUGG 17

( 2 ) INFORMATION FOR SEQ ID NO: 836:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 836:

AUGGUGCCCU GAUGANGAAA CAGGGAU 27

( 2 ) INFORMATION FOR SEQ ID NO: 837:

( i ) SEQUENCE CHARACTERISTICS:
    ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO: 837:

AUCCCUGUUG GCACCAU 17

(2) INFORMATION FOR SEQ ID NO: 838:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 838:

UAAUAAUCCU GAUGANGAAA CCCCAUG 27

(2) INFORMATION FOR SEQ ID NO: 839:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 839:

CAUGGGGUUG AUUAUUA 17

(2) INFORMATION FOR SEQ ID NO: 840:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 840:

AGGGUAAUCU GAUGANGAAA UCAACCC 27

(2) INFORMATION FOR SEQ ID NO: 841:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 841:

GGGUUGAUUA UUACCCU 17

(2) INFORMATION FOR SEQ ID NO: 842:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

( x i ) SEQUENCE DESCRIPTION: SEQ ID NO: 842:

CAGGGUAACU GAUGANGAAA AUCAACC                                                                                    27

( 2 ) INFORMATION FOR SEQ ID NO: 843:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO: 843:

GGUUGAUUAU UACCCUG                                                                                               17

( 2 ) INFORMATION FOR SEQ ID NO: 844:

( i ) SEQUENCE CHARACTERISTICS:
       ( A ) LENGTH: 27 base pairs
       ( B ) TYPE: nucleic acid
       ( C ) STRANDEDNESS: single
       ( D ) TOPOLOGY: linear ( i x ) FEATURE:
       ( D ) OTHER INFORMATION: The letter "N"stands for the stem II
             region of a HH ribozyme.

( x i ) SEQUENCE DESCRIPTION: SEQ ID NO: 844:

AUCAGGGUCU GAUGANGAAA UAAUCAA                                                                                    27

( 2 ) INFORMATION FOR SEQ ID NO: 845:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO: 845:

UUGAUUAUUA CCCUGAU                                                                                               17

( 2 ) INFORMATION FOR SEQ ID NO: 846:

( i ) SEQUENCE CHARACTERISTICS:
       ( A ) LENGTH: 27 base pairs
       ( B ) TYPE: nucleic acid
       ( C ) STRANDEDNESS: single
       ( D ) TOPOLOGY: linear ( i x ) FEATURE:
       ( D ) OTHER INFORMATION: The letter "N"stands for the stem II
             region of a HH ribozyme.

( x i ) SEQUENCE DESCRIPTION: SEQ ID NO: 846:

GAUCAGGGCU GAUGANGAAA AUAAUCA                                                                                    27

( 2 ) INFORMATION FOR SEQ ID NO: 847:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO: 847:

UGAUUAUUAC CCUGAUC                                                                                               17

( 2 ) INFORMATION FOR SEQ ID NO: 848:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 848:

UACACAAACU GAUGANGAAA UCAGGGU      27

( 2 ) INFORMATION FOR SEQ ID NO: 849:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 849:

ACCCUGAUCU UUGUGUA      17

( 2 ) INFORMATION FOR SEQ ID NO: 850:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 850:

AGUACACACU GAUGANGAAA GAUCAGG      27

( 2 ) INFORMATION FOR SEQ ID NO: 851:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 851:

CCUGAUCUUU GUGUACU      17

( 2 ) INFORMATION FOR SEQ ID NO: 852:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 852:

CAGUACACCU GAUGANGAAA AGAUCAG      27

( 2 ) INFORMATION FOR SEQ ID NO: 853:

( i ) SEQUENCE CHARACTERISTICS:
        ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO: 853:

CUGAUCUUUG UGUACUG                                                                                    17

(2) INFORMATION FOR SEQ ID NO: 854:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 854:

ACCAACAGCU GAUGANGAAA CACAAAG                                                                          27

(2) INFORMATION FOR SEQ ID NO: 855:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 855:

CUUUGUGUAC UGUUGGU                                                                                    17

(2) INFORMATION FOR SEQ ID NO: 856:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 856:

UUCCAACCCU GAUGANGAAA CAGUACA                                                                          27

(2) INFORMATION FOR SEQ ID NO: 857:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 857:

UGUACUGUUG GUUGGAA                                                                                    17

(2) INFORMATION FOR SEQ ID NO: 858:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

( x i ) SEQUENCE DESCRIPTION: SEQ ID NO: 858:

UUCGUUCCCU GAUGANGAAA CCAACAG 27

( 2 ) INFORMATION FOR SEQ ID NO: 859:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 859:

CUGUUGGUUG GAACGAA 17

( 2 ) INFORMATION FOR SEQ ID NO: 860:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for the stem II
         region of a HH ribozyme.

( x i ) SEQUENCE DESCRIPTION: SEQ ID NO: 860:

GGGAAUUGCU GAUGANGAAA GGCAUUC 27

( 2 ) INFORMATION FOR SEQ ID NO: 861:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 861:

GAAUGCCUCC AAUUCCC 17

( 2 ) INFORMATION FOR SEQ ID NO: 862:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for the stem II
         region of a HH ribozyme.

( x i ) SEQUENCE DESCRIPTION: SEQ ID NO: 862:

AUGGGGGCU GAUGANGAAA UUGGAGG 27

( 2 ) INFORMATION FOR SEQ ID NO: 863:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 863:

CCUCCAAUUC CCCCCAU 17

( 2 ) INFORMATION FOR SEQ ID NO: 864:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 864:

GAUGGGGCU GAUGANGAAA AUUGGAG    27

( 2 ) INFORMATION FOR SEQ ID NO: 865:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 865:

CUCCAAUUCC CCCCAUC    17

( 2 ) INFORMATION FOR SEQ ID NO: 866:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 866:

AGAUUCUUCU GAUGANGAAA UGGGGGG    27

( 2 ) INFORMATION FOR SEQ ID NO: 867:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 867:

CCCCCCAUCA AGAAUCU    17

( 2 ) INFORMATION FOR SEQ ID NO: 868:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II region of a HH ribozyme.

( x i ) SEQUENCE DESCRIPTION: SEQ ID NO: 868:

AUCCUCUACU GAUGANGAAA UUCUUGA    27

( 2 ) INFORMATION FOR SEQ ID NO: 869:

( i ) SEQUENCE CHARACTERISTICS:
    ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO: 869:

UCAAGAAUCU AGAGGAU 17

(2) INFORMATION FOR SEQ ID NO: 870:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 870:

AGAUCCUCCU GAUGANGAAA GAUUCUU 27

(2) INFORMATION FOR SEQ ID NO: 871:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 871:

AAGAAUCUAG AGGAUCU 17

(2) INFORMATION FOR SEQ ID NO: 872:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

(xi) SEQUENCE DESCRIPTION: SEQ ID NO: 872:

AGUAACCACU GAUGANGAAA UCCUCUA 27

(2) INFORMATION FOR SEQ ID NO: 873:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 873:

UAGAGGAUCU GGUUACU 17

(2) INFORMATION FOR SEQ ID NO: 874:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II region of a HH ribozyme.

( x i ) SEQUENCE DESCRIPTION: SEQ ID NO: 874:

UAUUCAGUCU GAUGANGAAA CCAGAUC 27

( 2 ) INFORMATION FOR SEQ ID NO: 875:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 875:

GAUCUGGUUA CUGAAUA 17

( 2 ) INFORMATION FOR SEQ ID NO: 876:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 876:

GUAUUCAGCU GAUGANGAAA ACCAGAU 27

( 2 ) INFORMATION FOR SEQ ID NO: 877:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 877:

AUCUGGUUAC UGAAUAC 17

( 2 ) INFORMATION FOR SEQ ID NO: 878:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 878:

UCCCUUGGCU GAUGANGAAA UUCAGUA 27

( 2 ) INFORMATION FOR SEQ ID NO: 879:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 879:

UACUGAAUAC CAAGGGA 17

( 2 ) INFORMATION FOR SEQ ID NO: 880:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 880:

AGGCCGAACU GAUGANGAAA GUUCCCU    27

( 2 ) INFORMATION FOR SEQ ID NO: 881:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 881:

AGGGAACUUU UCGGCCU    17

( 2 ) INFORMATION FOR SEQ ID NO: 882:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 882:

CAGGCCGACU GAUGANGAAA AGUUCCC    27

( 2 ) INFORMATION FOR SEQ ID NO: 883:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 883:

GGGAACUUUU CGGCCUG    17

( 2 ) INFORMATION FOR SEQ ID NO: 884:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 884:

CCAGGCCGCU GAUGANGAAA AAGUUCC    27

( 2 ) INFORMATION FOR SEQ ID NO: 885:

( i ) SEQUENCE CHARACTERISTICS:
        ( A ) LENGTH: 17 base pairs ( B ) TYPE: nucleic acid
            ( C ) STRANDEDNESS: single
            ( D ) TOPOLOGY: linear ( x i ) SEQUENCE DESCRIPTION: SEQ ID NO: 885:

GGAACUUUUC GGCCUGG                                                                                      17

( 2 ) INFORMATION FOR SEQ ID NO: 886:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i x ) FEATURE:
            ( D ) OTHER INFORMATION: The letter "N"stands for the stem II
                region of a HH ribozyme.

( x i ) SEQUENCE DESCRIPTION: SEQ ID NO: 886:

UCCAGGCCCU GAUGANGAAA AAAGUUC                                                                           27

( 2 ) INFORMATION FOR SEQ ID NO: 887:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 887:

GAACUUUUCG GCCUGGA                                                                                      17

( 2 ) INFORMATION FOR SEQ ID NO: 888:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i x ) FEATURE:
            ( D ) OTHER INFORMATION: The letter "N"stands for the stem II
                region of a HH ribozyme.

( x i ) SEQUENCE DESCRIPTION: SEQ ID NO: 888:

GCCCUUUACU GAUGANGAAA CACACCA                                                                           27

( 2 ) INFORMATION FOR SEQ ID NO: 889:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 889:

UGGUGUGUCU AAAGGGC                                                                                      17

( 2 ) INFORMATION FOR SEQ ID NO: 890:

( i ) SEQUENCE CHARACTERISTICS:
            ( A ) LENGTH: 27 base pairs
            ( B ) TYPE: nucleic acid
            ( C ) STRANDEDNESS: single
            ( D ) TOPOLOGY: linear ( i x ) FEATURE:
            ( D ) OTHER INFORMATION: The letter "N"stands for the stem II
                region of a HH ribozyme.

( x i ) SEQUENCE DESCRIPTION: SEQ ID NO: 890:

CAGCCCUUCU GAUGANGAAA GACACAC 27

( 2 ) INFORMATION FOR SEQ ID NO: 891:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 891:

GUGUGUCUAA AGGGCUG 17

( 2 ) INFORMATION FOR SEQ ID NO: 892:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 892:

UGGCUGCACU GAUGANGAAA CUCUCAG 27

( 2 ) INFORMATION FOR SEQ ID NO: 893:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 893:

CUGAGAGUCU GCAGCCA 17

( 2 ) INFORMATION FOR SEQ ID NO: 894:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 894:

GUUCACUGCU GAUGANGAAA GUCUGGC 27

( 2 ) INFORMATION FOR SEQ ID NO: 895:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 895:

GCCAGACUAC AGUGAAC 17

( 2 ) INFORMATION FOR SEQ ID NO: 896:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II
        region of a HH ribozyme.

( x i ) SEQUENCE DESCRIPTION: SEQ ID NO: 896:

CGUGGCAGCU GAUGANGAAA CCGUUCA 27

( 2 ) INFORMATION FOR SEQ ID NO: 897:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 897:

UGAACGGUUC UGCCACG 17

( 2 ) INFORMATION FOR SEQ ID NO: 898:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 898:

ACGUGGCACU GAUGANGAAA ACCGUUC 27

( 2 ) INFORMATION FOR SEQ ID NO: 899:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 899:

GAACGGUUCU GCCACGU 17

( 2 ) INFORMATION FOR SEQ ID NO: 900:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 900:

AUCUCGCUCU GAUGANGAAA CGUGGCA 27

( 2 ) INFORMATION FOR SEQ ID NO: 901:

( i ) SEQUENCE CHARACTERISTICS:
        ( A ) LENGTH: 17 base pairs (B) TYPE: nucleic acid
        (C) STRANDEDNESS: single
        (D) TOPOLOGY: linear (xi) SEQUENCE DESCRIPTION: SEQ ID NO: 901:

UGCCACGUCA GCGAGAU                                                                                          17

(2) INFORMATION FOR SEQ ID NO: 902:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 902:

UUGGGGGGCU GAUGANGAAA UCUCGCU                                                                               27

(2) INFORMATION FOR SEQ ID NO: 903:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 903:

AGCGAGAUUC CCCCCAA                                                                                          17

(2) INFORMATION FOR SEQ ID NO: 904:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

(xi) SEQUENCE DESCRIPTION: SEQ ID NO: 904:

UUUGGGGGCU GAUGANGAAA AUCUCGC                                                                               27

(2) INFORMATION FOR SEQ ID NO: 905:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 905:

GCGAGAUUCC CCCAAA                                                                                           17

(2) INFORMATION FOR SEQ ID NO: 906:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II
            region of a HH ribozyme.

( x i ) SEQUENCE DESCRIPTION: SEQ ID NO: 906:

CCCUCUCCCU GAUGANGAAA GGGCCCC 27

( 2 ) INFORMATION FOR SEQ ID NO: 907:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 907:

GGGGCCCUAG GAGAGGG 17

( 2 ) INFORMATION FOR SEQ ID NO: 908:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 908:

GCAAGGAGCU GAUGANGAAA CCUCCAG 27

( 2 ) INFORMATION FOR SEQ ID NO: 909:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 909:

CUGGAGGUUC UCCUUGC 17

( 2 ) INFORMATION FOR SEQ ID NO: 910:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 910:

UGCAAGGACU GAUGANGAAA ACCUCCA 27

( 2 ) INFORMATION FOR SEQ ID NO: 911:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 911:

UGGAGGUUCU CCUUGCA 17

( 2 ) INFORMATION FOR SEQ ID NO: 912:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 912:

GCUGCAAGCU GAUGANGAAA GAACCUC      27

( 2 ) INFORMATION FOR SEQ ID NO: 913:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 913:

GAGGUUCUCC UUGCAGC      17

( 2 ) INFORMATION FOR SEQ ID NO: 914:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 914:

CAGGCUGCCU GAUGANGAAA GGAGAAC      27

( 2 ) INFORMATION FOR SEQ ID NO: 915:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 915:

GUUCUCCUUG CAGCCUG      17

( 2 ) INFORMATION FOR SEQ ID NO: 916:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 916:

GUAAGGGCCU GAUGANGAAA UGCAGGC      27

( 2 ) INFORMATION FOR SEQ ID NO: 917:

( i ) SEQUENCE CHARACTERISTICS:
    ( A ) LENGTH: 17 base pairs (B) TYPE: nucleic acid
(C) STRANDEDNESS: single
(D) TOPOLOGY: linear (xi) SEQUENCE DESCRIPTION: SEQ ID NO: 917:

GCCUGCAUAG CCCUUAC                                                                                    17

(2) INFORMATION FOR SEQ ID NO: 918:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ix) FEATURE:
    (D) OTHER INFORMATION: The letter "N" stands for the stem II
        region of a HH ribozyme.

(xi) SEQUENCE DESCRIPTION: SEQ ID NO: 918:

AGGCCAGUCU GAUGANGAAA GGGCUAU                                                                         27

(2) INFORMATION FOR SEQ ID NO: 919:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO: 919:

AUAGCCCUUA CUGGCCU                                                                                    17

(2) INFORMATION FOR SEQ ID NO: 920:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ix) FEATURE:
    (D) OTHER INFORMATION: The letter "N" stands for the stem II
        region of a HH ribozyme.

(xi) SEQUENCE DESCRIPTION: SEQ ID NO: 920:

GAGGCCAGCU GAUGANGAAA AGGGCUA                                                                         27

(2) INFORMATION FOR SEQ ID NO: 921:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO: 921:

UAGCCCUUAC UGGCUC                                                                                     17

(2) INFORMATION FOR SEQ ID NO: 922:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ix) FEATURE:
    (D) OTHER INFORMATION: The letter "N" stands for the stem II
        region of a HH ribozyme.

( x i ) SEQUENCE DESCRIPTION: SEQ ID NO: 922:

ACAUGGGGCU GAUGANGAAA GGCCAGU    27

( 2 ) INFORMATION FOR SEQ ID NO: 923:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 923:

ACUGGCCUCC CCCAUGU    17

( 2 ) INFORMATION FOR SEQ ID NO: 924:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 924:

CAGAGAAUCU GAUGANGAAA CAUGGGG    27

( 2 ) INFORMATION FOR SEQ ID NO: 925:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 925:

CCCCAUGUUA UUCUCUG    17

( 2 ) INFORMATION FOR SEQ ID NO: 926:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 926:

UCAGAGAACU GAUGANGAAA ACAUGG    27

( 2 ) INFORMATION FOR SEQ ID NO: 927:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 927:

CCCAUGUUAU UCUCUGA    17

( 2 ) INFORMATION FOR SEQ ID NO: 928:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for the stem II
    region of a HH ribozyme.

( x i ) SEQUENCE DESCRIPTION: SEQ ID NO: 928:

CUUCAGAGCU GAUGANGAAA UAACAUG                        27

( 2 ) INFORMATION FOR SEQ ID NO: 929:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 929:

CAUGUUAUUC UCUGAAG                                  17

( 2 ) INFORMATION FOR SEQ ID NO: 930:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II
        region of a HH ribozyme.

( x i ) SEQUENCE DESCRIPTION: SEQ ID NO: 930:

GCUUCAGACU GAUGANGAAA AUAACAU                        27

( 2 ) INFORMATION FOR SEQ ID NO: 931:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 931:

AUGUUAUUCU CUGAAGC                                  17

( 2 ) INFORMATION FOR SEQ ID NO: 932:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II
        region of a HH ribozyme.

( x i ) SEQUENCE DESCRIPTION: SEQ ID NO: 932:

CGGCUUCACU GAUGANGAAA GAAUAAC                        27

( 2 ) INFORMATION FOR SEQ ID NO: 933:

( i ) SEQUENCE CHARACTERISTICS:
        ( A ) LENGTH: 17 base pairs (B) TYPE: nucleic acid
                (C) STRANDEDNESS: single
                (D) TOPOLOGY: linear (xi) SEQUENCE DESCRIPTION: SEQ ID NO: 933:

GUUAUUCUCU GAAGCCG                                                                                          17

(2) INFORMATION FOR SEQ ID NO: 934:

(i) SEQUENCE CHARACTERISTICS:
                (A) LENGTH: 27 base pairs
                (B) TYPE: nucleic acid
                (C) STRANDEDNESS: single
                (D) TOPOLOGY: linear (ix) FEATURE:
                (D) OTHER INFORMATION: The letter "N" stands for the stem II
                    region of a HH ribozyme.

(xi) SEQUENCE DESCRIPTION: SEQ ID NO: 934:

AAAGGAUUCU GAUGANGAAA UGUUCAG                                                                               27

(2) INFORMATION FOR SEQ ID NO: 935:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO: 935:

CUGAACAUCA AUCCUUU                                                                                          17

(2) INFORMATION FOR SEQ ID NO: 936:

(i) SEQUENCE CHARACTERISTICS:
                (A) LENGTH: 27 base pairs
                (B) TYPE: nucleic acid
                (C) STRANDEDNESS: single
                (D) TOPOLOGY: linear (ix) FEATURE:
                (D) OTHER INFORMATION: The letter "N" stands for the stem II
                    region of a HH ribozyme.

(xi) SEQUENCE DESCRIPTION: SEQ ID NO: 936:

CAUCAAAGCU GAUGANGAAA UUGAUGU                                                                               27

(2) INFORMATION FOR SEQ ID NO: 937:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (xi) SEQUENCE DESCRIPTION: SEQ ID NO: 937:

ACAUCAAUCC UUUGAUG                                                                                          17

(2) INFORMATION FOR SEQ ID NO: 938:

(i) SEQUENCE CHARACTERISTICS:
                (A) LENGTH: 27 base pairs
                (B) TYPE: nucleic acid
                (C) STRANDEDNESS: single
                (D) TOPOLOGY: linear (ix) FEATURE:
                (D) OTHER INFORMATION: The letter "N" stands for the stem II
                    region of a HH ribozyme.

( x i ) SEQUENCE DESCRIPTION: SEQ ID NO: 938:

UUCCAUCACU GAUGANGAAA GGAUUGA 27

( 2 ) INFORMATION FOR SEQ ID NO: 939:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 939:

UCAAUCCUUU GAUGGAA 17

( 2 ) INFORMATION FOR SEQ ID NO: 940:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 940:

GUUCCAUCCU GAUGANGAAA AGGAUUG 27

( 2 ) INFORMATION FOR SEQ ID NO: 941:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 941:

CAAUCCUUUG AUGGAAC 17

( 2 ) INFORMATION FOR SEQ ID NO: 942:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 942:

AGGACUUUCU GAUGANGAAA GGUUCCA 27

( 2 ) INFORMATION FOR SEQ ID NO: 943:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 943:

UGGAACCUCA AAGUCCU 17

( 2 ) INFORMATION FOR SEQ ID NO: 944:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 944:

GACUAUAGCU GAUGANGAAA CUUUGAG    27

( 2 ) INFORMATION FOR SEQ ID NO: 945:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 945:

CUCAAAGUCC UAUAGUC    17

( 2 ) INFORMATION FOR SEQ ID NO: 946:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 946:

UAGGACUACU GAUGANGAAA GGACUUU    27

( 2 ) INFORMATION FOR SEQ ID NO: 947:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 947:

AAAGUCCUAU AGUCCUA    17

( 2 ) INFORMATION FOR SEQ ID NO: 948:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 948:

CUUAGGACCU GAUGANGAAA UAGGACU    27

( 2 ) INFORMATION FOR SEQ ID NO: 949:

( i ) SEQUENCE CHARACTERISTICS:
    ( A ) LENGTH: 17 base pairs ( B ) TYPE: nucleic acid
( C ) STRANDEDNESS: single
( D ) TOPOLOGY: linear ( x i ) SEQUENCE DESCRIPTION: SEQ ID NO: 949:

AGUCCUAUAG UCCUAAG 17

( 2 ) INFORMATION FOR SEQ ID NO: 950:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II
region of a HH ribozyme.

( x i ) SEQUENCE DESCRIPTION: SEQ ID NO: 950:

UCACUUAGCU GAUGANGAAA CUAUAGG 27

( 2 ) INFORMATION FOR SEQ ID NO: 951:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 951:

CCUAUAGUCC UAAGUGA 17

( 2 ) INFORMATION FOR SEQ ID NO: 952:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO: 952:

GCAGGAGCAG AAGAAGGAAC CAGAGAAACA CACGUUGUGG UACAUUACCU GGUA 54

( 2 ) INFORMATION FOR SEQ ID NO: 953:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO: 953:

UCCUUCAGCU GCUCCUGC 18

( 2 ) INFORMATION FOR SEQ ID NO: 954:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO: 954:

UCAGCAGGAG AAGCUGAAAC CAGAGAAACA CACGUUGUGG UACAUUACCU GGUA 54

( 2 ) INFORMATION FOR SEQ ID NO: 955:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 955:

UUCAGCUGCU CCUGCUGA 18

( 2 ) INFORMATION FOR SEQ ID NO: 956:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 956:

CUGCCCUCAG AAGGAGCAAC CAGAGAAACA CACGUUGUGG UACAUUACCU GGUA 54

( 2 ) INFORMATION FOR SEQ ID NO: 957:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 957:

UGCUCCUGCU GAGGGCAG 18

( 2 ) INFORMATION FOR SEQ ID NO: 958:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 958:

AGGAUCAAAG AAGCUUUGAC CAGAGAAACA CACGUUGUGG UACAUUACCU GGUA 54

( 2 ) INFORMATION FOR SEQ ID NO: 959:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 959:

CAAAGCUGAU UUGAUCCU 18

( 2 ) INFORMATION FOR SEQ ID NO: 960:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 960:

CUGUAGAAAG AAGGAUCAAC CAGAGAAACA CACGUUGUGG UACAUUACCU GGUA 54

( 2 ) INFORMATION FOR SEQ ID NO: 961:

( i ) SEQUENCE CHARACTERISTICS:
    ( A ) LENGTH: 18 base pairs ( B ) TYPE: nucleic acid
( C ) STRANDEDNESS: single
( D ) TOPOLOGY: linear ( x i ) SEQUENCE DESCRIPTION: SEQ ID NO: 961:

UGAUCCUGAC UUCUACAG 18

( 2 ) INFORMATION FOR SEQ ID NO: 962:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO: 962:

UGUUCAGGAG AAGUAGAAAC CAGAGAAACA CACGUUGUGG UACAUUACCU GGUA 54

( 2 ) INFORMATION FOR SEQ ID NO: 963:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO: 963:

UUCUACAGCC CCUGAACA 18

( 2 ) INFORMATION FOR SEQ ID NO: 964:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO: 964:

CUGGAAGGAG AAGAGUAGAC CAGAGAAACA CACGUUGUGG UACAUUACCU GGUA 54

( 2 ) INFORMATION FOR SEQ ID NO: 965:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( x i ) SEQUENCE DESCRIPTION: SEQ ID NO: 965:

CUACUCUGCC CCUUCCAG 18

( 2 ) INFORMATION FOR SEQ ID NO: 966:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO: 966:

AGGCUCAGAG AAGCUAUUAC CAGAGAAACA CACGUUGUGG UACAUUACCU GGUA 54

( 2 ) INFORMATION FOR SEQ ID NO: 967:

( i ) SEQUENCE CHARACTERISTICS:
( A ) LENGTH: 18 base pairs
( B ) TYPE: nucleic acid
( C ) STRANDEDNESS: single ( D ) TOPOLOGY: linear ( x i ) SEQUENCE DESCRIPTION: SEQ ID NO: 967:

AAUAGCAGUU CUGAGCCU                                                                                           18

( 2 ) INFORMATION FOR SEQ ID NO: 968:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 968:

UCUGGUAGAG AAGGAUAUAC CAGAGAAACA CACGUUGUGG UACAUUACCU GGUA                                                    54

( 2 ) INFORMATION FOR SEQ ID NO: 969:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 969:

AUAUCCAGCU CUACCAGA                                                                                           18

( 2 ) INFORMATION FOR SEQ ID NO: 970:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 970:

GGUCCUGGAG AAGGACAAAC CAGAGAAACA CACGUUGUGG UACAUUACCU GGUA                                                    54

( 2 ) INFORMATION FOR SEQ ID NO: 971:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 971:

UUGUCCAGCU CCAGGACC                                                                                           18

( 2 ) INFORMATION FOR SEQ ID NO: 972:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 972:

GUAUUGUAAG AAGCGUUCAC CAGAGAAACA CACGUUGUGG UACAUUACCU GGUA                                                    54

( 2 ) INFORMATION FOR SEQ ID NO: 973:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 973:

GAACGCUGUU UACAAUAC 18

( 2 ) INFORMATION FOR SEQ ID NO: 974:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 974:

CCACACUAAG AAGGGAGAAC CAGAGAAACA CACGUUGUGG UACAUUACCU GGUA 54

( 2 ) INFORMATION FOR SEQ ID NO: 975:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 975:

UCUCCCUGCC UAGUGUGG 18

( 2 ) INFORMATION FOR SEQ ID NO: 976:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 976:

AGUGGACAAG AAGGCUCCAC CAGAGAAACA CACGUUGUGG UACAUUACCU GGUA 54

( 2 ) INFORMATION FOR SEQ ID NO: 977:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 977:

GGAGCCAGCC UGUCCACU 18

( 2 ) INFORMATION FOR SEQ ID NO: 978:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 978:

CCCCAGUGAG AAGGCUGGAC CAGAGAAACA CACGUUGUGG UACAUUACCU GGUA 54

( 2 ) INFORMATION FOR SEQ ID NO: 979:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 979:

CCAGCCUGUC CACUGGGG 18

( 2 ) INFORMATION FOR SEQ ID NO: 980:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 980:

AUGGUGCCAG AAGGGAUAAC CAGAGAAACA CACGUUGUGG UACAUUACCU GGUA 54

( 2 ) INFORMATION FOR SEQ ID NO: 981:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 981:

UAUCCCUGUU GGCACCAU 18

( 2 ) INFORMATION FOR SEQ ID NO: 982:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 982:

ACACAAAGAG AAGGGUAAAC CAGAGAAACA CACGUUGUGG UACAUUACCU GGUA 54

( 2 ) INFORMATION FOR SEQ ID NO: 983:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 983:

UUACCCUGAU CUUUGUGU 18

( 2 ) INFORMATION FOR SEQ ID NO: 984:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 984:

UUCCAACCAG AAGUACACAC CAGAGAAACA CACGUUGUGG UACAUUACCU GGUA 54

( 2 ) INFORMATION FOR SEQ ID NO: 985:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 985:

GUGUACUGUU GGUUGGAA 18

( 2 ) INFORMATION FOR SEQ ID NO: 986:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 986:

CCACUCCAAG AAGAAAAGAC CAGAGAAACA CACGUUGUGG UACAUUACCU GGUA     54

( 2 ) INFORMATION FOR SEQ ID NO: 987:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 987:

CUUUUCGGCC UGGAGUGG     18

( 2 ) INFORMATION FOR SEQ ID NO: 988:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 988:

GACUCUCAAG AAGCCCUUAC CAGAGAAACA CACGUUGUGG UACAUUACCU GGUA     54

( 2 ) INFORMATION FOR SEQ ID NO: 989:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 989:

AAGGGCUGAC UGAGAGUC     18

( 2 ) INFORMATION FOR SEQ ID NO: 990:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 990:

UCACUGUAAG AAGGCUGCAC CAGAGAAACA CACGUUGUGG UACAUUACCU GGUA     54

( 2 ) INFORMATION FOR SEQ ID NO: 991:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 991:

GCAGCCAGAC UACAGUGA     18

( 2 ) INFORMATION FOR SEQ ID NO: 992:

( i ) SEQUENCE CHARACTERISTICS:
  ( A ) LENGTH: 54 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 992:

CGUGGCAGAG AAGUUCACAC CAGAGAAACA CACGUUGUGG UACAUUACCU GGUA    54

( 2 ) INFORMATION FOR SEQ ID NO: 993:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 993:

GUGAACGGUU CUGCCACG    18

( 2 ) INFORMATION FOR SEQ ID NO: 994:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 994:

GCUAUGCAAG AAGCAAGGAC CAGAGAAACA CACGUUGUGG UACAUUACCU GGUA    54

( 2 ) INFORMATION FOR SEQ ID NO: 995:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 995:

CCUUGCAGCC UGCAUAGC    18

( 2 ) INFORMATION FOR SEQ ID NO: 996:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II
        region of a HH ribozyme.

( x i ) SEQUENCE DESCRIPTION: SEQ ID NO: 996:

UGAGUGGCCU GAUGANGAAA UGGUGGC    27

( 2 ) INFORMATION FOR SEQ ID NO: 997:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 997:

GCCACCAUUG CCACUCA    17

( 2 ) INFORMATION FOR SEQ ID NO: 998:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II region of a HH ribozyme.

( x i ) SEQUENCE DESCRIPTION: SEQ ID NO: 998:

AGGGAUCUCU GAUGANGAAA GUGGCAA 27

( 2 ) INFORMATION FOR SEQ ID NO: 999:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 999:

UUGCCACUCA GAUCCCU 17

( 2 ) INFORMATION FOR SEQ ID NO: 1000:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II region of a HH ribozyme.

( x i ) SEQUENCE DESCRIPTION: SEQ ID NO: 1000:

AUAAGAGGCU GAUGANGAAA UCUGAGU 27

( 2 ) INFORMATION FOR SEQ ID NO: 1001:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1001:

ACUCAGAUCC CUCUUAU 17

( 2 ) INFORMATION FOR SEQ ID NO: 1002:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II region of a HH ribozyme.

( x i ) SEQUENCE DESCRIPTION: SEQ ID NO: 1002:

AGGAAUAACU GAUGANGAAA GGGAUCU 27

( 2 ) INFORMATION FOR SEQ ID NO: 1003:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 1003:

AGAUCCCUCU UAUUCCU 17

( 2 ) INFORMATION FOR SEQ ID NO: 1004:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for the stem II region of a HH ribozyme.

( x i ) SEQUENCE DESCRIPTION: SEQ ID NO: 1004:

GCAGGAAUCU GAUGANGAAA GAGGGAU 27

( 2 ) INFORMATION FOR SEQ ID NO: 1005:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1005:

AUCCCUCUUA UUCCUGC 17

( 2 ) INFORMATION FOR SEQ ID NO: 1006:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for the stem II region of a HH ribozyme.

( x i ) SEQUENCE DESCRIPTION: SEQ ID NO: 1006:

UGCAGGAACU GAUGANGAAA AGAGGGA 27

( 2 ) INFORMATION FOR SEQ ID NO: 1007:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1007:

UCCCUCUUAU UCCUGCA 17

( 2 ) INFORMATION FOR SEQ ID NO: 1008:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:

(D) OTHER INFORMATION: The letter "N" stands for the stem II
region of a HH ribozyme.

(xi) SEQUENCE DESCRIPTION: SEQ ID NO: 1008:

GCUGCAGGCU GAUGANGAAA UAAGAGG 27

(2) INFORMATION FOR SEQ ID NO: 1009:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1009:

CCUCUUAUUC CUGCAGC 17

(2) INFORMATION FOR SEQ ID NO: 1010:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II
region of a HH ribozyme.

(xi) SEQUENCE DESCRIPTION: SEQ ID NO: 1010:

AGCUGCAGCU GAUGANGAAA AUAAGAG 27

(2) INFORMATION FOR SEQ ID NO: 1011:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1011:

CUCUUAUUCC UGCAGCU 17

(2) INFORMATION FOR SEQ ID NO: 1012:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II
region of a HH ribozyme.

(xi) SEQUENCE DESCRIPTION: SEQ ID NO: 1012:

CCAGCAGACU GAUGANGAAA CAGCUGC 27

(2) INFORMATION FOR SEQ ID NO: 1013:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1013:

GCAGCUGUCU CUGCUGG 17

( 2 ) INFORMATION FOR SEQ ID NO: 1014:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1014:

CCCCAGCACU GAUGANGAAA GACAGCU 27

( 2 ) INFORMATION FOR SEQ ID NO: 1015:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1015:

AGCUGUCUCU GCUGGGG 17

( 2 ) INFORMATION FOR SEQ ID NO: 1016:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1016:

GGACCGUGCU GAUGANGAAA GUUCAGC 27

( 2 ) INFORMATION FOR SEQ ID NO: 1017:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1017:

GCUGAACUCC ACGGUCC 17

( 2 ) INFORMATION FOR SEQ ID NO: 1018:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1018:

GGCAUGGGCU GAUGANGAAA CCGUGGA 27

( 2 ) INFORMATION FOR SEQ ID NO: 1019:

-continued ( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1019:

UCCACGGUCC CCAUGCC      17

( 2 ) INFORMATION FOR SEQ ID NO: 1020:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1020:

UCAGGUGUCU GAUGANGAAA UGUCUUC      27

( 2 ) INFORMATION FOR SEQ ID NO: 1021:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1021:

GAAGACAUCA CACCUGA      17

( 2 ) INFORMATION FOR SEQ ID NO: 1022:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1022:

CAGGAAGACU GAUGANGAAA UCAGGUG      27

( 2 ) INFORMATION FOR SEQ ID NO: 1023:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1023:

CACCUGAUUU CUUCCUG      17

( 2 ) INFORMATION FOR SEQ ID NO: 1024:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:

( D ) OTHER INFORMATION: The letter "N" stands for the stem II
region of a HH ribozyme.

( x i ) SEQUENCE DESCRIPTION: SEQ ID NO: 1024:

UCAGGAAGCU GAUGANGAAA AUCAGGU                     27

( 2 ) INFORMATION FOR SEQ ID NO: 1025:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1025:

ACCUGAUUUC UUCCUGA                                17

( 2 ) INFORMATION FOR SEQ ID NO: 1026:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II
        region of a HH ribozyme.

( x i ) SEQUENCE DESCRIPTION: SEQ ID NO: 1026:

GUCAGGAACU GAUGANGAAA AAUCAGG                     27

( 2 ) INFORMATION FOR SEQ ID NO: 1027:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1027:

CCUGAUUUCU UCCUGAC                                17

( 2 ) INFORMATION FOR SEQ ID NO: 1028:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II
        region of a HH ribozyme.

( x i ) SEQUENCE DESCRIPTION: SEQ ID NO: 1028:

CGGUCAGGCU GAUGANGAAA GAAAUCA                     27

( 2 ) INFORMATION FOR SEQ ID NO: 1029:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1029:

UGAUUUCUUC CUGACCG                                17

( 2 ) INFORMATION FOR SEQ ID NO: 1030:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II region of a HH ribozyme.

( x i ) SEQUENCE DESCRIPTION: SEQ ID NO: 1030:

GCGGUCAGCU GAUGANGAAA AGAAAUC 27

( 2 ) INFORMATION FOR SEQ ID NO: 1031:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1031:

GAUUCUUCC UGACCGC 17

( 2 ) INFORMATION FOR SEQ ID NO: 1032:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II region of a HH ribozyme.

( x i ) SEQUENCE DESCRIPTION: SEQ ID NO: 1032:

GGAGGGUGCU GAUGANGAAA GCGGUCA 27

( 2 ) INFORMATION FOR SEQ ID NO: 1033:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1033:

UGACCGCUAC ACCCUCC 17

( 2 ) INFORMATION FOR SEQ ID NO: 1034:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II region of a HH ribozyme.

( x i ) SEQUENCE DESCRIPTION: SEQ ID NO: 1034:

GGGUCUCGCU GAUGANGAAA GGGUGUA 27

( 2 ) INFORMATION FOR SEQ ID NO: 1035:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1035:

UACACCCUCC GAGACCC          17

( 2 ) INFORMATION FOR SEQ ID NO: 1036:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 1036:

GAAACACUCU GAUGANGAAA GGGUCUC          27

( 2 ) INFORMATION FOR SEQ ID NO: 1037:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1037:

GAGACCCUCA GUGUUUC          17

( 2 ) INFORMATION FOR SEQ ID NO: 1038:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 1038:

AGGGAGGACU GAUGANGAAA CACUGAG          27

( 2 ) INFORMATION FOR SEQ ID NO: 1039:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1039:

CUCAGUGUUU CCUCCCU          17

( 2 ) INFORMATION FOR SEQ ID NO: 1040:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:

-continued (D) OTHER INFORMATION: The letter "N" stands for the stem II
region of a HH ribozyme.

(xi) SEQUENCE DESCRIPTION: SEQ ID NO: 1040:

CAGGGAGGCU GAUGANGAAA ACACUGA 27

(2) INFORMATION FOR SEQ ID NO: 1041:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1041:

UCAGUGUUUC CUCCCUG 17

(2) INFORMATION FOR SEQ ID NO: 1042:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II
region of a HH ribozyme.

(xi) SEQUENCE DESCRIPTION: SEQ ID NO: 1042:

GCAGGGAGCU GAUGANGAAA AACACUG 27

(2) INFORMATION FOR SEQ ID NO: 1043:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1043:

CAGUGUUUCC UCCCUGC 17

(2) INFORMATION FOR SEQ ID NO: 1044:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II
region of a HH ribozyme.

(xi) SEQUENCE DESCRIPTION: SEQ ID NO: 1044:

GGGGCAGGCU GAUGANGAAA GGAAACA 27

(2) INFORMATION FOR SEQ ID NO: 1045:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1045:

UGUUUCCUCC CUGCCCC 17

( 2 ) INFORMATION FOR SEQ ID NO: 1046:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1046:

ACCUCUGGCU GAUGANGAAA GGGGCAG 27

( 2 ) INFORMATION FOR SEQ ID NO: 1047:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1047:

CUGCCCCUCC CAGAGGU 17

( 2 ) INFORMATION FOR SEQ ID NO: 1048:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1048:

AAACACUGCU GAUGANGAAA CCUCUGG 27

( 2 ) INFORMATION FOR SEQ ID NO: 1049:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1049:

CCAGAGGUCC AGUGUUU 17

( 2 ) INFORMATION FOR SEQ ID NO: 1050:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1050:

GAACACAACU GAUGANGAAA CACUGGA 27

( 2 ) INFORMATION FOR SEQ ID NO: 1051:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1051:

UCCAGUGUUU UGUGUUC                                                                                                  17

( 2 ) INFORMATION FOR SEQ ID NO: 1052:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
              region of a HH ribozyme.

( x i ) SEQUENCE DESCRIPTION: SEQ ID NO: 1052:

UGAACACACU GAUGANGAAA ACACUGG                                                                                       27

( 2 ) INFORMATION FOR SEQ ID NO: 1053:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1053:

CCAGUGUUUU GUGUUCA                                                                                                  17

( 2 ) INFORMATION FOR SEQ ID NO: 1054:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
              region of a HH ribozyme.

( x i ) SEQUENCE DESCRIPTION: SEQ ID NO: 1054:

UUGAACACCU GAUGANGAAA AACACUG                                                                                       27

( 2 ) INFORMATION FOR SEQ ID NO: 1055:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1055:

CAGUGUUUUG UGUUCAA                                                                                                  17

( 2 ) INFORMATION FOR SEQ ID NO: 1056:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:

( D ) OTHER INFORMATION: The letter "N"stands for the stem II
region of a HH ribozyme.

( x i ) SEQUENCE DESCRIPTION: SEQ ID NO: 1056:

CAACAUUGCU GAUGANGAAA CACAAAA 27

( 2 ) INFORMATION FOR SEQ ID NO: 1057:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1057:

UUUUGUGUUC AAUGUUG 17

( 2 ) INFORMATION FOR SEQ ID NO: 1058:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for the stem II
      region of a HH ribozyme.

( x i ) SEQUENCE DESCRIPTION: SEQ ID NO: 1058:

UCAACAUUCU GAUGANGAAA ACACAAA 27

( 2 ) INFORMATION FOR SEQ ID NO: 1059:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1059:

UUUGUGUUCA AUGUUGA 17

( 2 ) INFORMATION FOR SEQ ID NO: 1060:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for the stem II
      region of a HH ribozyme.

( x i ) SEQUENCE DESCRIPTION: SEQ ID NO: 1060:

AUGUACUCCU GAUGANGAAA CAUUGAA 27

( 2 ) INFORMATION FOR SEQ ID NO: 1061:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1061:

UUCAAUGUUG AGUACAU 17

( 2 ) INFORMATION FOR SEQ ID NO: 1062:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1062:

AAUUCAUGCU GAUGANGAAA CUCAACA        27

( 2 ) INFORMATION FOR SEQ ID NO: 1063:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1063:

UGUUGAGUAC AUGAAUU        17

( 2 ) INFORMATION FOR SEQ ID NO: 1064:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1064:

CCAAGUGCCU GAUGANGAAA UUCAUGU        27

( 2 ) INFORMATION FOR SEQ ID NO: 1065:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1065:

ACAUGAAUUG CACUUGG        17

( 2 ) INFORMATION FOR SEQ ID NO: 1066:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1066:

GCUGUUCCCU GAUGANGAAA GUGCAAU        27

( 2 ) INFORMATION FOR SEQ ID NO: 1067:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1067:

AUUGCACUUG GAACAGC                17

( 2 ) INFORMATION FOR SEQ ID NO: 1068:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II
          region of a HH ribozyme.

( x i ) SEQUENCE DESCRIPTION: SEQ ID NO: 1068:

GGGGCUCACU GAUGANGAAA GCUGCUG                27

( 2 ) INFORMATION FOR SEQ ID NO: 1069:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1069:

CAGCAGCUCU GAGCCCC                17

( 2 ) INFORMATION FOR SEQ ID NO: 1070:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II
          region of a HH ribozyme.

( x i ) SEQUENCE DESCRIPTION: SEQ ID NO: 1070:

UAUACCAGCU GAUGANGAAA GUGCAGG                27

( 2 ) INFORMATION FOR SEQ ID NO: 1071:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1071:

CCUGCACUAC UGGUAUA                17

( 2 ) INFORMATION FOR SEQ ID NO: 1072:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:

( D ) OTHER INFORMATION: The letter "N"stands for the stem II
region of a HH ribozyme.

( x i ) SEQUENCE DESCRIPTION: SEQ ID NO: 1072:

AGUUCUUACU GAUGANGAAA CCAGUAG 27

( 2 ) INFORMATION FOR SEQ ID NO: 1073:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1073:

CUACUGGUAU AAGAACU 17

( 2 ) INFORMATION FOR SEQ ID NO: 1074:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1074:

GGAGUUCUCU GAUGANGAAA UACCAGU 27

( 2 ) INFORMATION FOR SEQ ID NO: 1075:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1075:

ACUGGUAUAA GAACUCC 17

( 2 ) INFORMATION FOR SEQ ID NO: 1076:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1076:

CAUCAUUGCU GAUGANGAAA GUUCUUA 27

( 2 ) INFORMATION FOR SEQ ID NO: 1077:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1077:

UAAGAACUCC AAUGAUG 17

( 2 ) INFORMATION FOR SEQ ID NO: 1078:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1078:

CUGGACUUCU GAUGANGAAA UCAUCAU 27

( 2 ) INFORMATION FOR SEQ ID NO: 1079:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1079:

AUGAUGAUAA AGUCCAG 17

( 2 ) INFORMATION FOR SEQ ID NO: 1080:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1080:

CACUCCUGCU GAUGANGAAA CUUUAUC 27

( 2 ) INFORMATION FOR SEQ ID NO: 1081:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1081:

GAUAAAGUCC AGGAGUG 17

( 2 ) INFORMATION FOR SEQ ID NO: 1082:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1082:

AGAAUAGGCU GAUGANGAAA GUGGCCA 27

( 2 ) INFORMATION FOR SEQ ID NO: 1083:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1083:

UGGCCACUAC CUAUUCU     17

( 2 ) INFORMATION FOR SEQ ID NO: 1084:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 1084:

CUAGAGAACU GAUGANGAAA GGUAGUG     27

( 2 ) INFORMATION FOR SEQ ID NO: 1085:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1085:

CACUACCUAU UCUCUAG     17

( 2 ) INFORMATION FOR SEQ ID NO: 1086:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 1086:

CUCUAGAGCU GAUGANGAAA UAGGUAG     27

( 2 ) INFORMATION FOR SEQ ID NO: 1087:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1087:

CUACCUAUUC UCUAGAG     17

( 2 ) INFORMATION FOR SEQ ID NO: 1088:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:

( D ) OTHER INFORMATION: The letter "N"stands for the stem II
region of a HH ribozyme.

( x i ) SEQUENCE DESCRIPTION: SEQ ID NO: 1088:

UCUCUAGACU GAUGANGAAA AUAGGUA 27

( 2 ) INFORMATION FOR SEQ ID NO: 1089:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1089:

UACCUAUUCU CUAGAGA 17

( 2 ) INFORMATION FOR SEQ ID NO: 1090:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II
region of a HH ribozyme.

( x i ) SEQUENCE DESCRIPTION: SEQ ID NO: 1090:

CCUCUCUACU GAUGANGAAA GAAUAGG 27

( 2 ) INFORMATION FOR SEQ ID NO: 1091:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1091:

CCUAUUCUCU AGAGAGG 17

( 2 ) INFORMATION FOR SEQ ID NO: 1092:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II
region of a HH ribozyme.

( x i ) SEQUENCE DESCRIPTION: SEQ ID NO: 1092:

GACCUCUCCU GAUGANGAAA GAGAAUA 27

( 2 ) INFORMATION FOR SEQ ID NO: 1093:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1093:

UAUUCUCUAG AGAGGUC 17

( 2 ) INFORMATION FOR SEQ ID NO: 1094:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II region of a HH ribozyme.

( x i ) SEQUENCE DESCRIPTION: SEQ ID NO: 1094:

CCAGCAGUCU GAUGANGAAA CCUCUCU 27

( 2 ) INFORMATION FOR SEQ ID NO: 1095:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1095:

AGAGAGGUCA CUGCUGG 17

( 2 ) INFORMATION FOR SEQ ID NO: 1096:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II region of a HH ribozyme.

( x i ) SEQUENCE DESCRIPTION: SEQ ID NO: 1096:

CUGCAACCCU GAUGANGAAA CAGCCAG 27

( 2 ) INFORMATION FOR SEQ ID NO: 1097:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1097:

CUGGCUGUUG GUUGCAG 17

( 2 ) INFORMATION FOR SEQ ID NO: 1098:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II region of a HH ribozyme.

( x i ) SEQUENCE DESCRIPTION: SEQ ID NO: 1098:

CCUUCUGCCU GAUGANGAAA CCAACAG 27

( 2 ) INFORMATION FOR SEQ ID NO: 1099:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1099:

CUGUUGGUUG CAGAAGG　　　　　　　　　　　　　　17

( 2 ) INFORMATION FOR SEQ ID NO: 1100:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 1100:

UAGAGAUGCU GAUGANGAAA UCUCCUC　　　　　　　　27

( 2 ) INFORMATION FOR SEQ ID NO: 1101:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1101:

GAGGAGAUCC AUCUCUA　　　　　　　　　　　　　　17

( 2 ) INFORMATION FOR SEQ ID NO: 1102:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 1102:

UUCGUAGACU GAUGANGAAA UGGAUCU　　　　　　　　27

( 2 ) INFORMATION FOR SEQ ID NO: 1103:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1103:

AGAUCCAUCU CUACGAA　　　　　　　　　　　　　　17

( 2 ) INFORMATION FOR SEQ ID NO: 1104:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:

-continued (D) OTHER INFORMATION: The letter "N"stands for the stem II
region of a HH ribozyme.

(xi) SEQUENCE DESCRIPTION: SEQ ID NO: 1104:

GUUUCGUACU GAUGANGAAA GAUGGAU 27

(2) INFORMATION FOR SEQ ID NO: 1105:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1105:

AUCCAUCUCU ACGAAAC 17

(2) INFORMATION FOR SEQ ID NO: 1106:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N"stands for the stem II
region of a HH ribozyme.

(xi) SEQUENCE DESCRIPTION: SEQ ID NO: 1106:

AUGUUUCGCU GAUGANGAAA GAGAUGG 27

(2) INFORMATION FOR SEQ ID NO: 1107:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1107:

CCAUCUCUAC GAAACAU 17

(2) INFORMATION FOR SEQ ID NO: 1108:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N"stands for the stem II
region of a HH ribozyme.

(xi) SEQUENCE DESCRIPTION: SEQ ID NO: 1108:

GGACAACACU GAUGANGAAA UGUUUCG 27

(2) INFORMATION FOR SEQ ID NO: 1109:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1109:

CGAAACAUUU GUUGUCC 17

( 2 ) INFORMATION FOR SEQ ID NO: 1110:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II region of a HH ribozyme.

( x i ) SEQUENCE DESCRIPTION: SEQ ID NO: 1110:

UGGACAACCU GAUGANGAAA AUGUUUC 27

( 2 ) INFORMATION FOR SEQ ID NO: 1111:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1111:

GAAACAUUUG UUGUCCA 17

( 2 ) INFORMATION FOR SEQ ID NO: 1112:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II region of a HH ribozyme.

( x i ) SEQUENCE DESCRIPTION: SEQ ID NO: 1112:

AGCUGGACCU GAUGANGAAA CAAAUGU 27

( 2 ) INFORMATION FOR SEQ ID NO: 1113:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1113:

ACAUUUGUUG UCCAGCU 17

( 2 ) INFORMATION FOR SEQ ID NO: 1114:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II region of a HH ribozyme.

( x i ) SEQUENCE DESCRIPTION: SEQ ID NO: 1114:

CGGAGCUGCU GAUGANGAAA CAACAAA 27

( 2 ) INFORMATION FOR SEQ ID NO: 1115:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1115:

UUUGUUGUCC AGCUCCG 17

( 2 ) INFORMATION FOR SEQ ID NO: 1116:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II
      region of a HH ribozyme.

( x i ) SEQUENCE DESCRIPTION: SEQ ID NO: 1116:

GGGUCCCGCU GAUGANGAAA GCUGGAC 27

( 2 ) INFORMATION FOR SEQ ID NO: 1117:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1117:

GUCCAGCUCC GGGACCC 17

( 2 ) INFORMATION FOR SEQ ID NO: 1118:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II
      region of a HH ribozyme.

( x i ) SEQUENCE DESCRIPTION: SEQ ID NO: 1118:

UCUGUGUGCU GAUGANGAAA CUGCCUC 27

( 2 ) INFORMATION FOR SEQ ID NO: 1119:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1119:

GAGGCAGUCC ACACAGA 17

( 2 ) INFORMATION FOR SEQ ID NO: 1120:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:

( D ) OTHER INFORMATION: The letter "N"stands for the stem II
region of a HH ribozyme.

( x i ) SEQUENCE DESCRIPTION: SEQ ID NO: 1120:

UGCAGUUUCU GAUGANGAAA GCUUCUG 27

( 2 ) INFORMATION FOR SEQ ID NO: 1121:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1121:

CAGAAGCUAA AACUGCA 17

( 2 ) INFORMATION FOR SEQ ID NO: 1122:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II
region of a HH ribozyme.

( x i ) SEQUENCE DESCRIPTION: SEQ ID NO: 1122:

GAUCACCACU GAUGANGAAA UUUUGCA 27

( 2 ) INFORMATION FOR SEQ ID NO: 1123:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1123:

UGCAAAAUCU GGUGAUC 17

( 2 ) INFORMATION FOR SEQ ID NO: 1124:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II
region of a HH ribozyme.

( x i ) SEQUENCE DESCRIPTION: SEQ ID NO: 1124:

GCCCAGGGCU GAUGANGAAA UCACCAG 27

( 2 ) INFORMATION FOR SEQ ID NO: 1125:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1125:

CUGGUGAUCC CCUGGGC 17

( 2 ) INFORMATION FOR SEQ ID NO: 1126:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 1126:

GUUCUCCGCU GAUGANGAAA GCCCAGG 27

( 2 ) INFORMATION FOR SEQ ID NO: 1127:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1127:

CCUGGGCUCC GGAGAAC 17

( 2 ) INFORMATION FOR SEQ ID NO: 1128:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 1128:

UGAAGGGUCU GAUGANGAAA GGUUCUC 27

( 2 ) INFORMATION FOR SEQ ID NO: 1129:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1129:

GAGAACCUAA CCCUUCA 17

( 2 ) INFORMATION FOR SEQ ID NO: 1130:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 1130:

AGGUUGUGCU GAUGANGAAA GGGUUAG 27

( 2 ) INFORMATION FOR SEQ ID NO: 1131:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 1131:

CUAACCCUUC ACAACCU    17

( 2 ) INFORMATION FOR SEQ ID NO: 1132:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for the stem II
         region of a HH ribozyme.

( x i ) SEQUENCE DESCRIPTION: SEQ ID NO: 1132:

CAGGUUGUCU GAUGANGAAA AGGGUUA    27

( 2 ) INFORMATION FOR SEQ ID NO: 1133:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1133:

UAACCCUUCA CAACCUG    17

( 2 ) INFORMATION FOR SEQ ID NO: 1134:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for the stem II
         region of a HH ribozyme.

( x i ) SEQUENCE DESCRIPTION: SEQ ID NO: 1134:

CUAGCUGGCU GAUGANGAAA UUCGCUC    27

( 2 ) INFORMATION FOR SEQ ID NO: 1135:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1135:

GAGCGAAUCC CAGCUAG    17

( 2 ) INFORMATION FOR SEQ ID NO: 1136:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:

-continued (D) OTHER INFORMATION: The letter "N"stands for the stem II
region of a HH ribozyme.

( x i ) SEQUENCE DESCRIPTION: SEQ ID NO: 1136:

CUCAGUUCCU GAUGANGAAA GCUGGGA 27

( 2 ) INFORMATION FOR SEQ ID NO: 1137:

( i ) SEQUENCE CHARACTERISTICS:
(A) LENGTH: 17 base pairs
(B) TYPE: nucleic acid
(C) STRANDEDNESS: single
(D) TOPOLOGY: linear ( x i ) SEQUENCE DESCRIPTION: SEQ ID NO: 1137:

UCCCAGCUAG AACUGAG 17

( 2 ) INFORMATION FOR SEQ ID NO: 1138:

( i ) SEQUENCE CHARACTERISTICS:
(A) LENGTH: 27 base pairs
(B) TYPE: nucleic acid
(C) STRANDEDNESS: single
(D) TOPOLOGY: linear ( i x ) FEATURE:
(D) OTHER INFORMATION: The letter "N"stands for the stem II
region of a HH ribozyme.

( x i ) SEQUENCE DESCRIPTION: SEQ ID NO: 1138:

AGUGGUCCCU GAUGANGAAA GUGUCUG 27

( 2 ) INFORMATION FOR SEQ ID NO: 1139:

( i ) SEQUENCE CHARACTERISTICS:
(A) LENGTH: 17 base pairs
(B) TYPE: nucleic acid
(C) STRANDEDNESS: single
(D) TOPOLOGY: linear ( x i ) SEQUENCE DESCRIPTION: SEQ ID NO: 1139:

CAGACACUUG GACCACU 17

( 2 ) INFORMATION FOR SEQ ID NO: 1140:

( i ) SEQUENCE CHARACTERISTICS:
(A) LENGTH: 27 base pairs
(B) TYPE: nucleic acid
(C) STRANDEDNESS: single
(D) TOPOLOGY: linear ( i x ) FEATURE:
(D) OTHER INFORMATION: The letter "N"stands for the stem II
region of a HH ribozyme.

( x i ) SEQUENCE DESCRIPTION: SEQ ID NO: 1140:

AUGCUCCACU GAUGANGAAA CAGUGGU 27

( 2 ) INFORMATION FOR SEQ ID NO: 1141:

( i ) SEQUENCE CHARACTERISTICS:
(A) LENGTH: 17 base pairs
(B) TYPE: nucleic acid
(C) STRANDEDNESS: single
(D) TOPOLOGY: linear ( x i ) SEQUENCE DESCRIPTION: SEQ ID NO: 1141:

ACCACUGUUU GGAGCAU 17

( 2 ) INFORMATION FOR SEQ ID NO: 1142:

( i ) SEQUENCE CHARACTERISTICS:
           ( A ) LENGTH: 27 base pairs
           ( B ) TYPE: nucleic acid
           ( C ) STRANDEDNESS: single
           ( D ) TOPOLOGY: linear ( i x ) FEATURE:
           ( D ) OTHER INFORMATION: The letter "N"stands for the stem II
           region of a HH ribozyme.

( x i ) SEQUENCE DESCRIPTION: SEQ ID NO: 1142:

CAUGCUCCCU GAUGANGAAA ACAGUGG        27

( 2 ) INFORMATION FOR SEQ ID NO: 1143:

( i ) SEQUENCE CHARACTERISTICS:
           ( A ) LENGTH: 17 base pairs
           ( B ) TYPE: nucleic acid
           ( C ) STRANDEDNESS: single
           ( D ) TOPOLOGY: linear ( x i ) SEQUENCE DESCRIPTION: SEQ ID NO: 1143:

CCACUGUUUG GAGCAUG        17

( 2 ) INFORMATION FOR SEQ ID NO: 1144:

( i ) SEQUENCE CHARACTERISTICS:
           ( A ) LENGTH: 27 base pairs
           ( B ) TYPE: nucleic acid
           ( C ) STRANDEDNESS: single
           ( D ) TOPOLOGY: linear ( i x ) FEATURE:
           ( D ) OTHER INFORMATION: The letter "N"stands for the stem II
           region of a HH ribozyme.

( x i ) SEQUENCE DESCRIPTION: SEQ ID NO: 1144:

UACUGCACCU GAUGANGAAA CAUGCUC        27

( 2 ) INFORMATION FOR SEQ ID NO: 1145:

( i ) SEQUENCE CHARACTERISTICS:
           ( A ) LENGTH: 17 base pairs
           ( B ) TYPE: nucleic acid
           ( C ) STRANDEDNESS: single
           ( D ) TOPOLOGY: linear ( x i ) SEQUENCE DESCRIPTION: SEQ ID NO: 1145:

GAGCAUGUUG UGCAGUA        17

( 2 ) INFORMATION FOR SEQ ID NO: 1146:

( i ) SEQUENCE CHARACTERISTICS:
           ( A ) LENGTH: 27 base pairs
           ( B ) TYPE: nucleic acid
           ( C ) STRANDEDNESS: single
           ( D ) TOPOLOGY: linear ( i x ) FEATURE:
           ( D ) OTHER INFORMATION: The letter "N"stands for the stem II
           region of a HH ribozyme.

( x i ) SEQUENCE DESCRIPTION: SEQ ID NO: 1146:

CACUCCGGCU GAUGANGAAA CUGCACA        27

( 2 ) INFORMATION FOR SEQ ID NO: 1147:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1147:

UGUGCAGUAC CGGAGUG 17

( 2 ) INFORMATION FOR SEQ ID NO: 1148:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1148:

GGUCCACUCU GAUGANGAAA CUGUUCA 27

( 2 ) INFORMATION FOR SEQ ID NO: 1149:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1149:

UGAACAGUCA GUGGACC 17

( 2 ) INFORMATION FOR SEQ ID NO: 1150:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1150:

AGAGAAGCCU GAUGANGAAA UUUCGGU 27

( 2 ) INFORMATION FOR SEQ ID NO: 1151:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1151:

ACCGAAAUAG CUUCUCU 17

( 2 ) INFORMATION FOR SEQ ID NO: 1152:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:

( D ) OTHER INFORMATION: The letter "N"stands for the stem II
region of a HH ribozyme.

( x i ) SEQUENCE DESCRIPTION: SEQ ID NO: 1152:

GCAGAGAGCU GAUGANGAAA GCUAUUU 27

( 2 ) INFORMATION FOR SEQ ID NO: 1153:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1153:

AAAUAGCUUC UCUCUGC 17

( 2 ) INFORMATION FOR SEQ ID NO: 1154:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II
region of a HH ribozyme.

( x i ) SEQUENCE DESCRIPTION: SEQ ID NO: 1154:

GGCAGAGACU GAUGANGAAA AGCUAUU 27

( 2 ) INFORMATION FOR SEQ ID NO: 1155:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1155:

AAUAGCUUCU CUCUGCC 17

( 2 ) INFORMATION FOR SEQ ID NO: 1156:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II
region of a HH ribozyme.

( x i ) SEQUENCE DESCRIPTION: SEQ ID NO: 1156:

UAGGCAGACU GAUGANGAAA GAAGCUA 27

( 2 ) INFORMATION FOR SEQ ID NO: 1157:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1157:

UAGCUUCUCU CUGCCUA 17

( 2 ) INFORMATION FOR SEQ ID NO: 1158:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1158:

GCUAGGCACU GAUGANGAAA GAGAAGC      27

( 2 ) INFORMATION FOR SEQ ID NO: 1159:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1159:

GCUUCUCUCU GCCUAGC      17

( 2 ) INFORMATION FOR SEQ ID NO: 1160:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1160:

AUCCACGCCU GAUGANGAAA GGCAGAG      27

( 2 ) INFORMATION FOR SEQ ID NO: 1161:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1161:

CUCUGCCUAG CGUGGAU      17

( 2 ) INFORMATION FOR SEQ ID NO: 1162:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1162:

ACGUGUAGCU GAUGANGAAA CUUCUGC      27

( 2 ) INFORMATION FOR SEQ ID NO: 1163:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 1163:

GCAGAAGUUC UACACGU                                                                                                      17

( 2 ) INFORMATION FOR SEQ ID NO: 1164:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i x ) FEATURE:
                ( D ) OTHER INFORMATION: The letter "N"stands for the stem II
                        region of a HH ribozyme.

( x i ) SEQUENCE DESCRIPTION: SEQ ID NO: 1164:

AACGUGUACU GAUGANGAAA ACUUCUG                                                                                           27

( 2 ) INFORMATION FOR SEQ ID NO: 1165:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 1165:

CAGAAGUUCU ACACGUU                                                                                                      17

( 2 ) INFORMATION FOR SEQ ID NO: 1166:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i x ) FEATURE:
                ( D ) OTHER INFORMATION: The letter "N"stands for the stem II
                        region of a HH ribozyme.

( x i ) SEQUENCE DESCRIPTION: SEQ ID NO: 1166:

GGAACGUGCU GAUGANGAAA GAACUUC                                                                                           27

( 2 ) INFORMATION FOR SEQ ID NO: 1167:

( i ) SEQUENCE CHARACTERISTICS:
                ( A ) LENGTH: 17 base pairs
                ( B ) TYPE: nucleic acid
                ( C ) STRANDEDNESS: single
                ( D ) TOPOLOGY: linear ( x i ) SEQUENCE DESCRIPTION: SEQ ID NO: 1167:

GAAGUUCUAC ACGUUCC                                                                                                      17

( 2 ) INFORMATION FOR SEQ ID NO: 1168:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i x ) FEATURE:

( D ) OTHER INFORMATION: The letter "N" stands for the stem II
region of a HH ribozyme.

( x i ) SEQUENCE DESCRIPTION: SEQ ID NO: 1168:

GGACACGGCU GAUGANGAAA CGUGUAG 27

( 2 ) INFORMATION FOR SEQ ID NO: 1169:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1169:

CUACACGUUC CGUGUCC 17

( 2 ) INFORMATION FOR SEQ ID NO: 1170:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for the stem II
region of a HH ribozyme.

( x i ) SEQUENCE DESCRIPTION: SEQ ID NO: 1170:

CGGACACGCU GAUGANGAAA ACGUGUA 27

( 2 ) INFORMATION FOR SEQ ID NO: 1171:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1171:

UACACGUUCC GUGUCCG 17

( 2 ) INFORMATION FOR SEQ ID NO: 1172:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N" stands for the stem II
region of a HH ribozyme.

( x i ) SEQUENCE DESCRIPTION: SEQ ID NO: 1172:

CGGCUUCGCU GAUGANGAAA CACGGAA 27

( 2 ) INFORMATION FOR SEQ ID NO: 1173:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1173:

UUCCGUGUCC GAAGCCG 17

( 2 ) INFORMATION FOR SEQ ID NO: 1174:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1174:

GUGGGUUACU GAUGANGAAA GCGGCUU    27

( 2 ) INFORMATION FOR SEQ ID NO: 1175:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1175:

AAGCCGCUAU AACCCAC    17

( 2 ) INFORMATION FOR SEQ ID NO: 1176:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1176:

GAGUGGGUCU GAUGANGAAA UAGCGGC    27

( 2 ) INFORMATION FOR SEQ ID NO: 1177:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1177:

GCCGCUAUAA CCCACUC    17

( 2 ) INFORMATION FOR SEQ ID NO: 1178:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1178:

CUUCCACACU GAUGANGAAA GUGGGUU    27

( 2 ) INFORMATION FOR SEQ ID NO: 1179:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 1179:

AACCCACUCU GUGGAAG                    17

( 2 ) INFORMATION FOR SEQ ID NO: 1180:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for the stem II
         region of a HH ribozyme.

( x i ) SEQUENCE DESCRIPTION: SEQ ID NO: 1180:

CCAACGCUCU GAUGANGAAA GCGCUUC         27

( 2 ) INFORMATION FOR SEQ ID NO: 1181:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1181:

GAAGCGCUCA GCGUUGG                    17

( 2 ) INFORMATION FOR SEQ ID NO: 1182:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for the stem II
         region of a HH ribozyme.

( x i ) SEQUENCE DESCRIPTION: SEQ ID NO: 1182:

UUCACUCCCU GAUGANGAAA CGCUGAG         27

( 2 ) INFORMATION FOR SEQ ID NO: 1183:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1183:

CUCAGCGUUG GAGUGAA                    17

( 2 ) INFORMATION FOR SEQ ID NO: 1184:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:

(D) OTHER INFORMATION: The letter "N"stands for the stem II
region of a HH ribozyme.

(x i) SEQUENCE DESCRIPTION: SEQ ID NO: 1184:

CCAGUGGACU GAUGANGAAA GGGUGGC 27

(2) INFORMATION FOR SEQ ID NO: 1185:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO: 1185:

GCCACCCUAU CCACUGG 17

(2) INFORMATION FOR SEQ ID NO: 1186:

(i) SEQUENCE CHARACTERISTICS:
(A) LENGTH: 27 base pairs
(B) TYPE: nucleic acid
(C) STRANDEDNESS: single
(D) TOPOLOGY: linear (i x) FEATURE:
(D) OTHER INFORMATION: The letter "N"stands for the stem II
region of a HH ribozyme.

(x i) SEQUENCE DESCRIPTION: SEQ ID NO: 1186:

CCCCAGUGCU GAUGANGAAA UAGGGUG 27

(2) INFORMATION FOR SEQ ID NO: 1187:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO: 1187:

CACCCUAUCC ACUGGGG 17

(2) INFORMATION FOR SEQ ID NO: 1188:

(i) SEQUENCE CHARACTERISTICS:
(A) LENGTH: 27 base pairs
(B) TYPE: nucleic acid
(C) STRANDEDNESS: single
(D) TOPOLOGY: linear (i x) FEATURE:
(D) OTHER INFORMATION: The letter "N"stands for the stem II
region of a HH ribozyme.

(x i) SEQUENCE DESCRIPTION: SEQ ID NO: 1188:

CUUGGAGGCU GAUGANGAAA UUGCUCC 27

(2) INFORMATION FOR SEQ ID NO: 1189:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO: 1189:

GGAGCAAUAC CUCCAAG 17

( 2 ) INFORMATION FOR SEQ ID NO: 1190:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 1190:

UCUCCUUGCU GAUGANGAAA GGUAUUG      27

( 2 ) INFORMATION FOR SEQ ID NO: 1191:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1191:

CAAUACCUCC AAGGAGA      17

( 2 ) INFORMATION FOR SEQ ID NO: 1192:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 1192:

AAACAAAGCU GAUGANGAAA UUCUCCU      27

( 2 ) INFORMATION FOR SEQ ID NO: 1193:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1193:

AGGAGAAUCC UUUGUUU      17

( 2 ) INFORMATION FOR SEQ ID NO: 1194:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 1194:

UGCAAACACU GAUGANGAAA GGAUUCU      27

( 2 ) INFORMATION FOR SEQ ID NO: 1195:

-continued (i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO: 1195:

AGAAUCCUUU GUUUGCA     17

(2) INFORMATION FOR SEQ ID NO: 1196:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ix) FEATURE:
    (D) OTHER INFORMATION: The letter "N" stands for the stem II region of a HH ribozyme.

(xi) SEQUENCE DESCRIPTION: SEQ ID NO: 1196:

AUGCAAACCU GAUGANGAAA AGGAUUC     27

(2) INFORMATION FOR SEQ ID NO: 1197:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO: 1197:

GAAUCCUUUG UUUGCAU     17

(2) INFORMATION FOR SEQ ID NO: 1198:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ix) FEATURE:
    (D) OTHER INFORMATION: The letter "N" stands for the stem II region of a HH ribozyme.

(xi) SEQUENCE DESCRIPTION: SEQ ID NO: 1198:

CCGAUGCACU GAUGANGAAA CAAAGGA     27

(2) INFORMATION FOR SEQ ID NO: 1199:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (xi) SEQUENCE DESCRIPTION: SEQ ID NO: 1199:

UCCUUUGUUU GCAUCGG     17

(2) INFORMATION FOR SEQ ID NO: 1200:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ix) FEATURE:

( D ) OTHER INFORMATION: The letter "N" stands for the stem II
region of a HH ribozyme.

( x i ) SEQUENCE DESCRIPTION: SEQ ID NO: 1200:

UCCGAUGCCU GAUGANGAAA ACAAAGG 27

( 2 ) INFORMATION FOR SEQ ID NO: 1201:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1201:

CCUUUGUUUG CAUCGGA 17

( 2 ) INFORMATION FOR SEQ ID NO: 1202:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II
        region of a HH ribozyme.

( x i ) SEQUENCE DESCRIPTION: SEQ ID NO: 1202:

CAGCUUCCCU GAUGANGAAA UGCAAAC 27

( 2 ) INFORMATION FOR SEQ ID NO: 1203:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1203:

GUUUGCAUCG GAAGCUG 17

( 2 ) INFORMATION FOR SEQ ID NO: 1204:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N" stands for the stem II
        region of a HH ribozyme.

( x i ) SEQUENCE DESCRIPTION: SEQ ID NO: 1204:

AGGGGAUCU GAUGANGAAA GCACAGC 27

( 2 ) INFORMATION FOR SEQ ID NO: 1205:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1205:

GCUGUGCUUA UCCCCCU 17

( 2 ) INFORMATION FOR SEQ ID NO: 1206:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 1206:

AAGGGGACU GAUGANGAAA AGCACAG     27

( 2 ) INFORMATION FOR SEQ ID NO: 1207:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1207:

CUGUGCUUAU CCCCCUU     17

( 2 ) INFORMATION FOR SEQ ID NO: 1208:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 1208:

CCAAGGGCU GAUGANGAAA UAAGCAC     27

( 2 ) INFORMATION FOR SEQ ID NO: 1209:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1209:

GUGCUUAUCC CCCUUGG     17

( 2 ) INFORMATION FOR SEQ ID NO: 1210:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 1210:

AUGGAGCCCU GAUGANGAAA GGGGGAU     27

( 2 ) INFORMATION FOR SEQ ID NO: 1211:

( i ) SEQUENCE CHARACTERISTICS:
: ( A ) LENGTH: 17 base pairs
: ( B ) TYPE: nucleic acid
: ( C ) STRANDEDNESS: single
: ( D ) TOPOLOGY: linear ( x i ) SEQUENCE DESCRIPTION: SEQ ID NO: 1211:

AUCCCCUUG GCUCCAU 17

( 2 ) INFORMATION FOR SEQ ID NO: 1212:

: ( i ) SEQUENCE CHARACTERISTICS:
: : ( A ) LENGTH: 27 base pairs
: : ( B ) TYPE: nucleic acid
: : ( C ) STRANDEDNESS: single
: : ( D ) TOPOLOGY: linear : ( i x ) FEATURE:
: : ( D ) OTHER INFORMATION: The letter "N"stands for the stem II region of a HH ribozyme.

( x i ) SEQUENCE DESCRIPTION: SEQ ID NO: 1212:

AUCCCAUGCU GAUGANGAAA GCCAAGG 27

( 2 ) INFORMATION FOR SEQ ID NO: 1213:

: ( i ) SEQUENCE CHARACTERISTICS:
: : ( A ) LENGTH: 17 base pairs
: : ( B ) TYPE: nucleic acid
: : ( C ) STRANDEDNESS: single
: : ( D ) TOPOLOGY: linear ( x i ) SEQUENCE DESCRIPTION: SEQ ID NO: 1213:

CCUUGGCUCC AUGGGAU 17

( 2 ) INFORMATION FOR SEQ ID NO: 1214:

: ( i ) SEQUENCE CHARACTERISTICS:
: : ( A ) LENGTH: 27 base pairs
: : ( B ) TYPE: nucleic acid
: : ( C ) STRANDEDNESS: single
: : ( D ) TOPOLOGY: linear : ( i x ) FEATURE:
: : ( D ) OTHER INFORMATION: The letter "N"stands for the stem II region of a HH ribozyme.

( x i ) SEQUENCE DESCRIPTION: SEQ ID NO: 1214:

UAAUAAUCCU GAUGANGAAA UCCCAUG 27

( 2 ) INFORMATION FOR SEQ ID NO: 1215:

: ( i ) SEQUENCE CHARACTERISTICS:
: : ( A ) LENGTH: 17 base pairs
: : ( B ) TYPE: nucleic acid
: : ( C ) STRANDEDNESS: single
: : ( D ) TOPOLOGY: linear ( x i ) SEQUENCE DESCRIPTION: SEQ ID NO: 1215:

CAUGGGAUUG AUUAUUA 17

( 2 ) INFORMATION FOR SEQ ID NO: 1216:

: ( i ) SEQUENCE CHARACTERISTICS:
: : ( A ) LENGTH: 27 base pairs
: : ( B ) TYPE: nucleic acid
: : ( C ) STRANDEDNESS: single
: : ( D ) TOPOLOGY: linear : ( i x ) FEATURE:

( D ) OTHER INFORMATION: The letter "N"stands for the stem II
region of a HH ribozyme.

( x i ) SEQUENCE DESCRIPTION: SEQ ID NO: 1216:

AGGCUAAUCU GAUGANGAAA UCAAUCC                                                              27

( 2 ) INFORMATION FOR SEQ ID NO: 1217:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1217:

GGAUUGAUUA UUAGCCU                                                                          17

( 2 ) INFORMATION FOR SEQ ID NO: 1218:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1218:

AAGGCUAACU GAUGANGAAA AUCAAUC                                                              27

( 2 ) INFORMATION FOR SEQ ID NO: 1219:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1219:

GAUUGAUUAU UAGCCUU                                                                          17

( 2 ) INFORMATION FOR SEQ ID NO: 1220:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1220:

AUAAGGCUCU GAUGANGAAA UAAUCAA                                                              27

( 2 ) INFORMATION FOR SEQ ID NO: 1221:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1221:

UUGAUUAUUA GCCUUAU                                                                          17

( 2 ) INFORMATION FOR SEQ ID NO: 1222:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II
region of a HH ribozyme.

( x i ) SEQUENCE DESCRIPTION: SEQ ID NO: 1222:

GAUAAGGCCU GAUGANGAAA AUAAUCA 27

( 2 ) INFORMATION FOR SEQ ID NO: 1223:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1223:

UGAUUAUUAG CCUUAUC 17

( 2 ) INFORMATION FOR SEQ ID NO: 1224:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II
region of a HH ribozyme.

( x i ) SEQUENCE DESCRIPTION: SEQ ID NO: 1224:

ACACAGAUCU GAUGANGAAA GGCUAAU 27

( 2 ) INFORMATION FOR SEQ ID NO: 1225:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1225:

AUUAGCCUUA UCUGUGU 17

( 2 ) INFORMATION FOR SEQ ID NO: 1226:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II
region of a HH ribozyme.

( x i ) SEQUENCE DESCRIPTION: SEQ ID NO: 1226:

CACACAGACU GAUGANGAAA AGGCUAA 27

( 2 ) INFORMATION FOR SEQ ID NO: 1227:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1227:

UUAGCCUUAU CUGUGUG 17

( 2 ) INFORMATION FOR SEQ ID NO: 1228:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 1228:

UACACACACU GAUGANGAAA UAAGGCU 27

( 2 ) INFORMATION FOR SEQ ID NO: 1229:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1229:

AGCCUUAUCU GUGUGUA 17

( 2 ) INFORMATION FOR SEQ ID NO: 1230:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 1230:

GCCAGUAGCU GAUGANGAAA CACACAG 27

( 2 ) INFORMATION FOR SEQ ID NO: 1231:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1231:

CUGUGUGUAC UACUGGC 17

( 2 ) INFORMATION FOR SEQ ID NO: 1232:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:

( D ) OTHER INFORMATION: The letter "N"stands for the stem II
             region of a HH ribozyme.

( x i ) SEQUENCE DESCRIPTION: SEQ ID NO: 1232:

CCAGCCAGCU GAUGANGAAA GUACACA                                                27

( 2 ) INFORMATION FOR SEQ ID NO: 1233:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1233:

UGUGUACUAC UGGCUGG                                                           17

( 2 ) INFORMATION FOR SEQ ID NO: 1234:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
             region of a HH ribozyme.

( x i ) SEQUENCE DESCRIPTION: SEQ ID NO: 1234:

GGGGGAUCCU GAUGANGAAA CCGUUCC                                                27

( 2 ) INFORMATION FOR SEQ ID NO: 1235:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1235:

GGAACGGUCG AUCCCCC                                                           17

( 2 ) INFORMATION FOR SEQ ID NO: 1236:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
             region of a HH ribozyme.

( x i ) SEQUENCE DESCRIPTION: SEQ ID NO: 1236:

AUUCGGGGCU GAUGANGAAA UCGACCG                                                27

( 2 ) INFORMATION FOR SEQ ID NO: 1237:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1237:

CGGUCGAUCC CCCGAAU                                                           17

( 2 ) INFORMATION FOR SEQ ID NO: 1238:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1238:

AGGGUAGGCU GAUGANGAAA UUCGGGG                                      27

( 2 ) INFORMATION FOR SEQ ID NO: 1239:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1239:

CCCCGAAUUC CUACCCU                                                17

( 2 ) INFORMATION FOR SEQ ID NO: 1240:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1240:

GAGGGUAGCU GAUGANGAAA AUUCGGG                                      27

( 2 ) INFORMATION FOR SEQ ID NO: 1241:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1241:

CCCGAAUUCC UACCCUC                                               17

( 2 ) INFORMATION FOR SEQ ID NO: 1242:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1242:

CUUGAGGGCU GAUGANGAAA GGAAUUC                                      27

( 2 ) INFORMATION FOR SEQ ID NO: 1243:

( i ) SEQUENCE CHARACTERISTICS:
  ( A ) LENGTH: 17 base pairs
  ( B ) TYPE: nucleic acid
  ( C ) STRANDEDNESS: single
  ( D ) TOPOLOGY: linear ( x i ) SEQUENCE DESCRIPTION: SEQ ID NO: 1243:

GAAUUCCUAC CCUCAAG  17

( 2 ) INFORMATION FOR SEQ ID NO: 1244:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 1244:

AGGUUCUUCU GAUGANGAAA GGGUAGG  27

( 2 ) INFORMATION FOR SEQ ID NO: 1245:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1245:

CCUACCCUCA AGAACCU  17

( 2 ) INFORMATION FOR SEQ ID NO: 1246:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 1246:

AGUAACCACU GAUGANGAAA UCCUCCA  27

( 2 ) INFORMATION FOR SEQ ID NO: 1247:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1247:

UGGAGGAUCU GGUUACU  17

( 2 ) INFORMATION FOR SEQ ID NO: 1248:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:

-continued (D) OTHER INFORMATION: The letter "N" stands for the stem II
region of a HH ribozyme.

(xi) SEQUENCE DESCRIPTION: SEQ ID NO: 1248:

UAUUCAGUCU GAUGANGAAA CCAGAUC 27

(2) INFORMATION FOR SEQ ID NO: 1249:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1249:

GAUCUGGUUA CUGAAUA 17

(2) INFORMATION FOR SEQ ID NO: 1250:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II
region of a HH ribozyme.

(xi) SEQUENCE DESCRIPTION: SEQ ID NO: 1250:

AUAUUCAGCU GAUGANGAAA ACCAGAU 27

(2) INFORMATION FOR SEQ ID NO: 1251:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1251:

AUCUGGUUAC UGAAUAU 17

(2) INFORMATION FOR SEQ ID NO: 1252:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for the stem II
region of a HH ribozyme.

(xi) SEQUENCE DESCRIPTION: SEQ ID NO: 1252:

UCCCGUGACU GAUGANGAAA UUCAGUA 27

(2) INFORMATION FOR SEQ ID NO: 1253:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO: 1253:

UACUGAAUAU CACGGGA 17

( 2 ) INFORMATION FOR SEQ ID NO: 1254:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II
      region of a HH ribozyme.

( x i ) SEQUENCE DESCRIPTION: SEQ ID NO: 1254:

AUUCCCGUCU GAUGANGAAA UAUUCAG     27

( 2 ) INFORMATION FOR SEQ ID NO: 1255:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1255:

CUGAAUAUCA CGGGAAU     17

( 2 ) INFORMATION FOR SEQ ID NO: 1256:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II
      region of a HH ribozyme.

( x i ) SEQUENCE DESCRIPTION: SEQ ID NO: 1256:

GGCCGAAACU GAUGANGAAA UUCCCGU     27

( 2 ) INFORMATION FOR SEQ ID NO: 1257:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1257:

ACGGGAAUUU UUCGGCC     17

( 2 ) INFORMATION FOR SEQ ID NO: 1258:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II
      region of a HH ribozyme.

( x i ) SEQUENCE DESCRIPTION: SEQ ID NO: 1258:

AGGCCGAACU GAUGANGAAA AUUCCCG     27

( 2 ) INFORMATION FOR SEQ ID NO: 1259:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1259:

CGGGAAUUUU UCGGCCU 17

( 2 ) INFORMATION FOR SEQ ID NO: 1260:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 1260:

CAGGCCGACU GAUGANGAAA AAUUCCC 27

( 2 ) INFORMATION FOR SEQ ID NO: 1261:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1261:

GGGAAUUUUU CGGCCUG 17

( 2 ) INFORMATION FOR SEQ ID NO: 1262:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
            region of a HH ribozyme.

( x i ) SEQUENCE DESCRIPTION: SEQ ID NO: 1262:

CCAGGCCGCU GAUGANGAAA AAAUUCC 27

( 2 ) INFORMATION FOR SEQ ID NO: 1263:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1263:

GGAAUUUUUC GGCCUGG 17

( 2 ) INFORMATION FOR SEQ ID NO: 1264:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:

(D) OTHER INFORMATION: The letter "N"stands for the stem II
region of a HH ribozyme.

(x i) SEQUENCE DESCRIPTION: SEQ ID NO: 1264:

UCCAGGCCCU GAUGANGAAA AAAAUUC                27

(2) INFORMATION FOR SEQ ID NO: 1265:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO: 1265:

GAAUUUUUCG GCCUGGA                           17

(2) INFORMATION FOR SEQ ID NO: 1266:

(i) SEQUENCE CHARACTERISTICS:
(A) LENGTH: 27 base pairs
(B) TYPE: nucleic acid
(C) STRANDEDNESS: single
(D) TOPOLOGY: linear (i x) FEATURE:
(D) OTHER INFORMATION: The letter "N"stands for the stem II
region of a HH ribozyme.

(x i) SEQUENCE DESCRIPTION: SEQ ID NO: 1266:

GUCCCUUACU GAUGANGAAA CACUCCA                27

(2) INFORMATION FOR SEQ ID NO: 1267:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO: 1267:

UGGAGUGUCU AAGGGAC                           17

(2) INFORMATION FOR SEQ ID NO: 1268:

(i) SEQUENCE CHARACTERISTICS:
(A) LENGTH: 27 base pairs
(B) TYPE: nucleic acid
(C) STRANDEDNESS: single
(D) TOPOLOGY: linear (i x) FEATURE:
(D) OTHER INFORMATION: The letter "N"stands for the stem II
region of a HH ribozyme.

(x i) SEQUENCE DESCRIPTION: SEQ ID NO: 1268:

CAGUCCCUCU GAUGANGAAA GACACUC                27

(2) INFORMATION FOR SEQ ID NO: 1269:

(i) SEQUENCE CHARACTERISTICS:
(A) LENGTH: 17 base pairs
(B) TYPE: nucleic acid
(C) STRANDEDNESS: single
(D) TOPOLOGY: linear (x i) SEQUENCE DESCRIPTION: SEQ ID NO: 1269:

GAGUGUCUAA GGGACUG                           17

( 2 ) INFORMATION FOR SEQ ID NO: 1270:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1270:

UGGCUGCACU GAUGANGAAA CUCUCCG 27

( 2 ) INFORMATION FOR SEQ ID NO: 1271:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1271:

CGGAGAGUCU GCAGCCA 17

( 2 ) INFORMATION FOR SEQ ID NO: 1272:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1272:

AUUCACUGCU GAUGANGAAA GUCUGGC 27

( 2 ) INFORMATION FOR SEQ ID NO: 1273:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1273:

GCCAGACUAC AGUGAAU 17

( 2 ) INFORMATION FOR SEQ ID NO: 1274:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1274:

ACGUGGCACU GAUGANGAAA GCCAUUC 27

( 2 ) INFORMATION FOR SEQ ID NO: 1275:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1275:

GAAUGGCUCU GCCACGU     17

( 2 ) INFORMATION FOR SEQ ID NO: 1276:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 1276:

AUCUCACUCU GAUGANGAAA CGUGGCA     27

( 2 ) INFORMATION FOR SEQ ID NO: 1277:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1277:

UGCCACGUCA GUGAGAU     17

( 2 ) INFORMATION FOR SEQ ID NO: 1278:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 1278:

UUUGGGGGCU GAUGANGAAA UCUCACU     27

( 2 ) INFORMATION FOR SEQ ID NO: 1279:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1279:

AGUGAGAUUC CCCCAAA     17

( 2 ) INFORMATION FOR SEQ ID NO: 1280:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:

(D) OTHER INFORMATION: The letter "N" stands for the stem II
region of a HH ribozyme.

(x i) SEQUENCE DESCRIPTION: SEQ ID NO: 1280:

UUUUGGGCU GAUGANGAAA AUCUCAC                                    27

(2) INFORMATION FOR SEQ ID NO: 1281:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO: 1281:

GUGAGAUUCC CCCAAAA                                              17

(2) INFORMATION FOR SEQ ID NO: 1282:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (i x) FEATURE:
      (D) OTHER INFORMATION: The letter "N" stands for the stem II
          region of a HH ribozyme.

(x i) SEQUENCE DESCRIPTION: SEQ ID NO: 1282:

CUCCCCUGCU GAUGANGAAA GCCCCUC                                   27

(2) INFORMATION FOR SEQ ID NO: 1283:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO: 1283:

GAGGGGCUCC AGGGGAG                                              17

(2) INFORMATION FOR SEQ ID NO: 1284:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (i x) FEATURE:
      (D) OTHER INFORMATION: The letter "N" stands for the stem II
          region of a HH ribozyme.

(x i) SEQUENCE DESCRIPTION: SEQ ID NO: 1284:

GCCCCCAGCU GAUGANGAAA CCCUCCC                                   27

(2) INFORMATION FOR SEQ ID NO: 1285:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (x i) SEQUENCE DESCRIPTION: SEQ ID NO: 1285:

GGGAGGGUCC UGGGGGC                                              17

( 2 ) INFORMATION FOR SEQ ID NO: 1286:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1286:

UGCAGGGGCU GAUGANGAAA GCCCCCA 27

( 2 ) INFORMATION FOR SEQ ID NO: 1287:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1287:

UGGGGGCUCC CCCUGCA 17

( 2 ) INFORMATION FOR SEQ ID NO: 1288:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1288:

GUAGGGGCCU GAUGANGAAA UGCUGGC 27

( 2 ) INFORMATION FOR SEQ ID NO: 1289:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1289:

GCCAGCAUAG CCCCUAC 17

( 2 ) INFORMATION FOR SEQ ID NO: 1290:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II region of a HH ribozyme.

( x i ) SEQUENCE DESCRIPTION: SEQ ID NO: 1290:

GAGCCCAGCU GAUGANGAAA GGGGCUA 27

( 2 ) INFORMATION FOR SEQ ID NO: 1291:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1291:

UAGCCCUAC UGGGCUC 17

( 2 ) INFORMATION FOR SEQ ID NO: 1292:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1292:

ACAUGGGGCU GAUGANGAAA GCCCAGU 27

( 2 ) INFORMATION FOR SEQ ID NO: 1293:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1293:

ACUGGGCUCC CCCAUGU 17

( 2 ) INFORMATION FOR SEQ ID NO: 1294:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1294:

CAGGGUAUCU GAUGANGAAA CAUGGGG 27

( 2 ) INFORMATION FOR SEQ ID NO: 1295:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1295:

CCCCAUGUUA UACCCUG 17

( 2 ) INFORMATION FOR SEQ ID NO: 1296:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:

( D ) OTHER INFORMATION: The letter "N"stands for the stem II
region of a HH ribozyme.

( x i ) SEQUENCE DESCRIPTION: SEQ ID NO: 1296:

UCAGGGUACU GAUGANGAAA ACAUGGG 27

( 2 ) INFORMATION FOR SEQ ID NO: 1297:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1297:

CCCAUGUUAU ACCCUGA 17

( 2 ) INFORMATION FOR SEQ ID NO: 1298:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II
region of a HH ribozyme.

( x i ) SEQUENCE DESCRIPTION: SEQ ID NO: 1298:

UUUCAGGGCU GAUGANGAAA UAACAUG 27

( 2 ) INFORMATION FOR SEQ ID NO: 1299:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1299:

CAUGUUAUAC CCUGAAA 17

( 2 ) INFORMATION FOR SEQ ID NO: 1300:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i x ) FEATURE:
( D ) OTHER INFORMATION: The letter "N"stands for the stem II
region of a HH ribozyme.

( x i ) SEQUENCE DESCRIPTION: SEQ ID NO: 1300:

UGUCAGGGCU GAUGANGAAA UCAGGGC 27

( 2 ) INFORMATION FOR SEQ ID NO: 1301:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO: 1301:

GCCCUGAUAC CCUGACA 17

( 2 ) INFORMATION FOR SEQ ID NO: 1302:

( i ) SEQUENCE CHARACTERISTICS:
           ( A ) LENGTH: 27 base pairs
           ( B ) TYPE: nucleic acid
           ( C ) STRANDEDNESS: single
           ( D ) TOPOLOGY: linear ( i x ) FEATURE:
           ( D ) OTHER INFORMATION: The letter "N"stands for the stem II
               region of a HH ribozyme.

( x i ) SEQUENCE DESCRIPTION: SEQ ID NO: 1302:

AGGACUCUCU GAUGANGAAA GGUUCUG            27

( 2 ) INFORMATION FOR SEQ ID NO: 1303:

( i ) SEQUENCE CHARACTERISTICS:
           ( A ) LENGTH: 17 base pairs
           ( B ) TYPE: nucleic acid
           ( C ) STRANDEDNESS: single
           ( D ) TOPOLOGY: linear ( x i ) SEQUENCE DESCRIPTION: SEQ ID NO: 1303:

CAGAACCUCA GAGUCCU            17

( 2 ) INFORMATION FOR SEQ ID NO: 1304:

( i ) SEQUENCE CHARACTERISTICS:
           ( A ) LENGTH: 27 base pairs
           ( B ) TYPE: nucleic acid
           ( C ) STRANDEDNESS: single
           ( D ) TOPOLOGY: linear ( i x ) FEATURE:
           ( D ) OTHER INFORMATION: The letter "N"stands for the stem II
               region of a HH ribozyme.

( x i ) SEQUENCE DESCRIPTION: SEQ ID NO: 1304:

GAGGACAGCU GAUGANGAAA CUCUGAG            27

( 2 ) INFORMATION FOR SEQ ID NO: 1305:

( i ) SEQUENCE CHARACTERISTICS:
           ( A ) LENGTH: 17 base pairs
           ( B ) TYPE: nucleic acid
           ( C ) STRANDEDNESS: single
           ( D ) TOPOLOGY: linear ( x i ) SEQUENCE DESCRIPTION: SEQ ID NO: 1305:

CUCAGAGUCC UGUCCUC            17

( 2 ) INFORMATION FOR SEQ ID NO: 1306:

( i ) SEQUENCE CHARACTERISTICS:
           ( A ) LENGTH: 27 base pairs
           ( B ) TYPE: nucleic acid
           ( C ) STRANDEDNESS: single
           ( D ) TOPOLOGY: linear ( i x ) FEATURE:
           ( D ) OTHER INFORMATION: The letter "N"stands for the stem II
               region of a HH ribozyme.

( x i ) SEQUENCE DESCRIPTION: SEQ ID NO: 1306:

UAUAGGAGCU GAUGANGAAA CAGGACU            27

( 2 ) INFORMATION FOR SEQ ID NO: 1307:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1307:

AGUCCUGUCC UCCUAUA 17

( 2 ) INFORMATION FOR SEQ ID NO: 1308:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 1308:

CAAUAUAGCU GAUGANGAAA GGACAGG 27

( 2 ) INFORMATION FOR SEQ ID NO: 1309:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1309:

CCUGUCCUCC UAUAUUG 17

( 2 ) INFORMATION FOR SEQ ID NO: 1310:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N"stands for the stem II region of a HH ribozyme.

( x i ) SEQUENCE DESCRIPTION: SEQ ID NO: 1310:

GUACAAUACU GAUGANGAAA GGAGGAC 27

( 2 ) INFORMATION FOR SEQ ID NO: 1311:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 1311:

GUCCUCCUAU AUUGUAC 17

( 2 ) INFORMATION FOR SEQ ID NO: 1312:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i x ) FEATURE:

( D ) OTHER INFORMATION: The letter "N"stands for the stem II
region of a HH ribozyme.

( x i ) SEQUENCE DESCRIPTION: SEQ ID NO: 1312:

UAGUACAACU GAUGANGAAA UAGGAGG                              27

( 2 ) INFORMATION FOR SEQ ID NO: 1313:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1313:

CCUCCUAUAU UGUACUA                                         17

( 2 ) INFORMATION FOR SEQ ID NO: 1314:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1314:

GUUAGUACCU GAUGANGAAA UAUAGGA                              27

( 2 ) INFORMATION FOR SEQ ID NO: 1315:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1315:

UCCUAUAUUG UACUAAC                                         17

( 2 ) INFORMATION FOR SEQ ID NO: 1316:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1316:

GAAGUUAGCU GAUGANGAAA CAAUAUA                              27

( 2 ) INFORMATION FOR SEQ ID NO: 1317:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1317:

UAUAUUGUAC UAACUUC                                         17

( 2 ) INFORMATION FOR SEQ ID NO: 1318:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1318:

GGGGAAGUCU GAUGANGAAA GUACAAU                          27

( 2 ) INFORMATION FOR SEQ ID NO: 1319:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1319:

AUUGUACUAA CUUCCCC                                    17

( 2 ) INFORMATION FOR SEQ ID NO: 1320:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1320:

AUAAGGGCU GAUGANGAAA GUUAGUA                           27

( 2 ) INFORMATION FOR SEQ ID NO: 1321:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1321:

UACUAACUUC CCCUUAU                                    17

( 2 ) INFORMATION FOR SEQ ID NO: 1322:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for the stem II
        region of a HH ribozyme.

( x i ) SEQUENCE DESCRIPTION: SEQ ID NO: 1322:

GAUAAGGGCU GAUGANGAAA AGUUAGU                         27

( 2 ) INFORMATION FOR SEQ ID NO: 1323:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 1323:

ACUAACUUCC CCUUAUC  17

( 2 ) INFORMATION FOR SEQ ID NO: 1324:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for the stem II
         region of a HH ribozyme.

( x i ) SEQUENCE DESCRIPTION: SEQ ID NO: 1324:

GGUUAGAUCU GAUGANGAAA GGGGAAG  27

( 2 ) INFORMATION FOR SEQ ID NO: 1325:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1325:

CUUCCCUUA UCUAACC  17

( 2 ) INFORMATION FOR SEQ ID NO: 1326:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for the stem II
         region of a HH ribozyme.

( x i ) SEQUENCE DESCRIPTION: SEQ ID NO: 1326:

UGGUUAGACU GAUGANGAAA AGGGGAA  27

( 2 ) INFORMATION FOR SEQ ID NO: 1327:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1327:

UUCCCUUAU CUAACCA  17

( 2 ) INFORMATION FOR SEQ ID NO: 1328:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:

( D ) OTHER INFORMATION: The letter "N"stands for the stem II
region of a HH ribozyme.

( x i ) SEQUENCE DESCRIPTION: SEQ ID NO: 1328:

GUUGGUUACU GAUGANGAAA UAAGGGG   27

( 2 ) INFORMATION FOR SEQ ID NO: 1329:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1329:

CCCCUUAUCU AACCAAC   17

( 2 ) INFORMATION FOR SEQ ID NO: 1330:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for the stem II
      region of a HH ribozyme.

( x i ) SEQUENCE DESCRIPTION: SEQ ID NO: 1330:

AGGUUGGUCU GAUGANGAAA GAUAAGG   27

( 2 ) INFORMATION FOR SEQ ID NO: 1331:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1331:

CCUUAUCUAA CCAACCU   17

( 2 ) INFORMATION FOR SEQ ID NO: 1332:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i x ) FEATURE:
      ( D ) OTHER INFORMATION: The letter "N"stands for the stem II
      region of a HH ribozyme.

( x i ) SEQUENCE DESCRIPTION: SEQ ID NO: 1332:

GAGCAUUGCU GAUGANGAAA CCCAGGU   27

( 2 ) INFORMATION FOR SEQ ID NO: 1333:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1333:

ACCUGGGUCC AAUGCUC   17

(2) INFORMATION FOR SEQ ID NO: 1334:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (D) OTHER INFORMATION: The letter "N" stands for the stem II region of a HH ribozyme.

(xi) SEQUENCE DESCRIPTION: SEQ ID NO: 1334:

GGCGAGGUCU GAUGANGAAA GCAUUGG 27

(2) INFORMATION FOR SEQ ID NO: 1335:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 1335:

CCAAUGCUCA CCUCGCC 17

(2) INFORMATION FOR SEQ ID NO: 1336:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 1336:

UAAGAGGGAG AAGAGUGGAC CAGAGAAACA CACGUUGUGG UACAUUACCU GGUA 54

(2) INFORMATION FOR SEQ ID NO: 1337:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 1337:

CCACUCAGAU CCCUCUUA 18

(2) INFORMATION FOR SEQ ID NO: 1338:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 1338:

GCAGAGACAG AAGCAGGAAC CAGAGAAACA CACGUUGUGG UACAUUACCU GGUA 54

(2) INFORMATION FOR SEQ ID NO: 1339:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 1339:

UCCUGCAGCU GUCUCUGC 18

( 2 ) INFORMATION FOR SEQ ID NO: 1340:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1340:

CCAGCAGAAG AAGCUGCAAC CAGAGAAACA CACGUUGUGG UACAUUACCU GGUA 54

( 2 ) INFORMATION FOR SEQ ID NO: 1341:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1341:

UGCAGCUGUC UCUGCUGG 18

( 2 ) INFORMATION FOR SEQ ID NO: 1342:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1342:

CCACCCCAG AAGAGACAAC CAGAGAAACA CACGUUGUGG UACAUUACCU GGUA 54

( 2 ) INFORMATION FOR SEQ ID NO: 1343:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1343:

UGUCUCUGCU GGGGGUGG 18

( 2 ) INFORMATION FOR SEQ ID NO: 1344:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1344:

GGCAUGGGAG AAGUGGAGAC CAGAGAAACA CACGUUGUGG UACAUUACCU GGUA 54

( 2 ) INFORMATION FOR SEQ ID NO: 1345:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1345:

CUCCACGGUC CCCAUGCC 18

( 2 ) INFORMATION FOR SEQ ID NO: 1346:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1346:

AGGAAGAAAG AAGGUGUGAC CAGAGAAACA CACGUUGUGG UACAUUACCU GGUA    54

( 2 ) INFORMATION FOR SEQ ID NO: 1347:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1347:

CACACCUGAU UUCUUCCU    18

( 2 ) INFORMATION FOR SEQ ID NO: 1348:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1348:

GUGUAGCGAG AAGGAAGAAC CAGAGAAACA CACGUUGUGG UACAUUACCU GGUA    54

( 2 ) INFORMATION FOR SEQ ID NO: 1349:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1349:

UCUUCCUGAC CGCUACAC    18

( 2 ) INFORMATION FOR SEQ ID NO: 1350:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1350:

CUGGGAGGAG AAGGGAGGAC CAGAGAAACA CACGUUGUGG UACAUUACCU GGUA    54

( 2 ) INFORMATION FOR SEQ ID NO: 1351:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1351:

CCUCCCUGCC CCUCCCAG    18

( 2 ) INFORMATION FOR SEQ ID NO: 1352:

( i ) SEQUENCE CHARACTERISTICS:
   ( A ) LENGTH: 54 base pairs
   ( B ) TYPE: nucleic acid
   ( C ) STRANDEDNESS: single
   ( D ) TOPOLOGY: linear ( x i ) SEQUENCE DESCRIPTION: SEQ ID NO: 1352:

GGGCUCAGAG AAGCUGUUAC CAGAGAAACA CACGUUGUGG UACAUUACCU GGUA 54

( 2 ) INFORMATION FOR SEQ ID NO: 1353:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1353:

AACAGCAGCU CUGAGCCC 18

( 2 ) INFORMATION FOR SEQ ID NO: 1354:

( i ) SEQUENCE CHARACTERISTICS:
      ( A ) LENGTH: 54 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1354:

GGUUGGUGAG AAGGGCUAC CAGAGAAACA CACGUUGUGG UACAUUACCU GGUA 54

( 2 ) INFORMATION FOR SEQ ID NO: 1355:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1355:

AGCCCCGGCC CACCAACC 18

( 2 ) INFORMATION FOR SEQ ID NO: 1356:

( i ) SEQUENCE CHARACTERISTICS:
      ( A ) LENGTH: 54 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1356:

AGUGCAGGAG AAGGUUGGAC CAGAGAAACA CACGUUGUGG UACAUUACCU GGUA 54

( 2 ) INFORMATION FOR SEQ ID NO: 1357:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO: 1357:

CCAACCUGAC CCUGCACU 18

( 2 ) INFORMATION FOR SEQ ID NO: 1358:

( i ) SEQUENCE CHARACTERISTICS:

( A ) LENGTH: 54 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 1358:

CAACAGCCAG AAGUGACCAC CAGAGAAACA CACGUUGUGG UACAUUACCU GGUA    54

( 2 ) INFORMATION FOR SEQ ID NO: 1359:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 1359:

GGUCACUGCU GGCUGUUG    18

( 2 ) INFORMATION FOR SEQ ID NO: 1360:

( i ) SEQUENCE CHARACTERISTICS:
            ( A ) LENGTH: 54 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 1360:

CUGCAACCAG AAGCCAGCAC CAGAGAAACA CACGUUGUGG UACAUUACCU GGUA    54

( 2 ) INFORMATION FOR SEQ ID NO: 1361:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 1361:

GCUGGCUGUU GGUUGCAG    18

( 2 ) INFORMATION FOR SEQ ID NO: 1362:

( i ) SEQUENCE CHARACTERISTICS:
            ( A ) LENGTH: 54 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 1362:

GGUCCGGAG AAGGACAAAC CAGAGAAACA CACGUUGUGG UACAUUACCU GGUA    54

( 2 ) INFORMATION FOR SEQ ID NO: 1363:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( x i ) SEQUENCE DESCRIPTION: SEQ ID NO: 1363:

UUGUCCAGCU CCGGGACC    18

( 2 ) INFORMATION FOR SEQ ID NO: 1364:

( i ) SEQUENCE CHARACTERISTICS:
            ( A ) LENGTH: 54 base pairs
            ( B ) TYPE: nucleic acid (C) STRANDEDNESS: single
(D) TOPOLOGY: linear (x i) SEQUENCE DESCRIPTION: SEQ ID NO: 1364:

UCUGUGUGAG AAGCCUCCAC CAGAGAAACA CACGUUGUGG UACAUUACCU GGUA                54

(2) INFORMATION FOR SEQ ID NO: 1365:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (x i) SEQUENCE DESCRIPTION: SEQ ID NO: 1365:

GGAGGCAGUC CACACAGA                18

(2) INFORMATION FOR SEQ ID NO: 1366:

(i) SEQUENCE CHARACTERISTICS:
      (A) LENGTH: 54 base pairs
      (B) TYPE: nucleic acid
      (C) STRANDEDNESS: single
      (D) TOPOLOGY: linear (x i) SEQUENCE DESCRIPTION: SEQ ID NO: 1366:

AUGCUCCAAG AAGUGGUCAC CAGAGAAACA CACGUUGUGG UACAUUACCU GGUA                54

(2) INFORMATION FOR SEQ ID NO: 1367:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (x i) SEQUENCE DESCRIPTION: SEQ ID NO: 1367:

GACCACUGUU UGGAGCAU                18

(2) INFORMATION FOR SEQ ID NO: 1368:

(i) SEQUENCE CHARACTERISTICS:
      (A) LENGTH: 54 base pairs
      (B) TYPE: nucleic acid
      (C) STRANDEDNESS: single
      (D) TOPOLOGY: linear (x i) SEQUENCE DESCRIPTION: SEQ ID NO: 1368:

UUCAGUCCAG AAGCGGUCAC CAGAGAAACA CACGUUGUGG UACAUUACCU GGUA                54

(2) INFORMATION FOR SEQ ID NO: 1369:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (x i) SEQUENCE DESCRIPTION: SEQ ID NO: 1369:

GACCGCAGCU GGACUGAA                18

(2) INFORMATION FOR SEQ ID NO: 1370:

(i) SEQUENCE CHARACTERISTICS:
      (A) LENGTH: 54 base pairs
      (B) TYPE: nucleic acid
      (C) STRANDEDNESS: single
      (D) TOPOLOGY: linear ( x i ) SEQUENCE DESCRIPTION: SEQ ID NO: 1370:

CCACGCUAAG AAGAGAGAAC CAGAGAAACA CACGUUGUGG UACAUUACCU GGUA    54

( 2 ) INFORMATION FOR SEQ ID NO: 1371:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1371:

UCUCUCUGCC UAGCGUGG    18

( 2 ) INFORMATION FOR SEQ ID NO: 1372:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1372:

GGGGGAUCAG AAGUUCCAAC CAGAGAAACA CACGUUGUGG UACAUUACCU GGUA    54

( 2 ) INFORMATION FOR SEQ ID NO: 1373:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1373:

UGGAACGGUC GAUCCCCC    18

( 2 ) INFORMATION FOR SEQ ID NO: 1374:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1374:

CCACUCCAAG AAGAAAAAAC CAGAGAAACA CACGUUGUGG UACAUUACCU GGUA    54

( 2 ) INFORMATION FOR SEQ ID NO: 1375:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1375:

UUUUUCGGCC UGGAGUGG    18

( 2 ) INFORMATION FOR SEQ ID NO: 1376:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1376:

```
UCACUGUAAG  AAGGCUGCAC  CAGAGAAACA  CACGUUGUGG  UACAUUACCU  GGUA                54
```

(2) INFORMATION FOR SEQ ID NO: 1377:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 1377:

```
GCAGCCAGAC  UACAGUGA                                                            18
```

(2) INFORMATION FOR SEQ ID NO: 1378:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO: 1378:

```
UAUAGGAGAG  AAGGACUCAC  CAGAGAAACA  CACGUUGUGG  UACAUUACCU  GGUA                54
```

(2) INFORMATION FOR SEQ ID NO: 1379:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 1379:

```
GAGUCCUGUC  CUCCUAUA                                                            18
```